(12) United States Patent
Matsuoka et al.

(10) Patent No.: US 8,048,897 B2
(45) Date of Patent: Nov. 1, 2011

(54) CYCLOHEXANE DERIVATIVE, PRODRUG THEREOF AND SALT THEREOF, AND THERAPEUTIC AGENT CONTAINING THE SAME FOR DIABETES

(75) Inventors: Hiroharu Matsuoka, Gotenba (JP); Tsutomu Sato, Gotenba (JP); Masahiro Nishimoto, Gotenba (JP); Nobuo Shimma, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 936 days.

(21) Appl. No.: 11/658,400

(22) PCT Filed: Jul. 26, 2005

(86) PCT No.: PCT/JP2005/013634
§ 371 (c)(1),
(2), (4) Date: Jan. 26, 2007

(87) PCT Pub. No.: WO2006/011469
PCT Pub. Date: Feb. 2, 2006

(65) Prior Publication Data
US 2008/0318874 A1 Dec. 25, 2008

(30) Foreign Application Priority Data

Jul. 26, 2004 (JP) .................... 2004-217065
Nov. 25, 2004 (JP) .................... 2004-340104

(51) Int. Cl.
| | |
|---|---|
| A61K 31/7028 | (2006.01) |
| A61K 31/403 | (2006.01) |
| A61P 3/10 | (2006.01) |
| C07C 63/00 | (2006.01) |
| C07D 209/04 | (2006.01) |
| C07D 213/62 | (2006.01) |
| C07D 231/14 | (2006.01) |
| C07D 307/79 | (2006.01) |
| C07D 317/48 | (2006.01) |
| C07D 333/34 | (2006.01) |
| C07D 333/56 | (2006.01) |

(52) U.S. Cl. ...... 514/345; 514/738; 546/301; 548/376.1; 548/490; 549/58; 549/66; 549/445; 549/469; 562/405

(58) Field of Classification Search .......... None
See application file for complete search history.

(56) References Cited

U.S. PATENT DOCUMENTS

| | | | | |
|---|---|---|---|---|
| 5,962,686 A * | 10/1999 | Ichihara et al. | ............... | 544/364 |
| 6,048,842 A | 4/2000 | Tsujihara et al. | | |
| 2001/0041674 A1 | 11/2001 | Tomiyama et al. | | |
| 2002/0137903 A1 | 9/2002 | Ellsworth et al. | | |
| 2003/0114390 A1 | 6/2003 | Washburn et al. | | |
| 2004/0110693 A1 * | 6/2004 | Trepel et al. | ..................... | 514/25 |

FOREIGN PATENT DOCUMENTS

| | | |
|---|---|---|
| CA | 2493391 A1 | 1/2004 |
| CA | 2508024 A1 | 6/2004 |
| CA | 2508226 A1 | 6/2004 |
| EP | 0598359 A1 | 5/1994 |
| EP | 0684254 A1 | 11/1995 |
| EP | 1213296 A1 | 6/2002 |
| EP | 1270584 A1 | 1/2003 |
| EP | 1329456 A1 | 7/2003 |
| EP | 1338603 A1 | 8/2003 |
| EP | 1344780 A1 | 9/2003 |
| EP | 1354888 A1 | 10/2003 |
| EP | 1364957 A1 | 11/2003 |
| EP | 1364958 A1 | 11/2003 |
| EP | 1367060 A1 | 12/2003 |
| EP | 1389621 A1 | 2/2004 |
| EP | 1400529 A1 | 3/2004 |
| EP | 1405859 A1 | 4/2004 |
| EP | 1500403 A1 | 1/2005 |
| EP | 1528066 A1 | 5/2005 |
| EP | 1553094 A1 | 7/2005 |
| EP | 1577317 A1 | 9/2005 |
| JP | 827006 | 1/1996 |
| JP | 9124684 | 5/1997 |
| JP | 9124685 | 5/1997 |
| JP | 9188625 | 7/1997 |
| JP | 2000-80041 | 3/2000 |
| JP | 200080041 | 3/2000 |
| JP | 2001288178 | 10/2001 |
| JP | 200312686 | 1/2003 |
| WO | 0127128 A1 | 4/2001 |
| WO | WO 01/27128 A1 | 4/2001 |
| WO | 0158899 A1 | 8/2001 |
| WO | WO 01/68660 A1 | 9/2001 |
| WO | 0174834 A1 | 10/2001 |
| WO | 0174835 A1 | 10/2001 |
| WO | WO 02/064606 A1 | 8/2002 |
| WO | 02083066 A2 | 10/2002 |
| WO | WO 02/083066 A2 | 10/2002 |
| WO | 03011880 A1 | 2/2003 |
| WO | 03020737 A1 | 3/2003 |
| WO | 03099836 A1 | 12/2003 |
| WO | 2004007517 A1 | 1/2004 |
| WO | WO 2004/007517 A1 | 1/2004 |
| WO | WO 2004/013118 A1 | 2/2004 |
| WO | WO 2004/014931 A1 | 2/2004 |
| WO | 2004052902 A1 | 6/2004 |
| WO | 2004052903 A1 | 6/2004 |
| WO | WO2005051938 * | 6/2005 |

OTHER PUBLICATIONS

Adachi et al., Metabolism, "T-1095, a Renal Na+-Glucose Transporter Inhibitor, Improves Hyperglycemia in Streptozotocin-Induced Diabetic Rats", vol. 49, issue 8, pp. 990-995 (2000).*
MayoClinic.com "Type 1 diabetes"; aso available at http://www.mayoclinic.com/health/type-1-diabetes; last viewed Feb. 1, 2010.*
Testa, Bernard, Biochemical Pharmacology, "Prodrug research: futile or fertile?", vol. 68, pp. 2097-2106 (2004).*
Ettmayer, Peter, Journal of Medicinal Chemistry, "Lessons Learned from Marketed and Investigational Prodrugs", vol. 47, issue 10, pp. 2393-2404 (2004).*
WordNet Search 3.0 "prevent"; also available at http://wordnetweb.princeton.edu/perl/webwn; last viewed Nov. 14, 2007.*
Kenji Tsujihara et al., "Na+-Glucose Cotrans[orter Inhibitors as Antidiabetics. I. Synthesis and pharmacological Properties of 4'-Dehydroxyphlorizin Derivatives Based on a New Concept", Chem. Pharm. Bull., vol. 44, No. 6, 1996 Pharmaceutical Societyof Japan, pp. 1174-1180.
Mitsuya Honou et al., "Na+-Glucose Cotransporter Inhibitors as Autidiabetic Agents. III. Synthesis and Pharmacological Properties of 4'-Dehydroxyphlorizin Derivatives Modified at the OH Groups of the Glucose Moiety", Chem\Pharm vol. 46, No. 10, Oct. 1998, pp. 1545-1555.

Mitsuya Honou et al., "Na+-Glucose Cotransporter Inhibitors as Antidiabetic Agents. II. Synthesis ans Structure-Activity Relationships of 4'-Dehydroxyphlorizin Derivatives", Chem Pharm Bull., vol. 46, No. 1, 1998, p. 22-33.

Kenji Tsujihara et al., Na+-Glucose Cotransporter (SGLT) Inhibitors as Antidiabetic Agents. 4. Synthesis and Pharmacological Properties of 4'-Dehydroxyphlorizin Derivatives Substituted on the B Ring, J. Med. Chem. vol. 42, No. 26, Dec. 1999, pp. 5311-5324.

J.T.Link et al., "A method for preparing C-glycosides related to phlorizin", Tetrahedron Letters vol. 41, 2000, pp. 9213-9217.

Koji Obsumi et al., "Pyrazole-O-Glucosides as Novel Na+-Glucose Cotransporter (SGLT) Inhibitors", Bioorganic & Medicinal Chemistry Letters, vol. 13, 2003, pp. 2269-2272.

\* cited by examiner

*Primary Examiner* — Shaojia Anna Jiang

*Assistant Examiner* — Bahar Schmidtmann

(74) *Attorney, Agent, or Firm* — Browdy and Neimark, PLLC

(57) ABSTRACT

A cyclohexane derivative having the function of reducing a blood sugar level and having preferable properties required of medicines, such as long-lasting drug activity, metabolic stability, and safety; and a medicinal composition for use in the prevention or treatment of diseases attributable to hyperglycemia, such as diabetes, e.g., insulin dependent diabetes mellitus (type 1 diabetes) or noninsulin-dependent diabetes mellitus (type 2 diabetes), complications of diabetes, and obesity. The derivative is a copound represented by the formula (I):

[Formula 1]

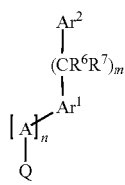

(I)

(wherein A is —O—, —$CH_2$—, or —NH—; n is an integer selected between 0 and 1; $R^6$ and $R^7$ each independently is hydrogen or $C_{1-6}$ alkyl; m is an integer selected among 1-3; Q is selected among the following formulae $Q^1$ to $Q^5$;

[Formula 2]

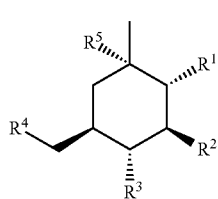

$Q^1$

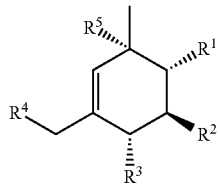
$Q^2$

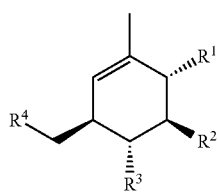
$Q^3$

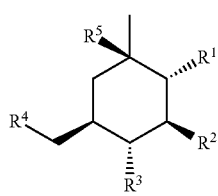
$Q^4$

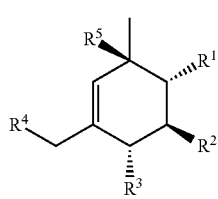
$Q^5$ $Ar^1$ is optionally substituted arylene or optionally substituted heteroarylene, provided that the heteroarylene may be bonded to an aromatic carbocycle or aromatic heterocycle to form a fused ring; and $Ar^2$ is optionally substituted aryl or optionally substituted heteroaryl), a prodrug of the compound, or a pharmaceutically acceptable salt of either. Also provided are a medicine, a medicinal composition, or the like each containing the compound.

17 Claims, No Drawings

CYCLOHEXANE DERIVATIVE, PRODRUG THEREOF AND SALT THEREOF, AND THERAPEUTIC AGENT CONTAINING THE SAME FOR DIABETES

TECHNICAL FIELD

The present invention relates to cyclohexane derivatives, their prodrugs and their pharmaceutically acceptable salts which are useful as drugs. Particularly, the present invention relates to cyclohexane derivatives, their prodrugs and their salts which are useful as prophylactic or therapeutic agents, which cause an effect by inhibiting $Na^+$-glucose co-transporter 2 (SGLT2), for diabetes such as insulin dependent diabetes (type I diabetes) and insulin independent diabetes (type II diabetes), diabetic complications and diseases such as obesity caused by hyperglycemia.

BACKGROUND ART

In recent years, the number of diabetic patients has increased due to the westernized dietary habits and chronic lack of exercise and the like. In diabetic patients, the insulin secretion and insulin sensitivity are both reduced by chronic hyperglycemia and this invites further rise in blood sugar levels to deteriorate the condition of the disease. As the therapeutic agents for diabetes, biguanide drugs, sulfonylurea drugs, glycosidase inhibitor drugs, insulin resistance improving agents and the like have been used. However, as the side effects associated with these agents, lactic acidosis is reported for the biguanide drugs, and hypoglycemia is reported for sulfonylurea drugs and diarrhea is reported for the glycosidase inhibitors, and therefore the actual condition is that the development of therapeutic agents for diabetes having a new mechanism of action different from that of these drugs is earnestly desired.

It was reported (see Non-patent Document 1) that phlorizin, a natural-occurring glucose derivative, inhibits reabsorption of excess glucose in the kidney by inhibiting sodium-dependent glucose co-transporter 2 (SGLT2) present in the S1 site of renal proximal convoluted tubule and promotes glucose excretion to exhibit lowering of blood sugar levels, and since then the study of therapeutic agents for diabetes based on the SGLT2 inhibition has been eagerly conducted.

For example, in Japanese Patent Publication 2000-080041 A (Patent Document 1), International Publication Nos. WO01/068660 (Patent Document 2), WO04/007517 (Patent Document 3) and the like, compounds used as SGLT2 inhibitors are reported. However, since phlorizin and the compounds described in the above-described Patent Applications have a glucose moiety as a common partial structure, and it is regarded as a problem that on oral administration, these compounds are easily hydrolyzed by glucosidase present in the small intestine or the like, and their pharmacological action quickly disappears. In the case of phlorizin, it is reported that phloretin, the aglycon of the phlorizin, strongly inhibits a sugar transporter of the facilitated diffusion type. For example, when phlorizin is intravenously administered to a rat, an adverse effect of reducing the intracerebral glucose concentration is reported (refer to, for example, Nonpatent Document 2).

Then, in order to prevent such decomposition and improve absorption efficiency, some attempt to convert such compounds to prodrugs thereof has been carried out. When a prodrug is administered, it is desired that the prodrug be appropriately metabolized in or near a target organ to change into an active compound. However, since various metabolic enzymes are present in a living body and individual variability is considerable, in many cases, it is difficult to provide an action of a prodrug stably. Further, the conversion of the glycoside bond of the compound to a carbon-carbon bond has been attempted (refer to Patent Documents 4 to 8). However, further improvement of the properties as a drug, including activity, metabolic stability and the like are demanded.

Patent Document 1: Japanese Patent Publication 2000-080041 A
Patent Document 2: International Publication No. WO01/068660 Pamphlet
Patent Document 3: International Publication No. WO04/007517 Pamphlet
Patent Document 4: US Patent Publication 2001/041674 A
Patent Document 5: US Patent Publication 2002/137903 A
Patent Document 6: International Publication No. WO01/027128 Pamphlet
Patent Document 7: International Publication No. WO02/083066 Pamphlet
Patent Document 8: International Publication No. WO04/013118 Pamphlet
Non-patent Document 1: J. Clin. Invest., 93, 1037 (1994)
Non-patent Document 2: Stroke, 14, 388 (1983)

DISCLOSURE OF THE INVENTION

Problem to be Solved by the Invention

An object of the present invention is to provide cyclohexane derivatives having suitable properties as a drug. An object of the present invention is particularly to provide cyclohexane derivatives which have blood sugar level lowering action and furthermore have suitable properties as drugs, such as prolonged effect, metabolic stability and safety. Furthermore, an object of the present invention is to provide pharmaceutical compositions which are used for preventing or treating diabetes such as insulin-dependent diabetes (type I diabetes) and insulin-independent diabetes (type II diabetes), diabetic complications, and diseases such as obesity caused by hyperglycemia.

Means to Solve the Problem

As the result of strenuous investigations by the present inventors in order to achieve the above-described objects, the inventors found that cyclohexane derivatives represented by formula (I) have excellent action of inhibiting SGLT2 and the present invention has been completed.

That is, according to one aspect of the present invention, there is provided a cyclohexane derivative represented by formula (I):

[Formula 1]

wherein
A is —O—, —CH$_2$—, or —NH—;
n is an integer selected from 0 and 1;

$R^6$ and $R^7$ are each independently a hydrogen atom, or a $C_1$-$C_6$ alkyl group m is an integer selected from 1 to 3;

Q is selected from $Q^1$ to $Q^5$ represented by the following formulae:

[Formula 2]

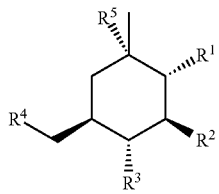
$Q^1$

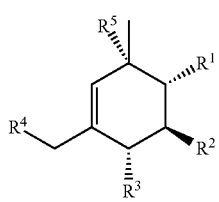
$Q^2$

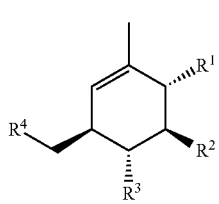
$Q^3$

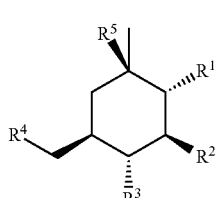
$Q^4$

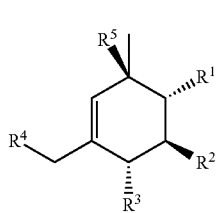
$Q^5$ wherein $R^1$, $R^2$, $R^3$, $R^4$, and $R^5$ are each independently selected from a hydrogen atom, a hydroxy group, a $C_1$-$C_6$ alkyl group which may be substituted with one or more Ra, a $C_1$-$C_6$ alkoxy group which may be substituted with one or more Ra, a $C_7$-$C_{14}$ aralkyloxy group which may be substituted with one or more Rb, and —OC(=O)Rx;

Rx is a $C_1$-$C_6$ alkyl group which may be substituted with one or more Ra, an aryl group which may be substituted with one or more Rb, a heteroaryl group which may be substituted with one or more Rb, a $C_1$-$C_6$ alkoxy group which may be substituted with one or more Ra, or —NReRf, $Ar^1$ is an arylene group which may be substituted with one or more Rb, or a heteroarylene group which may be substituted with one or more Rb, where the heteroarylene group may form a fused ring with an aromatic carbocycle or an aromatic heterocycle;

$Ar^2$ is an aryl group which may be substituted with one or more Rb, or a heteroaryl group which may be substituted with one or more Rb;

Ra is each independently selected from a halogen atom, a hydroxy group, a cyano group, a nitro group, a carboxy group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group, a $C_1$-$C_6$ alkylsulfinyl group, a $C_1$-$C_6$ alkylsulfonyl group, —NRfRg, and a $C_1$-$C_6$ alkylcarbonyl group which may be substituted with one or more Rc;

Rb is each independently selected from a $C_1$-$C_6$ alkyl group which may be substituted with one or more Rc, a $C_1$-$C_6$ alkenyl group which may be substituted with one or more Rc, a $C_3$-$C_8$ cycloalkyl group which may be substituted with one or more Rc, a $C_7$-$C_{14}$ aralkyl group which may be substituted with one or more Rd, a halogen atom, a hydroxy group, a cyano group, a nitro group, a carboxy group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group, a $C_1$-$C_6$ alkylsulfinyl group, a $C_1$-$C_6$ alkylsulfonyl group, —NRfRg, a $C_1$-$C_6$ alkylcarbonyl group which may be substituted with one or more Rc, a $C_1$-$C_3$ alkylenedioxy group, a heterocyclyl group, —$CO_2$Ri, and —CONRiRj;

Rc is each independently selected from a halogen atom, a hydroxy group, a cyano group, a nitro group, a carboxy group, a $C_1$-$C_6$ alkoxy group which may be substituted with one or more halogen atoms, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamino group, and a di($C_1$-$C_6$ alkyl)amino group;

Rd is each independently selected from a $C_1$-$C_6$ alkyl group which may be substituted with one or more halogen atoms, a $C_1$-$C_6$ alkoxy group which may be substituted with one or more halogen atoms, a $C_7$-$C_{14}$ aralkyl group which may be substituted with one or more halogen atoms, a halogen atom, a hydroxy group, a cyano group, a nitro group, an amino group, a $C_1$-$C_6$ alkylamino group, and a di($C_1$-$C_6$ alkyl)amino group;

Re is a hydrogen atom, a $C_1$-$C_6$ alkyl group which may be substituted with one or more Rc, an aryl group which may be substituted with one or more Rd, or a heteroaryl group which may be substituted with one or more Rd;

Rf is a hydrogen atom, or a $C_1$-$C_6$ alkyl group which may be substituted with one or more Rc;

Rg is a hydrogen atom, a $C_1$-$C_6$ alkyl group, which may be substituted with one or more Rc, a $C_1$-$C_6$ alkylcarbonyl group which may be substituted with one or more Rc, an aryl group which may be substituted with one or more Rd, a heteroaryl group which may be substituted with one or more Rd, a carbamoyl group, a $C_1$-$C_6$ alkoxycarboxy group which may be substituted with one or more Rc, or a $C_1$-$C_6$ alkylsulfonyl group which may be substituted with one or more Rc;

Re and Rf, and Rf and Rg may form a 4- to 7-membered heterocycle together with the nitrogen atom to which they are bonded, respectively; and Ri and Rj are each independently selected from a hydrogen atom, a $C_1$-$C_6$ alkyl group which may be substituted with one or more Rc, a $C_3$-$C_8$ cyclo-alkyl group which may be substituted with one or more Rc, and a $C_7$-$C_{14}$ aralkyl group which may be substituted with one or more Rd, or a prodrug or a pharmaceutically acceptable salt thereof.

According to another aspect of the present invention, there is provided a cyclohexane derivative represented by formula (I), wherein n is 1, or a prodrug or a pharmaceutically acceptable salt thereof. Herein, A is preferably —O— or —NH—. Further, the substitution system on $Ar^1$ is preferably that the substituent —$(CR^6R^7)_m$—$Ar^2$ is bonded to a ring atom adjacent to the ring atom to which the substituent A is bonded. For example, when $Ar^1$ is a phenylene group, an ortho substitution is preferred and, for example, when $Ar^1$ is a thienylene group, 2,3-substitution or 3,4-substitution is preferred and furthermore, for example, when $Ar^1$ is a pyridinylene group, 2,3-substitution, 3,4-substitution, 4,5-substitution or 5,6-substitution is preferred. Further, when $Ar^1$ is a pyrazolylene group, 3,4-substitution, 4,5-substitution or 1,5-substitution is preferred. The substituent A and the substituent —$(CR^6R^7)_m$—$Ar^2$ may be bonded to a ring nitrogen atom.

According to still another aspect of the present invention, there is provided a cyclohexane derivative represented by formula (I), wherein n is 0, or a prodrug or a pharmaceutically acceptable salt thereof. Herein, the substitution system on $Ar^1$ is preferably that the substituent —$(CR^6R^7)_m$—$Ar^2$ is bonded to the second ring atom departing from the ring atom to which Q is bonded. For example, when $Ar^1$ is a phenylene group, a meta substitution is preferred and, for example, when $Ar^1$ is a pyridinylene group, 2,4-substitution, 3,5-substitution, 4,6-substitution or 1,6-substitution is preferred. Further, when $Ar^1$ is an indolylene group, 1,3-substitution, 3,4-substitution, 4,6-substitution or 5,7-substitution is preferred. Further, when $Ar^1$ is a pyrazolylene group, 1,3-substitution, 3,5-substitution or 1,4-substitution is preferred. The substituent A and the substituent —$(CR^6R^7)_m$—$Ar^2$ may be bonded to a ring nitrogen atom.

In the above-described formula (I), m is preferably one. Further, $Ar^1$ is preferably a phenylene group, a naphthylene group, a thienylene group, a pyridinylene group, an indolylene group, or a pyrazolylene group, and particularly preferred are a phenylene group, a thienylene group, a pyridinylene group, and an indolylene group (and these groups may be substituted with one or more Rb).

In the above-described formula (I), m is preferably one, and further $Ar^2$ is preferably a phenyl group, a naphthyl group, a thienyl group, a benzofuranyl group, a benzothienyl group, a benzodioxolyl group, a 2,3-dihydrobenzofuranyl group, or a 2,3-dihyrobenzothienyl group, and particularly preferred are a phenyl group, a benzodioxolyl group, and a 2,3-dihydrobenzofuranyl group (and these groups may be substituted with one or more Rb).

In the above-described $Q^1$ to $Q^5$, it is preferred that $R^1$, $R^2$, $R^3$, $R^4$ and $R^5$ are each independently selected from a hydroxy group and —OC(=O)Rx.

According to a further aspect of the present invention, there is provided a compound of the above-described formula (I), wherein m is 1; n is 1; A is —O— or —NH—; $Ar^1$ is a phenylene group, a naphthylene group, a thienylene group, a pyridinylene group, an indolylene group or a pyrazolylene group (and these groups may be substituted with one or more Rb); $Ar^2$ is a phenyl group, a naphthyl group, a thienyl group, a benzofuranyl group, a benzothienyl group, a benzodioxolyl group, a 2,3-dihydrobenzofuranyl group or a 2,3-dihyrobenzothienyl group (and these groups may be substituted with one or more Rb); and $R^1$, $R^2$, $R^3$, $R^4$ and $R^5$ are each independently selected from a hydroxy group and —OC(=O)Rx, or a prodrug or a pharmaceutically acceptable salt thereof.

According to a still further aspect of the present invention, there is provided a compound of the above-described formula (I), wherein m is 1; n is 0; $Ar^1$ is a phenylene group, a naphthylene group, a thienylene group, a pyridinylene group, an indolylene group, or a pyrazolylene group (and these groups may be substituted with one or more Rb); $Ar^2$ is a phenyl group, a naphthyl group, a thienyl group, a benzofuranyl group, a benzothienyl group, a benzodioxolyl group, a 2,3-dihydrobenzofuranyl group, or a 2,3-dihyrobenzothienyl group (and these groups may be substituted with one or more Rb); and $R^1$, $R^2$, $R^3$, $R^4$ and $R^5$ are each independently selected from a hydroxy group and —OC(=O)Rx, or a prodrug or a pharmaceutically acceptable salt thereof.

According to a still further aspect of the present invention, there is provided a compound selected from:

[2-(4-methoxybenzyl)phenyl]-5a-carba-β-D-glucopyranoside;

[1S,2R,3R,4R,6S]-4-hydroxymethyl-6-[3-(4-methoxybenzyl)-phenyl]cyclohexane-1,2,3-triol;

[2-(4-trifluoromethoxybenzyl)phenyl]-5a-carba-β-D-glucopyranoside;

[2-(4-cyclopentylbenzyl)phenyl]-5a-carba-β-D-glucopyranoside;

[2-(4-chlorobenzyl)phenyl]-5a-carba-β-D-glucopyranoside;

(2-benzylphenyl)-5a-carba-β-D-glucopyranoside;

[2-(4-isopropylbenzyl)phenyl]-5a-carba-β-D-glucopyranoside;

[2-(4-cyclopropylbenzyl)phenyl]-5a-carba-β-D-glucopyranoside;

[2-(4-n-propylbenzyl)phenyl]-5a-carba-β-D-glucopyranoside;

[2-(4-trifluoromethylbenzyl)phenyl]-5a-carba-β-D-glucopyranoside;

[2-(4-methylsulfanylbenzyl)phenyl]-5a-carba-β-D-glucopyranoside;

[3-fluoro-2-(4-methoxybenzyl)phenyl]-5a-carba-β-D-glucopyranoside;

[2-(3-trifluoromethylbenzyl)phenyl]-5a-carba-β-D-glucopyranoside;

[2-(4-methoxybenzyl)-4-methylphenyl]-5a-carba-β-D-glucopyranoside;

[2-(3-methoxybenzyl)phenyl]-5a-carba-β-D-glucopyranoside;

[2-(4-methoxybenzyl)-4-methoxyphenyl]-5a-carba-β-D-glucopyranoside;

[2-(4-methoxybenzyl)-6-methylphenyl]-5a-carba-β-D-glucopyranoside;

[2-(4-methoxybenzyl)-4-fluorophenyl]-5a-carba-β-D-glucopyranoside;

[2-(3-fluorobenzyl)phenyl]-5a-carba-β-D-glucopyranoside;

[2-(3-methylbenzyl)phenyl]-5a-carba-β-D-glucopyranoside;

[5-fluoro-2-(4-methoxybenzyl)phenyl]-5a-carba-β-D-glucopyranoside;

[2-(4-methylsulfonylbenzyl)phenyl]-5a-carba-β-D-glucopyranoside;

[2-(4-fluorobenzyl)phenyl]-5a-carba-β-D-glucopyranoside;

[2-(3,4-dimethoxybenzyl)phenyl]-5a-carba-β-D-glucopyranoside;

[2-(4-ethylbenzyl)phenyl]-5a-carba-β-D-glucopyranoside;

[2-(4-hydroxybenzyl)phenyl]-5a-carba-β-D-glucopyranoside;

[2-(4-cyanobenzyl)phenyl]-5a-carba-β-D-glucopyranoside;
[2-(3-trifluoromethoxybenzyl)phenyl]-5a-carba-β-D-glucopyranoside;
[2-(4-aminomethylbenzyl)phenyl]-5a-carba-β-D-glucopyranoside;
[5-methoxy-2-(4-methoxybenzyl)phenyl]-5a-carba-β-D-glucopyranoside;
[2-(4-methoxycarbonylbenzyl)phenyl]-5a-carba-β-D-glucopyranoside;
[2-(4-carbamoylbenzyl)phenyl]-5a-carba-β-D-glucopyranoside;
[2-(4-N,N-dimethylcarbamoylbenzyl)phenyl]-5a-carba-β-D-glucopyranoside;
[2-(4-ethoxybenzyl)phenyl]-5a-carba-β-D-glucopyranoside;
[2-(4-difluoromethoxybenzyl)phenyl]-5a-carba-β-D-glucopyranoside;
[2-(4-tert-butylbenzyl)phenyl]-5a-carba-β-D-glucopyranoside;
[2-(4-methylbenzyl)phenyl]-5a-carba-β-D-glucopyranoside;
[2-(4-methoxybenzyl)phenyl]-5-trifluoromethylthiophen-3-yl]-5a-carba-β-D-glucopyranoside;
[3-methoxy-2-(4-methoxybenzyl)phenyl]-5a-carba-β-D-glucopyranoside;
[2-(4-methoxybenzyl)-3-methylphenyl]-5a-carba-β-D-glucopyranoside;
[2-(3-fluoro-4-methoxybenzyl)phenyl]-5a-carba-α-D-glucopyranoside;
[4-(4-cyclopropylbenzyl)pyridin-3-yl]-5a-carba-β-D-glucopyranoside;
[2-(4-carboxybenzyl)phenyl]-5a-carba-β-D-glucopyranoside;
[2-(4-vinylbenzyl)phenyl]-5a-carba-β-D-glucopyranoside;
{2-[4-(2,2-difluorovinyl)benzyl]phenyl}-5a-carba-β-D-glucopyranoside;
[2-(2,3-dihydrobenzofuran-5-ylmethyl)phenyl]-5a-carba-β-D-glucopyranoside;
[2-(3-fluoro-4-methylbenzyl)phenyl]-5a-carba-β-D-glucopyranoside;
[2-(4-methoxy-3-methylbenzyl)phenyl]-5a-carba-β-D-glucopyranoside;
[2-(4-pyrazol-1-ylbenzyl)phenyl]-5a-carba-β-D-glucopyranoside;
[2-(3-chloro-4-methoxybenzyl)phenyl]-5a-carba-β-D-glucopyranoside;
[2-(3,4-methylenedioxybenzyl)phenyl]-5a-carba-β-D-glucopyranoside;
[2-(4-cyclobutylbenzyl)phenyl]-5a-carba-β-D-glucopyranoside;
[2-(4-acetylbenzyl)phenyl]-5a-carba-β-D-glucopyranoside;
[2-(4-methoxybenzyl)-5-methylphenyl]-5a-carba-β-D-glucopyranoside;
[2-(4-ethylbenzyl)thiophen-3-yl]-5a-carba-β-D-glucopyranoside;
[2-(benzothiophen-2-yl)methylphenyl]-5a-carba-β-D-glucopyranoside;
(R)-{2-[1-(4-cyclopropylphenyl)ethyl]phenyl}-5a-carba-β-D-glucopyranoside;
(S)-{2-[1-(4-cyclopropylphenyl)ethyl]phenyl}-5a-carba-β-D-glucopyranoside;
[2-(4-cyclopropylbenzyl)-5-methylthiophen-3-yl]-5a-carba-β-D-glucopyranoside;
[2-(4-ethylbenzyl)-5-methylthiophen-3-yl]-5a-carba-β-D-glucopyranoside;
[5-chloro-2-(4-cyclopropylbenzyl)thiophen-3-yl]-5a-carba-β-D-glucopyranoside;
(1R,2S,3R,6R)-6-[2-(4-cyclopropylbenzyl)phenoxy]-4-(hydroxymethyl)cyclohex-4-ene-1,2,3-triol;
(1R,2S,3R,6R)-4-hydroxymethyl-6-[2-(4-methoxybenzyl)phenoxy]cyclohex-4-ene-1,2,3-triol;
(1R,2S,3S,6R)-4-[3-(4-ethylbenzyl)phenyl]-6-(hydroxymethyl)cyclohex-4-ene-1,2,3-triol;
(1R,2R,3S,4R,5R)-1-[3-(4-ethylbenzyl)-4-methoxyphenyl]-5-(hydroxymethyl)cyclohexane-1,2,3,4-tetraol;
(1R,2R,3S,4S,6R)-4-[3-(4-ethylbenzyl)-4-methoxyphenyl]-6-(hydroxymethyl)cyclohexane-1,2,3-triol;
(1R,2R,3S,4R,5R)-1-[2-ethoxy-5-(4-ethylbenzyl)phenyl]-5-(hydroxymethyl)cyclohexane-1,2,3,4-tetraol;
(1R,2R,3S,4S,6R)-4-[2-ethoxy-5-(4-ethylbenzyl)phenyl]-6-(hydroxymethyl)cyclohexane-1,2,3-triol;
(1R,2R,3S,4R,5R)-1-[5-(4-ethylbenzyl)-2,4-dimethoxyphenyl]-5-(hydroxymethyl)cyclohexane-1,2,3,4-tetraol;
(1R,2R,3S,4S,6R)-4-[5-(4-ethylbenzyl)-2,4-dimethoxyphenyl]-6-(hydroxymethyl)cyclohexane-1,2,3-triol;
(1R,2R,3S,4R,5R)-1-[5-(4-ethylbenzyl)-2-methylphenyl]-5-(hydroxymethyl)cyclohexane-1,2,3,4-tetraol;
(1R,2R,3S,4S,6R)-4-[5-(4-ethylbenzyl)-2-methylphenyl]-6-(hydroxymethyl)cyclohexane-1,2,3-triol;
(1R,2R,3S,4R,5R)-1-[5-(4-ethylbenzyl)-2-methoxyphenyl]-5-(hydroxymethyl)cyclohexane-1,2,3,4-tetraol;
(1R,2R,3S,4S,6R)-4-[5-(4-ethylbenzyl)-2-methoxyphenyl]-6-(hydroxymethyl)cyclohexane-1,2,3-triol;
(1R,2R,3S,4R,5R)-1-[5-(4-ethylbenzyl)-2-trifluoromethoxy-phenyl]-5-(hydroxymethyl)cyclohexane-1,2,3,4-tetraol;
(1R,2R,3S,4S,6R)-4-[5-(4-isopropylbenzyl)-2-methoxyphenyl]-6-(hydroxymethyl)cyclohexane-1,2,3-triol;
(1R,2R,3S,4S,6R)-4-[3-(4-ethylbenzyl)phenyl]-6-(hydroxymethyl)cyclohexane-1,2,3-triol;
(1R,2R,3S,4S,6R)-4-[3-(4-hydroxybenzyl)phenyl]-6-(hydroxymethyl)cyclohexane-1,2,3-triol;
(1R,2R,3S,4S,6R)-4-[5-(4-ethylbenzyl)-2-hydroxyphenyl]-6-(hydroxymethyl)cyclohexane-1,2,3-triol;
(1R,2R,3S,4S,6R)-4-[3-(4-cyclopropylbenzyl)phenyl]-6-(hydroxymethyl)cyclohexane-1,2,3-triol;
(1R,2R,3S,4R,5R)-1-[5-(4-ethylbenzyl)-2-fluorophenyl]-5-(hydroxymethyl)cyclohexane-1,2,3,4-tetraol;
(1S,2R,3S,4R,5R)-1-[5-(4-ethylbenzyl)-2-fluorophenyl]-5-(hydroxymethyl)cyclohexane-1,2,3,4-tetraol;
(1R,2R,3S,4R,5R)-5-hydroxymethyl-1-[3-(4-methoxybenzyl)-phenyl]cyclohexane-1,2,3,4-tetraol;
(1S,2R,3S,4R,5R)-5-hydroxymethyl-1-[3-(4-methoxybenzyl)-phenyl]cyclohexane-1,2,3,4-tetraol; and
(1R,2R,3S,4S,6R)-4-[1-(4-ethylbenzyl)-1H-indol-3-yl]-6-(hydroxymethyl)-cyclohexane-1,2,3-triol,
or a prodrug or a pharmaceutically acceptable salt thereof.

According to another aspect of the present invention, there is provided a pharmaceutical composition comprising the compound of the above-described formula (I) which is used as a $Na^+$-glucose co-transporter inhibitor.

According to still another aspect of the present invention, there is provided a pharmaceutical composition comprising the compound of the above-described formula (I), which is used for preventing or treating diabetes such as insulin-dependent diabetes (type I diabetes) and insulin-independent diabetes (type II diabetes), diabetic complications caused by hyperglycemia, or obesity.

According to a further aspect of the present invention, there is provided a method of preventing or treating diabetes such as insulin-dependent diabetes (type I diabetes) and insulin-independent diabetes (type II diabetes), diabetic complications caused by hyperglycemia and obesity, which comprises administering an effective amount of the compound of the above-described formula (I), or a pharmaceutically acceptable salt thereof to a patient.

In the above-described $Q^1$ to $Q^5$, the groups represented by $R^1$, $R^2$, $R^3$, $R^4$ and $R^5$ may be each independently, for example, a hydroxy group, a $C_1$-$C_6$ alkyloxy group, a $C_7$-$C_{14}$ aralkyloxy group or —OC(=O)Rx, and particularly $R^1$, $R^2$, $R^3$, $R^4$ and $R^5$ are preferably all hydroxy groups.

In the compounds of the present invention, n is preferably 1 and in this case, A is preferably —O— or —NH—, and particularly preferred is —O—.

In the above-described formula (I), $Ar^1$ and $Ar^2$ may be substituted with one to four substituents Rb and as the Rb, a halogen atom; a hydroxy group; a $C_1$-$C_6$ alkyl group and a $C_3$-$C_8$ cycloalkyl group which may be substituted with one to four substituents selected from a halogen atom, a hydroxy group and an amino group; a $C_1$-$C_6$ alkyloxy group and a $C_1$-$C_6$ alkylthio group which may be substituted with one to four substituents selected from a halogen atom, a hydroxy group and an amino group; a cyano group; a $C_1$-$C_6$ alkylsulfonyl group; a nitro group; a carboxy group; —NReRf (wherein Re is a hydrogen atom, a $C_1$-$C_6$ alkyl group, a $C_1$-$C_6$ alkylcarbonyl group, a carbamoyl group, a $C_1$-$C_6$ alkylsulfonyl group or a $C_1$-$C_6$ alkoxycarbonyl group; and Rf is a hydrogen atom or a $C_1$-$C_6$ alkyl group); 5- or 6-heteroaryl group; or a 4- to 6-membered heterocyclyl group is preferred.

Among the group represented by $Ar^1$, the arylene group is a divalent group composed of an aromatic carbocycle, preferably an aromatic carbocycle having 6 to 10 carbon atoms and includes, for example, a phenylene group and a naphthylene group. The heteroarylene group is a divalent group composed of an aromatic heterocycle, preferably a 6- to 10-membered aromatic heterocycle and includes, for example, a heteroarylene group containing a pyrrole ring, an indole ring, a thiophene ring, a benzothiophene group, a furan ring, a benzofuran ring, a pyridine ring, a quinoline ring, an isoquinoline group, a thiazole ring, a benzothiazole ring, an isothiazole ring, a benzoisothiazole ring, a pyrazole ring, an indazole ring, an oxazole ring, a benzoxazole ring, an isoxazole ring, a benzoisoxazole ring, an imidazole ring, a benzoimidazole ring, a triazole ring, a benzotriazole ring, a pyrimidine ring, a uridine ring, a pyrazine ring or a pyridazine ring. As the $Ar^1$, particularly a phenylene group, a naphthylene group and a heteroarylene group containing a pyridine ring, a pyrrole ring, an indole ring, a thiophene ring, a benzothiophene ring, a furan ring, a benzofuran ring or a pyrazole ring are preferred, and more preferred are a phenylene group, a thienylene group, a pyridinylene group and an indolyene group.

Among the group represented by $Ar^2$, the aryl group is a phenyl group, a naphthyl group or an azulenyl group, and the heteroaryl group is a pyrrolyl group, an indolyl group, a pyridyl group, a quinolyl group, an isoquinolyl group, a thienyl group, a benzothienyl group, a furyl group, a benzofuranyl group, a thiazolyl group, a benzothiazolyl group, an isothiazolyl group, a benzo-isothiazolyl group, a pyrazolyl group, an indazolyl group, an oxazolyl group, a benzoxazolyl group, an isoxazolyl group, a benzoisoxazolyl group, an imidazolyl group, a benzimidazolyl group, a triazolyl group, a benzotriazolyl group, a pyrimidinyl group, an uracilyl group, a pyrazinyl group, a pyridazinyl group or the like, and as the $Ar^2$, a phenyl group, a naphthyl group, a thienyl group, a benzothienyl group, a benzodioxolyl group, a furyl group, a benzofuranyl group, or 2,3-dihydrobenzofuranyl group is preferred, and furthermore preferred is a phenyl group, a benzodioxolyl group, or 2,3-dihydrobenzofuranyl group.

The term "$C_1$-$C_6$ alkyl group" as used herein means a linear or branched chain alkyl group having 1 to 6 carbon atoms and includes, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, and preferable $C_1$-$C_6$ alkyl groups include, for example, linear or branched chain alkyl groups having one to three carbon atoms, and particularly preferred are methyl and ethyl.

The term "$C_3$-$C_8$ cycloalkyl group" as used herein means a cyclic alkyl group having 3 to 8 carbon atoms and includes, for example, cyclopropyl, cyclobutyl, cyclopentyl, cyclohexyl, cycloheptyl, and cyclooctyl.

The term "$C_1$-$C_6$ alkoxy group" as used herein means an alkyloxy group having a linear or branched chain alkyl group having 1 to 6 carbon atoms as the alkyl moiety and includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, and 3-ethylbutoxy.

The term "aryl group" as used herein means an aryl group having an aromatic hydrocarbon ring having 6 to 10 carbon atoms and includes, for example, phenyl, 1-naphthyl and 2-naphthyl.

The term "$C_7$-$C_{14}$ aralkyl group" as used herein means an arylalkyl group having 7 to 14 carbon atoms and containing the already defined aryl group and includes, for example, benzyl, 1-phenethyl, 2-phenethyl, 1-naphthylmethyl, and 2-naphthylmethyl.

The term "$C_7$-$C_{14}$ aralkyloxy group" as used herein means an arylalkyloxy group having 7 to 14 carbon atoms and containing the already defined aralkyl group and includes, for example, benzyloxy, 1-phenethyloxy, 2-phenethyloxy, 1-naphthylmethyloxy and 2-naphthylmethyloxy.

The term "heteroaryl group" as used herein means a 5- to 10-membered aromatic heterocyclyl group containing one or more heteroatom independently selected from an oxygen atom, a nitrogen atom and a sulfur atom and includes, for example, furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidinyl, pyrazinyl, pyridazinyl, indolyl, quinolinyl, and isoquinolinyl. Preferred heteroaryl groups are 5- to 6-membered heteroaryl groups such as a pyrrolyl group, a pyrazolyl group, an imidazolyl group, and a pyridyl group, and particularly the pyrazolyl group is preferred.

The term "aryloxy group" as used herein means an aryloxy group having the already defined aromatic hydrocarbon group having 6 to 10 carbon atoms as the aryl moiety and includes, for example, phenoxy, 1-naphthoxy, and 2-naphthoxy.

The term "heteroaryloxy group" as used herein means a heteroaryloxy group having the already defined 5- to 10-membered aromatic heterocyclyl group which contains one or more heteroatom selected from an oxygen atom, a nitrogen atom and a sulfur as the heteroaryl moiety and includes, for example, furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridinyloxy, pyrimidinyloxy, pyrazinyloxy, pyridazinyloxy, indolyloxy, quinolinyloxy, and isoquinolinyloxy. Preferred heteroaryloxy groups are 5- to 6-membered heteroaryloxy groups.

The term "$C_1$-$C_6$ alkylamino group" as used herein means an alkylamino group having a linear or branched chain alkyl group having 1 to 6 carbon atoms as the alkyl moiety and includes, for example, methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, and 2-ethylbutylamino.

The term "di($C_1$-$C_6$ alkyl)amino group" as used herein means a dialkylamino group having a linear or branched chain alkyl group having 1 to 6 carbon atoms as the two alkyl moieties which may be the same or different. The "di($C_1$-$C_6$ alkyl)amino group" includes, for example, dimethylamino, diethylamino, di-n-propylamino, di-i-propylamino, di-n-butylamino, methyl-n-butylamino, methyl-s-butylamino, methyl-1-butylamino, methyl-t-butylamino, ethyl-n-butylamino, ethyl-s-butylamino, ethyl-1-butylamino, and ethyl-t-butylamino.

The term "$C_1$-$C_6$ alkylthio group" as used herein means an alkylthio group having a linear or branched chain alkyl group having 1 to 6 carbon atoms as the alkyl moiety and includes, for example, methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio.

The term "$C_1$-$C_6$ alkylsulfinyl group" as used herein means an alkylsulfinyl group (—SO—R) having a linear or branched chain alkyl group having 1 to 6 carbon atoms as the alkyl moiety and includes, for example, methylsulfinyl, ethylsulfinyl, n-propylsulfinyl, i-propylsulfinyl, n-butylsulfinyl, s-butylsulfinyl, i-butylsulfinyl, t-butylsulfinyl, n-pentylsulfinyl, 3-methylbutylsulfinyl, 2-methylbutylsulfinyl, 1-methylbutylsulfinyl, 1-ethylpropylsulfinyl, n-hexylsulfinyl, 4-methylpentylsulfinyl, 3-methylpentylsulfinyl, 2-methyl-pentylsulfinyl, 1-methylpentylsulfinyl, 3-ethylbutyl-sulfinyl and 2-ethylbutylsulfinyl.

The term "$C_1$-$C_6$ alkylsulfonyl group" as used herein means an alkylsulfonyl group having a linear or branched chain alkyl group having 1 to 6 carbon atoms as the alkyl moiety and includes, for example, methylsulfonyl, ethylsulfonyl, n-propylsulfonyl, i-propylsulfonyl, n-butylsulfonyl, s-butylsulfonyl, i-butylsulfonyl, t-butylsulfonyl, n-pentylsulfonyl, 3-methylbutylsulfonyl, 2-methylbutylsulfonyl, 1-methylbutylsulfonyl, 1-ethylpropylsulfonyl, n-hexylsulfonyl, 4-methylpentylsulfonyl, 3-methylpentylsulfonyl, 2-methylpentylsulfonyl, 1-methylpentylsulfonyl, 3-ethylbutyl-sulfonyl, and 2-ethylbutylsulfonyl.

The group "—OC(=O)—Rx" as used herein includes, for example, a $C_1$-$C_6$ alkylcarbonyloxy group, a $C_7$-$C_{14}$ aralkylcarbonyloxy group, a $C_1$-$C_6$ alkoxycarbonyloxy group, and a $C_7$-$C_{14}$ aralkyloxycarbonyloxy group. Here, the $C_1$-$C_6$ alkylcarbonyloxy group includes, for example, an acetyloxy group, a propionyloxy group, a butylyloxy group and pivaloyloxy group, and particularly the acetyloxy group is preferred. The $C_7$-$C_{14}$ aralkylcarbonyloxy group includes, for example, benzylcarbonyloxy group and naphthylmethylcarbonyloxy group, and the benzylcarbonyloxy group is preferred.

The $C_1$-$C_6$ alkoxycarbonyloxy group includes, for example, a methoxycarbonyloxy group, and an ethoxycarbonyloxy group, and preferred is methoxycarbonyloxy group. The $C_7$-$C_{14}$ aralkyloxycarbonyloxy group includes, for example, a benzyloxycarbonyloxy group and a naphthylmethyloxycarbonyloxy group, and preferred is benzyloxycarbonyloxy group.

The term "halogen atom" as used herein includes, for example, a fluorine atom, a chlorine atom, a bromine atom and an iodine atom.

The term "4- to 7-membered heterocycle" as used herein means a heterocycle which may be completely saturated or partially or completely unsaturated and contains one nitrogen and may further contain one or more heteroatoms independently selected from an oxygen atom, a nitrogen atom and a sulfur atom and includes, for example, azetidine, pyrrolidine, piperidine, and morpholine, and preferred is piperidine.

The term "aromatic carbocycle" as used herein means a 6- to 10-membered aromatic carbocycle and includes, for example, a benzene ring and a naphthalene ring.

The term "aromatic heterocycle" as used herein means a 5- to 6-membered aromatic heterocycle containing one or more heteroatom independently selected from an oxygen atom, a nitrogen atom and a sulfur atom and includes, for example, a pyrrole ring, an indole ring, a thiophene ring, a benzothiophene ring, a furan ring, a benzofuran ring, a pyridine ring, a quinoline ring, an isoquinoline ring, a thiazole ring, a benzothiazole ring, an isothiazole ring, a benzoisothiazole ring, a pyrazole ring, an indazole ring, an oxazole ring, a benzoxazole ring, an isoxazole ring, a benzoisoxazole ring, an imidazole ring, a benzoimidazole ring, a triazole ring, a benzotriazole ring, a pyrimidine ring, a uracil ring, a pyrazine ring, and a pyridazine ring.

The term "heterocyclyl group" as used herein means a 4- to 7-membered heterocyclyl group which contains one or more heteroatom independently selected from an oxygen atom, a nitrogen atom and a sulfur atom and may be completely saturated or partially or completely unsaturated and includes, for example, azetidinyl, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, pyridyl, pyrazinyl, pyrimidinyl, pyridazinyl, hexamethyleneimino, furyl, tetrahydrofuryl, thienyl, tetrahydrothienyl, dioxolanyl, oxathiolanyl, and dioxanyl. The substitution position on the heterocyclyl group is not particularly limited as far as it is the substitutable position on a carbon atom or a nitrogen atom.

The term "$C_1$-$C_3$ alkylenedioxy group" as used herein is a divalent group represented by the formula: —O—($C_1$-$C_3$ alkylene)-O— and includes, for example, a methylenedioxy group, an ethylenedioxy group and a dimethylmethyenedioxy group.

Further, the compounds of the present invention include mixtures of various types of tautomers, stereoisomers such as optical isomers and their isolated isomers.

The compounds of the present invention may form acid addition salts. Further depending on the type of the substituent, they may form salts with bases. Such salts include, for example, acid addition salts of mineral acids such as hydrochloric acid, hydrobromic acid, hydroiodic acid, sulfuric acid, nitric acid and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid; acidic amino acids such as asparaginic acid and glutamic acid. Further, salts formed with bases include salts with inorganic bases such as sodium, potassium, magnesium, calcium and aluminum; salts with organic bases such as methylamine, ethylamine and ethanolamine; salts with basic amino acids such as lysine and ornithine; and ammonium salts.

Furthermore, the compounds of the present invention include the hydrates and pharmaceutically acceptable various solvates, polymorphs and the like.

Further, the compounds of the present invention are not limited to the compounds as will be described in Examples below and include all cyclohexane derivatives represented by the above-described formula (I) and pharmaceutically acceptable salts thereof.

Further, the present invention includes the compounds which are converted to the compounds represented by the above-described formula (I) by the metabolism in a living body and their pharmaceutically acceptable salts, that is, so-called prodrugs. The groups which form the prodrugs of the compounds of the present invention include, for example, those described in Prog. Med., 5, 2157-2161 (1985) and those described in *Development of Drugs* (Molecular Designing) 7, 163-198, Hirokawa Shoten, 1990.

The compounds of the present invention can be produced by applying various known synthetic methods depending on the characteristic features based on the type of the basic skeleton or the substituent. In this instance, when there is a case such that the group is preferably protected with an appropriate protective group at the stage of the starting material or an intermediate from a production technique viewpoint, the protective group can be eliminated in later steps to obtain a desired compound. The groups which require protection in the production step include, for example, a hydroxy group and a carboxy group, and the protective groups for these groups include the protective groups described in Greene and Wuts: Protective Groups in Organic Synthesis, 2nd ed. The protective group used and the reaction conditions for introducing and eliminating the protective group are suitably selected based on known techniques such as the above-described documents.

The compounds of the present invention have an inhibitory activity of sodium-dependent glucose transporter 2 (SGLT2) (J. Clin. Invest., 93, 397 (1994)) relating to the renal glucose reabsortion. By the inhibition of SGLT2, the glucose reabsorptionia reduces, excess glucose is excreted and hyperglycemia is remedied without giving a load on the β-cells of the pancreas to bring about a therapeutic effect on diabetes and an improved effect on insulin resistance.

Thus, according to one aspect of the present invention, there is provided a drug for preventing or treating a disease or a condition, which can be improved by inhibiting the SGLT2 activity, for example, diabetes, diabetes-related diseases and diabetic complications.

The term "diabetes" as used herein includes, type I diabetes, type II diabetes and other types of diabetes due to specific causes. Further, the term "diabetes-related diseases" as used herein includes, for example, obesity, hyperinsulinemia, saccharometabolic disorder, hyperlipidemia, hypercholesterolemia, hypertriglyceridemia, disorder of lipid metabolism, hypertension, congestive heart failure, edema, hyperuricemia and gout.

Further, the term "diabetic complications" as used herein includes both acute complications and chronic complications. The "acute complications" include, for example, hyperglycemia (ketoacidosis and the like) and infectious diseases (such as skin, soft tissues, biliary tract, respiratory system and urinary tract) and the "chronic complications" include, for example, microangio-pathy (nephropathy and retinopathy), arteriosclerosis (such as atherosclerosis, myocardial infarction, cerebral thrombosis and lower limbo arterial obstruction), neuro-pathy (such as a sensory nerve, a motor nerve and an autonomic nerve) and foot gangrene. The major diabetic complications include, for example, diabetic retinopathy, diabetic nephropathy and diabetic neuropathy.

Further, the compounds of the present invention can be used in combination with a diabetes treating agent, a diabetic complication therapeutic agent, a hyperlipidemia therapeutic agent, a hypertension therapeutic agent or the like which has a mechanism of action different than that of SGLT2 activity inhibitors. By combining the compounds of the present invention with the other agents, an additive effect can be expected compared to the effect obtained from each single agent in the above diseases.

The "diabetes therapeutic agents and diabetic complication therapeutic agents" which are usable in combination include, for example, insulin sensitivity enhancers (such as PPAR γ agonist, PPAR α/γ agonist, PPAR δ agonist and PPAR α/γ/δ agonist), glycosidase inhibitors, biguanide drugs, insulin secretion promoters, insulin preparations, glucagon receptor antagonists, insulin receptor kinase promoters, tripeptiydly peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose bisphosphotase inhibitors, pyruvate dehydrogenase inhibitors, glucokinase activators, D-chiro-inositol, glycogen synthase kinase 3 inhibitors, glucagon-like peptide 1, glucagon-like peptide-1 analogs, glucagon-like peptide-1 agonists, amyrin, amyrin analogs, amyrin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKK β inhibitors, lipido-peroxidase inhibitors, N-acetylated-α-linked-acid-dipeptidase inhibitors, insulin-like growth factor-I, platelet-derived growth factor (PDGF), platelet-derived growth factor (PDGF) analogs, epidermal growth factor (EGF), nerve growth factor, carnitine derivatives, uridine, 5-hydroxy-1-methylhydantoin, EGB-761, bimoclomol, sulodexide, Y-128 and TAR-428.

As the diabetes therapeutic agents and the diabetic complication therapeutic agents, the following are illustrated.

"Biguanide drugs" include, for example, metformin hydrochloride and phenformin.

Among "insulin secretion promoters", sulfonylureas include, for example, glyburide (glibenclamide), glipizide, glyclazide and chlorpropamide, and non-sulfonylureas include, for example, nateglinide, repaglinide and mitiglinide.

"Insulin preparations" include recombinant human insulin and animal-derived-insulin, and are classified into three groups according to the time of action, that is, the immediate-acting type (human insulin and human neutral insulin), the medium type (an insulin-human isophane insulin aqueous suspension, a human neutral insulin-human isophane insulin aqueous suspension, a human insulin zinc aqueous suspension and an insulin zinc aqueous suspension) and the enlonged-acting type (a human crystalline insulin zinc suspension).

"Glycosidase inhibitors" include, for example, acarbose, voglibose and miglitol.

PPAR γ agonists of "insulin sensitivity enhancers" include, for example, troglitazone, pioglytazone and rosiglytazone, and PPAR α/γ dual agonists include, for example, MK-767 (KRP-297), tesaglitazar, LM 4156, LY 510929, DRF-4823 and TY-51501, and PPAR δ agonists include, for example, GW-501516.

"Tripeptidyl peptidase II inhibitors" include, for example, UCL-139.

"Dipeptidyl peptidase IV inhibitors" include, for example, NVP-DPP728A, LAF-237, MK-0431, P32/98 and TSL-225.

"Aldose reductase inhibitors" include, for example, ascorbyl gamolenate, tolrestat, epalrestat, fidarestat, sorbinil, ponalrestat, risarestat and zenarestat.

"γ-Aminobutyric acid receptor antagonists" include, for example, topiramate.

"Sodium channel antagonists" include, for example, mexiletin hydrochloride.

"Transcription factor NF-κB inhibitors" include, for example, dexlipotam.

"Lipoperoxidase inhibitors" include, for example, tirilazad mesylate.

"N-Acetylated α-linked-acid-dipeptidase inhibitors" include, for example, GPI-5693.

"Carnitine derivatives" include, for example, carnitine and levacecarnine hydrochloride.

"Hyperlipidemia therapeutic agents and the hypertension therapeutic agents" which can be used in combination include, for example, hydroxymethylglutaryl coenzyme A reductase inhibitors, fibrate compounds, $β_3$-adrenaline receptor agonists, AMPK activators, acyl coenzyme A: choresterol acyl transferase inhibitors, probucol, thyroid hormone receptor agonists, choresterol absorption inhibitors, lipase inhibitors, microsome triglyceride transfer protein inhibitors, lipoxygenase inhibitors, carnitine palmitoyl transferase inhibitors, squalene synthase inhibitors, low density lipoprotein receptor promoters, nicotinic acid derivatives, bile acid adsorbents, sodium conjugated bile acid transporter inhibitors, cholesteryl ester transfer protein inhibitors, angiotensin converting enzyme inhibitors, angiotensin II receptor antagonists, endothelin converting enzyme inhibitors, endothelin receptor antagonists, diuretics, calcium antagonists, vasodilating hypotensive agents, sympathetic blocking agents, central hypotensive agents, $α_2$-adrenergic receptor agonists, antiplatelet agents, uric acid formation inhibitors, uric acid excretion stimulants, urine alkalifying agents, anorectics, adiponectin receptor agonists, GPR40 agonists and GPR40 antagonists.

As the hyperlipemia therapeutic agents and the hypertension therapeutic agents, the following are illustrated.

"Hydroxymethylglutaryl coenzyme A reductase inhibitors" include, for example, fluvastatin, lovastatin, pravastatin, cerivastatin and pitavastatin.

"Fibrate compounds" include, for example, bezafibrate, beclobrate and binifibrate.

"Squalene synthase inhibitors" include, for example, TAK-475, α-phosphonosulfonate derivatives (as described in U.S. Pat. No. 5,712,396).

"Acyl coenzyme A: cholesterol acyl transferase inhibitors" include, for example, CI-1011, NTE-122, FCE-27677, RP-73163, MCC-147 and DPU-129.

"Low density lipoprotein receptor promoters" include, for example, MD-700 and LY-295427.

"Microsome triglyceride transfer protein inhibitors (MTP inhibitors)" include, for example, compounds as described in U.S. Pat. Nos. 5,739,135, 5,712,279, 5,760,246 and the like.

"Anorectics" include, for example, adrenaline-noradrenaline agonists (mazindol, ephedrine and the like), serotonin agonists (selective serotonin retake inhibitors such as fluvoxamine), adrenalin-serotonin agonists (sibutramine and the like), melanocortin 4 receptor (MC4R) agonists and α-melanocyte concentrating hormones (α-MCH), leptin, cocaine- and amphetamine-regulated transcript (CART) and the like.

"Thyroid hormone receptor agonists" include, for example, lyothyronine sodium and levothyroxine sodium.

"Cholesterol adsorption inhibitors" include, for example, ezetimibe.

"Lipase inhibitors" include, for example, orlistat.

"Carnitine palmitoyl transferase inhibitors" include, for example, etomoxir.

"Nicotinic acid derivatives" include, for example, nicotinic acid, nicotinamide, nicomol and nicorandil.

"Bile acid adsorbents" include, for example, cholestyramine, colestilan and cholesevelam hydrochloride.

"Angiotensin-converting enzyme inhibitors" include, for example, captopril, enalapril maleate, aracepril and cilazapril.

"Angiotensin II receptor antagonists" include, for example, candesartan cilexetil, losartan potassium and eprosartan mesylate.

"Endothelin-converting enzyme inhibitors" include, for example, CGS-31447 and CGS-35066.

"Endothelin receptor antagonists" include, for example, L-749805, TBC-3214 and BMS-182874.

For example, in the therapy of diabetes and the like, it is suitable that the compounds of the present invention are used together with one or more agent selected from the group consisting of insulin sensitivity enhancers (PPAR γ agonists, PPAR α/γ agonists, PPAR δ agonists, PPAR α/γ/δ agonists and the like), glycosidase inhibitors, biguanide drugs, insulin secretion promoters, insulin preparations and dipeptidyl peptidase IV inhibitors.

Further, it is suitable that the compounds of the present invention are used together with one or more agent selected from the group consisting of hydroxymethyl-glutaryl coenzyme A reductase inhibitors, fibrate compounds, squalene synthetase inhibitors, acyl coenzyme A: cholesterol acyl transferase inhibitors, low density lipoprotein receptor promoters, microsome triglyceride transfer protein inhibitors and anorectics.

The drugs of the present invention can be administered systemically or topically or orally or parenterally, for example, rectally, subcutaneously, intramuscularly, intravenously or percutaneously.

The compounds of the present invention which are used as drugs may be in any form of a solid composition, a liquid composition and another composition and are most suitably selected as the need arises. The drugs of the present invention can be produced by incorporating a pharmaceutically acceptable carrier into the compounds of the present invention. Specifically, a excipient, a filler, a binder, a disintegrator, a coating agent, a sugar-coating agent, a pH adjustor or a solubilizing agent which is conventionally used or an aqueous or nonaqeuous solvent is added to the compounds of the present invention to prepare tablets, pills, capsules, granule, dusting powders, powders, liquids and solutions, emulsions, suspensions, injections or the like by the conventionally employed techniques for pharmaceutical formulations. The excipients and fillers include, for example, lactose, magnesium stearate, starch, talc, gelatin, agar, pectin, acacia, olive oil, sesame oil, cacao butter, ethylene glycol and other substances usually used.

Further, the compounds of the present invention can be made into formulations by forming clathrate compounds with α-, β- or γ-cyclodextrin or methylated cyclodextrin.

The dose of the compounds of the present invention varies depending on the disease, the status of the disease, weight, age, sex and the route of administration, and is preferably 0.1 to 1,000 mg/kg weight/day, more preferably 10 to 200 mg/kg weight/day and can be administered once a day or dividedly several times a day.

The compounds of the present invention can be synthesized, for example, by the production methods as shown in the following Schemes. Further, "Bn" in the following Schemes represents a benzyl group.

2,3,4,6-Tetra-O-benzyl-5a-carba-α-D-glucopyranose (IV) of a key intermediate can be produced, for example, in the following manner.

Scheme 1

[Formula 3]

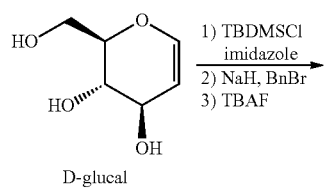

D-glucal

1) TBDMSCl imidazole
2) NaH, BnBr
3) TBAF

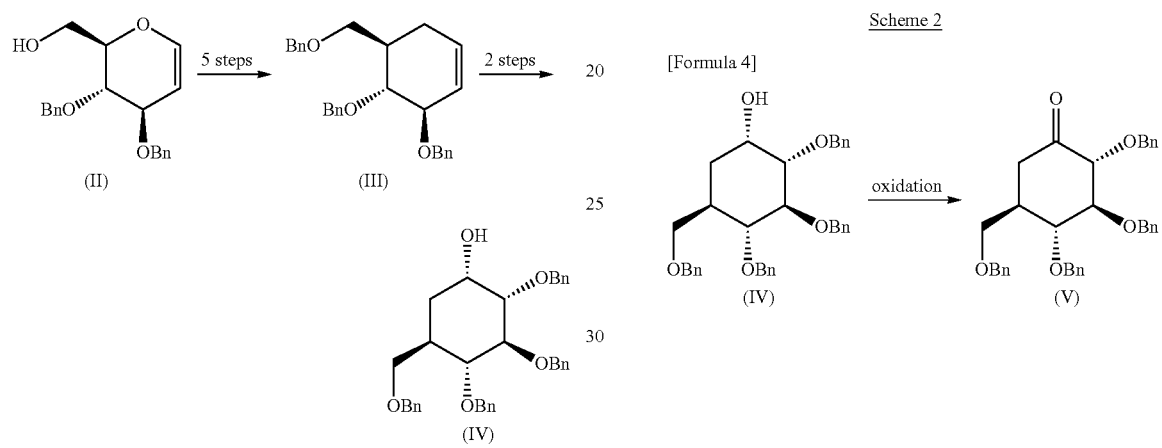

The compound (III) can be converted to 2,3,4,6-tetra-O-benzyl-5a-carba-α-D-glucopyranose (IV) via two steps [Liebigs. Ann. Chemi., p. 267 (1995)].

A compound (V) can be produced by the method as described in a document [J. Chem. Soc. Perkin Trans. 1, 3287 (1991)]. Further, as shown in the following Scheme 2, the compound (V) can be also produced from the compound (IV) by a suitable oxiding reagent (for example, activated DMSO in the Swern method or PCC, PDC, Dess-Martin periodinane or the like)

The compound (IV) can be converted to a compound (VII) as shown below.

Scheme 3

[Formula 5]

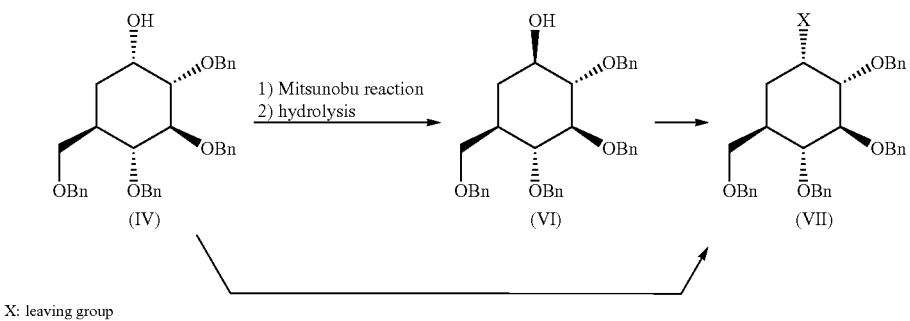

X: leaving group

First, after the primary hydroxy group of D-glucal is protected (for example, protection with a tert-butyl-dimethylsilyl group), two secondary hydroxy groups are protected by benzyl groups, and then the protective group of the primary hydroxy group is eliminated (for example, when the protective group is a tert-butyldimethylsilyl group, it is eliminated by tetrabutylammonium fluoride) to synthesize a 3,4-di-O-benzyl-D-glucal (II).

Next, the compound (II) can be converted to a 3,4,6-tri-O-benzyl-5a-carba-D-glucopyranose (III) via five steps [Chem. Commun., p. 925 (1998)].

The compound (IV) can be derivatized to 2,3,4,6-tetra-O-benzyl-5a-carba-β-D-glucopyranose (VI), for example, by performing hydrolysis after the Mitsunobu reaction with benzoic acid.

Next, a compound (VII) in which X is a halogen atom can be produced by allowing a suitable halogenation agent (for example, phosphorus oxychloride, phosphorus oxybromide, phosphorus trichloride, phosphorus tribromide, carbon tetrachloride-triphenylphosphine, carbon tetrabromide-triphenylphosphine, N-chlorosuccinimide-triphenylphosphine, N-bromosuccinimide-triphenylphosphine, iodine-triphenylphosphine or the like) to act on the compound (VI).

Further, a compound (VII) in which X is a methanesulfonyloxy group, p-toluenesulfonyloxy group, a trifluoromethanesulfonyloxy group or the like can be produced by allowing methanesulfonyl chloride, p-toluenesulfonyl chloride, anhydrous trifluoromethane-sulfonic acid or the like to act on the compound (IV) in a suitable solvent under basic conditions.

For example, a compound of the following formula:

[Formula 6]

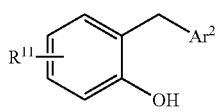

(VIII)

wherein $R^{11}$ is the same as the above defined Rb; and $Ar^2$ is the same as above defined, which is an intermediate of the compound of formula (I) can be synthesized with reference to the following documents: International Publication Nos. WO01/68660, WO01/074834, WO01/074835, WO02/28872, WO02/44192, WO02/064606, WO03/011880 and WO04/014931.

For example, the following compounds:

[Formula 7]

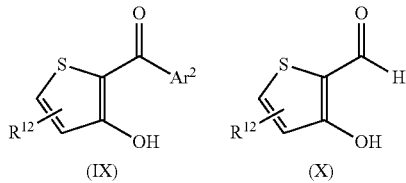

(IX)    (X)

wherein $R^{12}$ is the same as the above defined Rb; and $Ar^2$ is the same as above defined, which are intermediates of the compound of formula (I) can be synthesized with reference to the following document: International Publication No. WO04/007517.

For example, the following compound:

[Formula 8]

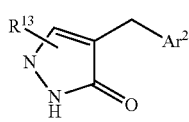

(XI)

wherein $R^{13}$ is the same as the above defined Rb; and $Ar^2$ is the same as above defined, which is an intermediate of the compound of formula (I) can be synthesized with reference to the following documents: International Publication Nos. WO01/16147, WO02/36602, WO02/053573, WO02/068439, WO02/068440, WO02/088157, WO02/098893, WO03/020737 and WO03/090783.

For example, the following compound:

[Formula 9]

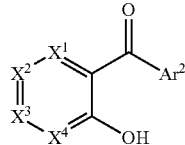

(XII)

wherein $X^1$, $X^2$, $X^3$ and $X^4$ are each a nitrogen atom or C—$R^{14}$ and one or two of $X^1$, $X^2$, $X^3$ and $X^4$ are nitrogen atoms; and $R^{14}$ is the same as the above defined Rb, which is an intermediate of the compound of formula (I) can be synthesized with reference to the following document: International Publication No. WO03/000712.

For example, the following compound:

[Formula 10]

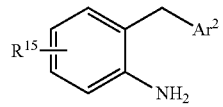

(XIII)

wherein $R^{15}$ is the same as the above defined Rb; and $Ar^2$ is the same as above defined, which is an intermediate of the compound of formula (I) can be prepared according to the following Scheme 4.

Scheme 4

[Formula 11]

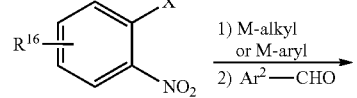

wherein $R^{16}$ is the same as the above defined Rb; M-alkyl and M-aryl are each an organometallic reagent such as n-butyllithium, phenyl lithium and phenyl magnesium bromide; X is a halogen such as chlorine, bromine and iodine; and $Ar^2$ is the same as above defined.

That is, the compound (XIII) can be synthesized by allowing a suitable organometallic reagent (n-butyllithium, phenyl lithium, phenyl magnesium bromide or the like) to act on a compound (XIV), then reacting the resulting compound with $Ar^2$—CHO to derivatize a compound (XV), and thereafter performing a suitable reduction reaction (catalytic hydrogenation using a palladium catalyst or the like).

The compounds of the present invention can be produced, for example, according to Scheme 5 as shown below.

Scheme 5

[Formula 12]

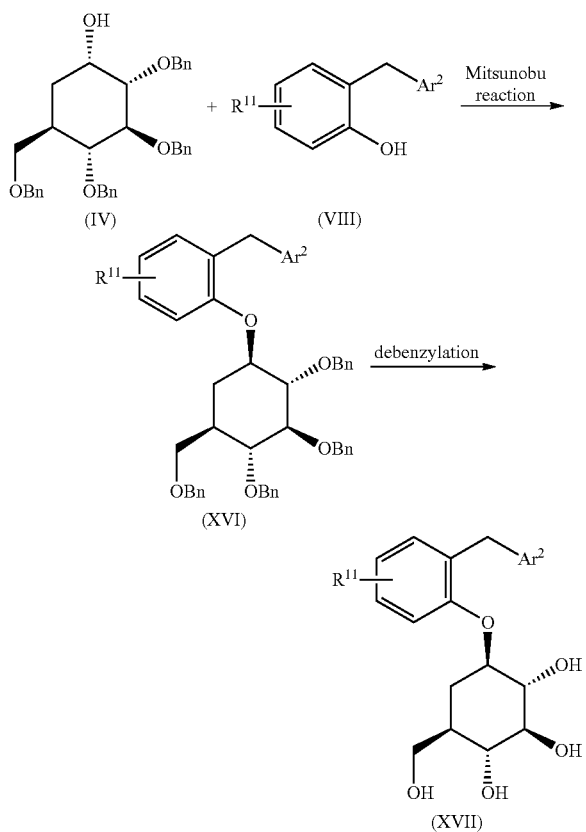

wherein $R^{11}$ is the same as the above defined Rb; and $Ar^2$ is the same as above defined.

That is, the compound of the present invention can be produced by condensing the compound (IV) with the compound (VIII) under the conditions of the Mitsunobu reaction using an azo reagent and a phosphine and then performing deprotection under catalytic hydrogenation conditions using a palladium catalyst or the like or performing deprotection by boron trifluoride-dimethylsulfide or the like. The azo reagents which can be used in the synthesis of the compounds of the present invention include, for example, diethyl azodicarboxylate, tetramethylazodicarboxamide and 1,6-dimethyl-1,5,7-hexahydro-1,4,6,7-tetrazocin-2,5-dione, and the phosphines include, for example, triphenylphosphine, tributylphosphine, 2-(dicyclohexylphosphino)biphenyl and tri(tert-butyl)phosphine. Further, the compounds of the present invention can be also synthesized by the Mitsunobu reaction using a phosphorane reagent. The phosphorane reagent which can be used herein includes, for example, (cyanomethylene)tributylphosphorane and (cyanomethylene)trimethylphosphorane. Further, the substituent $R^{11}$ of the compound (XVII) or the substituent of $Ar^2$ (a halogen, or a hydroxy group after converting to a triflate or the like) can be also converted with the use of a tin reagent, a boric acid or the like in the presence of a palladium catalyst.

Further, the compounds of the present invention can be also produced, for example, according to Scheme 6 as shown below.

Scheme 6

[Formula 13]

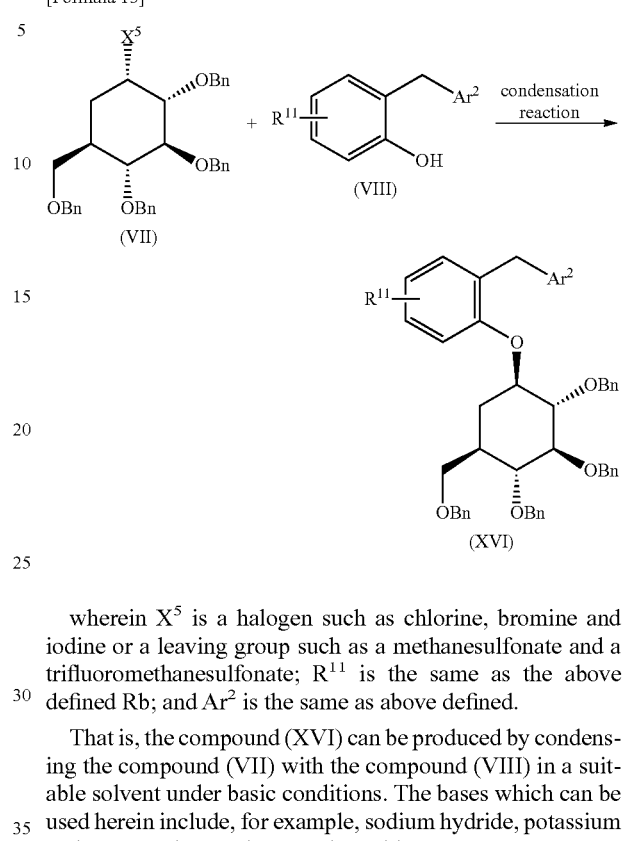

wherein $X^5$ is a halogen such as chlorine, bromine and iodine or a leaving group such as a methanesulfonate and a trifluoromethanesulfonate; $R^{11}$ is the same as the above defined Rb; and $Ar^2$ is the same as above defined.

That is, the compound (XVI) can be produced by condensing the compound (VII) with the compound (VIII) in a suitable solvent under basic conditions. The bases which can be used herein include, for example, sodium hydride, potassium carbonate and potassium tert-butoxide.

Further, the compounds of the present invention can be also produced, for example, according to Scheme 7 as shown below.

Scheme 7

[Formula 14]

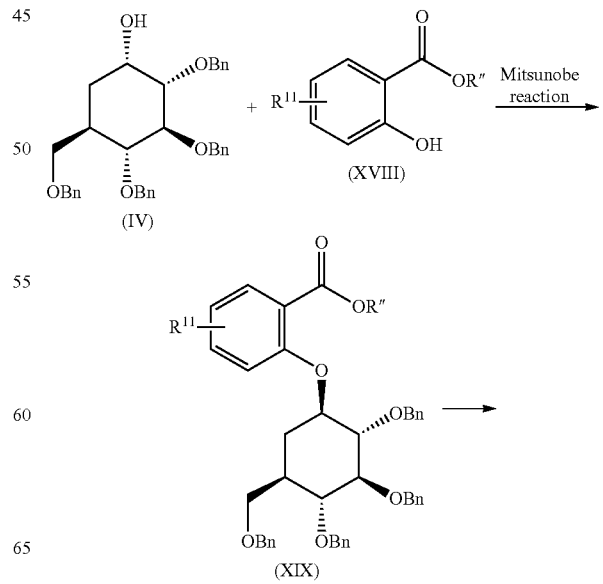

Scheme 8

[Formula 15]

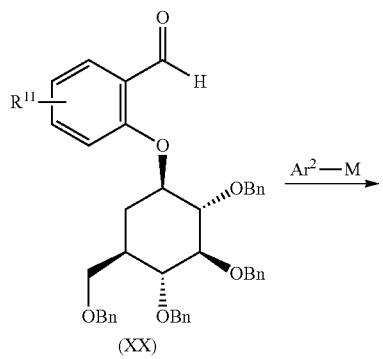

(XX)

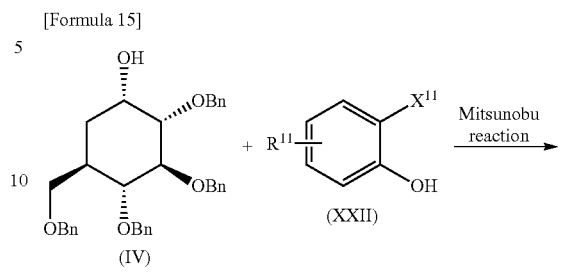

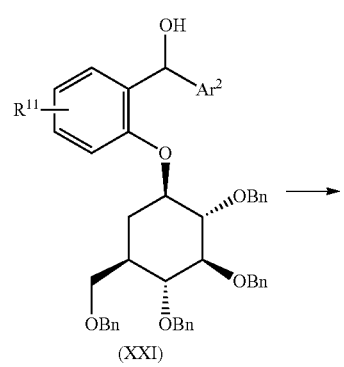

(XXI)

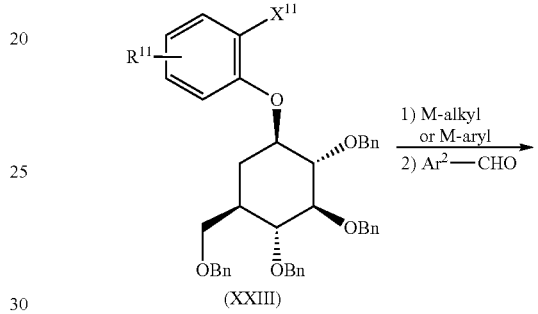

(XXIII)

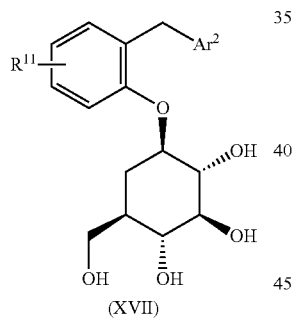

(XVII)

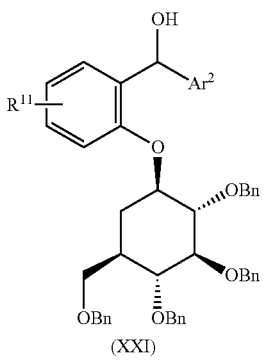

(XXI)

wherein $R^{11}$ is the same as the above defined Rb; R" is a $C_1$-$C_6$ alkyl group, a $C_7$-$C_{14}$ aralkyl group or an aryl group; and $Ar^2$ is the same as above defined.

That is, the compound (XVII) of the present invention can be produced by condensing the compound (1V) with the compound (XVIII) under the conditions of the Mitsunobu reaction using an azo reagent and a phosphine, then converting the alkoxycarbonyl group of the resulting compound to a formyl group by the conventional method to form a compound (XX), then allowing $Ar^2$-M (wherein M is lithium, a magnesium halide or the like) to act on the compound (XX) to be converted to a compound (XXI), and thereafter eliminating the hydroxy group and the benzyl groups simultaneously under catalytic hydrogenation conditions or eliminating them stepwise by reducing the hydroxy group with trimethylsilane or the like and then eliminating the benzyl groups with boron trifluoride-dimethylsulfide.

Further, the compounds of the present invention can be also produced, for example, according to Scheme 8 as shown below.

wherein $X^{11}$ is a halogen atom; $R^{11}$ is the same as the above defined Rb; and $Ar^2$ is the same as above defined.

That is, a compound (XXI) can be synthesized by derivatizing the compound (IV) and the compound (XXII) to a compound (XXIII) by the Mitsunobu reaction and then allowing an organometallic reagent (a lower alkyl lithium such as n-butyllithium or the like) to act on the compound (XXIII) to be reacted with $Ar^2$—CHO.

Further, the compounds of the present invention can be also produced, for example, according to Scheme 9 as shown below.

Scheme 9

[Formula 16]

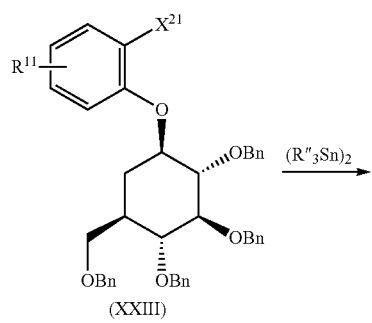

(XXIII)

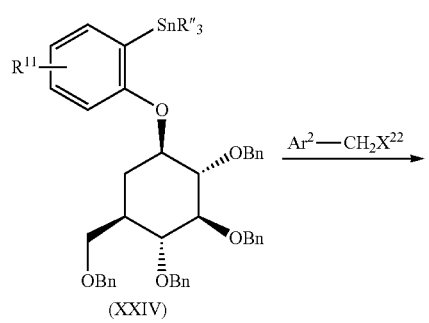

(XXIV)

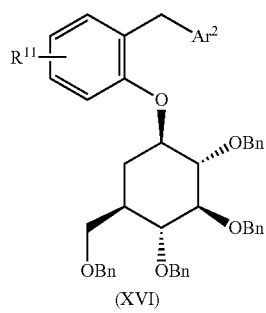

(XVI)

wherein $X^{21}$ and $X^{22}$ are each a halogen atom; R" is independently selected from a $C_1$-$C_6$ alkyl group; $R^{11}$ is the same as the above defined Rb; and $Ar^2$ is the same as above defined.

That is, a hexaalkylditin is allowed to act on a compound (XXIII) in the presence of a palladium catalyst to derivatize a compound (XXIV) which is then reacted with $Ar^2$—$CH_2X^{22}$ in the presence of a palladium catalyst to synthesize a compound (XVI). The hexaalkylditin as used herein includes, for example, hexamethylditin and hexabutylditin, and the palladium catalyst includes, for example, tetrakistriphenylphosphine palladium (0) and 1,2-bis(diphenylphosphorinoethane)dichloropalladium (II).

Further, the compounds of the present invention can be also produced, for example, according to Scheme 10 as shown below.

Scheme 10

[Formula 17]

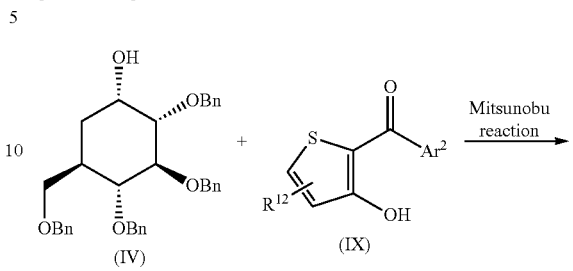

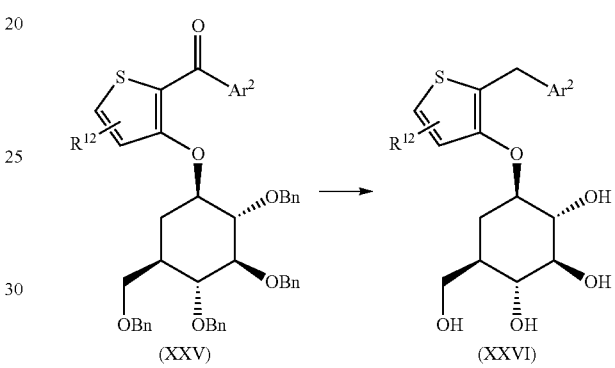

wherein $R^{12}$ is the same as the above defined Rb; and $Ar^2$ is the same as above defined.

That is, the compound (1V) is condensed with the compound (IX) under the conditions of the Mitsunobu reaction using an azo reagent and a phosphine to derivatize a compound (XXV), and thereafter the ketone reduction and the elimination of the benzyl groups are simultaneously performed under catalytic hydrogenation conditions using a palladium catalyst or the like, or performed stepwise by reduction of the ketone with sodium borohydride or the like and then the elimination of the benzyl groups with a palladium catalyst to produce a compound (XXVI) of the present invention.

Further, the compounds of the present invention can be also produced, for example, according to Scheme 11 as shown below.

Scheme 11

[Formula 18]

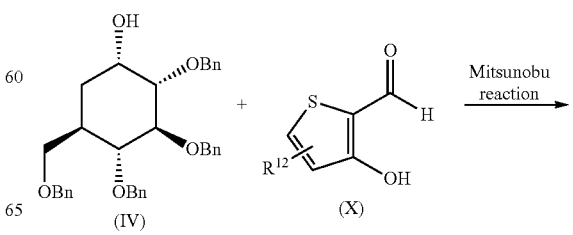

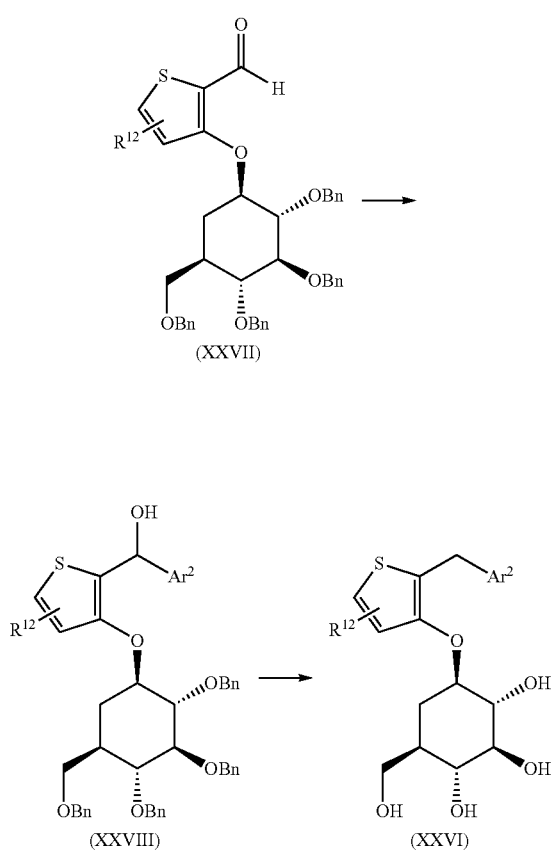

(XXVII)

(XXVIII) → (XXVI)

wherein $R^{12}$ is the same as the above defined Rb; and $Ar^2$ is the same as above defined.

That is, the compound (IV) is condensed with the compound (X) under the conditions of the Mitsunobu reaction using an azo reagent and a phosphine to derivatize a compound (XXVII), and thereafter $Ar^2$-M (wherein M is lithium, a magnesium halide or the like) is allowed to act on the compound (XXVII) to convert it to a compound (XXVIII), and thereafter the elimination of the hydroxy group and the benzyl groups is performed simultaneously or stepwise under catalytic hydrogenation conditions using a palladium catalyst or the like to produce a compound (XXVI) of this invention.

Further, the compounds of the present invention can be also produced, for example, according to Scheme 12 as shown below.

Scheme 12

[Formula 19]

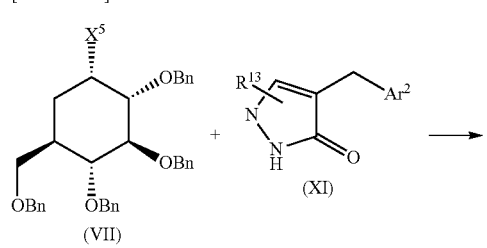

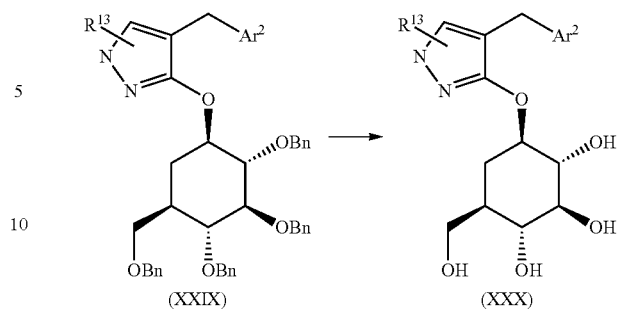

(XXIX) → (XXX)

wherein $X^5$ is the same as above defined; $R^{13}$ is the same as the above defined Rb; and $Ar^2$ is the same as above defined.

That is, the compound (XXX) of this invention can be produced by reacting the compound (VII) with the compound (XI) in a suitable solvent in the presence of a base to derivatize a compound (XXIX), and thereafter the elimination of the benzyl groups is performed under catalytic hydrogenation conditions using a palladium catalyst or the like to produce the desired compound.

Further, in the production method of Scheme 10, the compound (XXXI) (wherein $X^1$, $X^2$, $X^3$ and $X^4$ and $Ar^2$ is the same as above defined) of the present invention can be synthesized by using the compound (XII) instead of the compound (IX).

[Formula 20]

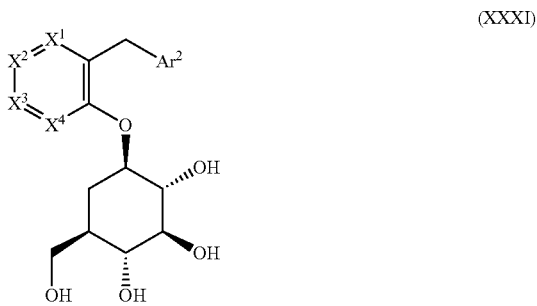

(XXXI)

Further, the compounds of the present invention can be also produced, for example, according to Scheme 13 as shown below.

Scheme 13

[Formula 21]

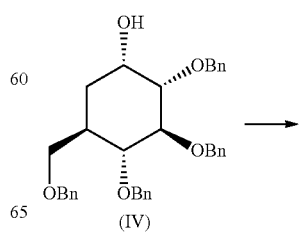

(IV)

-continued

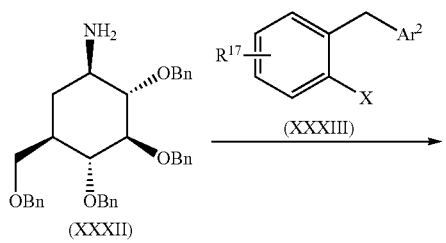

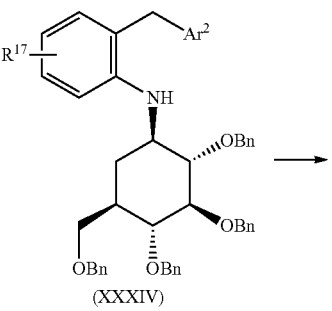

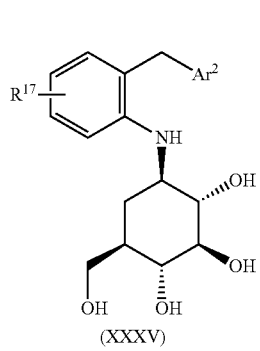

wherein X is a halogen atom; $R^{17}$ is the same as the above defined Rb; and $Ar^2$ is the same as above defined.

That is, the compound (XXXV) of this invention can be produced by subjecting the compound (1V) to the Mitsunobu reaction with phthalimide, allowing hydrazine or methylamine to act on the resulting compound to derivatize a compound (XXXII), then performing the coupling reaction with a compound (XXXIII) in the presence of a palladium catalyst [for example, tris(dibenzylideneacetone)di-palladium (0) or 1,1'-bis(diphenylphosphinoferrocene)-dichloropalladium (II)] or a copper reagent [for example, copper iodide (I)] to convert the compound (XXXII) to compound (XXXIV), and thereafter eliminating the benzyl groups under catalytic hydrogenation conditions using a palladium catalyst or the like.

Further, the compound (XXXII) can be synthesized by performing the Mitsunobu reaction of the compound (IV) with sodium azide or the like and thereafter allowing triphenylphosphine or the like to act on the resulting compound.

Further, the compound (XXXIII) can be produced according to Scheme 14 by allowing $Ar^2$-M to act on a compound (XXXVI) to derivatize a compound (XXXVII) and thereafter treating the compound (XXXVII) with triethylsilane in the presence of a boron trifluoride-diethylether complex, trifluoroacetic acid or the like.

Scheme 14

[Formula 22]

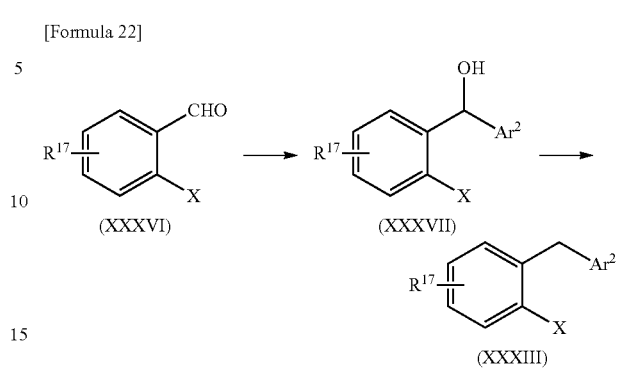

wherein X is the same as above defined; $R^{17}$ is the same as the above defined Rb; and $Ar^2$ is the same as above defined.

Further, the compounds of the present invention can be also produced, for example, according to Scheme 15 as shown below.

Scheme 15

[Formula 23]

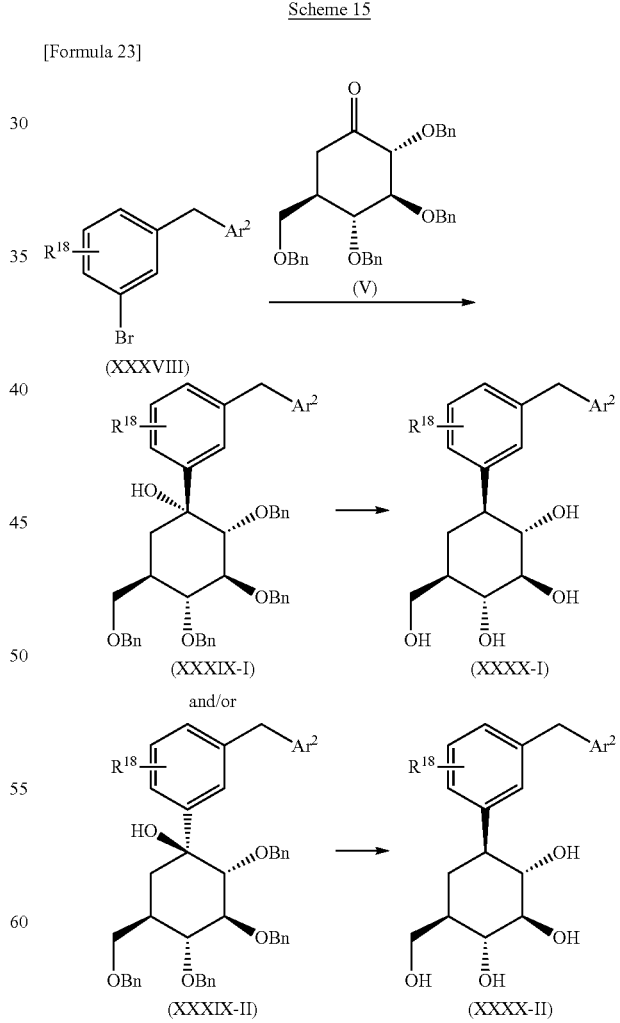

wherein $R^{18}$ is the same as the above defined Rb; and Ar is the same as above defined.

That is, a compound (XXXX-I) can be produced by allowing a suitable alkyl lithium (for example, n-butyllithium or the like) to act on a compound (XXXVIII) to be reacted with a compound (V) and catalytically hydrogenating the obtained compound (XXXIX-I) with a palladium catalyst or the like. In the same manner, a compound (XXXX-II) can be directly produced by catalytically hydrogenating the compound (XXXIX-II) with a palladium catalyst or can be produced by acetylating the hydroxy group and then eliminating the acetoxy group and the benzyl groups by catalytic hydrogenation reaction using a palladium catalyst or the like (if necessary, an acid such as hydrochloric acid is added). Herein, the compound (XXXVIII) can be synthesized, for example, by the method as described in International Publication No. WO01/27128.

The compound (XXXX) can be also produced, for example, according to the method of Scheme 16 as shown below.

Scheme 16

[Formula 24]

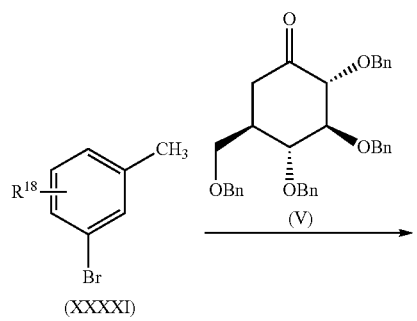

(XXXXI)

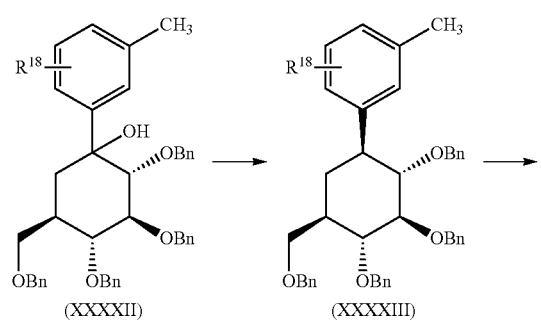

(XXXXII) (XXXXIII)

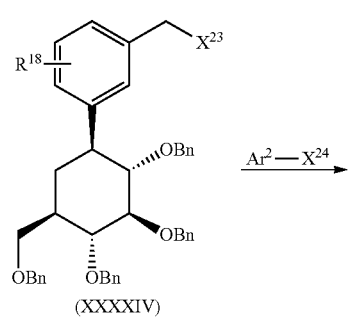

(XXXXIV)

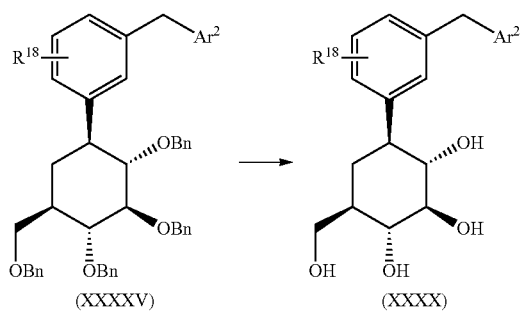

(XXXXV) (XXXX)

wherein $X^{23}$ and $X^{24}$ are halogen atoms; $R^{18}$ is the same as the above defined Rb; and $Ar^2$ is the same as above defined.

That is, a suitable alkyl lithium (for example, n-butyllithium or the like) is allowed to act on a compound (XXXXI) and is reacted with the compound (V) to derivatize a compound (XXXXII), and the resulting hydroxy group is converted to a thiocarbonyloxy group by methylthiocarbonylation or imidazolylthiocarbonylation, and then deoxygenation is performed by allowing a radical reaction agent (for example, a tin hydride reagent such as tributyltin hydride, a silane agent such as diphenylsilane, a combination of diphosphorous acid or diethyl phosphate with a tertiary amine) to act on the compound (XXXXII) in the presence of a suitable radical initiator (for example, 2,2'-azobisiso-butyronitrile, benzoyl peroxide or the like) to synthesize a compound (XXXXIII). Then, the compound (XXXXIII) is converted to the benzyl halide (XXXXIV) under suitable halogenation conditions (for example, by N-bromosuccinimide, bromine, hydrogen bromide or the like), and the benzyl halide (XXXXIV) is reacted with an aryl halide (including an heteroaryl halide) in the presence of a suitable catalyst [for example, tetrakistriphenyl-phosphine palladium (0), 1,2-bis (diphenylphosphinoethane)-dichloropalladium (II) or the like], and thereafter debenzylation is performed to derivatize a compound (XXXX).

The intermediate (XXXXIV) can be produced by the method of Scheme 17 as shown below.

Scheme 17

[Formula 25]

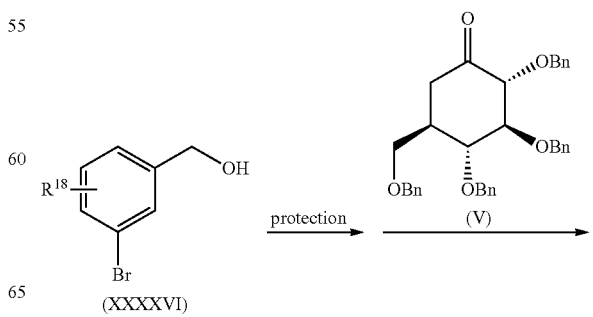

(XXXXVI)

-continued

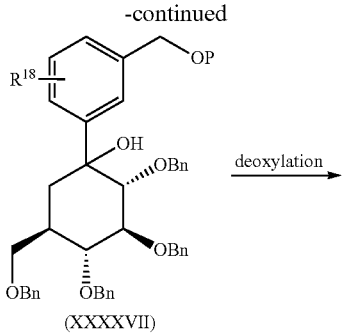

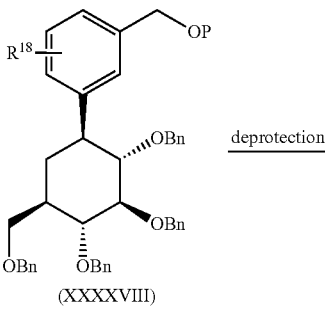

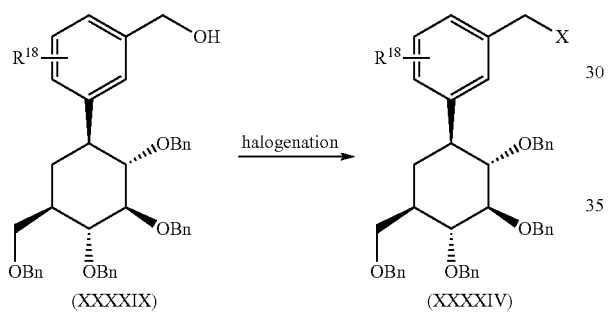

wherein $R^{18}$ is the same as the above defined Rb; P is a protective group; X is a halogen atom; and $Ar^2$ is the same as above defined.

That is, after the hydroxy group of a compound (XXXXVI) is protected by a suitable protective group (for example, a tert-butyldimethylsilyl group, a tetrahydro-pyranyl group or the like), a suitable alkyl lithium (for example, n-butyllithium or the like) is acted on the resulting compound and reacted with the compound (V) to derivatize a compound (XXXX-VII). Then, the tertiary hydroxy group is converted to, for example, a thio-carbonyloxy group by methylthiocarbonylation or imida-zolylthiocarbonylation, and then a radical reaction agent (for example, a tin hydride reagent such as tributyltin hydride, a silane agent such as diphenylsilane, a combination of diethyl phosphate or diphosphorous acid with a tertiary amine) is allowed to act on the resulting compound in the presence of a suitable radical initiator (for example, 2,2'-azobisisobutyronitrile, benzoyl peroxide) to convert it to a compound (XXXXVIII). Subsequently, the deprotection is performed to obtain a compound (XXXXIX), and thereafter by suitable halogenation conditions (for example, when X is bromine atom, the conditions using N-bromosuccinimide, bromine, carbon tetrabromide or the like in the presence of triphenylphosphine), the compound (XXXXIV) can be synthesized.

The compound (L) can be also produced, for example, according to Scheme 18 as shown below.

Scheme 18

[Formula 26]

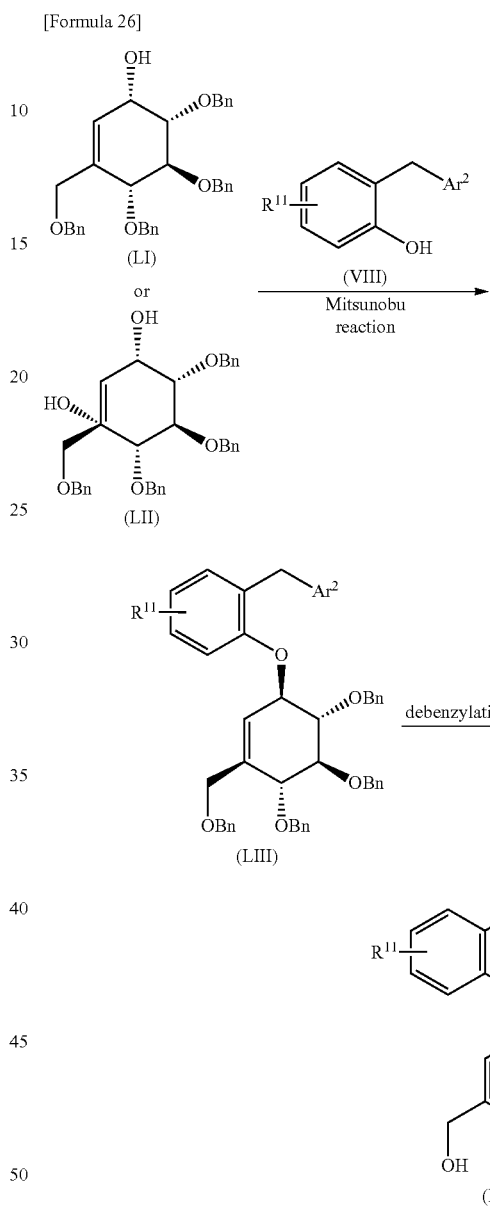

wherein $R^{11}$ is the same as the above defined Rb; and $Ar^2$ is the same as above defined.

That is, the compound (L) of the present invention can be produced by using the compound (LI) or the compound (LII) instead of the compound (IV) in the production method of Scheme 5. The compound (LI) can be synthesized by the method as described in a document [J. Org. Chem., 63, 5668 (1998)] and the compound (LII) can be synthesized by the method as described in a document [Tetrahedron, 56, 7109 (2000)]

Further, the compounds of the present invention can be also produced, for example, according to Scheme 19 as shown below.

Scheme 19

[Formula 27]

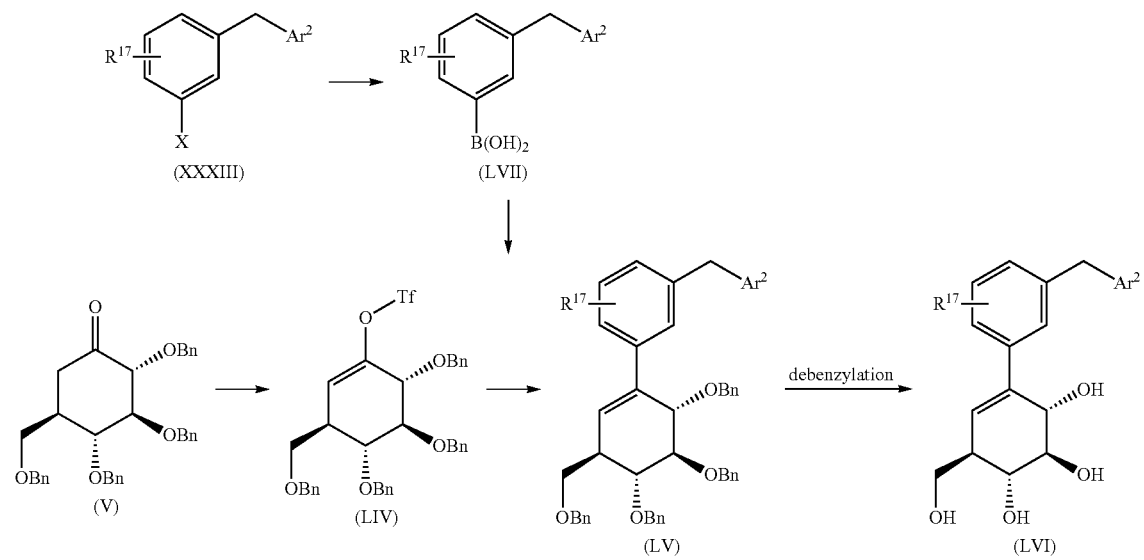

wherein $R^{17}$ is the same as the above defined Rb; X is the same as above defined; Tf is a trifluoromethane-sulfonyl group; and $Ar^2$ is the same as above defined.

That is, a compound (LV) can be produced by treating a compound (LIV) obtained by triflating the compound (V) together with a compound (LVII) obtained by allowing a suitable alkyl lithium (n-butyllithium or the like) to act on the compound (XXXIII) to be treated with a boric acid ester (trimethyl borate or the like) in the presence of a palladium catalyst (tetrakistriphenylphoxphine palladium or the like). A compound (LVI) can be produced by treating this compound (LV) with boron trichloride or the like in the presence of pentamethylbenzene or the like.

The method for producing the compounds of the present invention is not limited to the above-described methods. The compounds of the present invention can be synthesized, for example, by suitably combining the steps included in Schemes 1 to 19.

Effect of the Invention

The compounds of the present invention not only have SGLT2 inhibition action but also have suitable properties as drugs such as metabolic stability, oral absorbability, drug effect durability and safety. Thus, pharmaceutical compositions having an action of lowering blood sugar levels which are used for the prophylaxis or treatment of diabetes such as insulin-dependent diabetes (type I diabetes) and insulin-independent diabetes (type II diabetes), diabetic complications and obesity caused by hyperglycemia are provided by the present invention.

EXAMPLES

The contents of the present invention will be explained in further details by the following examples and experimental example but the present invention is not limited to their contents.

Each abbreviation in the following examples has the following meaning.

NMR: Nuclear magnetic resonance spectrum (TMS internal standard);
MS: Mass spectrometric analysis value;
HPLC: High-speed liquid chromatography;
NMR, MS and HPLC are measured by the following equipment.
NMR: JOEL JNM-EX-270 (270 MHz), Varian Mercury 300 (300 MHz) or JOEL JNM-ECP 400 (400 MHz);
MS: LCQ of Thermo Finigan or Micromass ZQ of Waters;
HPLC: 2690/2996 (Detector) of Waters.

The measurement conditions of HPLC are as follows unless otherwise described.
Column: YMC-Pack ODS-A 6.0×150 mm, 5 μm
Mobile Phase Elution by applying a gradient of from 0.1% TFA/MeCN (5%) plus 0.1% TFA/$H_2O$ (95%) to 0.1% TFA/MeCN (100%) for 20 minutes, and thereafter under the same condition [0.1% TFA/MeCN (100%)] for five minutes
Flow Rate: 1.5 mL/minute
Column Temperature Room temperature
Detection Condition Total plot of the entire wavelength of 230 to 400 nm Example 1

[2-(4-Methoxybenzyl)phenyl]-5a-carba-β-D-glucopyranoside (1) Synthesis of 2-(2,3,4,6-Tetra-O-benzyl-5a-carba-β-D-glucopyranosyl)benzoic Acid Methyl Ester To a methyl salicylate (72 μL, 0.557 mmol) THF solution (400 μL), triphenylphosphine (146 mg, 0.557 mmol) and 2,3,4,5,6-tetra-O-benzyl-5a-carba-α-D-glucopyranose (200 mg, 0.371 mmol) were added, and diethylazodi-carboxylate (DEAD, 88 μL, 0.557 mmol) was added dropwise thereto, and the mixture solution was stirred at room temperature for 10 hours. The reaction mixture was concentrated under reduced pressure, and the obtained residue was purified by preparative thin-layer chromatography (TLC) [developing solution=ethyl acetate:n-hexane (1:3)] to obtain the title compound (123 mg, 49%).

$^1$H-NMR (CDCl$_3$) δ: 1.60-1.80 (2H, m), 2.15-2.24 (1H, m), 3.48-3.64 (4H, m), 3.75-3.90 (1H, m), 3.83 (3H, s), 4.43 (3H, s), 4.53 (1H, d, J=10.7 Hz), 4.51-4.98 (6H, m), 6.95-7.02 (1H, m), 7.10-7.50 (22H, m), 7.78 (1H, dd, J=1.65, 7.75 Hz)

MS (ESI$^+$): 695 [M+Na]$^+$ (2) Synthesis of 2-(2,3,4,6-Tetra-O-benzyl-5a-carba-β-D-glucopyranosyl)benzyl Alcohol Lithium aluminum hydride (10.4 mg, 0.274 mmol) was added to a THF solution (360 μL) of 2-(2,3,4,6-tetra-O-benzyl-5a-carba-β-D-glucopyranosyl)benzoic acid methyl ester (123 mg, 0.183 mmol) in small portions and the reaction mixture was stirred in an oil bath (55° C.) for three hours. The reaction mixture was cooled to room temperature, and then water was added thereto and extracted with ethyl acetate. The organic layer was washed with a saturated sodium chloride aqueous solution and dried (anhydrous magnesium sulfate), and then the solvent was distilled under reduced pressure. The obtained residue was purified by preparative TLC [developing solution=ethyl acetate:n-hexane (1:3)] to obtain the title compound (95 mg, 81%).

$^1$H-NMR (CDCl$_3$) δ: 1.60-1.80 (2H, m), 2.16-2.22 (1H, m), 3.46-3.74 (5H, m), 4.43 (3H, s), 4.54 (1H, d, J=10.7 Hz), 4.66 (2H, br s), 4.81-4.96 (5H, m), 6.94-7.31 (24H, m)

MS (ESI$^+$): 667 [M+Na]$^+$ (3) Synthesis of 2-(2,3,4,6-Tetra-O-benzyl-5a-carba-β-D-glucopyranosyl)benzaldehyde To a 2-(2,3,4,6-tetra-O-benzyl-5a-carba-β-D-gluco-pyranosyl)benzyl alcohol (95 mg, 0.147 mmol) dichloro-methane solution (1.5 mL), a Dess-Martin reagent (94 mg, 0.221 mmol) was added, and the mixture solution was stirred at room temperature for 45 minutes. Insolubles were removed from the reaction mixture by filtration and the filtrate was concentrated under reduced pressure. The obtained residue was purified by preparative TLC [developing solution=ethyl acetate:n-hexane (1:3)] to obtain the title compound (77 mg, 81%).

$^1$H-NMR (CDCl$_3$) δ: 1.60-1.80 (2H, m), 2.17-2.23 (1H, m), 3.48-3.78 (5H, m), 4.44 (3H, s), 4.54 (1H, d, J=10.7 Hz), 4.73-4.97 (5H, m), 7.00-7.32 (22H, m), 7.50 (1H, dd, J=1.48, 7.83 Hz), 7.83 (1H, dd, J=1.49, 7.58 Hz), 10.4 (1H, s)

(4) Synthesis of [2-(2,3,4,6-Tetra-O-benzyl-5a-carba-β-D-glucopyranosyl)phenyl]-4-methoxyphenylmethanol To a diethyl ether solution (120 μL) of 2-(2,3,4,6-tetra-O-benzyl-5a-carba-β-D-gluco-pyranosyl)benzaldehyde (77 mg, 0.119 mmol), a 4-methoxyphenylmagnesium 0.5 M THF solution (480 μL, 0.238 mmol) was added, and the mixture solution was stirred at room temperature for 13 hours. A saturated ammonium chloride aqueous solution was added thereto and the mixture was extracted with ethyl acetate. The organic layer was dried (anhydrous magnesium sulfate) and the solvent was concentrated under reduced pressure. The obtained residue was purified by preparative TLC [developing solution=ethyl acetate:n-hexane (1:3)] to obtain the title compound (66 mg, 74%).

$^1$H-NMR (CDCl$_3$) δ: 1.60-1.80 (2H, m), 1.95-2.09 (1H, m), 2.66 (1H, d, J=4.78 Hz), 3.38-3.79 (5H, m), 3.65 (1.2H, s), 3.69 (1.8H, s), 4.33-4.93 (9H, m), 5.96-6.16 (1H, m), 6.73-7.42 (28H, m)

MS (ESI$^+$): 773 [M+Na]$^+$ (5) Synthesis of [2-(4-Methoxybenzyl)phenyl]-5a-carba-β-D-glucopyranoside To [2-(2,3,4,6-tetra-O-benzyl-5a-carba-β-D-gluco-pyrasyl)phenyl]-4-methoxyphenylmethanol (66 mg, 0.0879 mmol), hydro-chloric acid methanol solution (2 mL) containing a 20% palladium hydroxide carbon (10 mg) was added and the reaction mixture was stirred under a hydrogen atmosphere for three hours. After the reaction, the reaction mixture was filtered and the filtrate was concentrated under reduced pressure, and the obtained residue was purified by preparative TLC [developing solution=methanol:dichloro-methane (1:10)] to obtain the title compound (20 mg, 61%).

$^1$H-NMR (CD$_3$OD) δ: 0.89-1.03 (1H, m), 1.40-1.60 (1H, m), 2.02-2.10 (1H, m), 3.18-3.34 (2H, m), 3.45-3.51 (2H, m), 3.67-3.71 (1H, m), 3.73 (3H, s), 3.82-3.99 (2H, m), 4.13-4.22 (1H, m), 6.78 (2H, d, J=8.57 Hz), 6.80-6.86 (1H, m), 6.99-7.16 (5H, m)

MS (ESI$^+$): 397 [M+Na]$^+$

HPLC Retention Time: 10.6 minutes

Example 2

[1S,2R,3R,4R,6S]-4-Hydroxymethyl-6-[3-(4-methoxybenzyl)-phenyl]cyclohexane-1,2,3-triol (1) Synthesis of [2R,3S,4R,5R]-2,3,4-Trisbenzyloxy-5-benzyloxymethyl-1-[3-(4-methoxybenzyl)phenyl] cyclo-hexanol To a solution of 3-(4-methoxybenzyl)-1-bromobenzene (155 mg, 0.559 mmol) in THF (0.80 mL), an n-butyllithium 2.44 M hexane solution (0.23 mL, 0.559 mmol) was added dropwise at −78° C. and the mixture solution was stirred for 25 minutes. Then, a solution of 2,3,4-tribenzyloxy-5-(benzyloxy-methyl)cyclohexanone (200 mg, 0.373 mmol) in THF (0.70 mL) was added dropwise thereto and the reaction mixture was stirred for 75 minutes. To the reaction mixture was added a saturated ammonium chloride aqueous solution and the mixture was extracted with ethyl acetate, and the organic layer was washed with a saturated sodium chloride aqueous solution, and then dried over anhydrous magnesium sulfate. The solvent was concentrated and the obtained residue was purified by silica gel chromatography [developing solution=ethyl acetate:n-hexane (2:5)] to obtain the title compound (80 mg, 27%) as a mixture of 1R-isomer and 1S-isomer.

$^1$H-NMR (CDCl$_3$) δ: 1.82-1.92 (1H, m), 2.39-2.44 (1H, m), 2.56-2.64 (1H, m), 3.34-3.39 (1H, m), 3.55-3.80 (2H, m), 3.66 (3H, s), 3.78 (2H, s), 3.87-3.94 (2H, m), 4.42-5.04 (8H, m), 6.61-6.84 (4H, m), 7.06-7.40 (23H, m), 7.55-7.66 (1H, m)

(2) Synthesis of Acetic Acid [2R,3S,4R,5R]-2,3,4-Tris-benzyloxy-5-benzyloxymethyl-1-[3-(4-methoxybenzyl)-phenyl]cyclohexyl Ester To a solution of [2R,3S,4R,5R]-2,3,4-trisbenzyloxy-5-benzyloxymethyl-1-[3-(4-methoxybenzyl)phenyl]cyclohexanol (20 mg), triethylamine (0.008 mL) and 4-dimethylamino-pyridine (0.7 mg) in dichloromethane (0.10 mL), acetic anhydride (0.003 mL) was added under cooling with ice and the reaction mixture was stirred at room temperature for two hours. Then, acetyl chloride (0.003 mL) was added thereto under cooling with ice and the reaction mixture was stirred at room temperature for 30 minutes. a saturated sodium hydrogen-carbonate aqueous solution was added thereto and the mixture was extracted with dichloromethane, and the organic layer was dried over anhydrous magnesium sulfate. The solvent was concentrated and the obtained residue was purified by preparative TLC [developing solution=ethyl acetate:n-hexane (2:5)] to obtain the title compound (4.2 mg).

$^1$H-NMR (CDCl$_3$) δ: 1.85 (3H, s), 2.03-2.17 (2H, s), 3.20-3.49 (3H, m), 3.60-3.72 (2H, m), 3.67 (3H, s), 3.87 (2H, s), 4.07 (1H, d, J=9.9 Hz), 4.39-4.95 (8H, m), 6.72 (2H, d, J=8.6 Hz), 6.99-7.40 (24H, m), 7.54 (1H, d, J=7.8 Hz), 7.65 (1H, s)
MS (ESI$^+$): 794 [M+H$_2$O]$^+$ (3) Synthesis of [1S,2R,3R,4R,6S]-4-Hydroxymethyl-6-[3-(4-methoxybenzyl)phenyl]cyclohexane-1,2,3-triol To a methanol (0.2 mL)-THF (0.2 mL) solution of acetic acid [2R,3S,4R,5R]-2,3,4-trisbenzyloxy-5-benzyloxymethyl-1-[3-(4-methoxybenzyl)phenyl]cyclohexyl ester (4.2 mg), a 20% palladium hydroxide-carbon (3 mg) was added and the mixture solution was stirred under a hydrogen atmosphere for three hours. The reaction mixture was filtered and the filtrate was concentrated and the obtained residue was purified by preparative TLC [developing solution=dichloromethane:methanol (9:1)] to obtain the title compound (1.7 mg) as a single diastereomer.

$^1$H-NMR (DMSO-d$_6$) δ: 1.24 (1H, dd, J=12.9, 12.6 Hz), 1.48 (1H, m), 1.65 (1H, dt, J=13.8, 3.3 Hz), 2.43 (1H, dt, J=10.4, 4.2 Hz), 3.05-3.17 (2H, m), 3.26-3.40 (2H, m), 3.60 (1H, m), 3.71 (3H, s), 3.83 (2H, s), 4.15 (1H, d, J=4.8 Hz), 4.21 (1H, t, J=5.1 Hz), 4.45 (1H, br), 4.60 (1H, br), 6.84 (2H, m), 6.93-7.08 (3H, m), 7.10-7.20 (3H, m)
MS (ESI$^+$): 376 [M+H$_2$O]$^+$

Example 3

[2-(4-Trifluoromethoxybenzyl)phenyl]-5a-carba-β-D-gluco-pyrasnoide (1) Synthesis of (2-Benzyloxyphenyl)-(trifluoromethoxy-phenyl)methanol In a nitrogen stream, an n-butyllithium hexane solution (1.59 M, 8.7 mL) was added dropwise to a solution of 1-benzyloxy-2-bromobenzene (3.3 g, 12.64 mmol) in THF (126 mL) at −78° C. and the mixture solution was stirred at the same temperature for 15 minutes. To this solution, a solution of 4-trifluoromethoxybenzaldehyde (2.0 g, 10.52 mmol) in THF (42 mL) was added dropwise at −78° C. The reaction mixture was stirred at the same temperature for 40 minutes and at 0° C. for 45 minutes, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (3.03 g, 77%) as a colorless oil.

$^1$H-NMR (CDCl$_3$) δ: 2.98 (1H, d, J=5.8 Hz), 5.01 (2H, s), 6.02 (1H, d, J=5.6 Hz), 6.84-7.00 (2H, m), 7.03-7.37 (11H, m)

(2) Synthesis of 2-(4-Trifluoromethoxybenzyl)phenol

A 20% palladium hydroxide catalyst (150 mg) was added to a solution of (2-benzyloxyphenyl)-(4-trifluoromethoxyphenyl)methanol (1.5 g, 4.01 mmol) in methanol (27 mL) and furthermore 36% HCl (0.33 mL) was added thereto. The mixture solution was stirred under a hydrogen atmosphere for 16 hours, and then cooled to 0° C., potassium carbonate (0.54 g) added thereto and the mixture was stirred for 30 minutes, and then the catalyst was removed by filtration. The solvent was distilled under reduced pressure and the obtained residue was purified by silica gel column chromatography [developing solution=ethyl acetate:n-hexane (1:10)] to obtain a white solid title compound (1.05 g, 97%).

$^1$H-NMR (CDCl$_3$) δ: 3.98 (2H, s), 4.83 (1H, s), 6.77 (1H, d, J=7.7 Hz), 6.89 (1H, t, J=7.3 Hz), 6.99-7.13 (4H, m), 7.23 (2H, d, J=8.1 Hz)

(3) Synthesis of [2-(4-Trifluoromethoxybenzyl)phenyl]-5a-carba-β-D-glucopyranoside In a nitrogen stream, 2,3,4,6-tetra-O-benzyl-5a-carba-α-D-glucopyranose (400 mg, 0.74 mmol) and tributyl-phosphine (0.28 mL, 1.11 mmol) were added to a solution of 2-(4-tri-fluoromethoxybenzyl)phenol (298 mg, 1.11 mmol) in toluene (2.5 mL) under cooling with ice, and then tetramethylazodicarboxamide (TMAD, 191 mg, 1.11 mmol) was added thereto at the same temperature. The reaction mixture was stirred overnight while gradually raising its temperature to room temperature. The reaction mixture was concentrated under reduced pressure, and the obtained residue was treated with silica gel column chromatography [developing solution=ethyl acetate:n-hexane (1:10)] and furthermore preparative TLC [developing solution=ethyl acetate:n-hexane (1:5)]. The obtained crude product was dissolved in a tetrahydrofuran (1.4 mL)-methanol (2.8 mL) mixed solution, a 20% palladium hydroxide catalyst (40 mg) added thereto and the mixture was stirred under a hydrogen atmosphere for 1.75 hours, and then the catalyst was filtered off. The solvent was distilled under reduced pressure, and the obtained residue was purified by preparative TLC [developing solution=methylene chloride:methanol (10:1)] to obtain the title compound (67 mg, 21%).

$^1$H-NMR (CD$_3$OD) δ: 0.85-0.99 (1H, m), 1.44-1.61 (1H, m), 2.00-2.11 (1H, m), 3.12-3.33 (2H, m), 3.38-3.48 (2H, m), 3.64-3.73 (1H, m), 3.93 (1H, d, J=14.8 Hz), 4.07 (1H, d, J=14.8 Hz), 4.12-4.23 (1H, m), 6.86 (1H, t, J=7.3 Hz), 6.96-7.17 (5H, m), 7.29 (2H, d, J=8.6 Hz)
MS (ESI$^+$): 428 [M]$^+$
HPLC Retention Time: 12.7 minutes Example 4

[2-(4-Cyclopentylbenzyl)phenyl]-5a-carba-β-D-glucopyranoside (1) Synthesis of (2-Benzyloxyphenyl)-(4-bromophenyl)-methanol In a nitrogen stream, an n-butyllithium hexane solution (1.59 M, 11.57 mL) was added dropwise to a solution of 1-benzyloxy-2-bromobenzene (4.4 g, 16.72 mmol) in THF (168 mL) at −78° C. and the mixture solution was stirred at the same temperature for 15 minutes. To this solution, a solution of 4-bromobenzaldehyde (2.47 g, 13.34 mmol) in THF (50 mL) was added dropwise at −78° C. The reaction mixture was stirred at the same temperature for 30 minutes and at 0° C. for 30 minutes, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (4.08 g, 83%) as a colorless oil.

$^1$H-NMR (CDCl$_3$) δ: 2.96 (1H, d, J=6.1 Hz), 5.01 (2H, s), 5.97 (1H, d, J=5.9 Hz), 6.86-6.99 (2H, m), 7.09-7.39 (11H, m)

(2) Synthesis of 1-Benzyloxy-2-(4-bromobenzyl)benzene

In a nitrogen stream, triethylsilane (1.84 mL, 11.55 mmol) and a boron trifluoride-diethylether complex (1.33 mL, 10.5 mmol) were added to a solution of (2-benzyloxyphenyl)-(4-bromophenyl)methanol (3.88 g, 10.5 mmol) in acetonitrile (19.5 mL) at −40° C. and the mixture was stirred at the same temperature for 0.5 hour. A saturated potassium carbonate aqueous solution was added to the reaction mixture and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (2.86 g, 77%).

$^1$H-NMR (CDCl$_3$) δ: 3.95 (2H, s), 5.03 (2H, s), 6.81-6.92 (2H, m), 6.96-7.36 (11H, m)

(3) Synthesis of 1-[4-(2-Benzyloxybenzyl)phenyl]cyclo-pentanol

In a nitrogen stream, an n-butyllithium hexane solution (1.59 M, 2.94 mL) was added dropwise to a solution of 1-benzyloxy-2-(4-bromobenzyl)benzene (1.5 g, 4.25 mmol) in THF (16.5 mL) at −78° C. and the mixture was stirred at the same temperature for 30 minutes. To this mixture, a solution of cyclopentanone (357 mg, 4.25 mmol) in THF (4 mL) was added dropwise at −78° C. The reaction mixture was stirred at the same temperature for 50 minutes and at 0° C. for one hour, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (1.14 g, 75%) as a colorless oil.

$^1$H-NMR (CDCl$_3$) δ: 1.47-2.02 (8H, m), 4.00 (2H, s), 5.03 (2H, s), 6.79-6.89 (2H, m), 7.02-7.36 (11H, m)

(4) Synthesis of 2-(4-Cyclopentylbenzyl)phenol

To a solution of 1-[4-(2-benzyloxybenzyl)phenyl]-cyclopentanol (1.14 g, 3.19 mmol) in methanol (21 mL), a 20% palladium hydroxide catalyst (114 mg) was added, and furthermore 36% HCl (0.255 mL) was added thereto. The mixture was stirred under a hydrogen atmosphere overnight, and then cooled to 0° C., potassium carbonate (425 mg) was added thereto and the mixture was stirred for 20 minutes, and then the catalyst was filtered off. The solvent was distilled under reduced pressure and the obtained residue was purified by silica gel column chromatography [developing solution=ethyl acetate:n-hexane (1:20)] to obtain the title compound (744 mg, 92%) as a white solid.

$^1$H-NMR (CDCl$_3$) δ: 1.44-1.84 (6H, m), 1.93-2.09 (2H, m), 2.84-3.00 (1H, m), 3.95 (2H, s), 4.76 (1H, s), 6.76 (1H, d, J=8.1 Hz), 6.87 (1H, t, J=7.3 Hz), 7.02-7.20 (6H, m)

(5) Synthesis of [2-(4-Cyclopentylbenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-cyclopentylbenzyl)phenol (351 mg, 1.39 mmol) in toluene (3.1 mL) under cooling with ice, and then tetramethylazodicarboxamide (TMAD, 239 mg, 1.39 mmol) was added thereto at the same temperature. The reaction mixture was stirred overnight while gradually raising its temperature to room temperature. The reaction mixture was concentrated under reduced pressure, and the obtained residue was treated with silica gel column chromatography [developing solution=n-hexane:dichloromethane:acetone (12:3:1)] to obtain a crude product (555 mg). The obtained crude product was dissolved in a tetrahydrofuran (0.9 mL)-methanol (1.8 mL) mixed solution, a 20% palladium hydroxide catalyst (12.6 mg) was added thereto and the mixture was stirred under a hydrogen atmosphere for seven hours, and then the catalyst was filtered off. The solbent was distilled under reduced pressure and the obtained residue was purified by preparative TLC [developing solution=methylene chloride:methanol (10:1)] to obtain the title compound (40 mg, 58%).

$^1$H-NMR (CD$_3$OD) δ: 0.79-0.96 (1H, m), 1.44-1.86 (7H, m), 1.93-2.07 (3H, m), 2.84-2.99 (1H, m), 3.12-3.31 (2H, m), 3.37-3.48 (2H, m), 3.62-3.71 (1H, m), 3.86 (1H, d, J=14.8 Hz), 3.98 (1H, d, J=14.8 Hz), 4.08-4.20 (1H, m), 6.83 (1H, t, J=7.3 Hz), 6.93-7.14 (7H, m)

MS (ESI$^+$): 413 [M+H]$^+$

HPLC Retention Time: 14.5 minutes

Example 5

[2-(4-Chlorobenzyl)phenyl]-5a-carba-β-D-glucopyranoside

(1) Synthesis of (2-Benzyloxyphenyl)-(4-chlorophenyl)-methanol

In a nitrogen stream, an n-butyllithium hexane solution (2.44 M, 10.3 mL) was added dropwise to a solution of 1-benzyloxy-2-bromobenzene (6.0 g, 22.8 mmol) in THF (228 mL) at −78° C. and the mixture was stirred at the same temperature for 30 minutes. To this solution, a solution of 4-chlorobenzaldehyde (2.67 g, 19.0 mmol) in THF (76 mL) was added dropwise at −78° C. The reaction mixture was stirred at the same temperature for two hour and further more at 0° C. for one hour. Water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:5)] to obtain the title compound (4.76 g, 77%).

$^1$H-NMR (CDCl$_3$) δ: 2.94 (1H, s), 5.01 (2H, s), 5.99 (1H, s), 6.92-7.00 (22H, m), 7.17-7.41 (11H, m)

(2) Synthesis of 1-Benzyloxy-2-(4-chlorobenzyl)benzene

In a nitrogen stream, triethylsilane (2.8 mL, 17.6 mmol) and a boron trifluoride-diethyl ether complex (1.84 mL, 14.6 mmol) were added to a solution of (2-benzyloxyphenyl)-(4-chlorophenyl)methanol (4.76 g, 14.6 mmol) in acetonitrile (150 mL) at −40° C. and the reaction mixture was stirred at the same temperature for 2 hours and furthermore at 0° C. for one hour. Water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (3.85 g, 85%).

$^1$H-NMR (CDCl$_3$) δ: 3.97 (2H, s), 5.03 (2H, s), 6.87-6.92 (2H, m), 7.08-7.37 (11H, m)

(3) Synthesis of 2-(4-Chlorobenzyl)phenol

In a nitrogen stream, dimethylsulfide (105.1 μL, 2.43 mmol) and a boron trifluoride-diethyl ether complex (51.3 μL, 0.4 mmol) were added to a solution of 1-benzyloxy-2-(4-chlorobenzyl)benzene (50.0 mg, 0.16 mmol) in methylene chloride (2.0 mL) under cooling with ice, and the reaction mixture was stirred for 19 hours while gradually raising its temperature to room temperature. Thereafter water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:5)] to obtain the title compound (33.4 mg, 94%).

$^1$H-NMR (CDCl$_3$) δ: 3.95 (2H, s), 4.60 (1H, s), 6.75-6.78 (1H, m), 6.86-6.92 (1H, m), 7.07-7.27 (6H, m)

(4) Synthesis of [2-(4-Chlorobenzyl)phenyl]-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-chlorobenzyl)phenol (304 mg, 1.55 mmol) in toluene (2 mL) under cooling with ice, and then tetramethylazo-dicarboxamide (TMAD, 239 mg, 1.29 mmol) was added thereto at the same temperature. The reaction mixture was stirred for 20 hours while gradually raising its temperature to room temperature. The reaction mixture was concentrated under reduced pressure, and the obtained residue was treated with silica gel column chromatography [developing solution=ethyl acetate:n-hexane (1:10)]. The obtained crude product was dissolved in methylene chloride (8 mL), and dimethyl sulfide (2.17 mL, 50.2 mmol) and a boron trifluoride-diethyl ether complex (1.08 mL, 8.51 mmol) were added thereto under cooling with ice. The reaction mixture was stirred for 25 hours while gradually raising its temperature to room temperature, and then water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=methylene chloride:methanol (10:1)] to obtain the title compound (122.6 mg, 35%).

$^1$H-NMR (CD$_3$OD) δ: 0.95 (1H, dd, J=13.2, 11.1 Hz), 1.53 (1H, m), 2.00-2.09 (1H, m), 3.20 (1H, d, J=8.7 Hz), 3.25 (1H, d, J=5.1 Hz), 3.43-3.51 (2H, m), 3.68-3.71 (1H, dd, J=3.9, 3.9 Hz), 3.91 (1H, d, J=14.7 Hz), 3.99 (1H, d, J=15 Hz), 4.15-4.23 (1H, m), 6.85 (1H, t, J=7.5 Hz), 7.03 (1H, d, J=9.0 Hz), 7.08-7.23 (6H, m)

MS (ESI$^+$): 379 [M+H]$^+$

HPLC Retention Time: 11.7 minutes

Example 6

(2-Benzylphenyl)-5a-carba-β-D-glucopyranoside (1) Synthesis of 2-Benzylphenol

To a solution of 2-(4-chlorobenzyl)phenol (618.5 mg, 2.83 mmol) in methanol (20 mL), a 20% palladium hydroxide catalyst (240 mg) was added. The mixture was stirred under a hydrogen atmosphere for three days, and then the catalyst was filtered off. The solvent was distilled under reduced pressure and the obtained residue was purified by silica gel column chromatography [developing solution=ethyl acetate:n-hexane (1:4)] to obtain the title compound (348.4 mg, 67%).

$^1$H-NMR (CDCl$_3$) δ: 3.99 (2H, s), 4.65 (1H, s), 6.79 (1H, d, J=8.1 Hz), 6.89 (1H, t, J=7.5 Hz), 7.09-7.31 (6H, m)

(2) Synthesis of (2-Benzylphenyl)-5a-carba-β-D-gluco-pyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-benzyl-phenol (256.5 mg, 1.39 mmol) in toluene (2 mL) under cooling with ice, and then tetramethylazodi-carboxamide (TMAD, 239 mg, 1.39 mmol) was added thereto at the same temperature. The reaction mixture was stirred for 21 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:1) mixed solution (14 mL) and a 20% palladium hydroxide catalyst (118.8 mg) was added thereto and the mixture was stirred under a hydrogen atmosphere for 15 hours, and then the catalyst was filtered off. The solvent was distilled under reduced pressure and the obtained residue was purified by silica gel column chromatography [developing solution=methylene chloride: methanol (10:1)] to obtain the title compound (84 mg, 26%).

$^1$H-NMR (CD$_3$OD) δ: 0.95 (1H, dd, J=12.0, 11.7 Hz), 1.49-1.59 (1H, m), 2.03-2.09 (1H, m), 3.20 (1H, d, J=9.0 Hz), 3.25 (1H, d, J=5.7 Hz), 3.34 (4H, s), 3.44-3.50 (2H, m), 3.68 (1H, dd, J=3.9, 4.2 Hz), 3.94 (1H, d, J=15 Hz), 4.0 (1H, d, J=15 Hz), 4.13-4.22 (1H, m), 6.84 (1H, t, J=6.3 Hz), 7.03 (1H, d, J=6.3 Hz), 7.06-7.24 (7H, m)

MS (ESI$^+$): 345 [M+H]$^+$

HPLC Retention Time: 10.6 minutes

Example 7

[2-(4-Isopropylbenzyl)phenyl]-5a-carba-β-D-gluco-pyranoside (1) Synthesis of (2-Benzyloxyphenyl)-(4-isopropyl-phenyl)methanol In a nitrogen stream, an n-butyllithium hexane solution (2.44 M, 5.14 mL) was added dropwise to a solution of 1-benzyloxy-2-bromobenzene (3.0 g, 11.4 mmol) in THF (114 mL) at −78° C. and the reaction mixture was stirred at the same temperature for 30 minutes. To this solution, a solution of 4-isopropylbenzaldehyde (1.41 g, 9.49 mmol) in THF (38 mL) was added dropwise at −78° C. The reaction mixture was stirred at the same temperature for one hour and furthermore at 0° C. for one hour. Water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.63 g, 84%).

$^1$H-NMR (CDCl$_3$) δ: 1.26 (6H, d, J=7.8 Hz), 2.84-2.94 (1H, m), 5.02 (2H, s), 6.02 (1H, s), 6.90-7.00 (2H, m), 7.15-7.34 (11H, m)

(2) Synthesis of 2-(4-Isopropylbenzyl)phenol

To a solution of (2-benzyloxyphenyl)-(4-isopropylphenyl) methanol (2.63 g, 7.92 mmol) in methanol (50 mL), a 20% palladium hydroxide catalyst (263 mg) was added and furthermore 2N—HCl (0.4 mL) was added thereto, and the mixture solution was stirred under a hydrogen atmosphere for 15 hours, and then the catalyst was filtered off. The solvent was distilled under reduced pressure and the obtained residue was purified by silica gel column chromatography [developing solution=ethyl acetate:n-hexane (1:4)] to obtain the title compound (1.31 g, 73%).

$^1$H-NMR (CDCl$_3$) δ: 1.24 (6H, d, J=7.8 Hz), 2.82-2.92 (1H, m), 3.96 (2H, s), 4.67 (1H, s), 6.79 (1H, d, J=9.0 Hz), 6.88 (1H, t, J=8.4 Hz), 7.10-7.15 (6H, m)

(3) Synthesis of [2-(4-Isopropylbenzyl)phenyl-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-isopropylbenzyl)phenol (315.1 mg, 1.39 mmol) in toluene (2 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:1) mixed solution (14 mL) and a 20% palladium hydroxide catalyst (127.8 mg) was added thereto and the mixture was stirred under a hydrogen atmosphere for 15 hours, and then the catalyst was filtered off. The solvent was distilled under reduced pressure and the obtained residue was purified by silica gel column chromatography [developing solution=methylene chloride:methanol (10:1)] to obtain the title compound (97.1 mg, 27%).

$^1$H-NMR (CD$_3$OD) δ: 0.94 (1H, dd, J=12.9, 12.0 Hz), 1.22 (6H, d, J=6.9 Hz), 1.48-1.58 (1H, m), 2.02-2.09 (1H, dt, J=3.9, 4.2 Hz), 2.78-2.87 (1H, m), 3.12-3.24 (2H, m), 3.43-3.49 (2H, m), 3.68 (1H, dd, J=6.6, 4.2 Hz), 3.89 (1H, d, J=14.4 Hz), 4.01 (1H, d, J=14.7 Hz), 4.13-4.21 (1H, m), 6.84 (1H, t, J=6.3 Hz), 7.02 (1H, d, J=6.3 Hz), 7.06-7.15 (6H, m)

MS (ESI$^+$): 387 [M+H]$^+$

HPLC Retention Time: 13.1 minutes

Example 8

[2-(4-Cyclopropylbenzyl)phenyl]-5a-carba-β-D-glucopyranoside

(1) Synthesis of (2-Benzyloxyphenyl)-(4-cyclopropyl-phenyl)methanol

In a nitrogen stream, an n-butyllithium hexane solution (2.6 M, 3.5 mL) was added dropwise to a solution of 1-benzyloxy-2-bromobenzene (2.2 g, 8.3 mmol) in THF (83 mL) at −78° C. and the mixture was stirred at the same temperature for 30 minutes. To this solution, a solution of 4-cyclopropylbenzaldehyde (1.1 g, 6.9 mmol) in THF (280 mL) was added dropwise at −78° C. The reaction mixture was stirred at the same temperature for one hour. Water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (1.7 g, 75%).

$^1$H-NMR (CDCl$_3$) δ: 0.65-0.69 (2H, m), 0.92-0.97 (2H, m), 1.86-1.90 (1H, m), 2.88 (1H, d, J=6 Hz), 5.03 (2H, s), 6.03 (1H, d, J=6 Hz), 7.17-7.26 (5H, m), 7.32-7.35 (4H, m)

MS (ESI$^+$): 315 [M+Na]$^+$

(2) Synthesis of 1-Benzyloxyphenyl-2-(4-cyclopropyl-benzyl)benzene

In a nitrogen stream, triethylsilane (0.73 mL, 4.6 mmol) and a boron trifluoride-diethyl ether complex (0.5 mL, 4.0 mmol) were added to a solution of (2-benzyloxyphenyl)-(4-cyclopropylphenyl)methanol (1.3 g, 4.0 mmol) in acetonitrile (7 mL) at −40° C. and the mixture solution was stirred at the same temperature for 1.5 hours and furthermore at 0° C. for 30 minutes. Water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:7)] to obtain the title compound (1.2 g, 95%).

$^1$H-NMR (CDCl$_3$) δ: 0.63-0.67 (2H, m), 0.89-0.94 (2H, m), 1.84-1.87 (1H, m), 3.98 (2H, s), 5.06 (2H, s), 6.87-6.97 (4H, m), 7.08-7.26 (4H, m), 7.31-7.37 (5H, m)

MS (ESI$^+$): 332 [M+H$_2$O]$^+$

(3) Synthesis of 2-(4-Cyclopropylbenzyl)phenol

In a nitrogen stream, dimethyl sulfide (2.2 mL, 51.7 mmol) and a boron trifluoride-diethyl ether complex (1.1 mL, 8.8 mmol) were added to a solution of 1-benzyloxy-2-(4-cyclopropylbenzyl)benzene (1.1 g, 3.5 mmol) in methylene chloride (24 mL) under cooling with ice, and the reaction mixture was stirred for 23 hours while gradually raising its temperature to room temperature. Water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:4)] to obtain the title compound (620.7 mg, 79%).

$^1$H-NMR (CDCl$_3$) δ: 0.65-0.67 (2H, m), 0.90-0.94 (2H, m), 1.85-1.86 (1H, m), 3.95 (2H, s), 4.90 (1H, s), 6.79 (1H, d, J=8.1 Hz), 6.88 (1H, t, J=7.7 Hz), 7.11 (2H, d, J=8.1 Hz), 7.20 (4H, d, J=7.7 Hz)

MS (ESI$^+$): 247 [M+Na]$^+$ (4) Synthesis of [2-(4-Cyclopropylbenzyl)phenyl]-5a-carba-β-D-glucopyranoside In a nitrogen stream, 2,3,4,6-tetra-O-benzyl-5a-carba-α-D-glucopyranose (557 mg, 1.03 mmol) and tributyl-phosphine (0.37 mL, 1.55 mmol) were added to a solution of 2-(4-cyclopropylbenzyl)phenol (348 mg, 1.55 mmol) in toluene (3.5 mL) under cooling with ice, and then tetramethylazodicarboxamide (TMAD, 267 mg, 1.55 mmol) was added thereto at the same temperature. The reaction mixture was stirred for 15 hours while gradually raising its temperature to room temperature. The reaction mixture was concentrated under reduced pressure, and the obtained residue was treated with silica gel column chromatography [developing solution=ethyl acetate:n-hexane (1:10)]. The obtained crude product was dissolved in methylene chloride (3.5 mL), and dimethyl sulfide (1.3 mL, 30.3 mmol) and a boron trifluoride-diethyl ether complex (0.65 mL, 5.1 mmol) were added thereto. The reaction mixture was stirred for 14 hours while gradually raising its temperature to room temperature, and then water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=methylene chloride:methanol (9:1)] to obtain the title compound (97.8 mg, 25%).

$^1$H-NMR (CD$_3$OD) δ: 0.57-0.61 (2H, m), 0.81-0.95 (3H, m), 1.50 (1H, s), 1.79-1.85 (1H, m), 1.99-2.03 (1H, m), 3.15-3.33 (2H, m), 3.42-3.48 (2H, m), 3.66-3.72 (1H, m), 3.81-3.99 (2H, q, J=14.7 Hz), 4.41-4.85 (1H, m), 6.80-7.15 (8H, m)

MS (ESI$^+$): 407 [M+Na]$^+$
HPLC Retention Time: 12.3 minutes

Example 9

[2-(4-n-Propylbenzyl)phenyl]-5a-carba-β-D-glucopyranoside (1) Synthesis of [2-(4-n-Propylbenzyl)phenyl]-5a-carba-β-D-glucopyranoside 1-Benzyloxy-2-(4-cyclopropylenzyl)benzene (640.8 mg, 2.0 mmol) as synthesized in Example 8 was dissolved in 2,2-dimethylpropanol (12 mL), a 20% palladium hydroxide catalyst (64 mg) was added thereto and the mixture was stirred for two hours under a hydrogen atmosphere, and then the catalyst was filtered off. The solvent was distilled under reduced pressure, and the obtained residue was treated by silica gel column chromatography [developing solution=ethyl acetate:n-hexane (1:4)]. To a solution of the obtained crude product (348 mg) in toluene (3.5 mL), 2,3,4,6-tetra-O-benzyl-5a-carba-α-D-glucopyranose (557 mg, 1.03 mmol) and tributylphosphine (0.39 mL, 1.55 mmol) were added under cooling with ice, and then tetramethylazodicarboxamide (TMAD, 267 mg, 1.55 mmol) was added thereto at the same temperature. The reaction mixture was stirred for 20 hours while gradually raising its temperature to room temperature. The reaction mixture was concentrated under reduced pressure, and the obtained residue was treated with silica gel column chromatography [developing solution=ethyl acetate:n-hexane (1:5)]. The obtained crude product was dissolved in 2,2-dimethylpropanol (15 mL), a 20% palladium hydroxide catalyst (159 mg) was added thereto and the mixture was stirred under a hydrogen atmosphere for 17 hours, and the catalyst was filtered off. The solvent was distilled under reduced pressure, and the obtained residue was purified by silica gel column chromatography [developing solution=methylene chloride:methanol (9:1)] to obtain the title compound (164.4 mg).

$^1$H-NMR (CD$_3$OD) δ: 0.88-0.94 (4H, m), 1.48-1.63 (3H, m), 2.05-2.09 (1H, m), 2.52 (2H, t, J=7.7 Hz), 3.13-3.30 (2H, m), 3.46 (2H, m), 3.70 (1H, m), 3.87 (1H, d, J=15 Hz), 3.98 (1H, d, J=15 Hz), 4.60-4.88 (1H, m), 6.84 (1H, t, J=7.3 Hz), 7.00-7.16 (7H, m)

MS (ESI$^+$): 387 [M+H]$^+$
HPLC Retention Time: 13.3 minutes

Example 10

[2-(4-Trifluoromethylbenzyl)phenyl]-5a-carba-β-D-gluco-pyranoside (1) Synthesis of (2-Benzyloxyphenyl)-(4-trifluoromethyl-phenyl)methanol In a nitrogen stream, an n-butyllithium hexane solution (2.44 M, 4.0 mL) was added dropwise to a solution of 1-benzyloxy-2-bromobenzene (2.6 g, 9.9 mmol) in THF (100 mL) at −78° C. and the reaction mixture was stirred at the same temperature for 30 minutes. To this solution, 4-trifluoromethylbenzaldehyde (1.6 g, 9.0 mmol) was added dropwise at −78° C. The reaction mixture was stirred at the same temperature for two hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.6 g, 82%).

$^1$H-NMR (CDCl$_3$) δ: 3.01 (1H, d, J=6.3 Hz), 5.02 (2H, dd, J=11.4, 4.8 Hz), 6.05 (1H, d, J=6.3 Hz), 6.94-7.02 (2H, m), 6.96-7.16 (2H, m), 7.24-7.33 (5H, m), 7.44 (2H, d, J=7.1 Hz), 7.53 (2H, d, J=8.7 Hz)

MS (ESI$^+$): 359 [M+H]$^+$ (2) Synthesis of 2-(4-Trifluoromethylbenzyl)phenol

To a solution of (2-benzyloxyphenyl)-(4-trifluoromethylphenyl)-methanol (2.46 g, 6.85 mmol) in methanol (68.5 mL), a 20% palladium hydroxide catalyst (246 mg) was added and furthermore 36% HCl (0.59 mL) was added thereto, and the mixture solution was stirred under a hydrogen atmosphere for 3.5 hours, and then the catalyst was filtered off. The solvent was distilled under reduced pressure and the obtained residue was purified by silica gel column chromatography [developing solution=ethyl acetate:n-hexane (1:8)] to obtain the title compound (1.49 g, 86%).

$^1$H-NMR (CDCl$_3$) δ: 4.03 (2H, s), 4.72 (1H, s), 6.77 (1H, d, J=6.0 Hz), 6.89 (1H, t, J=4.8 Hz), 7.08-7.15 (2H, m), 7.33 (2H, d, J=6.0 Hz), 7.52 (2H, d, J=6.0 Hz)

MS (ESI$^+$): 275 [M+Na]$^+$ (3) Synthesis of [2-(4-Trifluoromethylbenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-trifluoromethylbenzyl)phenol (351 mg, 1.39 mmol) in toluene (3 mL) under cooling with ice, and then tetra-methylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:1) mixed solution (5 mL) and a 20% palladium hydroxide catalyst (20 mg) was added thereto and the mixture was stirred under a hydrogen atmosphere for 2 hours, and then the catalyst was filtered off. The solvent was distilled under reduced pressure and the obtained residue was purified by silica gel column chromatography [developing solution=methylene chloride:methanol (10:1)] to obtain the title compound (74 mg, 19%).

$^1$H-NMR (CD$_3$OD) δ: 0.89 (1H, dd, J=11.7, 12.9 Hz), 1.48-1.61 (1H, m), 2.05 (1H, dt, J=13.2, 4.2 Hz), 3.15-3.34 (2H, m), 3.42-3.49 (2H, m), 3.69 (1H, dd, J=3.9, 10.5 Hz), 3.96-4.15 (2H, dd, J=14.7, 28.2 Hz), 4.17-4.24 (1H, m), 6.87 (1H, dt, J=1.2, 7.5 Hz), 7.02-7.20 (3H, m), 7.38 (2H, d, J=8.1 Hz), 7.51 (2H, d, J=8.4 Hz)

MS (ESI$^+$): 435 [M+Na]$^+$

HPLC Retention Time: 12.3 minutes

Example 11

[2-(4-Methylsulfanylbenzyl)phenyl]-5a-carba-β-D-gluco-pyranoside (1) Synthesis of (2-Benzyloxyphenyl)-(4-methylsulfanyl-phenyl)methanol In a nitrogen stream, an n-butyllithium hexane solution (1.59 M, 6.92 mL) was added dropwise to a solution of 1-benzyloxy-2-bromobenzene (2.89 g, 11.0 mmol) in THF (38 mL) at –78° C. and the mixture solution was stirred at the same temperature for 30 minutes. To this solution, a solution of 4-methylsulfanylbenzaldehyde (1.67 g, 11.0 mmol) in THF (12 mL) was added dropwise at –78° C. The reaction mixture was stirred at the same temperature for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.14 g, 58%).

$^1$H-NMR (CDCl$_3$) δ: 2.47 (3H, s), 2.92 (1H, d, J=6.0 Hz), 5.03 (2H, s), 6.02 (1H, d, J=6.0 Hz), 6.92-7.00 (2H, m), 7.21-7.34 (11H, m)

(2) Synthesis of 1-Benzyloxy-2-(4-methylsulfanyl-benzyl)benzene

In a nitrogen stream, triethylsilane (1.23 mL, 7.72 mmol) and a boron trifluoride-diethyl ether complex (0.88 mL, 5.48 mmol) were added to a solution of (2-benzyloxy-phenyl)-(4-methylsulfanylphenyl)-methanol (2.13 g, 6.3 mmol) in acetonitrile (15 mL) at –40° C. and the mixture solution was stirred at the same temperature for 1.5 hours and further at 0° C. for 30 minutes, and then water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (1.9 g, 95%).

$^1$H-NMR (CDCl$_3$) δ: 2.46 (3H, s), 3.97 (2H, s), 5.05 (2H, s), 6.85-6.95 (2H, m), 7.10-7.35 (11H, m)

(3) Synthesis of 2-(4-Methylsulfanylbenzyl)phenol

In a nitrogen stream, dimethylsulfide (7.25 mL, 138 mmol) and a boron trifluoride-diethyl ether complex (2.1 mL, 8.8 mmol) were added to a solution of 1-benzyloxy-(4-methylsulfanylbenzyl)benzene (1.9 g, 5.9 mmol) in methylene chloride (15 mL) under cooling with ice, and the reaction mixture was stirred for 48 hours while gradually raising its temperature to room temperature. Water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (1.19 g, 91%).

$^1$H-NMR (CDCl$_3$) δ: 2.46 (3H, s), 3.95 (2H, s), 4.65-4.75 (1H, br s), 6.78 (1H, d, J=7.6 Hz), 6.89 (1H, t, J=7.6 Hz), 7.09-7.21 (6H, m)

(4) Synthesis of [2-(4-Methylsulfanylbenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methylsulfanybenzyl)phenol (320 mg, 1.39 mmol) in toluene (2 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in methylene chloride (10 mL), and dimethylsulfide (3.28 mL, 63 mmol) and a boron trifluoride-diethyl ether complex (0.94 mL, 5.9 mmol) were added thereto under cooling with ice. The reaction mixture was stirred for 20 hours while gradually raising its temperature to room temperature, and then water was added under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=methylene chloride:methanol (10:1)] to obtain the title compound (102 mg, 28%).

$^1$H-NMR (CD$_3$OD) δ: 0.80-0.95 (1H, m), 1.45-1.60 (1H, m), 2.00-2.10 (1H, m), 2.42 (3H, s), 3.12-3.33 (2H, m), 3.40-3.50 (2H, m), 3.63-3.70 (1H, m), 3.86 (1H, d, J=15 Hz), 4.00 (1H, d, J=15 Hz), 4.15-4.23 (1H, m), 6.84 (1H, t, J=7.0 Hz), 7.00-7.18 (7H, m)

MS (ESI$^+$): 391 [M+H]$^+$

HPLC Retention Time: 11.6 minutes

Example 12

[3-Fluoro-2-(4-methylbenzyl)phenyl]-5a-carba-β-D-gluco-pyranoside (1) Synthesis of (2-Benzyloxy-6-fluorophenyl)-(4-methoxyphenyl)methanol To a THF solution (50 mL) of 2-benzyloxy-6-fluoro-benzaldehyde (2.25 g, 9.8 mmol) as described in International Publication WO 04/048335, a 4-methoxyphenyl-magnesium bromide THF solution (0.5 M, 21.5 mL) was added dropwise in a nitrogen stream at room temperature. The reaction mixture was stirred at room temperature for 1.5 hours, and then a saturated ammonium chloride aqueous solution was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.82 g, 85%).

$^1$H-NMR (CDCl$_3$) δ: 3.78 (1H, d, J=12 Hz), 3.80 (3H, s), 4.98 (1H, d, J=12 Hz), 5.05 (1H, d, J=12 Hz), 6.20 (1H, d, J=12 Hz), 6.74-6.84 (4H, m), 7.11-7.31 (8H, m)

(2) Synthesis of 3-Fluoro-2-(4-methoxy)phenol

To a solution of (2-benzyloxy-6-fluorophenyl)-(4-methoxyphenyl)methanol (2.54, 7.51 mmol) in methanol (20 ml), a 20% palladium hydroxide catalyst (381 mg) was added and furthermore 2N—HCl (2 mL) was added thereto. The mixture solution was stirred under a hydrogen atmosphere for 24 hours, and then the catalyst was filtered off. The solvent was distilled under reduced pressure, and the obtained residue was purified by silica gel column chromatography [developing solution=ethyl acetate:n-hexane (1:4)] to obtain the title compound (1.48 g, 85%).

$^1$H-NMR (CDCl$_3$) δ: 3.76 (3H, s), 3.96 (2H, s), 4.90 (1H, br s), 6.57 (1H, d, J=8.0 Hz), 6.67 (1H, t, J=8.0 Hz), 6.82 (2H, d, J=9.0 Hz), 7.06 (1H, dd, J=8.0, 8.0 Hz), 7.19 (2H, d, J=9.0 Hz)

(3) Synthesis of [3-Fluoro-2-(4-methoxybenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 3-fluoro-2-(4-methoxybenzyl)phenol (323 mg, 1.39 mmol) in toluene (2 mL) under cooling with ice, and then tetra-methylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:4) mixed solution (5 mL) and a 20% palladium hydroxide catalyst (63 mg) was added thereto. The mixture was stirred under a hydrogen atmosphere for 24 hours, and then the catalyst was filtered off. The solvent was distilled under reduced pressure, and the obtained residue was purified by silica gel column chromatography [developing solution=methylene chloride:methanol (10:1)] to obtain the title compound (86 mg, 24%).

$^1$H-NMR (CD$_3$OD) δ: 0.90-1.05 (1H, m), 1.45-1.60 (1H, m), 2.00-2.10 (1H, m), 3.17-3.35 (2H, m), 3.45-3.52 (2H, m), 3.65-3.70 (1H, m), 3.72 (3H, s), 3.93 (2H, s), 4.15-4.25 (1H, m), 6.67 (1H, t, J=8.0 Hz), 6.76 (2H, d, J=9.0 Hz), 6.86 (1H, d, J=8.0 Hz), 7.09-7.18 (3H, m)

MS (ESI$^-$): 391 [M–H]$^-$

HPLC Retention Time: 10.8 minutes

Example 13

[2-(3-Trifluoromethylbenzyl)phenyl]-5a-carba-β-D-gluco-pyranoside (1) Synthesis of (2-Benzyloxyphenyl)-(3-trifluoromethyl-phenyl)methanol In a nitrogen stream, an n-butyllithium hexane solution (2.7 M, 3.4 mL) was added dropwise to a solution of 1-benzyloxy-2-bromobenzene (2.0 g, 7.6 mmol) in THF (50 mL) at −78° C. and the mixture solution was stirred at the same temperature for 30 minutes. To this solution, 4-trifluoromethylbenzaldehyde (2.0 g, 11.4 mmol) was added dropwise at −78° C. The reaction mixture was stirred at the same temperature for three hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (2.2 g, 80%).

$^1$H-NMR (CDCl$_3$) δ: 3.03 (1H, d, J=6.3 Hz), 4.97-5.07 (2H, m), 6.06 (1H, d, J=6.3 Hz), 6.95-7.03 (2H, m), 7.16-7.20 (2H, m), 7.26 (1H, dd, J=7.7, 2.0 Hz), 7.29-7.36 (4H, m), 7.39 (1H, d, J=7.7 Hz), 7.46-7.55 (2H, m), 7.67 (1H, s)

(2) Synthesis of 2-(3-Trifluoromethylbenzyl)phenol

To a solution of (2-benzyloxyphenyl)-(3-trifluoro-methylphenyl)methanol (3.32 g, 9.3 mmol) in methanol (50 ml), a 20% palladium hydroxide catalyst (166 mg) was added and furthermore 36% HCl (0.2 mL) was added thereto. The mixture solution was stirred under a hydrogen atmosphere for 72 hours, and then the catalyst was filtered off. The solvent was distilled under reduced pressure, and the obtained residue was purified by silica gel column chromatography [developing solution=ethyl acetate:n-hexane (1:4)] to obtain the title compound (2.26 g, 96%).

$^1$H-NMR (CDCl$_3$) δ: 4.04 (2H, s), 4.90 (1H, d, J=2.0 Hz), 6.76 (1H, d, J=8.1 Hz), 6.86-6.90 (1H, m), 7.09-7.16 (2H, m), 7.34-7.46 (3H, m), 7.50 (1H, s).

(3) Synthesis of [2-(3-Trifluoromethylbenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(3-tri-fluoromethylbenzyl)phenol (351 mg, 1.39 mmol) in toluene (3 mL) under cooling with ice, and then tetra-methylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (45 mg) was added thereto, and the mixture was stirred under a hydrogen atmosphere for 15 hours, and then the catalyst was filtered off. The solvent was distilled under reduced pressure and the obtained residue was purified by silica gel column chromatography [developing solution=methylene chloride:methanol (10:1)] to obtain the title compound (56 mg, 14%).

$^1$H-NMR (CD$_3$OD) δ: 0.88-1.02 (1H, m), 1.52-1.68 (1H, m), 2.10 (1H, dt, J=13.4, 3.9 Hz), 3.20-3.38 (2H, m), 3.45-3.55 (2H, m), 3.74 (1H, dd, J=4.1, 10.8 Hz), 3.99 (1H, d, J=14.7 Hz), 4.18 (1H, d, J=15.4 Hz), 4.20-4.32 (1H, m), 6.89-6.95 (1H, m), 7.08 (1H, d, J=7.7 Hz), 7.16-7.26 (2H, m), 7.42-7.58 (4H, m)

MS (ESI$^+$): 413 [M+H]$^+$

HPLC Retention Time: 12.0 minutes

Example 14

[2-(4-Methoxybenzyl)-4-methylphenyl]-5a-carba-β-D-gluco-pyranoside (1) Synthesis of 1-Benzyloxy-2-bromo-4-methylbenzene To a solution of 2-bromo-4-methylphenol (1.5 g, 8.0 mmol) in N,N-dimethylformamide (40 mL), potassium carbonate (1.32 g, 9.6 mmol) was added and furthermore benzyl bromide (1.05 mL, 8.8 mmol) was added thereto. The mixture solution was stirred at room temperature for 12 hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (1.72 g, 77%).

$^1$H-NMR (CDCl$_3$) δ: 2.30 (3H, s), 5.12 (2H, s), 6.82 (1H, d, J=8.4 Hz), 6.99-7.03 (1H, m), 7.28-7.41 (4H, m), 7.45-7.48 (2H, m)

(2) Synthesis of 2-Benzyloxy-5-methylphenyl)-(4-methoxyphenyl)methanol

In a nitrogen stream, an n-butyllithium hexane solution (2.7 M, 2.75 mL) was added dropwise to a solution of 1-benzyloxy-2-bromo-4-methylbenzene (1.72 g, 6.2 mmol) in THF (50 mL) at −78° C. and the mixture solution was stirred at the same temperature for 30 minutes. To this solution, 4-methoxybenzaldehyde (1.27 g, 9.3 mmol) was added dropwise at −78° C. The reaction mixture was stirred at the same temperature for two hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (1.46 g, 70%).

$^1$H-NMR (CDCl$_3$) δ: 2.28 (3H, s), 2.88 (1H, d, J=9.2 Hz), 3.80 (3H, s), 5.00 (2H, s), 5.99 (1H, d, J=5.6 Hz), 6.80-6.88 (3H, m), 7.00-7.05 (1H, m), 7.13 (1H, d, J=1.8 Hz), 7.19-7.34 (7H, m)

(3) Synthesis of 2-(4-Methoxybenzyl)-4-methylphenol

To a solution of (2-benzyloxy-5-methoxyphenyl)-(4-methoxyphenyl)-methanol (1.46 g, 4.3 mmol) in methanol (20 ml), a 20% palladium hydroxide catalyst (73 mg) was added and furthermore 36% HCl (0.1 mL) was added thereto. The mixture was stirred under a hydrogen atmosphere for 72 hours, and then the catalyst was filtered off. The solvent was distilled under reduced pressure, and the obtained residue was purified by silica gel column chromatography [developing solution=ethyl acetate:n-hexane (1:4)] to obtain the title compound (0.8 g, 80%).

$^1$H-NMR (CDCl$_3$) δ: 2.24 (3H, s), 3.77 (3H, s), 3.89 (2H, s), 4.55-4.56 (1H, m), 6.65-6.69 (1H, m), 6.80-6.86 (2H, m), 6.88-6.94 (2H, m), 7.11-7.16 (2H, m)

(4) Synthesis of [2-(4-Methoxybenzyl)-4-methylphenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methoxybenzyl)-4-methylphenol (317 mg, 1.39 mmol) in toluene (3 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (44 mg) was added thereto, and the mixture was stirred under a hydrogen atmosphere for 4 hours, and then the catalyst was filtered off. The solvent was distilled under reduced pressure and the obtained residue was purified by silica gel column chromatography [developing solution=methylene chloride:methanol (10:1)] to obtain the title compound (88 mg, 24%).

$^1$H-NMR (CD$_3$OD) δ: 0.88-1.02 (1H, m), 1.42-1.60 (1H, m), 2.04 (1H, dt, J=13.4, 4.0 Hz), 2.21 (3H, s), 3.17-3.32 (2H, m), 3.43-3.51 (2H, m), 3.70 (1H, dd, J=4.1, 10.7 Hz), 3.74 (3H, s), 3.82 (1H, d, J=14.7 Hz), 3.92 (1H, d, J=14.7 Hz), 4.06-4.16 (1H, m), 6.77-6.82 (2H, m), 6.86-6.96 (3H, m), 7.06-7.15 (2H, m)

MS (ESI$^+$): 389 [M+H]$^+$

HPLC Retention Time: 11.2 minutes

Example 15

[2-(3-Methoxybenzyl)phenyl]-5a-carba-β-D-glucopyranoside (1) Synthesis of (2-Benzyloxyphenyl)-(3-methoxyphenyl)-methanol To a solution of 2-benzyloxybenzaldehyde (3.0 g, 14.1 mmol) in THF (50 mL), a solution of 4-methoxyphenylmagnesium bromide in THF (1.0 M, 17.0 mL) was added dropwise in a nitrogen stream under cooling with ice. The mixture was stirred at room temperature for one hour, and then a saturated ammonium chloride aqueous solution was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (4.92 g, 100%).

¹H-NMR (CDCl₃) δ: 2.97 (1H, dd, J=1.1, 6.0 Hz), 3.73 (3H, s), 4.98-5.10 (2H, m), 6.03 (1H, d, J=6.0 Hz), 6.77-6.82 (1H, m), 6.88-7.01 (4H, m), 7.19-7.35 (9H, m)

(2) Synthesis of 2-(3-Methoxybenzyl)phenol

To a solution of (2-benzyloxyphenyl)-(3-methoxyphenyl)methanol (1.68 g, 5.24 mmol) in methanol (50 ml), a 20% palladium hydroxide catalyst (168 mg) was added and furthermore 36% HCl (0.2 mL) was added thereto. The mixture was stirred under a hydrogen atmosphere for 24 hours, and then the catalyst was filtered off. The solvent was distilled under reduced pressure, and the obtained residue was purified by silica gel column chromatography [developing solution=ethyl acetate:n-hexane (1:4)] to obtain the title compound (1.29 g, 100%).
¹H-NMR (CDCl₃) δ: 3.76 (3H, s), 3.97 (2H, s), 4.69 (1H, s), 6.73-6.92 (5H, m), 7.10-7.23 (3H, m)

(3) Synthesis of [2-(3-Methoxybenzyl)phenyl]-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(3-methoxybenzyl)phenol (298 mg, 1.39 mmol) in toluene (3 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (55 mg) was added thereto, and the mixture was stirred under a hydrogen atmosphere for four hours, and then the catalyst was filtered off. The solvent was distilled under reduced pressure and the obtained residue was purified by silica gel column chromatography [developing solution=methylene chloride:methanol (10:1)] to obtain the title compound (111 mg, 32%).
¹H-NMR (CD₃OD) δ: 0.97-1.11 (1H, m), 1.52-1.68 (1H, m), 2.12 (1H, dt, J=13.4, 4.0 Hz), 3.22-3.39 (2H, m), 3.49-3.56 (2H, m), 3.72-3.78 (1H, m), 3.78 (3H, s), 3.92 (1H, d, J=14.8 Hz), 4.05 (1H, d, J=14.8 Hz), 4.18-4.27 (1H, m), 6.72-6.92 (4H, m), 7.0577.22 (4H, m)
MS (ESI⁺): 375 [M+H]⁺
HPLC Retention Time: 10.6 minutes Example 16

[2-(4-Methoxybenzyl)-4-methoxyphenyl]-5a-carba-β-D-gluco-pyranoside (1) Synthesis of 2-Benzyloxy-5-methoxybenzaldehyde To a solution of 2-hydroxy-5-methoxybenzaldehyde (3.0 g, 19.7 mmol) in N,N-dimethylformamide (50 mL), potassium carbonate (3.27 g, 23.6 mmol) was added and furthermore benzyl bromide (2.6 mL, 21.7 mmol) was added thereto. The reaction mixture was stirred at room temperature for 24 hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (4.8 g, 100%).
¹H-NMR (CDCl₃) δ: 3.80 (3H, s), 5.15 (2H, s), 6.99 (1H, d, J=9.0 Hz), 7.11 (1H, dd, J=3.4, 9.1 Hz), 7.32-7.44 (6H, m), 10.50 (1H, s)

(2) Synthesis of (2-Benzyloxy-5-methoxyphenyl)-(4-methoxyphenyl)methanol

In a nitrogen stream, to a solution of 2-benzyloxy-5-methoxy-benzaldehyde (2.0 g, 8.25 mmol) in THF (50 mL), a solution of 4-methoxyphenylmagnesium bromide in THF (0.5 M, 19.8 mL) was added dropwise under cooling with ice. The mixture solution was stirred at room temperature for one hour, and then a saturated ammonium chloride aqueous solution was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:1)] to obtain the title compound (2.9 g, 100%).
¹H-NMR (CDCl₃) δ: 2.85 (1H, d, J=5.4 Hz), 3.76 (3H, s), 3.79 (3H, s), 4.96 (2H, s), 5.99 (1H, d, J=5.4 Hz), 6.74 (1H, dd, J=2.8, 9.0 Hz), 6.81-6.87 (3H, m), 6.94 (1H, d, J=4.1 Hz), 7.19-7.36 (7H, m)

(3) Synthesis of 2-(4-Methoxybenzyl)-4-methoxyphenol

To a solution of (2-benzyloxy-5-methoxyphenyl)-(4-methoxyphenyl)methanol (2.54 g, 7.25 mmol) in methanol (50 ml), a 20% palladium hydroxide catalyst (250 mg) was added and furthermore 36% HCl (0.25 mL) was added thereto. The mixture was stirred under a hydrogen atmosphere for 14 hours, and then the catalyst was filtered off. The solvent was distilled under reduced pressure, and the obtained residue was purified by silica gel column chromatography [developing solution=ethyl acetate:n-hexane (1:4)] to obtain the title compound (1.62 g, 91%).
¹H-NMR (CDCl₃) δ: 3.74 (3H, s), 3.78 (3H, s), 3.90 (2H, s), 4.41 (1H, br s), 6.64-6.86 (5H, m), 7.11-7.16 (2H, m)

(4) Synthesis of [2-(4-Methoxybenzyl)-4-methoxyphenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methoxybenzyl)-4-methoxyphenol (340 mg, 1.39 mmol) in toluene (3 mL) under cooling with ice, and then tetra-methylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (40 mg) was added thereto, and the mixture was stirred under a hydrogen atmosphere for 6 hours, and then the catalyst was filtered off. The solvent was distilled under reduced pressure and the obtained residue was purified by silica gel column chromatography [developing solution=methylene chloride:methanol (10:1)] to obtain the title compound (128 mg, 34%).

$^1$H-NMR (CD$_3$OD) δ: 0.94-1.08 (1H, m), 1.45-1.62 (1H, m), 2.06 (1H, dt, J=13.0, 4.0 Hz), 3.20-3.34 (2H, m), 3.46-3.56 (2H, m), 3.70-3.80 (1H, m), 3.73 (3H, s), 3.79 (3H, s), 3.88 (1H, d, J=14.8 Hz), 3.96 (1H, d, J=14.8 Hz), 4.04-4.14 (1H, m), 6.67 (1H, d, J=3.1 Hz), 6.74 (1H, dd, J=3.1, 8.7 Hz), 6.80-6.88 (2H, m), 7.00 (1H, d, J=8.7 Hz), 7.12-7.18 (2H, m)

MS (ESI$^+$): 405 [M+H]$^+$

HPLC Retention Time: 10.2 minutes

Example 17

[2-(4-Methoxybenzyl)-6-methylphenyl]-5a-carba-β-D-gluco-pyranoside (1) Synthesis of 2-Benzyloxy-3-methylbenzaldehyde To a solution of 2-hydroxy-3-methylbenzaldehyde (3.0 g, 22.07 mmol) in N,N-dimethylformamide (50 mL), potassium carbonate (3.65 g, 26.4 mmol) was added and furthermore benzyl bromide (2.9 mL, 24.2 mmol) was added thereto. The mixture was stirred at room temperature for 26 hours, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (5.0 g, 100%).

$^1$H-NMR (CDCl$_3$) δ: 2.36 (3H, s), 4.97 (2H, s), 7.16 (1H, t, J=7.4 Hz), 7.36-7.49 (6H, m), 7.68 (1H, dd, J=1.4, 7.8 Hz), 10.26 (1H, d, J=0.5 Hz)

(2) Synthesis of (2-Benzyloxy-3-methylphenyl)-(4-methoxyphenyl)methanol

In a nitrogen stream, to a solution of 2-benzyloxy-3-methyl-benzaldehyde (1.87 g, 8.25 mmol) in THF (50 mL), a solution of 4-methoxyphenylmagnesium bromide in THF (0.5 M, 19.8 mL) was added dropwise under cooling with ice. The mixture was stirred at room temperature for one hour, and then a saturated ammonium chloride aqueous solution was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:5)] to obtain the title compound (2.76 g, 100%).

$^1$H-NMR (CDCl$_3$) δ: 2.36 (3H, s), 2.63 (1H, d, J=5.0 Hz), 3.78 (3H, s), 4.64-4.73 (2H, m), 6.02 (1H, d, J=5.0 Hz), 6.77-6.86 (2H, m), 7.02-7.08 (1H, m), 7.15-7.21 (2H, m), 7.22-7.28 (2H, m), 7.34-7.40 (5H, m)

(3) Synthesis of 2-(4-Methoxybenzyl)-6-methylphenol

To a solution of (2-benzyloxy-3-methylphenyl)-(4-methoxyphenyl)-methanol (2.76 g, 8.25 mmol) in methanol (30 ml), a 20% palladium hydroxide catalyst (276 mg) was added and furthermore concentrated hydrochloric acid (0.27 mL) was added thereto. The mixture was stirred under a hydrogen atmosphere for 18 hours, and then the catalyst was filtered off. The solvent was distilled under reduced pressure, and the obtained residue was purified by silica gel column chromatography [developing solution=ethyl acetate:n-hexane (1:4)] to obtain the title compound (1.75 g, 93%).

$^1$H-NMR (CDCl$_3$) δ: 2.22 (3H, s), 3.78 (3H, s), 3.93 (2H, s), 4.63 (1H, br s), 6.77-6.86 (3H, m), 6.96-7.05 (2H, m), 7.11-7.17 (2H, m)

(4) Synthesis of [2-(4-Methoxybenzyl)-6-methylphenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methoxybenzyl)-6-methylphenol (318 mg, 1.39 mmol) in toluene (3 mL) under cooling with ice, and then tetramethylazodicarboxamide (TMAD, 239 mg, 1.39 mmol) was added thereto at the same temperature. The reaction mixture was stirred for 48 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (72 mg) was added thereto, and the mixture was stirred under a hydrogen atmosphere for 4 hours, and then the catalyst was filtered off. The solvent was distilled under reduced pressure and the obtained residue was purified by silica gel column chromatography [developing solution=methylene chloride:methanol (10:1)] to obtain the title compound (180 mg, 50%).

$^1$H-NMR (CD$_3$OD) δ: 1.16-1.35 (2H, m), 1.74-1.88 (1H, m), 2.33 (3H, s), 3.16-3.26 (2H, m), 3.42-3.52 (1H, m), 3.54-3.68 (2H, m), 3.74 (3H, s), 3.92-4.02 (2H, m), 4.08 (1H, d, J=15.3 Hz), 6.77-6.83 (2H, m), 6.86-6.91 (2H, m), 6.96-7.04 (1H, m), 7.05-7.12 (2H, m)

MS (ESI$^+$): 411 [M+Na]$^+$

HPLC Retention Time: 10.8 minutes

Example 18

[2-(4-Methoxybenzyl)-4-fluorophenyl]-5a-carba-β-D-gluco-pyranoside (1) Synthesis of (2-Benzyloxy-5-fluorophenyl)-(4-methoxyphenyl)methanol In a nitrogen stream, an n-butyllithium hexane solution (2.44 M, 2.4 mL) was added dropwise to a solution of 1-benzyloxy-2-bromo-4-fluorobenzene (1.5 g, 5.33 mmol) in THF (60 mL) at −78° C. and the mixture was stirred at the same temperature for 30 minutes. To this solution, a solution of 4-methoxybenzaldehyde (0.6 g, 4.42 mmol) in THF (20 mL) was added dropwise at −78° C. The reaction mixture was stirred at the same temperature for one hour, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (0.98 g, 66%).

$^1$H-NMR (CDCl$_3$) δ: 2.66 (1H, dd, J=0.8, 4.9 Hz), 3.80 (3H, s), 4.98 (2H, s), 6.01 (1H, d, J=4.9 Hz), 6.83-6.90 (4H, m), 7.14 (1H, dd, J=3.0, 9.0 Hz), 7.20-7.34 (7H, m)

(2) Synthesis of 4-Fluoro-2-(4-methoxy-benzyl)phenol

To a solution of (2-benzyloxy-5-fluorophenyl)-(4-methoxyphenyl)-methanol (0.98 g, 2.90 mmol) in methanol (18.6 mL), a 20% palladium hydroxide catalyst (98 mg) was added and furthermore 2N—HCl (1 mL) was added thereto. The mixture was stirred under a hydrogen atmosphere for 15 hours, and then the catalyst was filtered off. The solvent was distilled under reduced pressure, and the obtained residue was purified by silica gel column chromatography [developing solution=ethyl acetate:n-hexane (1:6)] to obtain the title compound (0.55 g, 82%).

$^1$H-NMR (CDCl$_3$) δ: 3.78 (3H, s), 3.89 (2H, s), 4.65 (1H, br s), 6.68-6.73 (1H, m), 6.77-6.87 (4H, m), 7.11-7.12 (2H, m)

(3) Synthesis of [2-(4-Methoxybenzyl)-4-fluorophenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methoxybenzyl)-4-fluorophenol (323 mg, 1.39 mmol) in toluene (3 mL) under cooling with ice, and then tetramethylazodicarboxamide (TMAD, 239 mg, 1.39 mmol) was added thereto at the same temperature. The reaction mixture was stirred for 48 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (22 mg) was added thereto, and the mixture was stirred under a hydrogen atmosphere for four hours, and then the catalyst was filtered off. The solvent was distilled under reduced pressure and the obtained residue was purified by silica gel column chromatography [developing solution=methylene chloride:methanol (10:1)] to obtain the title compound (103 mg, 29%).

$^1$H-NMR (CD$_3$OD) δ: 0.99-1.13 (1H, m), 1.50-1.65 (1H, m), 2.08 (1H, dt, J=13.4, 4.0 Hz), 3.22-3.35 (2H, m), 3.50-3.57 (2H, m), 3.75 (1H, dd, J=4.0, 10.7 Hz), 3.79 (3H, s), 3.87-4.02 (2H, m), 4.11-4.21 (1H, m), 6.79 (1H, dd, J=3.1, 9.4 Hz), 6.83-6.92 (3H, m), 7.06 (1H, dd, J=4.7, 8.9 Hz), 7.12-7.20 (2H, m)

MS (ESI$^+$): 415 [M+Na]$^+$
HPLC Retention Time: 10.9 minutes

Example 19

[2-(3-Fluorobenzyl)phenyl]-5a-carba-β-D-glucopyranoside

(1) Synthesis of (2-Benzyloxyphenyl)-(3-fluorophenyl)-methanol

In a nitrogen stream, an n-butyllithium hexane solution (2.44 M, 5.65 mL) was added dropwise to a solution of 1-benzyloxy-2-bromobenzene (3.3 g, 12.5 mmol) in THF (40 mL) at −78° C. and the mixture solution was stirred at the same temperature for 30 minutes. To this mixture, a solution of 3-fluorobenzaldehyde (1.40 g, 11.3 mmol) in THF (5 mL) was added dropwise at −78° C. The reaction mixture was stirred at the same temperature for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (2.26 g, 65%).

$^1$H-NMR (CDCl$_3$) δ: 3.00 (1H, d, J=6.3 Hz), 5.57 (1H, d, J=11.5 Hz), 5.60 (1H, d, J=11.5 Hz), 6.01 (1H, d, J=6.3 Hz), 6.85-7.15 (5H, m), 7.17-7.4 (7H, m)

MS (ESI$^+$): 308 [M]$^+$

(2) Synthesis of 2-(3-Fluorobenzyl)phenol

To a solution of (2-benzyloxyphenyl)-(3-fluorophenyl)methanol (2.54 g, 7.51 mmol) in methanol (30 ml), a 20% palladium hydroxide catalyst (300 mg) was added and furthermore 2N—HCl (0.3 mL) was added thereto. The mixture solution was stirred under a hydrogen atmosphere for five days, and then the catalyst was filtered off. The solvent was distilled under reduced pressure, and the obtained residue was purified by silica gel column chromatography [developing solution=ethyl acetate:n-hexane (1:10)] to obtain the title compound (620 mg, 42%).

$^1$H-NMR (CDCl$_3$) δ: 3.98 (2H, s), 4.70 (1H, s), 6.75-7.3 (8H, m)

MS (ESI$^-$): 201 [M−H]$^-$

(3) Synthesis of [2-(3-Fluorobenzyl)phenyl]-5a-carba-β-D-glucopyranoside

In a nitrogen stream, 2,3,4,6-tetra-O-benzyl-5a-carba-α-D-glucopyranose (400 mg, 0.743 mmol) and tributyl-phosphine (0.278 mL, 1.11 mmol) were added to a solution of 2-(3-fluorobenzyl)phenol (225 mg, 1.11 mmol) in toluene (2.5 mL) under cooling with ice, and then tetramethylazodicarboxamide (TMAD, 192 mg, 1.11 mmol) was added thereto at the same temperature. The reaction mixture was stirred for 14 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (5:2) mixed solution (7 mL) and a 20% palladium hydroxide catalyst (40 mg) was added thereto, and the mixture was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (76 mg, 28%).

$^1$H-NMR (CD$_3$OD) δ: 0.99 (1H, dd, J=24.7, 13.2 Hz), 1.45-1.62 (1H, m), 2.09 (1H, dt, J=12.6, 4 Hz), 3.16-3.3 (2H, m), 3.4-3.55 (2H, m), 3.71 (1H, dd, J=10.7, 3.8 Hz), 3.93 (1H, d, J=14.9 Hz), 4.05 (1H, d, J=14.9 Hz), 4.1-4.3 (1H, m), 6.8-6.95 (3H, m), 7.0-7.06 (2H, m), 7.08-7.27 (3H, m).

MS (ESI$^+$): 363 [M+H]$^+$, 385 [M+Na]$^+$
HPLC Retention Time: 10.9 minutes

Example 20

[2-(3-Methylbenzyl)phenyl]-5a-carba-β-D-glucopyranoside

(1) Synthesis of [2-(3-Methylbenzyl)phenyl]-5a-carba-β-D-glucopyranoside

In a nitrogen stream, 2,3,4,6-tetra-O-benzyl-5a-carba-β-D-glucopyranose (413 mg, 0.743 mmol) and tributyl-phosphine (0.233 mL, 1.15 mmol) were added to a toluene (2.5 mL) solution of 2-(3-methylbenzyl)phenol (228 mg, 1.15 mmol) as described in Uzbekskii Khimicheskii Zhurnal (1984), 6, 31-4 and the like under cooling with ice, and then tetramethylazodicarboxamide (TMAD, 198 mg, 1.15 mmol) was added thereto at the same temperature. The reaction mixture was stirred for 15 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (2:5) mixed solution (7 mL) and a 20% palladium hydroxide catalyst (40 mg) was added thereto, and the mixture was stirred under a hydrogen atmosphere for six hours, and then the catalyst was filtered off. The solvent was distilled under reduced pressure and the obtained residue was purified by silica gel column chromatography [developing solution=methylene chloride:methanol (10:1)] to obtain the title compound (109 mg, 40%).

$^1$H-NMR (CD$_3$OD) δ: 0.95 (1H, dd, J=24.4, 12.9 Hz), 1.45-1.62 (1H, m), 2.06 (1H, dt, J=13.1, 4.0 Hz), 2.27 (3H, s), 3.15-3.30 (2H, m), 3.42-3.52 (2H, m), 3.70 (1H, dd, J=10.7, 3.9 Hz), 3.87 (1H, d, J=14.8 Hz), 3.98 (1H, d, J=14.8 Hz), 4.1-4.25 (1H, m), 6.81-6.88 (1H, m), 6.9-7.2 (7H, m)

MS (ESI$^+$): 376 [M+NH$_4$]$^+$, 359 [M+H]$^+$

HPLC Retention Time: 11.4 minutes

Example 21

[5-Fluoro-2-(4-methoxybenzyl)phenyl]-5a-carba-β-D-gluco-pyranoside (1) Synthesis of 2-Benzyloxy-1-bromo-4-fluorobenzene Potassium carbonate (2.61 g, 18.8 mmol) was added to a solution of 2-bromo-5-fluorophenol (3.0 g, 15.7 mmol) in DMF (15.7 mL) and the mixture was stirred in a nitrogen stream at room temperature for 15 minutes. To this solution, benzyl bromide (2.69 g, 15.7 mmol) was added dropwise at the same temperature and the mixture solution was stirred at the same temperature overnight. To the reaction mixture was added a potassium hydrogensulfate aqueous solution, and the mixture was extracted with ethyl acetate. The organic layer was washed with a saturated sodium chloride aqueous solution and dried (anhydrous magnesium sulfate), and then the solvent was distilled under reduce pressure. The obtained residue was purified by silica gel column chromatography (developing solution=n-hexane) to obtain the title compound (4.31 g, 98%) as a colorless oil.

$^1$H-NMR (CDCl$_3$) δ: 5.14 (2H, s), 6.56-6.72 (2H, m), 7.31-7.52 (6H, m)

(2) Synthesis of (2-Benzyloxy-4-fluorophenyl)-(4-methoxyphenyl)methanol

In a nitrogen stream, an n-butyllithium hexane solution (1.59 M, 3.14 mL) was added dropwise to a solution of 2-benzyloxy-1-bromo-4-fluorobenzene (1.4 g, 5.0 mmol) in THF (50 ml) at −78° C. and the mixture was stirred at the same temperature for 15 minutes. To this solution, a solution of 4-methoxybenzaldehyde (680 mg, 4.99 mmol) in THF (15 mL) was added dropwise at −78° C. and the mixture was stirred at the same temperature for 1.5 hours, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=n-hexane:dichloro-methane:acetone (12:3:1)] to obtain the title compound (1.41 g, 83%) as a colorless oil.

$^1$H-NMR (CDCl$_3$) δ: 2.67 (1H, d, J=5.0 Hz), 3.79 (3H, s), 4.99 (2H, s), 6.00 (1H, d, J=3.8 Hz), 6.62-6.70 (2H, m), 6.81-6.86 (2H, m), 7.19-7.38 (8H, m)

(3) Synthesis of 2-(4-Methoxybenzyl)-5-fluorophenol

To a solution of (2-benzyloxy-4-fluorophenyl)-(4-methoxyphenyl)-methanol (2.095 g, 6.19 mmol) in methanol (20 mL), a 20% palladium hydroxide catalyst (200 mg) was added and furthermore 2N—HCl (0.3 mL) was added thereto. The mixture was stirred under a hydrogen atmosphere for 16 hours, and then the catalyst was filtered off. The solvent was distilled under reduced pressure, and the obtained residue was purified by silica gel column chromatography [developing solution=ethyl acetate:n-hexane (1:5)] to obtain the title compound (489 mg, 34%).

$^1$H-NMR (CDCl$_3$) δ: 3.78 (3H, s), 3.89 (2H, s), 4.88 (1H, s), 6.50-6.40 (2H, m), 6.80-6.88 (2H, m), 7.04 (1H, dd, J=6.6, 8.2 Hz), 7.08-7.15 (2H, m)

MS (ESI$^-$): 231 [M−H]$^-$ (4) Synthesis of [5-Fluoro-2-(4-methoxybenzyl)phenyl]-5a-carba-β-D-glucopyranoside In a nitrogen stream, 2,3,4,6-tetra-O-benzyl-5a-carba-β-D-glucopyranose (500 mg, 0.928 mmol) and tributyl-phosphine (0.346 mL, 1.39 mmol) were added to a solution of 2-(4-methoxybenzyl)-5-fluorophenol (323 mg, 1.39 mmol) in toluene (2.5 mL) under cooling with ice, and then tetramethylazodicarboxamide (TMAD, 240 mg, 1.39 mmol) was added thereto at the same temperature. The reaction mixture was stirred for 17 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (2:5) mixed solution (7 mL), and a 20% palladium hydroxide catalyst (40 mg) was added thereto and the mixture was stirred under a hydrogen atmosphere for 22 hours, and then the catalyst was filtered off. The solvent was distilled under reduced pressure. The obtained residue was purified by silica gel column chromatography [developing solution=methylene chloride:methanol (10:1)] to obtain the title compound (59 mg, 16%).

$^1$H-NMR (CD$_3$OD) δ: 1.00 (1H, dd, J=24.4, 12.9 Hz), 1.5-1.65 (1H, m), 2.04 (1H, dt, J=13.4, 4.1 Hz), 3.17-3.35 (2H, m), 3.43-3.55 (2H, m), 3.65-3.75 (1H, m), 3.73 (3H, s), 3.81 (1H, d, J=15.1 Hz), 3.90 (1H, d, J=15.1 Hz), 4.1-4.22 (1H, m), 6.56 (1H, dt, J=8.5, 2.7 Hz), 6.75-6.88 (3H, m), 7.0-7.13 (3H, m)

MS (ESI$^+$): 415 [M+Na]$^+$

HPLC Retention Time: 11.0 minutes

Example 22

[2-(4-Methylsulfonylbenzyl)phenyl]-5a-carba-β-D-gluco-pyranoside (1) Synthesis of (2-Benzyloxyphenyl)-(4-methylsulfanyl-phenyl)methanol In a nitrogen stream, a solution of 4-methylsulfanyl-phenylmagnesium bromide in THF (0.5 M, 35 mL) was added dropwise to a solution of 2-benzyloxybenzaldehyde (2.60 g, 12.2 mmol) in THF (24 mL) at 0° C. and the mixture was stirred at room temperature for two hours, and then a saturated ammonium chloride aqueous solution was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain the title compound (3.91 g, 95%).

$^1$H-NMR (CDCl$_3$) δ: 2.47 (3H, s), 2.91 (1H, d, J=5.8 Hz), 5.03 (2H, s), 6.01 (1H, d, J=6.0 Hz), 6.90-7.00 (2H, m), 7.15-7.35 (11H, m)

(2) Synthesis of (2-Benzyloxyphenyl)-(4-methanesulfonyl-phenyl)methanol

In a nitrogen stream, m-chloroperbenzoic acid (4.40 g, 22.2 mmol) was added to a solution of (2-benzyloxyphenyl)-(4-methyl-sulfanylphenyl)methanol (3.00 g, 8.92 mmol) in methylene chloride (25 mL) at 0° C. and the reaction mixture was stirred at the same temperature for 30 minutes. The precipitate was removed by filtration and the filtrate was washed with a 2N sodium hydroxide aqueous solution. The washed solution was extracted with methylene chloride, and the combined organic layer was washed with water and a saturated sodium chloride aqueous solution and dried (anhydrous magnesium sulfate), and then the solvent was distilled under reduced pressure to obtain the title compound (3.18 g, 97%).

$^1$H-NMR (CDCl$_3$) δ: 3.02 (3H, s), 3.03 (1H, d, J=6.3 Hz), 5.00 (1H, J=11.4 Hz), 5.04 (1H, d, J=11.5 Hz), 6.09 (1H, d, J=6.2 Hz), 6.95-7.03 (2H, m), 7.16-7.22 (2H, m), 7.24-7.38 (5H, m), 7.53 (2H, d, J=8.1 Hz), 7.84 (2H, d, J=8.6 Hz)

(3) Synthesis of 2-(4-Methanesulfonylbenzyl)phenol

In a nitrogen stream, a 20% palladium hydroxide catalyst (299 mg) and 36% HCl (150 μL, 1.78 mmol) were added to a solution of (2-benzyloxyphenyl)-(4-methane-sulfonylphenyl)methanol (3.00 g, 8.14 mmol) in a mixture of methanol (30 mL) and ethyl acetate (30 mL), and the mixture was stirred under a hydrogen atmosphere for six hours. To the reaction mixture was added sodium hydrogencarbonate and the mixture was stirred for 30 minutes to be neutralized, and then the catalyst was filtered off. The solvent was distilled under reduced pressure and the obtained residue was purified by silica gel column chromatography [developing solution=ethyl acetate:n-hexane (1:2)] to obtain the title compound (1.81 g, 85%).

$^1$H-NMR (CDCl$_3$) δ: 3.02 (3H, s), 4.06 (2H, s), 5.00 (1H, s), 6.77 (1H, d, J=7.9 Hz), 6.89 (1H, dt, J=7.5, 1.2 Hz), 7.08-7.17 (2H, m), 7.42 (2H, d, J=8.6 Hz), 7.82 (2H, d, J=8.4 Hz)

(4) Synthesis of [2-(4-Methanesulfonylbenzyl)phenyl]-5a-carba-β-D-glucopyranoside In a nitrogen stream, 2,3,4,6-tetra-O-benzyl-5a-carba-α-D-gluco-pyranose (500 mg, 0.928 mmol) and tributyl-phosphine (0.35 mL, 1.39 mmol) were added to a solution of 2-(4-methylsulfanylbenzyl)phenol (365 mg, 1.39 mmol) in a mixture of toluene (2 mL) and THF (1 mL) under cooling with ice, and then tetramethylazodicarboxamide (TMAD, 242 mg, 1.41 mmol) was added thereto at the same temperature. The reaction mixture was stirred for 25 hours while gradually raising its temperature to room temperature. The reaction mixture was concentrated under reduced pressure, and the obtained residue was treated by silica gel column chromatography [developing solution=ethyl acetate:n-hexane (1:4 to 1:2)]. The obtained crude product was dissolved in a mixture of methanol (3 mL) and THF (2 mL), and a 20% palladium hydroxide catalyst (27.2 mg) and one drop of 2N hydrochloric acid were added thereto, and the mixture was stirred under a hydrogen atmosphere for 2.5 hours. To the reaction mixture was added a sodium hydrogencarbonate aqueous solution to neutralize the mixture, and then the catalyst was filtered off. The solvent was distilled under reduced pressure, and the obtained residue was purified by silica gel column chromatography [developing solution=methylene chloride:methanol (8:1)] to obtain the title compound (120 mg, 31%).

$^1$H-NMR (CD$_3$OD) δ: 0.91 (1H, ddd, J=13.0, 13.0, 13.0 Hz), 1.53 (1H, m), 2.03 (1H, ddd, J=13.0, 4.0, 4.0 Hz), 3.07 (3H, s), 3.19 (1H, dd, J=8.9, 8.9 Hz), 3.28 (1H, dd, J=9.0, 9.0 Hz), 3.43 (1H, dd, J=9.0, 9.0 Hz), 3.50 (1H, dd, J=10.7, 6.1 Hz), 3.67 (1H, dd, J=10.7, 4.0 Hz), 4.02 (1H, d, J=14.5 Hz), 4.16 (1H, d, J=14.5 Hz), 4.14-4.26 (1H, m), 6.88 (1H, t, J=6.2 Hz), 7.04 (1H, d, J=8.1 Hz), 7.17 (1H, d, J=7.5 Hz), 7.18 (1H, t, J=7.5 Hz), 7.48 (1H, d, J=8.4 Hz), 7.80 (1H, d, J=8.4 Hz)

MS (ESI$^+$): 423 [M+H]$^+$, 440 [M+NH$_4$]$^+$, 445 [M+Na]$^+$

HPLC Retention Time: 9.0 minutes

Example 23

[2-(4-Fluorobenzyl)phenyl]-5a-carba-β-D-glucopyranoside (1) Synthesis of 2-(4-Fluorobenzyl)phenol In a nitrogen stream, an n-butyllithium hexane solution (1.59 M, 4.9 mL) was added dropwise to a solution of 1-benzyloxy-2-bromobenzene (2.04 g, 7.75 mmol) in THF (60 mL) at −78° C. and the mixture was stirred at the same temperature for 20 minutes. To this solution, a solution of 4-fluorobenzaldehyde (801 mg, 6.45 mmol) in THF (10 mL) was added dropwise at −78° C. The mixture was stirred at the same temperature for 1.5 hours, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure to obtain a crude product (2.35 g) of the title compound. To a solution of the obtained crude product in methanol (15 mL), a 20% palladium hydroxide catalyst (186 mg) was added and furthermore 2N—HCl (400 μL) was added thereto. The mixture was stirred under a hydrogen atmosphere for three hours, and then the catalyst was filtered. The solvent was distilled under reduced pressure and the obtained residue was purified by silica gel column chromatography [developing solution=ethyl acetate:n-hexane (1:5)] to obtain the title compound (996 mg, 77%).

$^1$H-NMR (CDCl$_3$) δ: 3.95 (2H, s), 4.72 (1H, s), 7.77 (1H, dd, J=7.9, 1.1 Hz), 6.88 (1H, td, J=7.5, 1.1 Hz), 6.96 (1H, dd, J=8.7, 8.7 Hz), 7.06-7.20 (4H, m)

(2) Synthesis of [2-(4-Fluorobenzyl)phenyl]-5a-carba-β-D-glucopyranoside

In a nitrogen stream, 2,3,4,6-tetra-O-benzyl-5a-carba-α-D-glucopyranose (500 mg, 0.928 mmol) and tributyl-phosphine (0.35 mL, 1.40 mmol) were added to a solution of 2-(4-fluorobenzyl)phenol (284 mg, 1.40 mmol) in toluene (3 mL) under cooling with ice, and then tetramethylazo-dicarboxamide (TMAD, 241 mg, 1.40 mmol) was added thereto at the same temperature. The reaction mixture was stirred for 21 hours while gradually raising its temperature to room temperature. The reaction mixture was concentrated under reduced pressure, and the obtained residue was treated by silica gel column chromatography [developing solution=ethyl acetate:n-hexane (1:8 to 1:3)]. The obtained crude product was dissolved in a methanol (4 mL)-THF (2 mL) mixed solvent and a 20% palladium hydroxide catalyst (18.4 mg) and a drop of 2N hydrochloric acid were added thereto, and the mixture was stirred under a hydrogen atmosphere for 1.5 hours. To the reaction mixture was added a saturated sodium hydrogencarbonate aqueous solution to neutralize the mixture, and the catalyst was filtered off. The solvent was distilled under reduced pressure and the obtained residue was purified by silica gel column chromatography [developing solution=methylene chloride:methanol (10:1 to 8:1)] to obtain the title compound (153 mg, 46%).

$^1$H-NMR (CD$_3$OD) δ: 0.99 (1H, ddd, J=12.9, 12.9, 12.9 Hz), 1.55 (1H, m), 2.08 (1H, ddd, J=13.2, 3.9, 3.9 Hz), 3.22 (1H, dd, J=9.0, 9.0 Hz), 3.30 (1H, dd, J=9.0, 9.0 Hz), 3.48 (1H, dd, J=8.7, 8.7 Hz), 3.51 (1H, dd, J=10.8, 6.0 Hz), 3.70 (1H, dd, J=10.8, 4.2 Hz), 3.90 (1H, d, J=14.7 Hz), 4.02 (1H, d, J=14.7 Hz), 4.20 (1H, ddd, J=11.4, 9.0, 4.8 Hz), 6.85 (1H, t, J=7.5 Hz), 6.93 (1H, dd, J=8.9, 8.9 Hz), 7.02 (1H, d, J=8.1 Hz), 7.06-7.23 (4H, m)

MS (ESI$^+$): 363 [M+H]$^+$

HPLC Retention Time: 10.9 minutes

Example 24

[2-(3,4-Dimethoxybenzyl)phenyl]-5a-carba-β-D-gluco-pyranoside (1) Synthesis of 2-(3,4-Dimethoxybenzyl)phenol In a nitrogen stream, an n-butyllithium hexane solution (1.59 M, 4.4 mL) was added dropwise to a solution of 1-benzyloxy-2-bromobenzene (1.74 g, 6.61 mmol) in THF (30 mL) at −78° C. and the mixture solution was stirred at the same temperature for one hour. To this solution, a solution of 3,4-dimethoxybenzaldehyde (1.00 g, 6.02 mmol) in THF (8 mL) was added dropwise at −78° C. The reaction mixture was stirred at the same temperature for 1.5 hours, and then a saturated ammonium chloride aqueous solution was added thereto and the mixture was extracted with ethyl acetate. The organic layer was washed with a saturated sodium chloride aqueous solution and dried (anhydrous magnesium sulfate), and then the solvent was distilled under reduced pressure to obtain a crude product (2.38 g). The obtained crude product was dissolved in methanol (20 mL) and a 20% palladium hydroxide catalyst (196 mg) was added and furthermore 2N—HCl (30 µL) was added thereto. The mixture solution was stirred under a hydrogen atmosphere for 23 hours, and then the catalyst was filtered off. The solvent was distilled under reduced pressure and the obtained residue was purified by silica gel column chromatography [developing solution=ethyl acetate:n-hexane (1:5)] to obtain the title compound (653 mg, 44%).

$^1$H-NMR (CDCl$_3$) δ: 3.82 (3H, s), 3.85 (3H, s), 3.94 (2H, s), 4.73 (1H, s), 6.74-6.82 (2H, m), 6.78 (1H, s), 6.89 (1H, td, J=7.5, 1.1 Hz), 7.08-7.17 (2H, m)

(2) Synthesis of [2-(3,4-Dimethoxybenzyl)phenyl]-5a-carba-β-D-glucopyranoside

In a nitrogen stream, 2,3,4,6-tetra-O-benzyl-5a-carba-α-D-glucopyranose (504 mg, 0.936 mmol) and tributyl-phosphine (0.35 mL, 1.40 mmol) were added to a solution of 2-(3,4-dimethoxybenzyl)phenol (342 mg, 1.40 mmol) in a mixture of toluene (2.5 mL) and THF (1.0 mL) under cooling with ice, and then tetramethylazodicarboxamide (TMAD, 242 mg, 1.41 mmol) was added thereto at the same temperature. The reaction mixture was stirred for 22 hours while gradually raising its temperature to room temperature. The reaction mixture was concentrated under reduced pressure and the obtained residue was treated by silica gel column chromatography [developing solution=ethyl acetate:n-hexane (1:3)]. The obtained crude product was dissolved in a methanol (2 mL)-THF (2 mL) mixed solvent and a 20% palladium hydroxide catalyst (21.9 mg) was added thereto. The mixture solution was stirred under a hydrogen atmosphere for five hours, and then the catalyst was filtered off. The solvent was distilled under reduced pressure and the obtained residue was purified by silica gel column chromatography [developing solution=methylene chloride:methanol (10:1)] to obtain the title compound (108 mg, 38%).

$^1$H-NMR (CD$_3$OD) δ: 1.01 (1H, ddd, J=13.1, 13.1, 11.6 Hz), 1.55 (1H, m), 2.08 (1H, ddd, J=13.3, 3.8, 3.8 Hz), 3.21 (1H, dd, J=9.2, 9.2 Hz), 3.29 (1H, dd, J=8.9, 8.9 Hz), 3.48 (1H, dd, J=9.2, 9.2 Hz), 3.49 (1H, dd, J=10.7, 6.3 Hz), 3.70 (1H, dd, J=10.7, 4.1 Hz), 3.76 (3H, s), 3.78 (3H, s), 3.87 (1H, d, J=14.8 Hz), 3.96 (1H, d, J=14.8 Hz), 4.19 (1H, ddd, J=11.5, 9.0, 4.6 Hz), 6.73 (1H, dd, J=8.3, 2.0 Hz), 6.81 (1H, s), 6.82 (1H, d, J=8.3 Hz), 6.84 (1H, td, J=7.5, 1.2 Hz), 7.02 (1H, d, J=7.5 Hz), 7.08 (1H, dd, J=7.5, 1.5 Hz), 7.14 (1H, td, J=7.2, 1.7 Hz)

MS (ESI$^+$): 405 [M+H]$^+$

HPLC Retention Time: 9.7 minutes

Example 25

[2-(4-Ethylbenzyl)phenyl]-5a-carba-β-D-glucopyranoside (1) Synthesis of [2-(4-Ethylbenzyl)phenyl]-5a-carba-β-D-glucopyranoside In a nitrogen stream, 2,3,4,6-tetra-O-benzyl-5a-carba-α-D-glucopyranose (400 mg, 0.74 mmol) and tributyl-phosphine (0.28 mL, 1.11 mmol) were added to a toluene (2.5 mL) solution of 2-(4-ethylbenzyl)phenol (236 mg, 1.11 mmol) as described in International Publication Nos. WO04/052902, WO01/074834 and the like under cooling with ice, and then tetramethylazodicarboxamide (TMAD, 191 mg, 1.11 mmol) was added thereto at the same temperature. The reaction mixture was stirred for 25 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:2) mixed solution (4 mL) and a 20% palladium hydroxide catalyst (20 mg) was added thereto. The mixture was stirred under a hydrogen atmosphere for 1.5 hours, and then the catalyst was filtered off. The solvent was distilled under reduced pressure and the obtained residue was purified by TLC [developing solution=methylene chloride:methanol (10:1)] to obtain the title compound (40 mg, 14%).

¹H-NMR (CD₃OD) δ: 0.86-1.00 (1H, m), 1.19 (3H, t, J=7.6 Hz), 1.45-1.62 (1H, m), 2.00-2.11 (1H, m), 2.57 (2H, q, J=7.6 Hz), 3.16-3.30 (2H, m), 3.43-3.49 (2H, m), 3.70 (1H, dd, J=10.6, 4.1 Hz), 3.84-4.02 (2H, m), 4.12-4.24 (1H, m), 6.83 (1H, t, J=7.4 Hz), 6.99-7.16 (7H, m)

MS (ESI⁺): 395 [M+Na]⁺

HPLC Retention Time: 12.3 minutes

Example 26

[2-(4-Hydroxybenzyl)phenyl]-5a-carba-β-D-glucopyranoside (1) Synthesis of [2-(4-Hydroxybenzyl)phenyl]-5a-carba-β-D-glucopyranoside Under a nitrogen atmosphere, a solution of boron tribromide in dichloromethane (1.0 M, 0.80 mL, 0.80 mmol) was added to a solution of [2-(4-methoxybenzyl)phenyl]-5a-carba-β-D-glucopyranoside (100 mg, 0.27 mmol) as obtained in Example 1 in dichloromethane (1.3 mL) at −78° C. The cooling bath was removed and the reaction mixture was stirred at room temperature for one hour. The reaction mixture was concentrated under reduced pressure and the obtained residue was purified by HPLC (developing solution=methanol:20 mM ammonium acetate aqueous solution) to obtain the title compound (45 mg, 47%).

¹H-NMR (CD₃OD) δ: 0.92-1.06 (1H, m), 1.47-1.67 (1H, m), 2.03-2.11 (1H, m), 3.18-3.34 (2H, m), 3.45-3.52 (2H, m), 3.71 (1H, dd, J=10.7, 4.1 Hz), 3.79-3.95 (2H, m), 4.12-4.22 (1H, m), 6.65 (2H, d, J=8.4 Hz), 6.83 (1H, t, J=7.3 Hz), 6.99-7.16 (5H, m)

MS (ESI⁺): 361 [M+H]⁺

HPLC Retention Time: 8.9 minutes

Example 27

[2-(4-Cyanobenzyl)phenyl]-5a-carba-β-D-glucopyranoside (1) Synthesis of [2-(4-Cyanobenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-cyano-benzyl)phenol (291 mg, 1.39 mmol) in a mixture of toluene (2 mL) and THF (1 mL) under cooling with ice, and then tetramethylazodicarboxamide (TMAD, 239 mg, 1.39 mmol) was added thereto at the same temperature. The reaction mixture was stirred for 14 hours while gradually raising its temperature to room temperature. The reaction mixture was concentrated under reduced pressure, and the obtained residue was treated by silica gel column chromatography [developing solution=ethyl acetate:n-hexane (1:5)] and preparative TLC [developing solution=ethyl acetate:n-hexane (1:3)] to obtain a crude product (130 mg). The obtained crude product (55 mg) was dissolved in methylene chloride (0.50 mL), and dimethyl-sulfide (0.19 mL, 4.4 mmol) and a boron trifluoride-diethyl ether complex (0.095 mL, 0.75 mmol) were added thereto under cooling with ice. The reaction mixture was stirred at room temperature for five hours, and then water was added thereto under cooling with ice and the mixture was extracted with ethyl acetate. The organic layer was washed with a saturated sodium chloride aqueous solution and dried (anhydrous magnesium sulfate), and then the solvent was distilled under reduced pressure. The obtained residue was purified by TLC [developing solution=methylene chloride:methanol (10:1)] to obtain the title compound (17.5 mg, 12%).

¹H-NMR (CD₃OD) δ: 0.83-0.96 (1H, m), 1.44-1.60 (1H, m), 1.99-2.07 (1H, m), 3.14-3.32 (2H, m), 3.38-3.50 (2H, m), 3.67 (1H, dd, J=10.7, 4.0 Hz), 3.93-4.13 (2H, m), 4.15-4.22 (1H, m), 6.85 (1H, t, J=7.3 Hz), 7.01 (1H, d, J=7.9 Hz), 7.11-7.18 (2H, m), 7.37 (2H, d, J=8.2 Hz), 7.55 (2H, d, J=8.1 Hz)

MS (ESI⁺): 392 [M+Na]⁺

HPLC Retention Time: 10.2 minutes

Example 28

[2-(3-Trifluoromethoxybenzyl)phenyl]-5a-carba-β-D-gluco-pyranoside (1) Synthesis of 2-(3-Trifluoromethoxybenzyl)phenol In a nitrogen stream, an n-butyllithium hexane solution (2.44 M, 4.3 mL) was added dropwise to a solution of 1-benzyloxy-2-bromobenzene (2.5 g, 9.5 mmol) in THF (95 mL) at −78° C. and the mixture was stirred at the same temperature for 30 minutes. To this mixture, a solution of 3-trifluoromethoxybenzaldehyde (1.5 g, 7.9 mmol) in THF (32 mL) was added dropwise at −78° C. The reaction mixture was stirred at the same temperature for two hours and furthermore at 0° C. for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was treated by silica gel column chromatography [developing solution=ethyl acetate:n-hexane (1:5)]. The obtained crude product was dissolved in methanol (20 mL) and a 20% palladium hydroxide catalyst (200 mg) was added and furthermore 2N—HCl (0.187 mL) was added thereto. The mixture was stirred under a hydrogen atmosphere for 13 hours. Potassium carbonate (850 mg) was added to the reaction mixture and the mixture was stirred at room temperature for 30 minutes, and then the catalyst was filtered off. The solvent was distilled under reduced pressure and the obtained residue was purified by silica gel column chromatography [developing solution=ethyl acetate:n-hexane (1:5)] to obtain the title compound (1.40 g, 99%).

¹H-NMR (CDCl₃) δ: 3.99 (2H, s), 4.71 (1H, br s), 6.76 (1H, d, J=7.9 Hz), 6.92-6.86 (1H, m), 7.02-7.15 (5H, m), 7.29 (1H, d, J=7.3 Hz)

(2) Synthesis of [2-(3-Trifluoromethoxybenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(3-trifluoromethoxybenzyl)phenol (373 mg, 1.39 mmol) in toluene (2 mL) under cooling with ice, and then tetra-methylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:2) mixed solvent (10 mL) and a 20% palladium hydroxide catalyst (100 mg) was added thereto, and the reaction mixture was stirred under a hydrogen atmosphere for 13 hours, and then the catalyst was filtered off. The solvent was distilled under reduced pressure and the obtained residue was purified by TLC [developing solution=methylene chloride:methanol (10:1)] to obtain the title compound (104 mg, 26%).

$^1$H-NMR (CD$_3$OD) δ: 0.86-1.00 (1H, m), 1.45-1.60 (1H, m), 2.01-2.09 (1H, m), 3.15-3.31 (2H, m), 3.41-3.48 (2H, m), 3.68 (1H, dd, J=10.7, 4.1 Hz), 3.88-4.11 (2H, m), 4.13-4.95 (1H, m), 6.82-6.87 (1H, m), 7.00-7.30 (7H, m)

MS (ESI$^+$): 429 [M+H]$^+$

HPLC Retention Time: 12.4 minutes

Example 29

[2-(4-Aminomethylbenzyl)phenyl]-5a-carba-β-D-glucopyranoside acetic acid salt (1) Synthesis of [2-(4-Aminomethylbenzyl)phenyl]-5a-carba-β-D-glucopyranoside acetic acid salt The crude product (63 mg) of [2-(4-cyanobenzyl)-phenyl]-2,3,4,6-tetra-O-benzyl-5a-carba-β-D-glucopyranoside as obtained in Example 27 was dissolved in a methanol-THF (1:2) mixed solvent (1 mL) and a 20% palladium hydroxide catalyst was added thereto and the mixture solution was stirred under a hydrogen atmosphere for 23 hours. The catalyst was filtered, and the solvent was distilled under reduced pressure to obtain a crude product of [2-(4-aminomethylbenzyl)phenyl]-2,3,4,6-tetra-O-benzyl-5a-carba-β-D-glucopyranoside. This crude product was dissolved in methylene chloride (0.55 mL) and dimethyl sulfide (0.22 mL, 5.1 mmol) and a boron tri-fluoride-diethyl ether complex (0.11 mL, 0.86 mmol) were added thereto under cooling with ice, and the mixture was stirred at room temperature for 22 hours. The reaction mixture was concentrated under reduced pressure and the obtained residue was purified by HPLC (developing solution=methanol:20 mM ammonium acetate aqueous solution) to obtain the title compound (19 mg).

$^1$H-NMR (CD$_3$OD) δ: 0.85-0.99 (1H, m), 1.42-1.58 (1H, m), 1.88 (3H, s), 1.93-2.01 (1H, m), 3.14-3.67 (5H, m), 3.87-4.07 (2H, m), 4.01 (2H, s), 4.11-4.20 (1H, m), 6.79-6.85 (1H, m), 6.99 (1H, d, J=4.1H), 7.01-7.16 (2H, m), 7.25 (2H, d, J=8.4 Hz), 7.29 (2H, d, J=8.5 Hz)

MS (ESI$^+$): 374 [M+H]$^+$

HPLC Retention Time: 7.3 minutes

Example 30

[5-Methoxy-2-(4-methoxybenzyl)phenyl]-5a-carba-β-D-gluco-pyranoside (1) Synthesis of [5-Methoxy-2-(4-methoxybenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 5-methoxy-2-(4-methoxybenzyl)phenol (340 mg, 1.39 mmol) as described in International Publication Nos. WO04/058682, WO02/064606, WO02/044192 or the like in toluene (3 mL) under cooling with ice, and then tetramethylazodicarboxamide (TMAD, 239 mg, 1.39 mmol) was added thereto at the same temperature. The reaction mixture was stirred for 17 hours while gradually raising its temperature to room temperature. The reaction mixture was concentrated under reduced pressure, and the obtained residue was treated by silica gel column chromatography [developing solution=ethyl acetate:n-hexane (1:3)]. The obtained crude product was dissolved in a methanol-THF (1:2) mixed solvent (5 mL) and a 20% palladium hydroxide catalyst (50 mg) was added thereto, and the reaction mixture was stirred under a hydrogen atmosphere for three hours, and then the catalyst was filtered off. The solvent was distilled under reduced pressure and the obtained residue was purified by TLC [developing solution=methylene chloride:methanol (10:1)] to obtain the title compound (119 mg, 32%).

$^1$H-NMR (CD$_3$OD) δ: 0.84-0.98 (1H, m), 1.44-1.60 (1H, m), 1.98-2.06 (1H, m), 3.13-3.47 (5H, m), 3.77 (3H, s), 3.82 (3H, s), 3.71-3.88 (2H, m), 4.06-4.16 (1H, m), 6.41 (1H, dd, J=2.3, 8.2 Hz), 6.58 (1H, d, J=2.1 Hz), 6.75 (2H, d, J=8.7 Hz), 6.94 (1H, d, J=8.2 Hz), 7.05 (2H, d, J=8.6 Hz)

MS (ESI$^+$): 405 [M+H]$^+$

HPLC Retention Time: 10.7 minutes

Example 31

[2-(4-Methoxycarbonylbenzyl)phenyl]-5a-carba-β-D-gluco-pyranoside (1) Synthesis of 4-[(2-Benzyloxyphenyl)hydroxymethyl]-benzoic Acid Methyl Ester In a nitrogen stream, an n-butyllithium hexane solution (2.71 M, 12.1 mL) was added dropwise to a solution of 1-benzyloxy-2-bromobenzene (7.84 g, 29.8 mmol) in THF (300 mL) at −78° C. and the reaction mixture was stirred at the same temperature for 30 minutes. To this mixture, a solution of 4-methyl ester-benzaldehyde (4.78 g, 29.1 mmol) in THF (100 mL) was added dropwise at −78° C. The reaction mixture was stirred at the same temperature for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (4.15 g, 41%).

$^1$H-NMR (CDCl$_3$) δ: 3.06 (1H, d, J=6.2 Hz), 3.91 (3H, s), 5.02 (2H, dd, J=5.8, 11.4 Hz), 6.07 (1H, d, J=6.2 Hz), 6.94-7.00 (2H, m), 7.18-7.42 (9H, m), 7.96 (2H, d, J=8.4 Hz)

(2) Synthesis of 4-(2-Benzyloxybenzyl)benzoic Acid Methyl Ester

In a nitrogen stream, triethylsilane (2.27 mL, 13.5 mmol) and a boron trifluoride-diethyl ether complex (1.52 mL, 11.88 mmol) were added to a solution of 4-[(2-benzyloxyphenyl)-hydroxymethyl]benzoic acid methyl ester (4.15 g, 11.9 mmol) in acetonitrile (22.7 mL) at −40° C. and the mixture solution was stirred at the same temperature for 1.5 hours and further at 0° C. for 30 minutes. Water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (2.39 g, 62%).

$^1$H-NMR (CDCl$_3$) δ: 3.89 (3H, s), 4.05 (2H, s), 5.02 (2H, d, J=5.8 Hz), 6.92 (2H, d, J=7.9 Hz), 7.12-7.36 (9H, m), 7.91 (2H, d, J=8.0 Hz)

MS (ESI$^+$): 333 [M+H]$^+$

(3) Synthesis of 4-(2-Hydroxybenzyl)benzoic Acid Methyl Ester

To a solution of 4-(2-benzyloxybenzyl)benzoic acid methyl ester (2.39 g, 7.19 mmol) in methanol (70 mL), a 20% palladium hydroxide catalyst (239 mg) was added. The mixture was stirred under a hydrogen atmosphere for five hours, and then the catalyst was filtered off. The solvent was distilled under reduced pressure to obtain the title compound (1.16 g, 96%).

$^1$H-NMR (CDCl$_3$) δ: 3.89 (3H, s), 4.04 (2H, s), 4.76 (1H, s), 6.77 (1H, d, J=8.0 Hz), 6.89 (1H, t, J=7.3 Hz), 7.13 (2H, m), 7.29 (2H, d, J=8.4 Hz), 7.94 (2H, d, J=8.0 Hz)

MS (ESI$^+$): 243 [M+H]$^+$

(4) Synthesis of [2-(4-Methoxycarbonylbenzyl)phenyl]-2,3,4,6-tetra-O-benzyl-5a-carba-β-D-glucopyranoside In a nitrogen stream, 2,3,4,6-tetra-O-benzyl-5a-carba-α-D-glucopyranose (1.10 g, 2.04 mmol) and tributyl-phosphine (0.77 mL, 3.06 mmol) were added to a solution of 4-(2-hydroxybenzyl)benzoic acid methyl ester (741.4 mg, 3.06 mmol) in toluene (6.9 mL) under cooling with ice, and then tetramethylazodicarboxamide (TMAD, 526.5 mg, 3.06 mmol) was added thereto at the same temperature. The reaction mixture was stirred for 20 hours while gradually raising its temperature to room temperature. The reaction mixture was concentrated under reduced pressure, and the obtained residue was purified by silica gel column chromatography [developing solution=ethyl acetate:n-hexane (1:10)] to obtain the title compound (429.0 mg, 28%).

$^1$H-NMR (CD$_3$OD) δ: 1.40 (1H, dd, J=12.0, 12.0 Hz), 1.65-1.74 (1H, m), 2.00-2.09 (1H, m), 3.43-3.59 (2H, m), 3.84 (3H, s), 4.00 (2H, s), 4.32-3.92 (8H, m), 6.91 (1H, t, J=8.0 Hz), 7.04-7.32 (25H, m), 7.87 (2H, d, J=8.0 Hz)

(5) Synthesis of [2-(4-Methoxycarbonylbenzyl)phenyl]-5a-carba-β-D-glucopyranoside

[2-(4-Methoxycarbonylbenzyl)phenyl]-2,3,4,6-tetra-O-benzyl-5a-carba-β-D-glucopyranose (38.1 mg, 0.05 mmol) was dissolved in a methanol-THF (2:1) mixed solvent (1.5 mL) and a 20% palladium hydroxide catalyst (5 mg) was added thereto. The mixture was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (12.9 mg, 65%).

$^1$H-NMR (CD$_3$OD) δ: 0.89-1.00 (1H, m), 1.47-1.62 (1H, m), 2.03-2.09 (1H, m), 3.16-3.23 (2H, m), 3.42-3.49 (2H, m), 3.51-3.87 (1H, m), 3.95 (3H, s), 4.00-4.17 (2H, m), 4.19-4.23 (1H, m), 6.87 (1H, d, J=7.4 Hz), 7.31 (1H, d, J=7.6 Hz), 7.12-7.20 (2H, m), 7.32 (2H, d, J=8.4 Hz), 7.88 (2H, d, J=8.4 Hz)

MS (ESI$^+$): 403 [M+Na]$^+$

Example 32

[2-(4-Carbamoylbenzyl)phenyl]-5a-carba-β-D-glucopyranoside

(1) Synthesis of [2-(4-Carboxybenzyl)phenyl]-2,3,4,6-tetra-O-benzyl-5a-carba-β-D-glucopyranoside Under a nitrogen atmosphere, a 5N-sodium hydroxide aqueous solution (0.15 mL) was added to a solution of [2-(4-methoxycarbonyl-benzyl)phenyl]-2,3,4,6-tetra-O-benzyl-5a-carba-β-D-glucopyranose (100.0 mg, 0.13 mmol) in ethanol-THF (4:1) mixed solvent (1.5 mL) at room temperature and the mixture solution was stirred for 22 hours. Thereafter, to the reaction mixture was added a 5N-hydrochloric acid aqueous solution under cooling with ice to neutralize the mixture. The resulting mixture was extracted with methylene chloride and dried (sodium sulfate) and concentrated under reduced pressure to obtain the title compound (91.3 mg, 94%).

$^1$H-NMR (CDCl$_3$) δ: 1.42 (1H, ddd, J=12.4, 12.4, 12.4 Hz), 1.55-1.67 (1H, m), 2.00-2.04 (1H, m), 3.41-3.61 (2H, m), 4.02 (2H, s), 4.35-3.92 (8H, m), 6.92 (1H, t, J=7.3 Hz), 7.05-7.32 (25H, m), 7.92 (2H, d, J=7.7 Hz)

MS (ESI$^+$): 749 [M+H]$^+$

(2) Synthesis of [2-(4-Carbamoylbenzyl)phenyl]-2,3,4,6-tetra-O-benzyl-5a-carba-β-D-glucopyranoside Under a nitrogen atmosphere, 1-hydroxybenzotrizole monohydrate (9.0 mg, 0.07 mmol) and 1-ethyl-3-(3-dimethyl-aminopropyl)carbodiimide hydrochloride (12.0 mg, 0.07 mmol) were added to a solution of [2-(4-hydroxycarbonylbenzyl)-phenyl]-2,3,4,6-tetra-O-benzyl-5a-carba-β-D-glucopyranoside (45.0 mg, 0.06 mmol) in N,N-dimethylformamide (1.2 mL) at room temperature and the reaction mixture was stirred for one hour, and then ammonia water (0.5 mL) was added thereto under cooling with ice and the mixture was stirred for 27 hours. The reaction mixture was concentrated under reduced pressure and purified by TLC (developing solution=methanol:methylene chloride=1:10) to obtain the title compound (39.1 mg, 89%).

$^1$H-NMR (CDCl$_3$) δ: 1.31-1.49 (1H, m), 1.62-1.76 (1H, m), 1.96-2.08 (1H, m), 3.39-3.66 (2H, m), 4.02 (2H, s), 4.33-4.96 (8H, m), 6.88-6.97 (1H, m), 7.04-7.39 (25H, m), 7.54-7.61 (2H, m)

MS (ESI$^+$): 748 [M+H]$^+$

(3) Synthesis of [2-(4-Carbamoylbenzyl)phenyl]-5a-carba-β-D-glucopyranoside

To a solution (3 mL) of [2-(4-carbamolybenzyl)-phenyl]-2,3,4,6-tetra-O-benzyl-5a-carba-β-D-glucopyranoside (39.1 mg, 0.05 mmol) in methanol-THF (2:1) solvent (3 mL), a 20% palladium hydroxide catalyst (5 mg) was added. The mixture solution was stirred under a hydrogen atmosphere for 24 hours, and then the catalyst was filtered off. The solvent was distilled under reduced pressure and the obtained residue was purified by TLC [developing solution=methanol:methylene chloride (1:5)] to obtain the title compound (19.2 g, 99%).

$^1$H-NMR (CD$_3$OD) δ: 0.92 (1H, dd, J=11.7, 11.7 Hz), 1.48-1.62 (1H, m), 1.96-2.08 (1H, m), 3.16-3.33 (4H, m), 3.42-3.59 (2H, m), 3.65-3.73 (1H, m), 3.93-4.26 (3H, m), 6.87 (1H, t, J=7.3 Hz), 7.02-7.21 (3H, m), 7.31 (2H, d, J=8.2 Hz), 7.74 (2H, d, J=8.1 Hz)

MS (ESI$^+$): 388 [M+H]$^+$

HPLC Retention Time: 8.0 minutes

Example 33

[2-(4-N,N-Dimethylcarbamoylbenzyl)phenyl]-5a-carba-β-D-glucopyranoside

(1) Synthesis of [2-(4-N,N-Dimethylcarbamoylbenzyl)-phenyl]-2,3,4,6-tetra-O-benzyl-5a-carba-β-D-gluco-pyranoside Under a nitrogen atmosphere, 1-hydroxybenzotrizole monohydrate (9.0 mg, 0.07 mmol) and 1-ethyl-3-(3-dimethyl-aminopropyl)carbodiimide hydrochloride (12.0 mg, 0.07 mmol) were added to a solution of [2-(4-carboxybenzyl) phenyl]-2,3,4,6-tetra-O-benzyl-5a-carba-β-D-glucopyranoside (45.0 mg, 0.06 mmol) as obtained in Example 32 in N,N-dimethylformamide (1.2 mL) at room temperature and the reaction mixture was stirred for one hour. A N,N-dimethylamine aqueous solution (0.5 mL) was added thereto under cooling with ice and the mixture was stirred for 27 hours. The reaction mixture was concentrated under reduced pressure and purified by preparative TLC (developing solution=methanol:methylene chloride=1:10) to obtain the title compound (44.1 mg, 96%).

$^1$H-NMR (CDCl$_3$) δ: 1.42-1.52 (1H, m), 1.66-1.78 (1H, m), 2.05-2.14 (1H, m), 2.83 (3H, s), 3.04 (3H, s), 3.44-3.68 (5H, m), 3.99 (2H, s), 4.35-4.53 (1H, m), 4.68 (2H, s), 4.83-4.94 (3H, m), 6.91 (1H, t, J=7.3 Hz), 7.04-7.36 (27H, m)

MS (ESI$^+$): 776 [M+H]$^+$ (2) Synthesis of [2-(4-N,N-Dimethylcarbamoylbenzyl)-phenyl]-5a-carba-β-D-glucopyranoside To a methanol-THF (2:1) solution (3 mL) of [2-(4-N,N-dimethylcarbamolybenzyl)phenyl]-2,3,4,6-tetra-O-benzyl-5a-carba-β-D-glucopyranoside (44.1 mg, 0.06 mmol), a 20% palladium hydroxide catalyst (5 mg) was added. The mixture solution was stirred under a hydrogen atmosphere for 24 hours, and then the catalyst was filtered off. The solvent was distilled under reduced pressure and the obtained residue was purified by TLC [developing solution=methanol:methylene chloride (1:5)] to obtain the title compound (20.1 mg, 87%).

$^1$H-NMR (CD$_3$OD) δ: 0.86-1.00 (1H, m), 1.45-1.58 (1H, m), 1.98-2.06 (1H, m), 2.95 (3H, s), 3.03 (3H, s), 3.13-3.49 (5H, m), 3.62-3.68 (1H, m), 3.88-4.21 (3H, m), 6.91 (1H, t, J=7.2 Hz), 6.98-7.15 (3H, m), 7.26 (4H, s)

MS (ESI$^+$): 416 [M+H]$^+$

HPLC Retention Time: 8.9 minutes

Example 34

[2-(4-Ethoxybenzyl)phenyl]-5a-carba-β-D-glucopyranoside (1) Synthesis of 2-(4-Ethyoxybenzyl)phenol In a nitrogen stream, an n-butyllithium hexane solution (2.71 M, 3.8 mL) was added dropwise to a solution of 1-benzyloxy-2-bromobenzene (2.5 g, 9.5 mmol) in THF (90 mL) at −78° C. and the mixture solution was stirred at the same temperature for 30 minutes. To this mixture, a solution of 4-ethoxybenzaldehyde (1.29 mL, 1.86 mmol) in THF (30 mL) was added dropwise at −78° C. The reaction mixture was stirred at the same temperature for two hours, and then water was added thereto and the mixture was extracted with ethyl acetate. The organic layer was washed with a saturated sodium chloride aqueous solution and dried (anhydrous magnesium sulfate), and then the solvent was distilled under reduced pressure and the obtained residue was treated by silica gel column chromatography [developing solution=ethyl acetate:n-hexane (1:5)]. To a methanol solution (26.8 mL) of the obtained crude product, a 20% palladium hydroxide catalyst (147 mg) was added and furthermore 36% HCl (0.4 mL) was added thereto. The mixture was stirred under a hydrogen atmosphere for 24 hours, and then the catalyst was filtered off. The solvent was distilled under reduced pressure and the obtained residue was purified by silica gel column chromatography [developing solution=ethyl acetate:n-hexane (1:5)] to obtain the title compound (828.1 mg, 38%).

$^1$H-NMR (CDCl$_3$) δ: 1.39 (3H, t, J=7.0 Hz), 3.93 (2H, s), 3.99 (2H, q, J=7.0 Hz), 6.77-6.90 (4H, m), 7.09-7.14 (4H, m)

(2) Synthesis of [2-(4-Ethoxybenzyl)phenyl]-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-ethoxybenzyl)phenol (319.6 mg, 1.4 mmol) in toluene (3.2 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in methanol (5 mL) and a 20% palladium hydroxide catalyst (56 mg) was added thereto, and the reaction mixture was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (133.5 mg, 36%).

$^1$H-NMR (CD$_3$OD) δ: 0.89-1.03 (1H, m), 1.35 (3H, t, J=7.1 Hz), 1.48-1.62 (1H, m), 2.02-2.11 (1H, m), 3.18-3.33 (3H, m), 3.35 (2H, s), 3.44-3.52 (2H, m), 3.68-3.74 (1H, m), 3.81-4.02 (4H, m), 4.13-4.23 (1H, m), 6.74-6.87 (4H, m), 6.99-7.17 (4H, m)

MS (ESI$^+$): 411 [M+Na]$^+$

HPLC Retention Time: 11.4 minutes

Example 35

[2-(4-Difluoromethoxybenzyl)phenyl]-5a-carba-β-D-gluco-pyranoside (1) Synthesis of 2-(4-Difluoromethoxybenzyl)phenol In a nitrogen stream, an n-butyllithium hexane solution (2.71 M, 3.8 mL) was added dropwise to a solution of 1-benzyloxy-2-bromobenzene (2.5 g, 9.5 mmol) in THF (90 mL) at −78° C. and the mixture solution was stirred at the same temperature for 30 minutes. To this solution, a solution of 4-difluoromethoxybenzaldehyde (1.23 mL, 1.86 mmol) in THF (30 mL) was added dropwise at −78° C. The reaction mixture was stirred at the same temperature for two hours, and then water was added thereto and the mixture was extracted with ethyl acetate. The organic layer was washed with a saturated sodium chloride aqueous solution and dried (anhydrous magnesium sulfate), and then the solvent was distilled under reduced pressure and the obtained residue was treated by silica gel column chromatography [developing solution=ethyl acetate:n-hexane (1:5)] to obtain a crude product. To a solution of the obtained crude product in methanol (26.8 mL), a 20% palladium hydroxide catalyst (147 mg) was added and furthermore concentrated hydrochloric acid (0.4 mL) was added thereto. The mixture solution was stirred under a hydrogen atmosphere for 24 hours, and then the catalyst was filtered off. The solvent was distilled under reduced pressure and the obtained residue was purified by silica gel column chromatography [developing solution=ethyl acetate:n-hexane (1:5)] to obtain the title compound (1.03 g, 42%).

$^1$H-NMR (CDCl$_3$) δ: 3.97 (2H, s), 6.46 (1H, t, J=74.4 Hz), 6.77 (1H, d, J=8.0 Hz), 6.87-6.91 (1H, t, J=7.3 Hz), 7.03 (2H, d, J=8.4 Hz), 7.09-7.15 (2H, m), 7.21 (2H, d, J=8.0 Hz)

(2) Synthesis of [2-(4-Difluoromethoxybenzyl)phenyl]-5a-carba-β-D-glucopyranoside In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-di-fluoromethoxybenzyl)phenol (350.0 mg, 1.4 mmol) in toluene (3.2 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in methanol (5 mL) and a 20% palladium hydroxide catalyst (69 mg) was added thereto, and the mixture solution was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (153.1 mg, 40%).

$^1$H-NMR (CD$_3$OD) δ: 0.87-1.01 (1H, m), 1.48-1.62 (1H, m), 2.01-2.11 (1H, m), 3.17-3.34 (2H, m), 3.43-3.54 (2H, m), 3.67-3.73 (1H, m), 3.96 (2H, dd, J=22.9, 14.7 Hz), 4.14-4.26 (1H, m), 6.72 (1H, t, J=74.5 Hz), 6.83-7.25 (8H, m)

MS (ESI$^+$): 433 [M+Na]$^+$
HPLC Retention Time: 11.6 minutes

Example 36

[2-(4-tert-Butylbenzyl)phenyl]-5a-carba-β-D-glucopyranoside (1) Synthesis of (2-Benzyloxyphenyl)-(4-tert-butylphenyl)methanol In a nitrogen stream, an n-butyllithium hexane solution (2.44 M, 5.65 mL) was added dropwise to a solution of 1-benzyloxy-2-bromobenzene (3.3 g, 12.5 mmol) in THF (126 mL) at −78° C. and the mixture solution was stirred at the same temperature for 30 minutes. To this solution, a solution of 4-tert-butylbenzaldehyde (1.68 g, 10.4 mmol) in THF (42 mL) was added at −78° C. The reaction mixture was stirred at the same temperature for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.17 g, 60%).

$^1$H-NMR (CDCl$_3$) δ: 1.32 (9H, s), 2.86 (1H, br s), 5.02 (2H, s), 6.03 (1H, s), 6.03-7.00 (2H, m), 7.13-7.39 (11H, m)

(2) Synthesis of 2-(4-tert-Butylbenzyl)phenol

To a solution of (2-benzyloxyphenyl)-(4-tert-butylphenyl)methanol (2.17 g, 6.26 mmol) in methanol (27 mL), a 20% palladium hydroxide catalyst (217 mg) was added and furthermore 2N—HCl (0.52 mL) was added thereto. The mixture was stirred under a hydrogen atmosphere for 24 hours, and then the catalyst was filtered off. The solvent was distilled and the obtained residue was purified by silica gel column chromatography [developing solution=ethyl acetate:n-hexane (1:10)] to obtain the title compound (1.3 g, 86%).

$^1$H-NMR (CDCl$_3$) δ: 1.29 (9H, s), 3.96 (2H, s), 4.65 (1H, s), 6.75-6.91 (2H, m), 7.09-7.32 (6H, m)

(3) Synthesis of [2-(4-tert-Butylbenzyl)phenyl]-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-tert-butylbenzyl)phenol (334 mg, 1.39 mmol) in toluene (2 mL) under cooling with ice, and then tetramethylazodicarboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:1) mixed solvent (12 mL) and a 20% palladium hydroxide catalyst (60 mg) was added thereto, and the mixture was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (57 mg, 15%).

$^1$H-NMR (CD$_3$OD) δ: 0.89-1.01 (1H, m), 1.29 (9H, s), 1.53-1.59 (1H, m), 2.04-2.11 (1H, m), 3.19-3.34 (2H, m), 3.45-3.51 (2H, m), 3.71 (1H, dd, J=10.8, 4.5 Hz), 3.95 (2H, m), 4.19 (1H, m), 6.84 (1H, m), 7.01-7.17 (5H, m), 7.26-7.28 (2H, m)

MS (ESI$^+$): 401 [M+H]$^+$
HPLC Retention Time: 13.7 minutes

Example 37

[2-(4-Methylbenzyl)phenyl]-5a-carba-β-D-glucopyranoside (1) Synthesis of (2-Benzyloxyphenyl)-p-tolylmethanol In a nitrogen stream, an n-butyllithium hexane solution (2.44 M, 5.65 mL) was added dropwise to a solution of 1-benzyloxy-2-bromobenzene (3.3 g, 12.54 mmol) in THF (126 mL) at −78° C. and the mixture was stirred at the same temperature for 30 minutes. To this mixture, a solution of 4-methylbenzaldehyde (1.28 g, 10.6 mmol) in THF (42 mL) was added at −78° C. The reaction mixture was stirred at the same temperature for one hour, and then water was added thereto and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.3 g, 71%).

$^1$H-NMR CDCl$_3$) δ: 2.33 (3H, s), 2.87 (1H, s), 5.02 (2H, s), 6.03 (1H, s), 6.09-6.99 (2H, m), 7.09-7.34 (11H, m)

(2) Synthesis of 2-(4-Methylbenzyl)phenol

To a solution of (2-benzyloxyphenyl)-p-tolylmethanol (1.5 g, 4.43 mmol) in methanol (27 mL), a 20% palladium hydroxide catalyst (150 mg) was added and furthermore 2N—HCl (0.37 mL) was added thereto. The mixture was stirred under a hydrogen atmosphere for 24 hours, and then the catalyst was filtered off. The solvent was distilled under reduced pressure and the obtained residue was purified by silica gel column chromatography [developing solution=ethyl acetate:n-hexane (1:10)] to obtain the title compound (617 mg, 70%).

$^1$H-NMR (CDCl$_3$) δ: 1.55 (3H, s), 3.95 (2H, s), 4.65 (1H, s), 6.75-6, 90 (2H, m), 7.09-7.25 (6H, m)

(3) Synthesis of [2-(4-Methylbenzyl)phenyl]-5a-carba-β-D-glucopyranoside

In a nitrogen stream, 2,3,4,6-tetra-O-benzyl-5a-carba-α-D-glucopyranose (500 mg, 0.93 mmol) and tributyl-phosphine (0.35 mL, 1.39 mmol) were added to a solution of 2-(4-methylbenzyl)phenol (275 mg, 1.39 mmol) in toluene (2 mL) under cooling with ice, and then tetramethylazodi-carboxamide (TMAD, 239 mg, 1.39 mmol) was added thereto at the same temperature. The reaction mixture was stirred for 20 hours while gradually raising its temperature to room temperature. The reaction mixture was concentrated under reduced pressure, and the obtained residue was treated by silica gel column chromatography [developing solution=ethyl acetate:n-hexane (1:10)]. The obtained crude product was dissolved in a methanol-THF (1:1) mixed solvent (8 mL) and a 20% palladium hydroxide catalyst (44 mg) was added thereto, and the mixture was stirred under a hydrogen atmosphere for 24 hours, and then the catalyst was filtered off. The solvent was distilled under reduced pressure and the obtained residue was purified by silica gel column chromatography [developing solution=methylene chloride:methanol (10:1)] to obtain the title compound (20 mg, 6%).

$^1$H-NMR (CD$_3$OD) δ: 0.84-0.97 (1H, m), 1.44-2.03 (1H, m), 1.96-2.03 (1H, m), 2.22 (3H, s), 3.13-3.30 (2H, m), 3.39-3.46 (2H, m), 3.64 (1H, dd, J=10.8, 4.5 Hz), 3.95 (2H, m), 4.12 (1H, m), 6.76-6.81 (1H, m), 6.92-7.03 (5H, m), 7.06-7.11 (2H, m)

MS (ESI$^+$): 381 [M+Na]$^+$

HPLC Retention Time: 11.4 minutes

Example 38

[2-(4-Methoxybenzyl)-5-trifluoromethylthiophen-3-yl]-5a-carba-β-D-glucopyranoside

(1) Synthesis of 3-Benzyloxy-2-(4-methoxybenzyl)-5-tri-fluoromethylthiophene To a solution of (3-benzyloxy-5-trifluoromethylthiophen-2-yl)-(4-methoxy-phenyl)methanone (220.2 mg, 0.56 mmol) as synthesized by the method described in International Publication No. WO04/007517 and triethylsilane (1.34 mL, 8.41 mmol) in dichloromethane (1.1 mL), trifluoroacetic acid (3 mL) was added at 0° C. in a nitrogen stream over five minutes. The reaction mixture was stirred at the same temperature for 6.75 hours, and then triethylsilane (0.9 mL, 5.61 mmol) was added thereto. The reaction mixture was stirred at the same temperature for 16.75 hours, and then concentrated under reduced pressure. The obtained residue was purified by silica gel column chromatography [developing solution=ethyl acetate:n-hexane (1:10)] to obtain the title compound (108.8 mg, 51%).

$^1$H-NMR (CDCl$_3$) δ: 3.79 (3H, s), 3.96 (2H, s), 5.04 (2H, s), 6.82 (2H, d, J=8.6 Hz), 7.11 (2H, d, J=8.6 Hz), 7.16 (1H, s), 7.30-7.41 (5H, m)

(2) Synthesis of 2-(4-Methoxybenzyl)-5-trifluoromethyl-thiophen-3-ol

To a solution of (3-benzyloxy-2-(4-methoxybenzyl)-5-trifluoromethylthiophene (170.5 mg, 0.45 mmol) in dichloromethane (4.5 mL), a solution of boron tribromide-dimethylsulfide complex in dichloromethane (0.47 mL, 0.47 mmol) was added at −78° C. in a nitrogen stream. The reaction mixture was stirred at the same temperature for five minutes and then at 0° C. for 11 hours. To the reaction mixture, water was added and the resulting mixture was extracted with methylene chloride. The organic layer was washed with a saturated sodium hydrogencarbonate aqueous solution and a saturated sodium chloride aqueous solution and dried (anhydrous sodium sulfate), and then the solvent was distilled under reduced pressure. The obtained residue was purified by silica gel column chromatography [developing solution=ethyl acetate:n-hexane (1:5)] to obtain the title compound (117.0 mg, 90%).

$^1$H-NMR (CDCl$_3$) δ: 3.80 (3H, s), 3.97 (2H, s), 4.47 (1H, s), 6.87 (2H, d, J=8.6 Hz), 6.98 (1H, s), 7.19 (2H, d, J=8.6 Hz)

(3) Synthesis of [2-(4-Methoxybenzyl)-5-trifluoromethyl-thiophen-3-yl]-2,3,4,6-tetra-O-benzyl-5a-carba-β-D-glucopyranoside In a nitrogen stream, 2,3,4,6-tetra-O-benzyl-5a-carba-α-D-glucopyranose (146 mg, 0.27 mmol) and tributyl-phosphine (0.10 mL, 0.41 mmol) were added to a solution of 2-(4-methylbenzyl)-5-trifluoromethylthiophen-3-ol (117 mg, 0.41 mmol) in toluene (0.85 mL) under cooling with ice, and then tetramethylazodicarboxamide (TMAD, 70 mg, 0.41 mmol) was added thereto at the same temperature. The reaction mixture was stirred at room temperature for 18.5 hours. The reaction mixture was treated by silica gel column chromatography [developing solution=ethyl acetate: n-hexane (1:10 to 1:8)]. The obtained product was purified by preparative TLC [developing solution=ethyl acetate:n-hexane (1:8)] to obtain the title compound (47.2 mg).

$^1$H-NMR (CDCl$_3$) δ: 1.56-1.80 (2H, m), 1.96-2.10 (1H, m), 3.40-3.70 (5H, m), 3.75 (3H, s), 3.96 (2H, s), 3.96-4.16 (1H, m), 4.44 (2H, s), 4.53 (1H, d, J=11.0 Hz), 4.70-5.00 (5H, m), 6.79 (2H, d, J=8.6 Hz), 7.06-7.38 (23H, m)

(4) Synthesis of [2-(4-Methoxybenzyl)-5-trifluoromethyl-thiophen-3-yl]-5a-carba-β-D-glucopyranoside In a nitrogen stream, [2-(4-methoxybenzyl)-5-tri-fluoromethylthiophen-3-yl]-2,3,4,6-tetra-O-benzyl-5a-carba-β-D-glucopyranoside (45.2 mg, 0.056 mmol) was dissolved in methylene chloride (0.5 mL), and dimethylsulfide (0.145 mL, 3.35 mmol) and a boron trifluoride-diethyl ether complex (0.07 mL, 0.56 mmol) were added thereto under cooling with ice. The reaction mixture was stirred at the same temperature for five minutes and then at room temperature for 19 hours, and then a saturated sodium hydrogencarbonate aqueous solution and water were added thereto under cooling with ice and extracted with methylene chloride. The organic layer was washed with a saturated sodium chloride aqueous solution and dried (anhydrous sodium sulfate), and then the solvent was distilled under reduced pressure. The obtained residue was purified by TLC [developing solution=n-hexane:acetone (1:1)] to obtain the title compound (12.2 mg, 49%).

$^1$H-NMR (CD$_3$OD) δ: 1.15-1.35 (1H, m), 1.40-1.65 (1H, m), 1.95-2.15 (1H, m), 3.15-3.35 (2H, m), 3.35-3.60 (2H, m), 3.65-3.80 (1H, m), 3.75 (3H, m), 3.90-4.06 (1H, m), 4.01 (2H, m), 6.84 (2H, d, J=8.3 Hz), 7.16 (2H, d, J=8.3 Hz), 7.40 (1H, s)

MS (ESI$^+$): 448 [M]$^+$

HPLC Retention Time: 12.4 minutes

Example 39

[3-Methoxy-2-(4-methoxybenzyl)phenyl]-5a-carba-β-D-gluco-pyranoside (1) Synthesis of 2-Benzyloxy-6-methoxybenzoic Acid Benzyl Ester While stirring a mixture of 6-methoxysalicylic acid (5.07 g, 30.15 mmol) and sodium hydride (60% w/w, 3.02 g, 75.38 mmol) under cooling with ice, DMF (30 mL) was added thereto. The mixture solution was stirred at the same temperature for 10 minutes, and then benzyl bromide (8.95 mL, 75.38 mmol) was added thereto over 5 minutes and the reaction mixture was stirred at the same temperature for 30 minutes and at room temperature for 2.5 hours. To the reaction mixture was added a saturated ammonium chloride aqueous solution and water under cooling with ice, and the mixture was extracted with ether. The organic layer was washed with water and a saturated ammonium chloride aqueous solution and dried (anhydrous sodium sulfate), and then the solvent was distilled under reduce pressure. The obtained residue was purified by silica gel column chromatography [developing solution=ethyl acetate:n-hexane (1:10 to 1:5)] to obtain the title compound (6.24 g, 59%).

$^1$H-NMR (CDCl$_3$) δ: 3.81 (3H, s), 5.08 (2H, s), 5.35 (2H, s), 6.55 (1H, d, J=5.9 Hz), 6.58 (1H, d, J=5.9 Hz), 7.15-7.45 (11H, m)

(2) (2-Benzyloxy-6-methoxyphenyl)methanol

In a nitrogen stream, to a suspension of lithium aluminum hydride (0.88 g, 23.14 mmol) in ether (35 mL), a solution of 2-benzyloxy-6-methoxybenzoic acid benzyl ester (6.2 g, 17.80 mmol) in ether (20 mL) was added at room temperature over 15 minutes. The reaction mixture was stirred for two hours under heating to reflux. Ethyl acetate (2 mL) was added dropwise to the reaction mixture under cooling with ice and then a saturated Rochelle salt aqueous solution (20 mL) was added dropwise thereto and the mixture was stirred at room temperature for 20 hours. The reaction mixture was subjected to Celite filtration and to the filtrate was added a saturated Rochelle salt aqueous solution (15 mL) and the mixture was extracted with ether. The organic layer was washed with a saturated sodium chloride aqueous solution and dried (anhydrous sodium sulfate), and then the solvent was distilled under reduced pressure. The obtained residue was purified by silica gel column chromatography [developing solution=ether: n-hexane (1:1)] to obtain the title compound (4.75 g, 100%).

$^1$H-NMR (CDCl$_3$) δ: 2.48 (1H, t, J=6.8 Hz), 3.85 (3H, s), 4.84 (2H, d, J=6.8 Hz), 5.10 (2H, s), 6.58 (1H, d, J=8.4 Hz), 6.62 (1H, d, J=8.2 Hz), 7.20 (1H, dd, J=8.4, 8.2 Hz), 7.28-7.47 (5H, m)

(3) Synthesis of (2-Benzyloxy-6-methoxyphenyl)-(4-methoxyphenyl)methanol

In a nitrogen stream, a solution of (2-benzyloxy-6-methoxyphenyl)-methanol (3.52 g, 14.41 mmol) and N-methyl-morpholine N-oxide (NMO, 2.53 g, 21.61 mmol) in dichloromethane (14.5 mL) was cooled in a water bath, and tetra-n-propylammonium perruthenate (TPAP, 152 mg, 0.43 mmol) was added thereto. The reaction mixture was stirred for 20 minutes at the same temperature and at room temperature for 1.75 hours, and then subjected to Celite filtration and the solvent was distilled under reduced pressure. The obtained residue was treated by silica gel column chromatography [developing solution=ethyl acetate: n-hexane (1:3 to 1:2.5)]. The obtained compound was dissolved in THF and cooled in a water bath, and a solution of 4-methoxyphenylmagnesium bromide in THF (0.5 M, 30.3 mL) was added dropwise thereto in a nitrogen stream. The reaction mixture was stirred at room temperature for 1.25 hours, and then a saturated ammonium chloride aqueous solution was added thereto at room temperature and the mixture was extracted with ether. The organic layer was washed with a saturated ammonium chloride aqueous solution and dried (anhydrous sodium sulfate), and then the solvent was distilled under reduce pressure. The obtained residue was purified by silica gel column chromatography [developing solution=ethyl acetate:n-hexane (1:4 to 1:3.5)] to obtain the title compound (3.66 g, 72%).

$^1$H-NMR (CDCl$_3$) δ: 3.78 (3H, s), 3.81 (3H, s), 4.28 (1H, d, J=11.7 Hz), 4.99 (1H, d, J=11.5 Hz), 5.06 (1H, d, J=11.5 Hz), 6.33 (1H, d, J=11.7 Hz), 6.61 (1H, d, J=7.6 Hz), 6.64 (1H, d, J=7.6 Hz), 6.80 (2H, d, J=8.7 Hz), 7.10-7.40 (8H, m)

(4) 3-Methoxy-2-(4-methoxybenzyl)phenol

To a solution of (2-benzyloxy-6-methoxyphenyl)-(4-methoxyphenyl)-methanol (2.13 g, 6.08 mmol) in methanol (50 mL), a 20% palladium hydroxide catalyst (0.32 g) was added and furthermore 2N—HCl (1.8 mL) was added thereto. The reaction mixture was stirred under a hydrogen atmosphere for 24 hours, and then the catalyst was filtered off. The solvent was distilled under reduced pressure and the obtained residue was purified by silica gel column chromatography [developing solution=ethyl acetate:n-hexane (1:4)] to obtain the title compound (1.31 g, 89%).

$^1$H-NMR (CDCl$_3$) δ: 3.76 (3H, s), 3.82 (3H, s), 3.98 (2H, s), 4.67 (1H, s), 6.45 (1H, d, J=8.1 Hz), 6.52 (1H, d, J=8.2 Hz), 6.79 (1H, d, J=8.6 Hz), 7.07 (1H, dd, J=8.1, 8.2 Hz), 7.17 (1H, d, J=8.6 Hz)

(5) Synthesis of [3-Methoxy-2-(4-methoxybenzyl)phenyl]-5a-carba-β-D-glucopyranoside In a nitrogen stream, to a solution of 3-methoxy-2-(4-methoxybenzyl)phenol (343 mg, 1.40 mmol) in toluene-THF mixed solvent (toluene 2.5 mL, THF 0.3 mL), 2,3,4,6-tetra-O-benzyl-5a-carba-α-D-glucopyranose (504 mg, 0.94 mmol) and tributylphosphine (0.35 mL, 1.40 mmol) were added under cooling with ice, and tetramethylazodicarboxamide (TMAD, 242 mg, 1.40 mmol) was added thereto at the same temperature. The reaction mixture was stirred for 1.25 hours under cooling with ice and then at room temperature for 22 hours. The reaction mixture was treated by silica gel column chromatography [developing solution=ethyl acetate:n-hexane (1:10 to 1:5)]. The obtained crude product was dissolved in a methanol-THF (1:4) mixed solution (10 mL), and a 20% palladium hydroxide catalyst (94 mg) was added thereto and the mixture solution was stirred under a hydrogen atmosphere for 5 hours, and then the catalyst was filtered off. The solvent was distilled under reduced pressure and the obtained residue was purified by silica gel column chromatography [developing solution=methylene chloride:methanol (15:1 to 10:1)] to obtain the title compound (121 mg, 32%).

$^1$H-NMR (CD$_3$OD) δ: 0.85-1.05 (1H, m), 1.40-1.65 (1H, m), 1.95-2.15 (1H, m), 3.10-3.30 (2H, m), 3.40-3.55 (2H, m), 3.60-3.75 (1H, m), 3.71 (3H, s), 3.79 (3H, s), 3.92 (2H, s), 4.05-4.25 (1H, m), 6.59 (1H, d, J=8.2 Hz), 6.65-6.75 (3H, m), 7.05-7.15 (3H, m)

MS (ESI$^+$): 405 [M+H]$^+$

HPLC Retention Time: 10.6 minutes

Example 40

[2-(4-Methoxybenzyl)-3-methylphenyl]-5a-carba-β-D-gluco-pyranoside (1) Synthesis of (2-Benzyloxy-6-methoxyphenyl)methanol In a nitrogen stream, to a suspension of lithium aluminum hydride (0.82 g, 21.50 mmol) in ether (30 mL), a solution of 2-benzyloxy-6-methyl-benzoic acid ethyl ester (4.47 g, 16.54 mmol) in ether (15 mL) was added at room temperature over 10 minutes. The reaction mixture was stirred under heating to reflux for one hour. Ethyl acetate (2 mL) was added dropwise to the reaction mixture under cooling with ice, and then a saturated Rochelle salt aqueous solution (20 mL) was added thereto dropwise and the mixture was stirred at room temperature for one hour. The reaction mixture was subjected to Celite filtration. To the filtrate was added a saturated Rochelle salt aqueous solution (10 mL) and the mixture was extracted with ether. The organic layer was washed with a saturated sodium chloride aqueous solution and dried (anhydrous sodium sulfate), and then the solvent was distilled under reduced pressure. The obtained residue was purified by silica gel column chromatography [developing solution=ethyl acetate:n-hexane (1:4)] to obtain the title compound (3.84 g, 100%).

$^1$H-NMR (CDCl$_3$) δ: 2.20 (1H, d, J=6.6 Hz), 2.40 (3H, s), 4.79 (2H, d, J=6.6 Hz), 5.11 (2H, s), 6.83 (2H, d, J=7.9 Hz), 7.15 (1H, t, J=7.9 Hz), 7.25-7.50 (5H, m)

(2) Synthesis of 2-Benzyloxy-6-methylbenzaldehyde

In a nitrogen stream, a solution of (2-benzyloxy-6-methoxyphenyl)-methanol (3.46 g, 15.16 mmol) and N-methyl-morpholine N-oxide (NMO, 2.66 g, 22.73 mmol) in dichloromethane (10 mL) was cooled in a water bath and tetra-n-propyl-ammonium perruthenate (TPAP, 152 mg, 0.43 mmol) was added thereto. The reaction mixture was stirred at the same temperature for 1.75 hours, and then subjected to Celite filtration and the solvent was distilled under reduce pressure. The obtained residue was purified by silica gel column chromatography [developing solution=ethyl acetate: n-hexane (1:5)] to obtain the title compound (3.08 g, 90%).

$^1$H-NMR (CDCl$_3$) δ: 2.59 (3H, s), 5.16 (2H, s), 6.82 (1H, d, J=7.3 Hz), 6.90 (1H, d, J=8.4 Hz), 7.25-7.50 (6H, m), 10.73 (1H, s)

(3) Synthesis of (2-Benzyloxy-6-methylphenyl)-(4-methoxyphenyl)methanol

In a nitrogen stream, a solution of 2-benzyloxy-6-methoxybenzaldehyde (3.08 g, 13.6 mmol) in THF (10 mL) was cooled in a water bath, and a solution of 4-methoxyphenyl-magnesium bromide THF (0.5 M, 30.3 mL) was added dropwise thereto. The mixture solution was stirred at room temperature for 1.75 hours, and then a saturated ammonium chloride aqueous solution was added thereto under cooling with ice and the mixture was extracted with ether. The organic layer was washed with a saturated ammonium chloride aqueous solution and dried (anhydrous sodium sulfate), and then the solvent was distilled under reduced pressure. The obtained residue was purified by silica gel column chromatography [developing solution=ethyl acetate:n-hexane (1:6 to 1:5)] to obtain the title compound (4.75 g, 100%).

$^1$H-NMR (CDCl$_3$) δ: 2.38 (3H, s), 3.80 (3H, s), 4.09 (1H, d, J=11.2 Hz), 4.88 (1H, d, J=11.5 Hz), 5.00 (1H, d, J=11.5 Hz), 6.03 (1H, d, J=11.2 Hz), 6.75-6.90 (4H, m), 6.90-7.05 (2H, m), 7.10-7.35 (6H, m)

(4) Synthesis of 2-(4-Methoxybenzyl)-3-methylphenol

To a solution of (2-benzyloxy-6-methylphenyl)-(4-methoxyphenyl)-methanol (2.39 g, 7.15 mmol) in methanol (50 mL), a 20% palladium hydroxide catalyst (0.36 g) was added and furthermore 36% HCl (0.36 mL) was added thereto. The mixture was stirred under a hydrogen atmosphere for 11 hours, and then the catalyst was filtered off. The solvent was distilled under reduced pressure and the obtained residue was purified by silica gel column chromatography [developing solution=ethyl acetate:n-hexane (1:5)] to obtain the title compound (1.40 g, 86%).

$^1$H-NMR (CDCl$_3$) δ: 2.28 (3H, s), 3.76 (3H, s), 3.99 (2H, s), 4.61 (1H, s), 6.67 (1H, d, J=8.1 Hz), 6.70-6.85 (3H, m), 6.95-7.15 (3H, m)

(5) Synthesis of [2-(4-Methoxybenzyl)-3-methylphenyl]-5a-carba-β-D-glucopyranoside In a nitrogen stream, to a solution of 2-(4-methoxy-benzyl)-3-methylphenol (318 mg, 1.39 mmol) toluene-THF mixed solvent (toluene 1 mL, THF 0.1 mL), 2,3,4,6-tetra-O-benzyl-5a-carba-α-D-glucopyranose (500 mg, 0.93 mmol) and tributylphosphine (0.35 mL, 1.39 mmol) were added under cooling with ice, and tetramethylazodicarboxamide (TMAD, 242 mg, 1.40 mmol) was added thereto at the same temperature. The reaction mixture was stirred for 10 minute under cooling with ice and then at room temperature for 23 hours. The reaction mixture was treated by silica gel column chromatography [developing solution=ethyl acetate:n-hexane (1:7 to 1:6)]. The obtained crude product was dissolved in a methanol-THF (1:3) mixed solvent (4 mL), and a 20% palladium hydroxide catalyst (66 mg) was added thereto and the mixture solution was stirred under a hydrogen atmosphere for 6.5 hours, and then the catalyst was filtered off. The solvent was distilled under reduced pressure and the obtained reside was purified by silica gel column chromatography [developing solution=methylene chloride:methanol (10:1)] to obtain the title compound (55 mg, 15%).

$^1$H-NMR (CD$_3$OD) δ: 0.85-1.05 (1H, m), 1.45-1.65 (1H, m), 2.00-2.15 (1H, m), 2.21 (3H, s), 3.15-3.30 (2H, m), 3.40-3.55 (2H, m), 3.65-3.75 (1H, m), 3.72 (3H, s), 3.94 (1H, d, J=15.0 Hz), 4.06 (1H, d, J=15.0 Hz), 4.05-4.20 (1H, m), 6.70-6.80 (3H, m), 6.91 (1H, d, J=8.2 Hz), 6.95-7.10 (3H, m)

MS (ESI$^+$): 411 [M+Na]$^+$

HPLC Retention Time: 11.2 minutes

Example 41

[2-(3-Fluoro-4-methoxybenzyl)phenyl]-5a-carba-α-D-glucopyranoside (1) Synthesis of (2-Benzyloxyphenyl)-(3-fluoro-4-methoxyphenyl)methanol In a nitrogen stream, an n-butyllithium hexane solution (1.54 M, 6.79 mL) was added dropwise to a solution of 1-benzyloxy-2-bromobenzene (2.5 g, 9.50 mmol) in THF (30 mL) at −78° C. and the mixture was stirred at the same temperature for 30 minutes. To this solution, a solution of 3-fluoro-4-methoxybenzaldehyde (1.32 g, 8.56 mmol) in THF (8 mL) was added dropwise at −78° C. The mixture was stirred at the same temperature for one hour, and then a saturated ammonium chloride aqueous solution was added thereto and the mixture was extracted with ethyl acetate, and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (2.79 g, 96%).

$^1$H-NMR (CDCl$_3$) δ: 2.92 (1H, d, J=5.8 Hz), 3.87 (3H, s), 5.03 (2H, s), 5.98 (1H, d, J=6.0 Hz), 6.85-7.10 (5H, m), 7.21-7.35 (7H, m).

(2) Synthesis of 2-(3-Fluoro-4-methoxybenzyl)phenol

To a (2-benzyloxyphenyl)-(3-fluoro-4-methoxyphenyl)-methanol (1.50 g, 4.43 mmol) methanol solution (29 mL), a 20% palladium hydroxide catalyst (150 mg) was added, and furthermore 2N—HCl (2 mL) was added thereto. The mixture was stirred under a hydrogen atmosphere for 15 hours, and then the catalyst was filtered off. The solvent was distilled under reduced pressure and the obtained residue was purified by silica gel column chromatography [developing solution=ethyl acetate:n-hexane (1:5)] to obtain the title compound (0.95 g, 92%).

$^1$H-NMR (CDCl$_3$) δ: 3.85 (3H, s), 3.91 (2H, s), 4.69 (1H, br s), 6.77 (1H, dd, J=1.1, 8.0 Hz), 6.84-6.97 (4H, m), 7.09-7.16 (2H, m)

(3) Synthesis of [2-(3-Fluoro-4-methoxybenzyl)phenyl]-5a-carba-β-D-glucopyranoside In a nitrogen stream, to a solution of 2-(3-fluoro-4-methoxybenzyl)phenol (323 mg, 1.39 mmol) in toluene (3 mL), 2,3,4,6-tetra-O-benzyl-5a-carba-α-D-glucopyranose (500 mg, 0.93 mmol) and tributylphosphine (0.35 mL, 1.39 mmol) were added under cooling with ice, and tetramethylazodicarboxamide (TMAD, 242 mg, 1.40 mmol) was added thereto at the same temperature. The reaction mixture was stirred for 40.5 hours while gradually raising its temperature to room temperature. The reaction mixture was treated by silica gel column chromatography [developing solution=ethyl acetate:n-hexane (1:6)]. The obtained crude product was dissolved in a methanol-THF (1:2) mixed solvent (6 mL), and a 20% palladium hydroxide catalyst (65 mg) was added thereto and the mixture was stirred under a hydrogen atmosphere for two hours, and then the catalyst was filtered off. The solvent was distilled under reduced pressure and the obtained reside was purified by silica gel column chromatography [developing solution=methylene chloride:methanol (10:1)] to obtain the title compound (78 mg, 21%).

$^1$H-NMR (CD$_3$OD) δ: 0.85-1.05 (1H, m), 1.40-1.65 (1H, m), 1.95-2.15 (1H, m), 3.35-3.60 (2H, m), 3.60-4.00 (3H, m), 3.81 (3H, s), 4.05-4.25 (1H, m), 6.70-7.20 (7H, m)

MS (ESI$^+$): 392 [M]$^+$

HPLC Retention Time: 10.7 minutes

Example 42

[4-(4-Cyclopropylbenzyl)pyridin-3-yl]-5a-carba-β-D-gluco-pyranoside

(1) Synthesis of 3-(2-Trimethylsilylethoxymethoxy)-pyridine

Sodium hydride (3.85 g, 96.3 mmol) was washed with hexane and dimethoxyethane (90 mL) was added thereto. 3-Hydroxypyridine (4.97 g, 52.3 mmol) was added to the obtained mixture under cooling with ice over 10 minutes and the reaction mixture was stirred for 10 minutes, and then 2-(trimethylsilyl)ethoxymethyl chloride (10.0 mL, 56.5 mmol) was added thereto under cooling with ice over 25 minutes. The reaction mixture was stirred at room temperature for 14.5 hours. Under cooling with ice, to the reaction mixture was added water and the mixture was extracted with ether and the organic layer was dried over anhydrous magnesium sulfate and concentrated under reduced pressure. The obtained residue was purified by silica gel flash column chromatography [developing solution=n-hexane:ethyl acetate (3:1)] to obtain the title product (10.8 g, 92%).

$^1$H-NMR (CDCl$_3$) δ: 0.00 (9H, s), 0.93-0.98 (2H, m), 3.73-3.79 (2H, m), 5.24 (2H, s), 7.18-7.23 (1H, m), 7.34-7.38 (1H, m), 8.25 (1H, dd, J=4.7, 1.4 Hz), 8.40 (1H, dd, J=3.0, 0.6 Hz)

(2) Synthesis of (4-Cyclopropylphenyl)-[3-(2-trimethyl-silylethoxymethoxy)pyridin-4-yl]methanol In a nitrogen stream, a t-butyllithium n-pentane solution (1.47 M, 6.20 mmol) was added dropwise to a solution of 3-(2-trimethylsilylethoxymethoxy)pyridine (1.77 g, 7.85 mmol) in anhydrous THF (31 mL) at −78° C. over 25 minutes. The mixture was stirred at −70° C. for one hour, and then a solution of 4-cyclopropylbenzaldehyde (1.49 g, 10.19 mmol) in ether (10 mL) was added thereto over 25 minutes, and the reaction mixture was stirred at −70° C. for two hours and at room temperature for two hours. To the reaction mixture was added a saturated ammonium chloride aqueous solution, and the mixture was extracted with ether, and the organic layer was dried over anhydrous magnesium sulfate. After filtration, the solvent was distilled under reduced pressure, and the obtained residue was purified by silica gel flash column chromatography [developing solution=n-hexane:ethyl acetate (2:1)] to obtain the title product (2.17 g, 74%).

$^1$H-NMR (CDCl$_3$) δ: −0.04 (9H, s), 0.61-0.66 (2H, m), 0.84-0.96 (4H, m), 1.79-1.90 (1H, m), 3.48-3.59 (2H, m), 5.13 (2H, dd, J=22.8, 6.9 Hz), 6.00 (1H, s), 6.97-6.99 (2H, m), 7.20-7.23 (2H, m), 7.48 (1H, d, J=4.9 Hz), 8.18 (1H, d, J=4.9 Hz), 8.27 (1H, s)

(3) Synthesis of (4-Cyclopropylphenyl)-[3-(2-trimethyl-silylethoxymethoxy)pyridin-4-yl]methanone In a nitrogen stream, Dess-Martin Periodinane (2.71 g, 6.39 mmol) was added to a solution of (4-cyclopropyl-phenyl)-[3-(2-trimethylsilylethoxy-methoxy)pyridin-4-yl] methanol (2.17 g, 5.84 mmol) in methylene chloride (31 mL), and the reaction mixture was stirred at room temperature for 1.5 hours. Furthermore, the Dess-Martin Periodinane (0.27 g, 0.64 mmol) was added to the reaction mixture and the obtained mixture was stirred for 1.5 hours. Insolubles were filtered and the filtrate was washed with a saturated sodium hydrogencarbonate aqueous solution and a saturated sodium chloride and dried over anhydrous magnesium sulfate), and then the solvent was distilled under reduced pressure. The obtained residue was purified by amino silica gel column chromatography [developing solution=ethyl acetate:n-hexane (1:1)] to obtain the title product (1.96 g, 91%).

$^1$H-NMR (CDCl$_3$) δ: −0.04 (9H, s), 0.76-0.90 (4H, m), 1.05-1.12 (2H, m), 1.92-1.98 (1H, m), 3.56-3.62 (2H, m), 5.17 (2H, s), 7.09-7.13 (2H, m), 7.19-7.21 (1H, m), 7.67-7.71 (2H, m), 8.40 (1H, d, J=4.67 Hz), 8.65 (1H, s)

(4) Synthesis of (4-Cyclopropylphenyl)-(3-hydroxypyridin-4-yl)methanone p-Toluenesulfonic acid monohydrate (3.03 g, 15.9 mmol) was added to a solution of (4-cyclopropylphenyl)-[3-(2-trimethylsilylethoxymethoxy)pyridin-4-yl]methanone (1.96 g, 5.30 mmol) in THF (49 mL) and the mixture solution was stirred at 65° C. for one hour. The reaction mixture was cooled to room temperature and a saturated sodium hydrogencarbonate aqueous solution was added thereto and the mixture was extracted with ether, and the organic layer was dried over anhydrous magnesium sulfate. After filtration, the solvent was distilled under reduced pressure, and the obtained residue was purified by silica gel flash column chromatography [developing solution=n-hexane:ethyl acetate (2:3)] to obtain the title product (1.10 g, 87%).

$^1$H-NMR (CDCl$_3$) δ: 0.80-0.86 (2H, m), 1.09-1.16 (2H, m), 1.97-2.03 (1H, m), 7.18-7.22 (2H, m), 7.42 (1H, dd, J=5.2, 0.6 Hz), 7.63-7.68 (2H, m), 8.24 (1H, d, J=5.2 Hz), 8.59 (1H, d, J=0.6 Hz), 11.15 (1H, s)

(5) Synthesis of (4-Cyclopropylphenyl)-[3-((1R,2S,3S,4R,5R)-2,3,4-trisbenzyloxy-5-benzyloxymethyl-cyclo-hexyloxy)pyridin-4-yl]methanone In a nitrogen stream, diisopropylazodicarboxylate (0.14 mL, 0.72 mmol) was slowly added dropwise to a mixture of (4-cyclopropylphenyl)-(3-hydroxypyridin-4-yl)methanone (0.18 g, 0.74 mmol), (1S,2S,3S,4R,5R)-2,3,4-trisbenzyloxy-5-benzyloxymethylcyclohexanol (0.20 g, 0.37 mmol), triphenylphosphine (0.19 g, 0.74 mmol) and toluene (1.3 mL) under cooling with ice. The reaction mixture was stirred at room temperature for three hours, and then the solvent was distilled under reduced pressure and the obtained residue was purified by silica gel flash column chromatography [developing solution=n-hexane:ethyl acetate (2:3)] to obtain the title product (0.20 g, 71%).

$^1$H-NMR (CDCl$_3$) δ: 0.67-0.73 (2H, m), 1.00-1.06 (2H, m), 1.39-1.47 (1H, m), 1.81-1.88 (1H, m), 2.09-2.16 (1H, m), 3.37-3.58 (5H, m), 4.36-4.51 (6H, m), 4.76-4.86 (3H, m), 6.98-7.07 (4H, m), 7.13-7.35 (19H, m), 7.62-7.66 (2H, m), 8.34 (1H, d, J=4.9 Hz), 8.54 (1H, s)

(6) Synthesis of (4-Cyclopropylphenyl)-[3-((1R,2S,3S,4R,5R)-2,3,4-trisbenzyloxy-5-benzyloxymethyl-cyclo-hexyloxy)pyridin-4-yl]methanol Sodium borohydride (40 mg, 1.06 mmol) was added to a solution of (4-cyclo-propylphenyl)-[3-((1R,2S,3S,4R,5R)-2,3,4-trisbenzyloxy-5-benzyloxymethylcyclohexyloxy)pyridin-4-yl]methanone (0.20 g, 0.26 mmol) in THF (1.37 mL) and water (0.67 mL) under cooling with ice and the reaction mixture was stirred at room temperature for 14.5 hours. To the reaction mixture, THF was added, and concentrated sulfuric acid (0.2 mL) was added thereto under cooling with ice and the reaction mixture was stirred for 10 minutes. To the obtained reaction mixture was added a saturated sodium hydrogencarbonate aqueous solution and the mixture was stirred at room temperature for 10 minutes. The resulting mixture was extracted with ethyl acetate and the organic layer was dried (anhydrous magnesium sulfate), and then the solvent was distilled under reduced pressure. The obtained residue was purified by silica gel column chromatography [developing solution=ethyl acetate:n-hexane (3:2)] to obtain the title product (0.20 g, 100%) as a diastereomeric mixture.

$^1$H-NMR (CDCl$_3$) δ: 0.47-0.53 (1H, m), 0.58-0.63 (1H, m), 0.80-0.92 (2H, m), 1.09-1.27 (2H, m), 1.68-1.84 (2H, m), 3.32-3.64 (5H, m), 4.34-4.53 (4H, m), 4.70-4.88 (5H, m), 5.84 (0.5H, s), 5.96 (0.5H, s), 6.85-6.97 (3H, m), 7.05-7.35 (21H, m), 7.43-7.48 (1H, m), 8.20-8.24 (2H, m)

MS (ESI$^+$): 762 [M+H]$^+$ (7) Synthesis of 4-[Chloro-(4-cyclopropylphenyl)methyl-3-((1R,2S,3S,4R,5R)-2,3,4-trisbenzyloxy-5-benzyloxymethylcyclohexyloxy)pyridine In a nitrogen stream, thionyl chloride (0.05 mL, 0.68 mmol) was added to a solution of (4-cyclopropylphenyl)-[3-((1R,2S,3S,4R,5R)-2,3,4-trisbenzyloxy-5-benzyloxymethyl-cyclohexyloxy)pyridin-4-yl]methanol (0.20 g, 0.26 mmol) in methylene chloride (3.0 mL) under cooling with ice and the mixture was stirred at room temperature for two hours. To the reaction mixture was added a saturated sodium hydrogencarbonate aqueous solution and the mixture was extracted with methylene chloride and the organic layer was dried (anhydrous magnesium sulfate), and then the solvent was distilled under reduced pressure. The obtained residue was purified by silica gel column chromatography [developing solution=ethyl acetate:n-hexane (1:1)] to obtain the title product (0.20 g, 100%) as a diastereomeric mixture.

$^1$H-NMR (CDCl$_3$) δ: 0.51-0.53 (1H, m), 0.61-0.64 (1H, m), 0.83-0.93 (2H, m), 1.10-1.18 (1H, m), 1.66-1.77 (3H, m), 2.15-2.27 (1H, m), 3.30-3.66 (5H, m), 4.38-4.55 (4H, m), 4.83-4.91 (4H, m), 6.23 (0.5H, s), 6.39 (0.5H, s), 6.85-6.96 (3H, m), 7.11-7.33 (21H, m), 7.54-7.58 (1H, m), 8.26-8.42 (2H, m)

MS (ESI$^+$): 780[M+H]$^+$ (8) Synthesis of 4-(4-Cyclopropylbenzyl)-3-((1R,2S,3S,4R,5R)-2,3,4-trisbenzyloxy-5-benzyloxymethyl-cyclo-hexyloxy)pyridine In a nitrogen stream, zinc (0.14 g, 2.14 mmol) was added to a solution of 4-[chloro-(4-cyclopropylphenyl)-methyl]-3-((1R,2S,3S,4R,5R)-2,3,4-trisbenzyloxy-5-benzyloxymethyl-cyclohexyloxy)pyridine (0.22 g, 0.28 mmol) in methylene chloride (4.1 mL) and acetic acid (12.4 mL), and the mixture solution was stirred at room temperature for 14 hours. To the reaction mixture was added ethyl acetate and the mixture was washed with a saturated hydrogencarbonate aqueous solution and dried (anhydrous magnesium sulfate), and then the solvent was distilled under reduced pressure. The obtained residue was purified by silica gel column chromatography [developing solution=ethyl acetate:n-hexane (1:1)] to obtain the title product (0.14 g, 67%).

$^1$H-NMR (CDCl$_3$) δ: 0.57-0.62 (2H, m), 0.86-0.92 (2H, m), 1.51-1.59 (1H, m), 1.70-1.85 (2H, m), 2.08-2.15 (1H, m), 3.44 (1H, dd, J=9.1, 2.5 Hz), 3.53-3.70 (4H, m), 3.87 (2H, d, J=1.6 Hz), 4.42-4.54 (4H, m), 4.71 (2H, dd, J=17.6, 10.7 Hz), 4.83-4.93 (3H, m), 6.90-7.34 (25H, m), 8.11 (1H, d, J=4.7 Hz), 8.35 (1H, s)

(9) Synthesis of [4-(4-Cyclopropylbenzyl)pyridin-3-yl]-5a-carba-β-D-glucopyranoside In a nitrogen stream, entamethylbenzene (0.40 g, 2.70 mmol) and a solution of boron trichloride in methylene chloride (1.0 M, 1.00 mL, 1.00 mmol) was added to a solution of 4-(4-cyclopropylphenyl)-[3-((1R,2S,3S,4R,5R)-2,3,4-trisbenzyloxy-5-benzyloxymethyl-cyclohexyloxy)pyridine (136 mg, 0.18 mmol) in methylene chloride (7.1 mL) at −78° C. and the mixture was stirred at −78° C. for 3.5 hours. To the reaction mixture, methanol (1.7 mL) was added, and then a sodium methoxide methanol solution (1.0 M, 4 mL) was added thereto and the reaction mixture was stirred at room temperature for 10 minutes. Insolubles were filtered and the filtrate was concentrated under reduced pressure. The obtained residue was purified by silica gel column chromatography [developing solution=methylene chloride:methanol (5:1)] to obtain the title product (66 mg, 95%).

$^1$H-NMR (CD$_3$OD) δ: 0.60-0.65 (2H, m), 0.88-0.95 (2H, m), 1.06-1.19 (1H, m), 1.56-1.61 (1H, m), 1.81-1.88 (1H, m), 2.05-2.12 (1H, m), 3.20-3.27 (2H, m), 3.47-3.55 (2H, m), 3.72 (1H, dd, J=10.7, 3.8 Hz), 3.90-4.03 (2H, m), 4.28-4.36 (1H, m), 6.97 (2H, td, J=8.2, 1.9 Hz), 7.07-7.10 (3H, m), 8.00 (1H, d, J=4.7 Hz), 8.30 (1H, s)

MS (ESI$^+$): 386 [M+H]$^+$

HPLC Retention Time: 8.40 minutes

Example 43

[2-(4-Carboxybenzyl)phenyl]-5a-carba-β-D-glucopyranoside

To a methanol-THF solution (10 mL-5 mL) of [2-(4-methoxycarbonylbenzyl)phenyl]-5a-carba-β-D-glucopyranoside (72.0 mg, 0.1 mmol) as obtained in Example 31, a 20% palladium hydroxide catalyst (7.2 mg) was added. The mixture was stirred under a hydrogen atmosphere for 15 hours, and then the catalyst was filtered off. The solvent was distilled under reduced pressure to obtain the title compound (38.2 mg, 100%).

$^1$H-NMR (CD$_3$OD) δ: 0.86-1.00 (1H, m), 1.51-1.58 (1H, m), 2.01-2.11 (1H, m), 3.16-3.34 (2H, m), 3.43-3.50 (2H, m), 3.67-3.73 (1H, m), 3.95-4.88 (3H, m), 6.87 (1H, t, J=13.5 Hz), 7.03 (1H, d, J=7.4 Hz), 7.12-7.21 (2H, m), 7.30 (2H, d, J=8.1 Hz), 7.88 (2H, d, J=8.1 Hz)

MS (ESI$^+$): 389 [M+H]$^+$

HPLC Retention Time: 10.6 minutes

Example 44

[2-(4-Vinylbenzyl)phenyl]-5a-carba-β-D-glucopyranoside (1) Synthesis of 2-(4-Bromobenzyl)phenol In a nitrogen stream, dimethylsulfide (1.83 mL, 42.46 mmol) and boron trifluoride-diethyl ether complex (0.9 mL, 7.07 mmol) were added to a solution of 1-benzlyoxy-2-(4-bromobenzyl)benzene (1.0 g, 2.83 mmol) in methylene chloride (30.0 mL) under cooling with ice. The reaction mixture was stirred for 19 hours while gradually raising its temperature to room temperature, and then water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (527 mg, 70.8%).

$^1$H-NMR (CDCl$_3$) δ: 3.92 (2H, s), 4.62 (1H, s), 6.73-6.76 (1H, m), 6.85-6.99 (1H, m), 7.06-7.14 (4H, m), 7.35-7.40 (2H, m)

(2) Synthesis of Trifluoromethanesulfonic acid (1S,2R,3S,4R,5R)-Trisbenzyloxy-5-(benzyloxymethyl) cyclohexyl Ester Pyridine (205 μL, 2.53 mmol) was added to a solution of (1S,2R,3S,4R,5R)-tris-benzyloxy-5-(benzyloxymethyl)-cyclohexanol (300 mg, 0.557 mmol) in methylene chloride (5.5 mL) and the mixture was cooled to 0° C., and then trifluoromethanesulfonic acid anhydride (210 μL, 1.25 mmol) was added thereto. The reaction mixture was stirred at the same temperature for one hour, and then a saturated sodium hydrogencarbonate aqueous solution was added thereto and the mixture was extracted with methylene chloride. The combined organic layer was washed with a saturated potassium hydrogensulfate aqueous solution and a saturated sodium chloride aqueous solution, and dried over magnesium sulfate. The solvent was distilled to obtain a crude product (380 mg).

$^1$H-NMR (CDCl$_3$) δ: 1.83 (1H, dd, J=15.9, 14.0 Hz), 2.00-2.14 (2H, m), 3.39 (1H, dd, J=9.2, 2.3 Hz), 3.50 (1H, dd, J=9.6, 2.6 Hz), 3.56 (1H, dd, J=10.2, 9.3 Hz), 3.75 (1H, dd, J=9.2, 3.4 Hz), 3.86 (1H, dd, J=9.5, 9.3 Hz), 4.40 (2H, s), 4.50 (1H, d, J=10.8 Hz), 4.62 (1H, d, J=11.4 Hz), 4.79 (1H, dd, J=10.7 Hz), 4.82 (1H, d, J=11.5 Hz), 4.89 (1H, d, J=10.7 Hz), 4.92 (1H, d, J=10.7 Hz), 5.33 (1H, br), 7.15-7.30 (20H, m)

(3) Synthesis of [2-(4-Bromobenzyl)phenyl]-5a-carba-β-D-glucopyranoside

In a nitrogen stream, a solution of 1-benzyloxy-2-(4-bromo-benzyl)benzene (386 mg, 1.46 mmol) in DMF (1 mL) was cooled in an ice bath, and NaH (60%, 52 mg) was added thereto. The reaction mixture was stirred at the same temperature for 10 minutes, and then this reaction mixture was added dropwise to a suspension of trifluoromethane-sulfonic acid (1S,2R,3S,4R,5R)-trisbenzyloxy-5-(benzyloxy-methyl)cyclohexyl ester (655 mg, 0.97 mmol) in DMF (2.5 mL) at −40° C. The reaction mixture was stirred at the same temperature for two minutes, at from −40° C. to 0° C. for 30 minutes and then at 0° C. for one hour. To the reaction mixture was added a saturated sodium chloride aqueous solution and water. The resulting solution was extracted with ether, and the organic layer was washed with water and a saturated sodium chloride aqueous solution and dried over sodium sulfate. The residue obtained by distilling the solvent was roughly purified by silica gel column chromatography [developing solution=ethyl acetate:n-hexane (1:5)] to obtain a crude product (200 mg). The obtained crude product was dissolved in methylene chloride (2.5 mL) in a nitrogen stream. Dimethylsulfide (0.6 mL, 13.48 mmol) and a boron trifluoride-diethyl ether complex (284 μL, 2.2 mmol) were added thereto under cooling with ice. The reaction mixture was stirred for 25 hours while gradually raising its temperature to room temperature, then water was added thereto under cooling with ice and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=methylene chloride:methanol (10:1)] to obtain the title product (40.0 mg, 42.9%).

$^1$H-NMR (CD$_3$OD) δ: 0.85 (1H, q, J=13.2, J=11.1 Hz), 1.44-1.59 (1H, m), 2.03-2.09 (1H, m), 3.13 (1H, d, J=8.7 Hz), 3.19 (1H, d, J=5.1 Hz), 3.23-3.26 (2H, m), 3.37-3.45 (2H, m), 3.63-3.68 (1H, dd, J=10.6, 3.9 Hz), 3.81 (1H, d, J=14.4 Hz), 4.10 (1H, d, J=14.4 Hz), 4.09-4.18 (1H, m), 6.79 (1H, t, J=7.5 Hz), 6.96 (1H, d, J=9.0 Hz), 7.03-7.13 (4H, m), 7.27-7.32 (2H, m)

(4) Synthesis of [2-(4-Vinylbenzyl)phenyl]-5a-carba-β-D-glucopyranoside

In a nitrogen stream, [2-(4-bromobenzyl)phenyl]-5a-carba-β-D-glucopyranoside (40 mg, 0.094 mmol) was dissolved in toluene (2 mL), and tributylvinyltin (36 mg, 0.11 mmol), tetrakis(triphenylphosphine)palladium (0) (2.7 mg) and 2,6-di-tert-butyl-4-methylphenol were added thereto, and the mixture was refluxed at 110° C. for 15 hours. The reaction mixture was cooled to room temperature and the solvent was distilled under reduced pressure. The obtained residue was purified by preparative TLC [developing solution=methanol:methylene chloride (1:10)] to obtain the title product (9 mg, 25.7%).

$^1$H-NMR (CD$_3$OD) δ: 0.86 (1H, q, J=12.0, 11.7), 1.42-1.55 (1H, m), 1.96-2.03 (1H, m), 3.10-3.19 (2H, m), 3.22-3.25 (2H, m), 3.36-3.44 (2H, m), 3.63 (1H, dd, J=10.6, 4.1 Hz), 3.81-4.08 (2H, m), 4.09-4.16 (1H, m), 5.07 (1H, dd, J=11.0, 1.2 Hz), 5.63 (1H, dd, J=18.0, 1.2 Hz), 6.61 (1H, dd, J=18.0, 11.0 Hz), 6.78 (1H, t, J=7.3 Hz), 7.03 (1H, d, J=6.3 Hz), 7.02-7.24 (6H, m)

MS (ESI$^+$): 370 [M]$^+$

HPLC Retention Time: 11.8 minutes

Example 45

{2-[4-(2,2-Difluorovinyl)benzyl]phenyl}-5a-carba-β-D-glucopyranoside (1) Synthesis of 1-Diethoxymethyl-4-(2,2-difluorovinyl)-benzene In a nitrogen stream, an n-butyllithium hexane solution (2.44 M, 9.94 mL) was added dropwise to diiso-propylamine (3.40 mL, 24.2 mmol) cooled in an ice bath and then THF (20 mL) was added thereto. The obtained mixture was cooled to −78° C., and diethyl (difluoromethyl)-phosphonate (3.62 mL, 23.1 mmol) was added dropwise thereto. The reaction mixture was stirred at the same temperature for five minutes, and then terephthalaldehyde monodiethylacetal (4.2 mL, 21.0 mmol) was added dropwise thereto. The reaction mixture was stirred at the same temperature for 50 minutes, at room temperature for 20 minutes and at a temperature of 70° C. to 75° C. for 34 hours. After cooling the reaction mixture, a saturated ammonium chloride aqueous solution and water were added to the reaction mixture and the resulting mixture was extracted with ether. The organic layer was washed with a saturated ammonium chloride aqueous solution and dried over sodium sulfate. The residue obtained by distilling the solvent under reduced pressure was purified by silica gel column chromatography [developing solution=ethyl acetate:n-hexane (1:20)] to obtain the title compound (1.10 g, 22%).

$^1$H-NMR (CDCl$_3$) δ: 1.24 (6H, t, J=7.1 Hz), 3.45-3.68 (4H, m), 5.27 (1H, dd, J=26.4, 3.8 Hz), 5.49 (1H, s), 7.32 (2H, d, J=8.4 Hz), 7.44 (2H, d, J=8.4 Hz)

(2) Synthesis of 4-(2,2-Difluorovinyl)benzaldehyde

In a nitrogen stream, a 2M hydrochloric acid aqueous solution (2.5 mL) was added to a solution of 1-diethoxymethyl-4-(2,2-difluorovinyl)benzene (998.1 mg, 4.12 mmol) in ether (4 mL) cooled in an ice bath and the reaction mixture was stirred at the same temperature for three minutes and at room temperature for 3.75 hours. The reaction mixture was extracted with ether and the organic layer was washed with a saturated sodium hydrogen carbonate aqueous solution and a saturated sodium chloride aqueous solution, and dried over sodium sulfate. The solvent was distilled under reduced pressure to obtain a crude compound.

$^1$H-NMR (CDCl$_3$) δ: 5.37 (1H, dd, J=25.7, 3.5 Hz), 7.49 (2H, d, J=8.4 Hz), 7.85 (2H, d, J=8.4 Hz), 9.98 (1H, s)

(3) Synthesis of (2-Benzyloxyphenyl)-[4-(2,2-difluoro-vinyl)phenyl]methanol

In a nitrogen stream, a solution of 2-benzyloxybromobenzene (1.63 g, 6.18 mmol) in THF (4 mL) was cooled to −78° C., and an n-butyllithium hexane solution (2.44 M, 2.66 mL) was added dropwise thereto. The reaction mixture was stirred at the same temperature for 25 minutes, and then a solution of 4-(2,2-difluorovinyl)benzaldehyde previously prepared in THF (1 mL) was added dropwise thereto. The reaction mixture was stirred at the same temperature for 1.25 hours, and then a saturated ammonium chloride aqueous solution and water was added thereto. The resulting mixture was extracted with ether and the organic layer was washed with a saturated ammonium chloride aqueous solution and dried over sodium sulfate. The residue obtained by distilling the solvent under reduced pressure was purified by silica gel column chromatography [developing solution=ethyl acetate:n-hexane (1:5)] to obtain the title compound (1.17 g, 81%).

$^1$H-NMR (CDCl$_3$) δ: 2.94 (1H, d, J=6.1 Hz), 4.98-5.04 (2H, m), 5.26 (1H, dd, J=26.4, 3.8 Hz), 6.03 (1H, d, J=6.1 Hz), 6.88-7.04 (2H, m), 7.14-7.38 (11H, m)

(4) Synthesis of 1-Benzyloxy-2-[4-(2,2-difluorovi-nyl)-benzyl]benzene

In a nitrogen stream, a solution of (2-benzyloxyphenyl)-[4-(2,2-fluorovinyl)-phenyl]methanol (1.14 g, 3.24 mmol) in methylene chloride (10 mL) was cooled to −78° C., and triethylsilane (5.17 mL, 32.35 mmol) was added thereto. A boron trifluoride-diethyl ether complex (0.49 mL, 3.88 mmol) was added dropwise to the reaction mixture over five minutes and the reaction mixture was stirred at −78° C. for five minutes and then under cooling with ice for 10 minutes. A saturated sodium hydrogencarbonate aqueous solution and water were added thereto and the resulting mixture solution was extracted with methylene chloride. The organic layer was washed with a saturated sodium chloride aqueous solution and dried over sodium sulfate. The residue obtained by distilling the solvent under reduced pressure was purified by silica gel column chromatography [developing solution=ethyl acetate:n-hexane (1:30)] to obtain the title compound (984.5 mg, 90%).

$^1$H-NMR (CDCl$_3$) δ: 4.00 (2H, s), 5.05 (2H, s), 5.23 (1H, dd, J=26.2, 3.8 Hz), 6.85-6.95 (2H, m), 7.05-7.40 (11H, m)

(5) Synthesis of 2-[4-(2,2-Difluorovinyl)benzyl]phenol

In a nitrogen stream, a solution of 1-benzyloxy-2-[4-(2,2-Difluorovinyl)benzyl]benzene (984.5 mg, 2.93 mmol) in methylene chloride (12 mL) was cooled to −78° C., and a boron tribromide-dimethylsulfide methylene chloride solution (1.0 M, 7.32 mL) was added dropwise thereto. The reaction mixture was stirred at the same temperature for two minutes and under cooling with ice for two hours, and furthermore the boron trifluoride-dimethylsulfide methylene chloride solution (4.39 mL) was added dropwise thereto. The reaction mixture was stirred at the same temperature for 3.5 hours, then a sodium hydroxide aqueous solution and a saturated sodium hydrogencarbonate aqueous solution was added thereto and the mixture was extracted with methylene chloride, and the organic layer was washed with a saturated sodium chloride aqueous solution and dried over sodium sulfate. The residue obtained by distilling the solvent under reduced pressure was purified by silica gel column chromatography [developing solution=ethyl acetate:n-hexane (1:7)] to obtain the title compound (647.5 mg, 90%).

$^1$H-NMR (CDCl$_3$) δ: 3.98 (2H, s), 4.62 (1H, s), 5.24 (1H, dd, J=26.2, 3.8 Hz), 6.78 (1H, d, J=8.1 Hz), 6.84-6.94 (1H, m), 7.04-7.32 (6H, m)

(6) Synthesis of {2-[4-(2,2-Difluorovinyl)benzyl]-phenyl}-5a-carba-β-D-glucopyranoside In a nitrogen stream, a solution of 2-[4-(2,2-difluorovinyl) benzyl]phenol (80 mg, 0.324 mmol) in DMF (1 mL) was cooled in an ice bath, and NaH (60%, 13 mg) was added thereto. The reaction mixture was stirred at the same temperature for 10 minutes, and then this reaction mixture was added dropwise to a suspension of trifluoromethane-sulfonic acid (1S,2R,3S,4R,5R)-trisbenzyloxy-5-(benzyloxy-methyl)cyclohexyl ester (181 mg, 0.270 mmol) in DMF (2.5 mL) at −40° C. The reaction mixture was stirred at the same temperature for two minutes, at −40° C. to 0° C. for 30 minutes and at 0° C. for one hour. To the reaction mixture was added a saturated sodium chloride aqueous solution and water and the mixture was extracted with ether, and the organic layer was washed with water and a saturated sodium chloride aqueous solution and dried over sodium sulfate. The residue obtained by distilling the solvent under reduced pressure was purified by silica gel column chromatography [developing solution=ethyl acetate: n-hexane (1:7)] to obtain a target product (180.7 mg). In a nitrogen stream, 65 mg (0.0848 mmol) out of the product was mixed with pentamethylbenzene (188 mg, 1.27 mmol) in a nitrogen stream and dissolved in methylene chloride (2.5 mL). After cooling the mixture solution to −78° C., a boron trichloride methylene chloride solution (1.0 M, 0.42 mL) was added dropwise thereto. The reaction mixture was stirred at the same temperature for 2.25 hours, and then methanol (0.5 mL) was added dropwise thereto. At the same temperature, a sodium methoxide methanol solution (1 M, 1.26 mL) was added dropwise, and the reaction mixture was stirred at room temperature for 15 minutes. The mixture was filtered and the filtrate was concentrated under reduced pressure and the obtained residue was purified by preparative TLC [developing solution=methanol: methylene chloride (1:10)] to obtain the title product (22.1 mg, 64%).

$^1$H-NMR (CD$_3$OD) δ: 0.82-1.04 (1H, m), 1.44-1.64 (1H, m), 1.98-2.12 (1H, m), 3.12-3.28 (2H, m), 3.40-3.54 (2H, m), 3.69 (1H, dd, J=10.7, 4.0 Hz), 3.89 (1H, d, J=14.8 Hz), 4.02 (1H, d, J=14.8 Hz), 4.10-4.26 (1H, m), 5.40 (1H, dd, J=27.0, 4.0 Hz), 6.78-6.90 (1H, m), 6.96-7.30 (7H, m)

MS (ESI$^+$): 406 [M]$^+$

HPLC Retention Time: 18.51 minutes

Measurement Conditions of HPLC

Column: YMC-Pack ODS-A 6.0×150 mm, 5 μm

Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes Flow Rate: 1.5 mL/minute Column Temperature Room temperature Detection Condition Total plot of the entire wavelength of 230 to 400 nm

Examples 46 to 58

The target compound was obtained by performing the same operation as in the above-described Examples with the use of the corresponding starting materials and reagents, respectively.

Example 46

[2-(2,3-Dihydrobenzofuran-5-ylmethyl)phenyl]-5a-carba-β-D-glucopyranoside $^1$H-NMR (CD$_3$OD) δ: 0.93 (1H, q, J=13.2 Hz, J=11.4 Hz), 1.49-1.58 (1H, m), 2.01-2.07 (1H, dt, J=13.2, 4.5 Hz), 3.12 (1H, t, J=8.4 Hz), 3.20 (1H, d, J=9.3 Hz), 3.25 (1H, d, J=4.8 Hz), 3.30-3.53 (2H, m), 3.69 (1H, dd, J=6.6, 4.2 Hz), 3.85 (1H, d, J=15 Hz), 3.91 (1H, d, J=15 Hz), 4.13-4.21 (1H, m), 4.47 (2H, t, J=8.7 Hz), 6.59 (1H, d, J=8.4 Hz), 6.83 (1H, t, J=7.2 Hz), 6.89 (1H, d, J=8.1 Hz), 6.99-7.15 (4H, m)

MS (ESI$^+$): 386 [M]$^+$

HPLC Retention Time: 10.5 minutes

Example 47

[2-(3-Fluoro-4-methylbenzyl)phenyl]-5a-carba-β-D-gluco-pyranoside $^1$H-NMR (CD$_3$OD) δ: 0.99 (1H, q, J=12.6 Hz), 1.48-1.59 (1H, m), 2.04-2.10 (1H, dt, J=13.2, 4.2 Hz), 2.18 (3H, s), 3.18-3.32 (2H, m), 3.44-3.51 (2H, m), 3.68 (1H, dd, J=6.9, 3.9 Hz), 3.89 (1H, d, J=15 Hz), 3.97 (1H, d, J=15 Hz), 4.14-4.22 (1H, m), 6.81-6.90 (3H, m), 7.00-7.17 (4H, m)

MS (ESI$^+$): 376.4 [M]$^+$

HPLC Retention Time: 11.7 minutes

Example 48

[2-(4-Methoxy-3-methylbenzyl)phenyl]-5a-carba-β-D-gluco-pyranoside $^1$H-NMR (CD$_3$OD) δ: 0.94 (1H, q, J=12.9, 11.7 Hz), 1.47-1.57 (1H, m), 2.01-2.08 (1H, dt, J=13.2, 4.2 Hz), 2.12 (3H, s), 3.18-3.34 (2H, m), 3.45-3.52 (2H, m), 3.68 (1H, dd, J=6.6, 4.2 Hz), 3.75 (3H, s), 3.84 (1H, d, J=14.7 Hz), 3.90 (1H, d, J=14.7 Hz), 4.14-4.21 (1H, m), 6.76 (1H, d, J=8.7 Hz), 6.83 (1H, t, J=7.5 Hz), 6.95-7.15 (5H, m)

MS (ESI$^+$):389 [M+H]$^+$

HPLC Retention Time: 11.5 minutes

Example 49

[2-(4-Pyrazol-1-ylbenzyl)phenyl]-5a-carba-β-D-gluco-pyranoside $^1$H-NMR (CD$_3$OD) δ: 0.95 (1H, q, J=12.9, 11.4 Hz), 1.49-1.59 (1H, m), 2.02-2.09 (1H, dt, J=12.3, 4.2 Hz), 3.20 (1H, d, J=9.0 Hz), 3.23 (1H, d, J=6.3 Hz), 3.43-3.53 (2H, m), 3.67 (1H, dd, J=6.6, 4.2 Hz), 3.98 (1H, d, J=14.7 Hz), 4.07 (1H, d, J=15 Hz), 4.16-4.24 (1H, m), 6.49 (1H, s), 6.87 (1H, t, J=7.5 Hz), 7.05 (1H, d, J=8.1 Hz), 7.14 (2H, d, J=7.5 Hz), 7.35 (2H, d, J=8.4 Hz), 7.56 (2H, d, J=8.4 Hz), 7.68 (1H, s), 8.12 (1H, s)

MS (ESI$^+$): 411 [M+H]$^+$

HPLC Retention Time: 10.5 minutes

Example 50

[2-(3-Chloro-4-methylbenzyl)phenyl]-5a-carba-β-D-gluco-pyranoside

¹H-NMR (CD₃OD) δ: 0.94 (1H, dd, J=24.4, 13.2 Hz), 1.5-1.65 (1H, m), 2.05 (1H, dt, J=13.5, 4.1 Hz), 3.18-3.35 (2H, m), 3.43-3.55 (2H, m), 3.70 (1H, dd, J=10.7, 4.1 Hz), 3.82 (3H, s), 3.82 (1H, d, J=14.8 Hz), 3.97 (1H, d, J=14.8 Hz), 4.15-4.25 (1H, m), 6.86 (1H, td, J=7.4, 1.1 Hz), 6.92 (1H, d, J=8.2 Hz), 7.0-7.2 (5H, m)
MS (ESI⁺):409 [M+H]⁺, 431 [M+Na]⁺
HPLC Retention Time: 11.25 minutes

Example 51

[2-(3,4-Methylenedioxybenzyl)phenyl]-5a-carba-β-D-gluco-pyranoside

¹H-NMR (CD₃OD) δ: 1.01 (1H, q, J=12.7 Hz), 1.45-1.64 (1H, m), 2.04-2.13 (1H, m), 3.19-3.35 (4H, m), 3.46-3.54 (2H, m), 3.69-3.74 (1H, m), 3.89 (2H, q, J=16.1 Hz), 4.15-4.22 (1H, m), 5.86 (2H, s), 6.68 (3H, s), 6.85 (1H, t, J=6.1 Hz), 7.00-7.18 (3H, m)
MS (ESI⁺): 389 [M+H]⁺
HPLC Retention Time: 10.6 minutes

Example 52

[2-(4-Cyclobutylbenzyl)phenyl]-5a-carba-β-D-glucopyranoside

¹H-NMR (CD₃OD) δ: 0.81-0.96 (1H, m), 1.45-1.61 (1H, m), 1.78-2.37 (7H, m), 3.15-3.34 (5H, m), 3.40-3.55 (2H, m), 3.66-4.76 (1H, m), 3.95 (2H, q, J=13.7 Hz), 4.13-4.24 (1H, m), 6.87 (1H, t, J=8.1 Hz), 6.97-7.17 (7H, m)
MS (ESI⁺): 425 [M+Na]⁺
HPLC Retention Time: 13.6 minutes

Example 53

[2-(4-Acetylbenzyl)phenyl]-5a-carba-β-D-glucopyranoside

¹H-NMR (CD₃OD) δ: 0.84-0.98 (1H, m), 1.50-1.56 (1H, m), 2.00-2.08 (1H, m), 2.55 (3H, s), 3.15-3.32 (3H, m), 3.42-3.50 (2H, m), 3.65-3.70 (1H, m), 3.94-4.24 (3H, m), 4.89 (2H, s), 6.86 (1H, t, J=7.3 Hz), 7.03 (1H, d, J=8.1 Hz), 7.12-7.20 (2H, m), 7.34 (2H, d, J=8.1 Hz), 7.86 (2H, d, J=8.1 Hz)
MS (ESI⁺): 386[M+1]⁺
HPLC Retention Time: 9.8 minutes

Example 54

[2-(4-Methoxybenzyl)-5-methylphenyl]-5a-carba-β-D-gluco-pyranoside

¹H-NMR (CD₃OD) δ: 0.92-1.06 (1H, m), 1.51-1.66 (1H, m), 2.08 (1H, dt, J=13.2, 4.0 Hz), 2.32 (3H, s), 3.21-3.40 (2H, m), 3.47-3.56 (2H, m), 3.71-3.78 (1H, m), 3.77 (3H, s), 3.84 (1H, d, J=14.2 Hz), 3.95 (1H, d, J=14.2 Hz), 4.14-4.26 (1H, m), 6.68-6.72 (1H, m), 6.78-6.85 (2H, m), 6.86-6.91 (1H, m), 6.97 (1H, d, J=7.8 Hz), 7.10-7.16 (2H, m)
MS (ESI⁺): 388 [M]⁺
HPLC Retention Time: 11.26 minutes

Example 55

[2-(4-Ethylbenzyl)thiophen-3-yl]-5a-carba-β-D-gluco-pyranoside

¹H-NMR (CD₃OD) δ: 1.20 (1H, t, J=7.6 Hz), 1.40-1.80 (1H, m), 2.04-2.09 (1H, m), 2.59 (2H, q, J=7.58 Hz), 3.19-3.55 (5H, m), 3.88-3.96 (1H, m), 3.99 (2H, m), 6.89 (2H, d, J=5.4 Hz), 7.06-7.15 (5H, m)
MS (ESI⁺): 378 [M]⁺
HPLC Retention Time: 11.9 minutes

Example 56

[(Benzothiophen-2-yl)methylphenyl]-5a-carba-β-D-gluco-pyranoside

¹H-NMR (CD₃OD) δ: 1.04 (1H, m), 1.40-1.80 (1H, m), 2.08-2.16 (1H, m), 3.14-3.67 (5H, m), 4.14 (1H, d, J=15.7 Hz), 4.19-4.27 (1H, m), 4.36 (1H, d, J=15.5 Hz), 6.89 (1H, dd, J=8.1, 6.6 Hz), 7.02 (1H, s), 7.07 (1H, d, J=8.1 Hz), 7.17-7.28 (4H, m), 7.63 (1H, d, J=7.6 Hz), 7.71 (1H, d, J=7.6 Hz)
MS (ESI⁺): 400 [M]⁺
HPLC Retention Time: 12.0 minutes

Example 57

{2-[1-(4-Cyclopropylphenyl)ethyl]phenyl}-5a-carba-β-D-glucopyranoside [less polar-isomer isolated by preparative TLC (developing solution:methanol:methylene chloride=1:10)]

¹H-NMR (CD₃OD) δ: 0.40 (1H, dd, J=9.3, 9.0 Hz), 0.56-0.66 (2H, m), 0.84-0.96 (2H, m), 1.36-1.54 (1H, m), 1.52 (3H, d, J=6.6 Hz), 1.76-1.88 (2H, m), 3.04-3.12 (1H, dd, J=10.8, 9.9 Hz), 3.25 (1H, t, J=10.8 Hz), 3.26-3.40 (1H, m), 3.42 (1H, t, J=9.9 Hz), 3.64 (1H, dd, J=10.4, 4.8 Hz), 4.08-4.22 (1H, m), 4.50 (1H, dd, J=12.0, 6.3 Hz), 6.84-6.99 (4H, m), 6.99-7.06 (2H, m), 7.06-7.28 (1H, m), 7.20-7.26 (1H, m)
MS (ESI⁺): 399 [M+H]⁺
HPLC Retention Time: 12.7 minutes

Example 58

{2-[1-(4-Cyclopropylphenyl)ethyl]phenyl}-5a-carba-β-D-glucopyranoside [more polar-isomer isolated by preparative TLC (developing solution:methanol:methylene chloride=1:10)]

¹H-NMR (CD₃OD) δ: 0.56-0.66 (2H, m), 0.84-0.96 (2H, m), 1.10 (1H, dd, J=9.6, 9.0 Hz), 1.44-1.64 (1H, m), 1.53 (3H, d, J=6.6 Hz), 1.76-1.88 (1H, m), 2.13 (1H, ddd, J=12.2, 4.5, 3.3 Hz), 3.20-3.28 (2H, m), 3.44 (1H, t, J=10.5 Hz), 3.53 (1H, dd, J=11.4, 6.6 Hz), 3.73 (1H, dd, J=11.4, 2.4 Hz), 4.06-4.22 (1H, m), 4.50 (1H, dd, J=12.0, 6.3 Hz), 6.82-7.03 (4H, m), 7.06-7.16 (4H, m)
MS (ESI⁺): 399 [M+H]⁺
HPLC Retention Time: 12.7 minutes

Example 59

[2-(4-Cyclopropylbenzyl)-5-methylthiophen-3-yl]-5a-carba-β-D-glucopyranoside

(1) Synthesis of (4-Cyclopropylphenyl)-(3-methoxy-5-methylthiophen-2-yl)methanone Methyl iodide (2.53 mL, 40.6 mmol) was added to a solution of (4-cyclopropylphenyl)-(3-methoxy-5-thiophen-2-yl)methanone (1.05 g, 4.06 mmol) as synthesized in the same manner as in Example 38 in THF (20 mL) under a nitrogen atmosphere. This solution was cooled to −78° C., and a lithium diisopropylamide heptane-THF-ethylbenzene solution (2.0 M, 2.44 mL, 4.88 mmol) was added thereto over 20 minutes. The reaction mixture was stirred at the same temperature for three hours. To this solution, furthermore the lithium diisopropylamide heptane-THF-ethylbenzene solution (2.0 M, 2.44 mL, 4.88 mmol) was added over 20 minutes and the reaction mixture was stirred for two hours, and a saturated ammonium chloride solution was added thereto. The resulting mixture was extracted with ethyl acetate and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:5)] to obtain the title compound (589 mg, 53%).

$^1$H-NMR (CDCl$_3$) δ: 0.74-0.80 (2H, m), 1.00-1.06 (2H, m), 1.91-1.97 (1H, m), 2.49 (3H, s), 3.81 (3H, s), 6.62 (1H, s), 7.08 (2H, d, J=7.9 Hz), 7.68 (2H, d, J=8.3 Hz)

(2) Synthesis of (4-Cyclopropylphenyl)-(3-hydroxy-5-methylthiophen-2-yl)methanone In a nitrogen stream, a boron trichloride methylene chloride solution (1.0 M, 6.4 mL, 6.4 mmol) was added to a solution of (4-cyclopropylphenyl)-(3-methoxy-5-methylthiophen-2-yl)methanone (582 mg, 2.14 mmol) in methylene chloride (12 mL) at −15° C. and the reaction mixture was stirred for one hour. Water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=methanol:methylene chloride (1:100)] to obtain the title compound (497 mg, 90%).

$^1$H-NMR (CDCl$_3$) δ: 0.76-0.82 (2H, m), 1.03-1.10 (2H, m), 1.93-1.98 (1H, m), 2.49 (3H, s), 6.57 (1H, s), 7.15 (2H, d, J=8.4 Hz), 7.85 (2H, d, J=8.4 Hz), 12.80 (1H, s)

(3) Synthesis of (4-Cyclopropylphenyl)-[5-methyl-3-((1R,2S,3S,4R,5R)-2,3,4-trisbenzyloxy-5-benzyloxy-methylcyclohexyloxy)thiophen-2-yl]methanone In a nitrogen stream, diisopropylazodicarboxylate (0.27 mL, 1.39 mmol) was added dropwise to a mixture of (4-cyclopropylphenyl)-(3-hydroxy-5-methylthiophen-2-yl)methanone (360 mg, 1.39 mmol), (1S,2S,3S,4R,5R)-2,3,4-trisbenzyloxy-5-benzyloxymethylcyclohexanol (500 mg, 0.93 mmol), triphenylphosphine (365 mg, 1.39 mmol) and toluene (3.1 mL) under cooling with ice. The mixture was stirred at room temperature for 15 hours, and then the solvent was distilled under reduced pressure and the obtained residue was purified by silica gel flash column chromatography [developing solution=n-hexane:ethyl acetate (4:1)] to obtain the title compound (237 mg, 33%).

$^1$H-NMR (CDCl$_3$) δ: 0.70-0.73 (2H, m), 0.99-1.02 (2H, m), 1.35-1.50 (1H, m), 1.64-1.72 (1H, m), 1.87-1.94 (1H, m), 2.07-2.14 (1H, m), 2.44 (3H, s), 3.36-3.56 (5H, m), 4.07-4.13 (1H, m), 4.33-4.88 (8H, m), 6.61 (1H, s), 7.01 (2H, d, J=7.9 Hz), 7.05-7.35 (22H, m), 7.62 (2H, d, J=8.2 Hz)

(4) Synthesis of 2-(4-Cyclopropylbenzyl)-5-methyl-3-[(1R,2S,3S,4R,5R)-2,3,4-trisbenzyloxy-5-(benzyloxy-methyl)cyclohexyloxy]thiophene In a nitrogen stream, chlorotrimethylsilane (0.46 mL, 3.56 mmol) and sodium cyanoborohydride (230 mg, 3.65 mmol) were added to an solution of (4-cyclopropylphenyl)-[5-methyl-3-((1R,2S,3S,4R,5R)-2,3,4-trisbenzyloxy-5-benzyloxymethylcyclohexyloxy)thiophen-2-yl]methanone (237 mg, 0.30 mmol) in acetonitrile (5 mL) under cooling with ice and the reaction mixture was stirred at 0° C. for one hour. Methylene chloride was added thereto and the mixture was subjected to Celite filtration, and the solvent of the filtrate was distilled under reduced pressure. The obtained residue was purified by silica gel column chromatography [developing solution=ethyl acetate:n-hexane (1:10)] to obtain the title compound (135 mg, 58%).

$^1$H-NMR (CDCl$_3$) δ: 0.58-0.65 (2H, m), 0.86-0.94 (2H, m), 1.23-1.28 (1H, m), 1.57-1.65 (1H, m), 1.77-1.86 (1H, m), 2.06-2.12 (1H, m), 2.33 (3H, s), 3.43-3.65 (5H, m), 3.93 (2H, s), 3.98-4.08 (1H, m), 4.44 (2H, s), 4.51 (1H, d, J=10.8 Hz), 4.75-4.97 (5H, m), 6.55 (1H, s), 6.92 (2H, d, J=8.1 Hz), 7.10 (2H, d, J=8.1 Hz), 7.18-7.37 (20H, m)

(5) Synthesis of [2-(4-Cyclopropylbenzyl)-5-methyl-thiophen-3-yl]-5a-carba-β-D-glucopyranoside In a nitrogen stream, pentamethylbenzene (390 mg, 2.63 mmol) and a boron trichloride methylene chloride solution (1.0 M, 0.88 mL, 0.88 mmol) were added to a solution of 2-(4-cyclopropylbenzyl)-5-methyl-3-[(1R,2S,3S,4R,5R)-2,3,4-trisbenzyloxy-5-(benzyloxymethyl)-cyclohexyloxy]thiophene (134 mg, 0.18 mmol) in methylene chloride (6 mL) at −78° C. and the reaction mixture was stirred at −78° C. for one hour. Methanol was added to the reaction mixture and the solvent was distilled under reduced pressure. The obtained residue was purified by silica gel column chromatography [developing solution=methylene chloride:ethanol (20:1)] to obtain the title compound (35 mg, 49%).

$^1$H-NMR (CD$_3$OD) δ: 0.62-0.68 (2H, m), 0.90-0.97 (2H, m), 1.10-1.21 (1H, m), 1.43-1.56 (1H, m), 1.82-1.95 (1H, m), 2.03-2.11 (1H, m), 2.36 (3H, s), 3.25-3.90 (6H, m), 3.94 (2H, m), 6.63 (1H, m), 6.98 (2H, d, J=8.4 Hz), 7.11 (2H, d, J=7.9 Hz)

MS (ESI$^-$): 403 [M−H]$^-$

Example 60

[2-(4-Ethylbenzyl)-5-methylthiophen-3-yl]-5a-carba-β-D-glucopyranoside

The target compound was obtained by performing the same operation as in Example 59 with the use of the corresponding starting material and reagents.

$^1$H-NMR (CD$_3$OD) δ: 1.10-1.22 (4H, m), 1.40-1.54 (1H, m), 2.02-2.09 (1H, m), 2.33 (3H, s), 2.58 (2H, d, J=7.6 Hz), 3.22-3.25 (2H, m), 3.28-3.35 (2H, m), 3.39-3.45 (1H, m), 3.52 (1H, dd, J=10.7, 6.2 Hz), 3.71 (1H, dd, J=10.7, 4.0 Hz), 3.83-3.90 (1H, m), 6.60 (1H, s), 7.06 (2H, d, J=8.2 Hz), 7.11 (2H, d, J=8.2 Hz)
MS (ESI+): 393 [M+H]+, 415 [M+Na]+

Example 61

[5-Chloro-2-(4-cyclopropylbenzyl)thiophen-3-yl]-5a-carba-β-D-glucopyranoside (1) Synthesis of 4-Cyclopropyl-N-methoxy-N-methyl-benzamide In a nitrogen stream, an n-butyllithium hexane solution (1.6 M, 6.0 mL, 9.59 mmol) was added dropwise to an solution of 1-bromo-4-cyclopropylbenzene (1.8 g, 9.13 mmol) in anhydrous THF (30 mL) at −78° C. over 15 minutes. This solution was stirred at −78° C. for 10 minutes, and a solution of N,N'-dimethoxy-N,N'-dimethylurea (1.42 g, 9.59 mmol) in THF (15 mL) was added dropwise thereto. The reaction mixture was stirred at room temperature for 30 minutes. To the reaction mixture was added a saturated ammonium chloride aqueous solution and the mixture was extracted with ether, and the organic layer was dried over anhydrous magnesium sulfate. After filtration, the solvent was distilled under reduced pressure, and the obtained residue was purified by silica gel column chromatography [developing solution=n-hexane:ethyl acetate (4:1)] to obtain the title compound (875 mg, 95%).
1H-NMR (CDCl3) δ: 0.73-0.78 (2H, m), 0.97-1.03 (2H, m), 1.87-1.94 (1H, m), 3.34 (3H, s), 3.56 (3H, s), 7.08 (2H, d, J=8.3 Hz), 7.60 (2H, d, J=8.3 Hz)

(2) Synthesis of (5-Chloro-3-methoxythiophen-2-yl)-(4-cyclopropylphenyl)methanone In a nitrogen stream, an n-butyllithium n-hexane solution (1.6 M, 2.43 mL, 3.88 mmol) was added dropwise to a solution of 2-bromo-5-chloro-3-methoxythiophene (882 mg, 3.88 mmol) as synthesized by the method described in a document [L. Org. Chem., 58, 4629-4633 (1993)] in anhydrous THF (15 mL) at −78° C. This mixture was stirred at −78° C. for ten minutes, and a solution of 4-cyclopropyl-N-methoxy-N-methylbenzamide (875 mg, 4.26 mmol) in THF (3 mL) was added dropwise thereto. The reaction mixture was stirred at −78° C. for 30 minutes. A saturated ammonium chloride aqueous solution was added to the reaction mixture and the resulting mixture was extracted with ethyl acetate, and the organic layer was dried over anhydrous magnesium sulfate. After filtration, the solvent was distilled under reduced pressure, and the obtained residue was purified by silica gel column chromatography [developing solution=n-hexane:ethyl acetate (4:1)] to obtain the title compound (714 mg, 63%).
1H-NMR (CDCl3) δ: 0.75-0.81 (2H, m), 1.02-1.08 (2H, m), 1.92-1.98 (1H, m), 3.80 (3H, s), 6.78 (1H, s), 7.10 (2H, d, J=8.3 Hz), 7.68 (2H, d, J=8.3 Hz)

(3) Synthesis of [5-Chloro-2-(4-cyclopropylbenzyl)-thiophen-3-yl]-5a-carba-β-D-glucopyranoside The target compound was obtained by performing the same operation as in Example 59 with the use of the synthesized (5-chloro-3-methoxythiophen-2-yl)-(4-cyclo-propylphenyl) methanone and the corresponding reagents.
1H-NMR (CD3OD) δ: 0.63-0.66 (2H, m), 0.88-0.93 (2H, m), 1.15-1.21 (1H, m), 1.61-1.67 (1H, m), 1.82-1.87 (1H, m), 1.99-2.03 (1H, m), 3.22-3.57 (4H, m), 3.70-3.74 (1H, m), 3.87-3.91 (1H, m), 3.92 (2H, s), 6.86 (1H, s), 6.97 (2H, d, J=8.1 Hz), 7.09 (2H, d, J=8.1 Hz)
MS (ESI+): 425 [M+H]+

Example 62

(1R,2S,3R,6R)-6-[2-(4-Cyclopropylbenzyl)phenoxy]-4-(hydroxymethyl)cyclohex-4-ene-1,2,3-triol (1) Synthesis of 1-(4-Cyclopropylphenyl)methyl-2-[(1R,4R,5S,6S)-4,5,6-trisbenzyloxy-3-(benzyloxymethyl)-cyclohex-2-enyloxy]benzene In a nitrogen stream, 2-(4-cyclopropylbenzyl)phenol and tributylphosphine (70 μL, 0.28 mmol) were added to a solution of (1S,4R,5S,6S)-4,5,6-tris(benzyloxy)-3-(benzyloxymethyl)cyclohex-2-enol (51 mg, 0.095 mmol) as described in a document [J. Org. Chem., 63, 5668-5671 (1998)] in toluene (300 μL) under cooling with ice, and then tetramethylazodicarboxamide (48 mg, 0.28 mmol) was added thereto at the same temperature. The reaction mixture was stirred at the same temperature for 20 hours and then hexane was added thereto and the precipitate was filtered and the solvent of the filtrate was distilled. The obtained residue was purified by preparative TLC [developing solution=ethyl acetate:n-hexane (1:5) to obtain the title compound (44 mg, 62%).
1H-NMR (CDCl3) δ: 0.54 (2H, m), 0.84 (2H, m), 1.75 (1H, m), 3.82-3.92 (3H, m), 3.93 (2H, s), 4.19 (1H, d, J=12.5 Hz), 4.35 (1H, br), 4.41 (1H, d, J=11.7 Hz), 4.46 (1H, d, J=11.8 Hz), 4.61 (1H, d, J=10.7 Hz), 4.68 (1H, d, J=10.2 Hz), 4.72 (1H, d, J=10.5 Hz), 4.79 (1H, d, J=10.8 Hz), 4.85 (1H, d, J=10.7 Hz), 4.99 (1H, d, J=11.0 Hz), 5.04 (1H, br), 5.65 (1H, s), 6.8-7.4 (28H, m)

(2) Synthesis of (1R,2S,3R,6R)-6-[2-(4-Cyclopropyl-benzyl)phenoxy]-4-(hydroxymethyl)cyclohex-4-ene-1,2,3-triol In a nitrogen stream, a boron trichloride 1.0 M methylene chloride solution (160 μL, 0.16 mmol) was added to a solution of 1-(4-cyclopropylphenyl)methyl-2-[(1R,4R,5S,6S)-4,5,6-tris-benzyloxy-3-(benzyloxymethyl)-cyclohex-2-enyloxy] benzene (12 mg, 0.016 mmol) and pentamethylbenzene (24 mg, 0.17 mmol) in methylene chloride (300 μL) at −78° C., and the mixture was stirred at the same temperature for 1.5 hours. After addition of methanol, the temperature of the resulting solution was raised to room temperature and the solvent was distilled under reduced pressure. The obtained residue was purified by preparative TLC [developing solution=methanol:methylene chloride (1:8)] to obtain the title compound (4.1 mg, 70%).
1H-NMR (CD3OD) δ: 0.61 (2H, m), 0.89 (2H, m), 1.83 (1H, m), 3.55 (1H, dd, J=10.5, 7.8 Hz), 3.72 (1H, dd, J=10.5, 7.8 Hz), 3.89 (1H, d, J=14.8 Hz), 3.93 (1H, d, J=14.9 Hz), 4.11 (2H, br s), 4.15 (1H, d, J=7.8 Hz), 4.80 (1H, d, J=7.6 Hz), 5.60 (1H, t, J=1.5 Hz), 6.84 (1H, t, J=7.3 Hz), 6.93 (2H, d, J=8.1 Hz), 7.06 (1H, d, J=8.2 Hz), 6.97-7.18 (3H, m)
MS (ESI+): 405 [M+Na]+
HPLC Retention Time: 12.5 minutes Example 63

(1R,2S,3R,6R)-4-Hydroxymethyl-6-[2-(4-methoxybenzyl)-phenoxy]cyclohex-4-ene-1,2,3-triol (1) Synthesis of 1-(4-Methoxyphenyl)methyl-2-[(1R,4R,5S,6S)-4,5,6-trisbenzyloxy-3-(benzyloxymethyl)-cyclohex-2-enyloxy]benzene In a nitrogen stream, 2-(4-methoxybenzyl)phenol (299 mg, 1.40 mmol) and tributylphosphine (380 μL, 1.53 mmol)

were added to a solution of (1S,3S,4S,5R,6R)-4,5,6-trisbenzyloxy-1-(benzyloxymethyl)cyclohane-1,3-diol (561 mg, 1.01 mmol) as described in a document [Tetrahedron, 56, 7109-7122 (2000)] in toluene (3 mL) under cooling with ice, and then tetramethylazodicarboxamide (261 mg, 1.52 mmol) was added thereto at the same temperature. The reaction mixture was stirred at the same temperature for 20 hours and then hexane was added thereto, and the precipitate was filtered and the solvent of the filtrate was distilled.

The obtained residue was purified by silica gel column chromatography [developing solution=ethyl acetate:n-hexane (1:7 to 1:1) to obtain the title compound (312 mg, 42%).

$^1$H-NMR (CDCl$_3$) δ: 3.64 (3H, s), 3.80-3.95 (3H, m), 3.92 (2H, s), 4.19 (1H, d, J=13.6 Hz), 4.36 (1H, br), 4.41 (1H, d, J=11.9 Hz), 4.46 (1H, d, J=11.8 Hz), 4.64 (1H, d, J=11.0 Hz), 4.69 (1H, d, J=10.8 Hz), 4.71 (1H, d, J=10.8 Hz), 4.79 (1H, d, J=10.8 Hz), 4.85 (1H, d, J=11.0 Hz), 4.99 (1H, d, J=11.0 Hz), 5.05 (1H, br), 5.67 (1H, s), 6.71 (2H, d, J=8.7 Hz), 6.80-7.40 (26H, m)

MS (ESI$^+$): 755 [M+Na]$^+$ (2) Synthesis of (1R,2S,3R,6R)-4-Hydroxymethyl-6-[2-(4-methoxybenzyl)phenoxy]cyclohex-4-ene-1,2,3-triol In a nitrogen stream, a boron trichloride 1.0 M methylene chloride solution (6.0 mL, 6.0 mmol) was added to a solution of 1-(4-methoxyphenyl)methyl-2-[(1R,4R,5S,6S)-4,5,6-trisbenzyloxy-3-(benzyloxymethyl)cyclohex-2-enyloxy]benzene (312 mg, 0.426 mmol) in methylene chloride (12 mL) at –78° C., and the mixture was stirred at the temperature for 1.5 hours. After addition of methanol, the temperature of the resulting solution was raised to room temperature and the solvent was distilled under reduced pressure. The obtained residue was purified by silica gel column chromatography [developing solution=methanol:methylene chloride (1:8)] to obtain the title compound (37.9 mg, 24%).

$^1$H-NMR (CD$_3$OD) δ: 3.56 (1H, dd, J=10.5, 8.0 Hz), 3.73 (1H, m), 3.73 (3H, s), 3.88 (1H, d, J=14.9 Hz), 3.92 (1H, d, J=14.9 Hz), 4.11 (2H, br s), 4.16 (1H, m), 4.81 (1H, m), 5.61 (1H, t, J=1.7 Hz), 6.77 (2H, d, J=8.7 Hz), 6.84 (1H, t, J=7.3 Hz), 6.99 (1H, d, J=8.1 Hz), 7.04 (1H, d, J=7.5 Hz), 7.10 (2H, d, J=8.9 Hz), 7.13 (1H, m)

MS (ESI$^+$): 395 [M+Na]$^+$
HPLC Retention Time: 10.8 minutes

Example 64

(1R,2S,3S,6R)-4-[3-(4-Ethylbenzyl)phenyl]-6-(hydroxy-methyl)cyclohex-4-ene-1,2,3-triol (1) Synthesis of 3-(4-Ethylbenzyl)phenylboronic Acid In a nitrogen stream, a solution of 1-bromo-3-(4-ethylbenzyl)benzene (2.19 g, 7.96 mmol) in THF (20 mL) was cooled to –78° C., and an n-butyllithium hexane solution (2.44 M, 3.42 mL) was added dropwise thereto and the mixture solution was stirred at the same temperature for 20 minutes. After addition of trimethyl borate (2.68 mL, 23.87 mmol), the reaction mixture was stirred at the temperature for five minutes and at room temperature for 12.5 hours. After cooling the reaction mixture in an ice bath, concentrated sulfuric acid (10 mL) was added dropwise thereto and the mixture solution was stirred at the same temperature for one hour. The mixture was extracted with ether and the organic layer was washed with water and then dried over sodium sulfate. To a white solid obtained by distilling the solvent under reduced pressure was added hexane-ethyl acetate (10:1)(5 mL), the mixture was filterated and then the obtained solid was washed with hexane-ethyl acetate (10:1). The obtained white powder was dried under reduced pressure to obtain the title compound (604.2 mg, 32%).

$^1$H-NMR (CDCl$_3$) δ: 1.22 (3H, t, J=7.6 Hz), 2.62 (2H, q, J=7.6 Hz), 4.07 (2H, s), 7.10-7.20 (4H, m), 7.36-7.44 (2H, m), 8.00-8.10 (2H, m)

(2) Synthesis of Trifluoromethanesulfonic Acid (3R,4R,5S, 6R)-4,5,6-Trisbenzyloxy-3-(benzyloxymethyl)cyclohex-1-enyl Ester In a nitrogen stream, an n-butyllithium hexane solution (322 μL, 0.787 mmol) was added dropwise to diisopropylamine (113 μL, 0.806 mmol) cooled in an ice bath, and THF (0.8 mL) was added thereto. The obtained solution was cooled to –78° C., and a solution of (2R,3S,4R,5R)-2,4,5-trisbenzyloxy-5-(benzyloxymethyl)-cyclohexanone (205.9 mg, 0.384 mmol) in THF (1 mL) was added dropwise, and the mixture was stirred at the same temperature for 12 minutes. A solution of N-(5-chloro-2-pyridyl)triflimide (452 mg, 1.15 mmol) in THF (1.2 mL) was added dropwise thereto and the reaction mixture was stirred at the same temperature for 2.5 hours. A saturated sodium hydrogencarbonate aqueous solution and water were added thereto to stop the reaction and the resulting mixture was extracted with ether. The organic layer was washed with a saturated sodium chloride aqueous solution and dried over sodium sulfate. The solvent was distilled under reduces pressure and the obtained residue was purified by silica gel column chromatography [developing solution=ethyl acetate:n-hexane (1:10 to 1:8) to obtain the title compound (161.4 mg, 63%).

$^1$H-NMR (CDCl$_3$) δ: 2.60-2.70 (1H, m), 3.40-3.58 (2H, m), 3.70 (1H, dd, J=9.9, 9.7 Hz), 3.90 (1H, dd, J=9.7, 7.1 Hz), 4.32-4.54 (4H, m), 4.70-4.94 (5H, m), 5.76-5.83 (1H, m), 7.10-7.40 (20H, m)

(3) Synthesis of 1-(4-Ethylbenzyl)-3-[(3R,4R,5S,6S)-4,5,6-trisbenzyloxy-3-(benzyloxymethyl)cyclohex-1-enyl]-benzene In a nitrogen stream, dioxane-water (10:1)(12 mL) was added to a mixture of trifluoromethanesulfonic acid (3R,4R,5S,6R)-4,5,6-trisbenzyloxy-3-(benzyloxymethyl)cyclohex-1-enyl ester (656 mg, 0.981 mmol), K$_3$PO$_3$ (250 mg, 1.18 mmol), KBr (140 mg, 1.18 mmol), 3-(4-ethylbenzyl)phenylboronic acid (283 mg, 1.18 mmol) and Pd(PPh$_3$)$_4$ (56.6 mg, 0.049 mmol), and the reaction mixture was heated and stirred at a temperature of 100° C. to 105° C. for 26 hours. After cooling the reaction mixture, a saturated sodium chloride aqueous solution and water were added thereto. The resulting solution was extracted with ether, and the organic layer was washed with a saturated sodium chloride aqueous solution and dried over sodium sulfate. The solvent was distilled under reduced pressure, and the obtained residue was purified by silica gel column chromatography [developing solution=ethyl acetate:n-hexane (1:10 to 1:8) to obtain the title compound (510.0 mg, 73%).

$^1$H-NMR (CDCl$_3$) δ: 1.19 (3H, t, J=7.6 Hz), 2.58 (2H, q, J=7.6 Hz), 2.64-2.75 (1H, m), 3.54 (1H, dd, J=8.9, 5.9 Hz), 3.64 (1H, dd, J=8.9, 3.5 Hz), 3.68-3.79 (1H, m), 3.92 (2H, s), 4.07 (1H, dd, J=9.7, 7.3 Hz), 4.31 (1H, d, J=10.6 Hz), 4.45 (2H, s), 4.48 (1H, d, J=10.6 Hz), 4.54 (1H, d, J=10.9 Hz), 4.79-5.00 (4H, m), 5.85-5.92 (1H, m), 6.73-6.82 (2H, m), 6.98-7.42 (26H, m)

(4) Synthesis of (1R,2S,3S,6R)-4-[3-(4-Ethylbenzyl)-phenyl]-6-(hydroxymethyl)cyclohex-4-ene-1,2,3-triol In a nitrogen stream, a solution of 1-(4-ethylbenzyl-3-[(3R,4R,5S,6S)-4,5,6-trisbenzyloxy-3-(benzyloxymethyl)-cyclohex-2-enyloxy]benzene (494.5 mg, 0.692 mmol) and pentamethylbenzene (1.05 g, 7.06 mmol) in methylene chloride (38 mL) was cooled to −78° C., and a $BCl_3$ methylene chloride solution (1.0 M, 7.54 mL) was added dropwise thereto. The reaction mixture was stirred at the temperature for ten minutes and at −70° C. for 1.5 hours, and then methanol (20 mL) was added thereto. The residue obtained by distilling the solvent under reduced pressure was roughly purified by silica gel column chromatography [developing solution=methanol:methylene chloride (1:20 to 1:10) and then purified by preparative TLC [developing solution=methanol:methylene chloride (1:10)] to obtain the title compound (46.2 mg, 19%).

$^1$H-NMR (CD$_3$OD) δ: 1.19 (3H, t, J=7.6 Hz), 2.27-2.44 (1H, m), 2.58 (2H, q, J=7.6 Hz), 3.44-3.68 (3H, m), 3.76-3.94 (3H, m), 4.45-4.57 (1H, m), 5.74-5.84 (1H, m), 6.95-7.25 (8H, m)

MS (ESI$^+$): 372 [M+H$_2$O]$^+$

HPLC Retention Time: 18.37 minutes

Measurement Conditions of HPLC

Column: YMC-Pack ODS-A 6.0×150 mm, 5 μm

Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes Flow Rate: 1.5 mL/minute Column Temperature Room temperature Detection Condition Total plot of the entire wavelength of 230 to 400 nm

Example 65

(1R,2R,3S,4R,5R)-1-[3-(4-Ethylbenzyl)-4-methoxyphenyl]-5-(hydroxymethyl)cyclohexane-1,2,3,4-tetraol (1) Synthesis of (1R,2R,3S,4R,5R)-2,3,4-trisbenzyloxy-5-(benzyloxymethyl)-1-[3-(4-ethylbenzyl)-4-methoxy-phenyl]cyclohexanol and (1S,2R,3S,4R,5R)-2,3,4-trisbenzyloxy-5-(benzyloxymethyl)-1-[3-(4-ethyl-benzyl)-4-methoxyphenyl]cyclohexanol In a nitrogen stream, an n-butyllithium hexane solution (2.70 M, 1.03 mL) was added dropwise to a solution of 4-bromo-2-(4-ethylbenzyl)-1-methoxybenzene (908 mg, 2.98 mmol) in THF (10 mL) while being cooled to −78° C. The reaction mixture was stirred at the same temperature for 10 minutes. To this solution, a solution of (2R,3S,4R,5R)-2,3,4-trisbenzyoxy-5-(benzyloxymethyl)-cyclohexanone (1.00 g, 1.86 mmol) in THF (2 mL) was added dropwise and the resulting solution was stirred at −78° C. for 30 minutes. The reaction was stopped by addition of a saturated ammonium chloride aqueous solution and water. The obtained solution was extracted with ethyl acetate, and the organic layer was washed with water and then dried over sodium sulfate. The residue obtained by distilling the solvent under reduced pressure was purified by silica gel column chromatography [developing solution=ethyl acetate:n-hexane (1:5 to 1:1) to obtain (1R,2R,3S,4R,5R)-2,3,4-tris-benzyloxy-5-(benzyloxymethyl)-1-[3-(4-ethylbenzyl)-4-methoxyphenyl]cyclohexanol (0.32 g, 23%) and (1S,2R,3S,4R, 5R)-2,3,4-trisbenzyloxy-5-(benzyloxymethyl)-1-[3-(4-ethylbenzyl)-4-methoxyphenyl]cyclohexanol (0.89 g, 64%).

(1R)-Isomer: $^1$H-NMR (CDCl$_3$) δ: 1.17 (3H, t, J=7.6 Hz), 1.80-2.00 (2H, m), 2.20-2.36 (1H, m), 2.55 (2H, d, J=7.6 Hz), 2.91 (1H, d, J=2.0 Hz), 3.35-3.42 (1H, m), 3.65-4.05 (10H, m), 4.41-4.45 (3H, m), 4.59 (1H, d, J=10.7 Hz), 4.81 (1H, d, J=10.7 Hz), 4.87 (1H, d, J=10.7 Hz), 4.90 (1H, d, J=10.7 Hz), 6.78-6.84 (3H, m), 6.99-7.20 (6H, m), 7.20-7.40 (18H, m)

(1S)-Isomer: $^1$H-NMR (CDCl$_3$) δ: 1.12 (3H, t, J=7.6 Hz), 1.40-1.54 (2H, m), 1.78-1.88 (1H, m), 2.35 (1H, dd, J=3.3, 13.7 Hz), 2.43 (1H, s), 2.47 (2H, q, J=7.6 Hz), 3.34 (1H, dd, J=0.9, 8.9 Hz), 3.53-3.72 (4H, m), 3.80 (3H, s), 3.86-3.93 (2H, m), 4.41 (2H, s), 4.49 (1H, d, J=10.7 Hz), 4.67-4.79 (2H, m), 4.83 (1H, d, J=10.7 Hz), 5.02 (1H, d, J=11.7 Hz), 6.78 (1H, d, J=8.4 Hz), 7.00 (2H, d, J=7.9 Hz), 7.10 (2H, d, J=7.9 Hz), 7.14-7.20 (2H, m), 7.21-7.40 (18H, m), 7.56-7.63 (2H, m)

(2) Synthesis of (1R,2R,3S,4R,5R)-1-[3-(4-Ethylbenzyl)-4-methoxyphenyl]-5-(hydroxymethyl)cyclohenane-1,2,3,4-tetraol To a solution of (1R,2R,3S,4R,5R)-2,3,4-trisbenzyloxy-5-(benzyloxymethyl)-1-[3-(4-ethylbenzyl)-4-methoxyphenyl] cyclohexanol (50.0 mg, 0.067 mmol) in THF (0.5 mL) and methanol (2 mL), a 20% palladium hydroxide catalyst (10 mg) was added and the mixture was stirred under a hydrogen atmosphere at room temperature for 15 hours. After filtering the catalyst, the filtrate was concentrated under reduced pressure. The obtained residue was purified by preparative TLC [developing solution=methanol:methylene chloride (1:10)] to obtain the title compound (20 mg, 74%).

$^1$H-NMR (CD$_3$OD) δ: 1.22 (3H, t, J=7.6 Hz), 1.65-1.84 (2H, m), 2.01-2.14 (1H, m), 2.60 (2H, q, J=7.6 Hz), 3.39-3.46 (1H, m), 3.62-3.75 (4H, m), 3.82 (3H, s), 3.94 (2H, s), 6.94 (1H, d, J=8.4 Hz), 7.06 (2H, d, J=8.2 Hz), 7.13 (2H, d, J=8.2 Hz), 7.30-7.38 (2H, m)

MS (ESI$^+$): 420 [M+H$_2$O]$^+$

HPLC Retention Time: 17.70 minutes

Measurement Conditions of HPLC

Column: YMC-Pack ODS-A 6.0×150 mm, 5 μm

Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes Flow Rate: 1.5 mL/minute Column Temperature Room temperature Detection Condition Total plot of the entire wavelength of 230 to 400 nm

Example 66

(1R,2R,3S,4S,6R)-4-[3-(4-Ethylbenzyl)-4-methoxyphenyl]-6-(hydroxymethyl)cyclohexane-1,2,3-triol (1) Synthesis of 2-(4-Ethylbenzyl)-1-methoxy-4-[(1S,2S, 3R,4R,5R)-2,3,4-trisbenzyloxy-5-(benzyloxymethyl)-cyclohexyl]benzene A solution of the (1S,2R,3S,4R,5R)-2,3,4-trisbenzyloxy-5-(benzyloxymethyl)-1-[3-(4-ethylbenzyl)-4-methoxyphenyl]cyclohexanol (124 mg, 0.16 mmol) as obtained in Example 65 in methylene chloride (2 mL) was cooled to −5° C., and triethylsilane (0.39 mL, 2.44 mmol) was added thereto. To the mixture, triofluoroacetic acid (0.12 mL, 1.6 mmol) was added and the reaction mixture was stirred at −5°

C. for one hour, and then a saturated sodium hydrogen-carbonate was added thereto. The resulting mixture was extracted with methylene chloride and the organic layer was washed with a saturated sodium chloride aqueous solution and then dried over sodium sulfate. The solvent was distilled under reduced pressure and the obtained residue was purified by silica gel column chromatography [developing solution=ethyl acetate:n-hexane (1:9)] to obtain the title compound (10 mg, 8%).

$^1$H-NMR (CDCl$_3$) δ: 1.17 (3H, t, J=7.6 Hz), 1.58-1.96 (3H, m), 2.56 (2H, q, J=7.6 Hz), 2.55-2.70 (1H, m), 3.43-3.62 (5H, m), 3.78-4.00 (6H, m), 4.43 (2H, s), 4.44 (1H, d, J=9.9 Hz), 4.56 (1H, d, J=10.8 Hz), 4.82-4.93 (3H, m), 6.75-6.82 (3H, m), 6.99-7.18 (9H, m), 7.20-7.38 (15H, m)

(2) Synthesis of (1R,2R,3S,4S,6R)-4-[3-(4-Ethylbenzyl)-4-methoxyphenyl]-6-(hydroxymethyl)cyclohexane-1,2,3-triol To a solution of 2-(4-ethylbenzyl)-1-methoxy-4-[(1S,2S,3R,4R,5R)-2,3,4-tris-benzyloxy-5-(benzyloxymethyl)cyclohexyl]benzene (10 mg, 0.013 mmol) in THF (0.2 mL) and methanol (1 mL), a 20% palladium hydroxide catalyst (10 mg) was added and the mixture was stirred under a hydrogen atmosphere at room temperature for 13 hours. After filtering the catalyst, the filtrate was concentrated under reduced pressure. The obtained residue was purified by preparative TLC [developing solution=methanol:methylene chloride (1:10)] to obtain the title compound (3.9 mg, 75%).

$^1$H-NMR (CD$_3$OD) δ: 1.23 (3H, t, J=7.4 Hz), 1.34-1.48 (1H, m), 1.60-1.76 (1H, m), 1.83 (1H, dt, J=13.5, 3.5 Hz), 2.48-2.66 (3H, m), 3.30-3.38 (2H, m), 3.42-3.52 (1H, m), 3.58-3.65 (1H, m), 3.77 (1H, d, J=4.0 Hz), 3.82 (3H, s), 3.92 (2H, s), 6.91 (1H, d, J=8.2 Hz), 7.02-7.14 (6H, m)

MS (ESI$^+$): 406 [M+H$_2$O]$^+$

HPLC Retention Time: 12.53 minutes

Measurement Conditions of HPLC
Column: YMC-Pack ODS-A 6.0×150 mm, 5 μm
Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes
Flow Rate: 1.5 mL/minute
Column Temperature Room temperature
Detection Condition Total plot of the entire wavelength of 230 to 400 nm Example 67

(1R,2R,3S,4R,5R)-1-[2-Ethyl-5-(4-ethylbenzyl)phenyl]-5-(hydroxymethyl)cyclohexane-1,2,3,4-tetraol (1) Synthesis of (3-Bromo-4-ethoxyphenyl)-(4-ethylphenyl)methanol THF (10 mL) was added to magnesium (353 mg, 14.5 mmol), and furthermore 1-bromo-4-ethylbenzene (2 mL, 14.5 mmol) was added dropwise thereto and the mixture was heated to reflux for one hour. The reaction mixture was cooled to 0° C., and a solution of 3-bromo-4-ethoxybenzaldehyde (2.21 g, 9.68 mmol) in THF (5 mL) was added thereto and the reaction mixture was stirred at the same temperature for 1.5 hours. To the reaction mixture, a saturated ammonium chloride aqueous solution was added and the resulting mixture was extracted with ethyl acetate. The extract was washed with a saturated sodium chloride aqueous solution and dried over magnesium sulfate. The residue obtained by distilling the solvent under reduced pressure was purified by silica gel column chromatography [developing solution=n-hexane to n-hexane:ethyl acetate (3:1)] to obtain the title compound (2.83 g, 88%).

$^1$H-NMR (CDCl$_3$) δ: 1.22 (3H, t, J=7.6 Hz), 1.45 (3H, t, J=7.0 Hz), 2.14 (1H, d, J=3.5 Hz), 2.63 (2H, q, J=7.5 Hz), 4.07 (2H, q, J=7.0 Hz), 5.74 (1H, d, J=3.5 Hz), 6.83 (1H, d, J=8.4 Hz), 7.17 (2H, d, J=8.1 Hz), 7.20-7.30 (3H, m), 7.56 (1H, d, J=2.1 Hz)

(2) Synthesis of 2-Bromo-1-ethoxy-4-(4-ethylbenzyl)-benzene

Triethylsilane (2.7 mL, 16.9 mmol) and a boron trifluoride-diethyl ether complex (1.2 mL, 9.47 mmol) were added to a solution of (3-bromo-4-ethoxyphenyl)-(4-ethylphenyl)methanol (2.83 g, 8.44 mmol) in methylene chloride (20 mL) at 0° C. and the mixture was stirred for three hours. Methanol (50%)-water (4 mL) was added to the reaction mixture and the resulting mixture was extracted with methylene chloride. The extract was washed with a saturated sodium chloride aqueous solution, and then dried over magnesium sulfate. The residue obtained by distilling the solvent under reduced pressure was purified by silica gel column chromatography {developing solution=n-hexane to n-hexane-ethyl acetate [4% (v/v)]} to obtain the title compound (2.69 g, 100%).

$^1$H-NMR (CDCl$_3$) δ: 1.22 (3H, t, J=7.6 Hz), 1.45 (3H, t, J=7.0 Hz), 2.62 (2H, q, J=7.6 Hz), 3.85 (2H, s), 4.06 (2H, q, J=7.0 Hz), 6.79 (1H, d, J=8.4 Hz), 7.00-7.15 (3H, m), 7.36 (1H, d, J=2.1 Hz)

(3) Synthesis of (1R,2R,3S,4R,5R)- and (1S,2R,3S,4R,5R)-2,3,4-Trisbenzyloxy-5-benzyloxymethyl-1-[2-ethoxy-5-(4-ethylbenzyl)phenyl]cyclohexanol In a nitrogen stream, an n-butyllithium hexane solution (1.59 M, 2.30 mL, 3.66 mmol) was added dropwise to a solution of 2-bromo-1-ethoxy-4-(4-ethyl-benzyl)benzene (1.18 g, 3.70 mmol) in THF (9 mL) while being cooled to −78° C. The reaction mixture was stirred at the same temperature for one hour, and then a solution of (2R,3S,4R,5R)-2,3,4-trisbenzyloxy-5-(benzyloxymethyl)-cyclohexanone (1.50 g, 2.80 mmol) in THF (4.5 mL) was added dropwise thereto and the reaction mixture was stirred at −78° C. for 10 minutes. A saturated ammonium chloride aqueous solution was added thereto to stop the reaction. The resulting mixture was extracted with ethyl acetate, and the organic layer was washed with a saturated sodium chloride aqueous solution and then dried over magnesium sulfate. The residue obtained by distilling the solvent under reduced pressure was purified by silica gel column chromatography [developing solution=ethyl acetate:n-hexane (1:4)] to obtain a (1R)-isomer (884 mg, 41%) and a (1S)-isomer (740 mg, 34%).

(1R)-Isomer: $^1$H-NMR (CDCl$_3$) δ: 1.23 (3H, t, J=7.6 Hz), 1.37 (3H, t, J=7.0 Hz), 1.70 (1H, dd, J=14.3, 4.1 Hz), 2.20-2.35 (1H, m), 2.62 (2H, q, J=7.6 Hz), 2.67-2.82 (1H, m), 3.0-3.3 (1H, br), 3.43 (1H, dd, J=8.8, 2.0 Hz), 3.71 (1H, dd, J=9.8, 9.8 Hz), 3.83 (1H, dd, J=8.9, 4.0 Hz), 3.86-4.10 (3H, m), 3.91 (2H, s), 4.44 (2H, s), 4.48 (1H, d, J=10.3 Hz), 4.58 (1H, br), 4.63 (1H, d, J=10.3 Hz), 4.85 (1H, d, J=11.0 Hz), 4.88 (1H, d, J=11.0 Hz), 4.95 (1H, d, J=10.8 Hz), 6.75 (1H, d, J=8.4 Hz), 6.79 (2H, d, J=7.0 Hz), 7.00-7.40 (24H, m), 7.53 (1H, d, J=2.0 Hz)

(1S)-Isomer: $^1$H-NMR (CDCl$_3$) δ: 1.12 (3H, t, J=7.6 Hz), 1.30 (3H, t, J=7.2 Hz), 1.40-1.55 (1H, m), 1.76 (1H, dd, J=13.3, 13.3 Hz), 2.50 (2H, q, J=7.6 Hz), 2.74 (1H, dd, J=13.7, 3.2 Hz), 3.38 (1H, dd, J=9.0, 2.8 Hz), 3.54 (1H, dd, J=9.0, 5.3 Hz), 3.64 (1H, dd, J=10.8, 8.7 Hz), 3.86 (1H, dd, J=9.5, 9.5 Hz), 3.89 (2H, s), 4.0-4.1 (2H, m), 4.39 (2H, s), 4.53 (1H, dd, J=11.0 Hz), 4.64-4.72 (3H, m), 4.77 (1H, d, J=11.7 Hz), 4.79 (1H, d, J=10.5 Hz), 4.87 (1H, d, J=10.8 Hz), 4.98 (1H, d, J=11.7 Hz), 6.98-7.42 (25H, m), 7.67 (1H, d, J=1.8 Hz)

(4) Synthesis of (1R,2R,3S,4R,5R)-1-[2-Ethoxy-5-(4-ethyl-benzyl)phenyl]-5-(hydroxymethyl)cyclohexane-1,2,3,4-tetraol To a solution of (1R,2R,3S,4R,5R)-2,3,4-trisbenzyl-oxy-5-(benzyloxymethyl)-1-[2-ethoxy-5-(4-ethylbenzyl)-phenyl]cyclohexanol (600 mg, 0.772 mmol) in THF (6 mL) and methanol (3 mL), a 20% palladium hydroxide catalyst (60 mg) was added and the mixture was stirred under a hydrogen atmosphere for 2.5 hours. After filtering the catalyst, the filtrate was concentrated under reduced pressure. The obtained residue was purified by silica gel column chromatography (developing solution=methylene to methylene chloride methanol [12% (v/v)]) to obtain the title compound (197 mg, 61%).
$^1$H-NMR (CD$_3$OD) δ: 1.18 (3H, t, J=7.6 Hz), 1.43 (3H, t, J=7.0 Hz), 1.60 (1H, dd, J=14.3, 4.1 Hz), 2.01 (1H, m), 2.43 (1H, dd, J=14.0, 13.0 Hz), 2.57 (2H, q, J=7.5 Hz), 3.39 (1H, dd, J=10.5, 9.3 Hz), 3.60-3.68 (3H, m), 3.85 (2H, s), 4.03 (2H, m), 4.34 (1H, d, J=9.2 Hz), 6.82 (1H, d, J=8.2 Hz), 6.99 (1H, dd, J=8.4 Hz, 2.3 Hz), 7.45 (1H, d, J=2.3 Hz)
MS (ESI$^+$): 434 [M+H$_2$O]$^+$
HPLC Retention Time: 18.71 minutes
Measurement Conditions of HPLC
  Column: YMC-Pack ODS-A 6.0×150 mm, 5 μm
  Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes
  Flow Rate: 1.5 mL/minute
  Column Temperature Room temperature
  Detection Condition Total plot of the entire wavelength of 230 to 400 nm Example 68

(1R,2R,3S,4S,6R)-4-[2-Ethoxy-5-(4-ethylbenzyl)phenyl]-6-(hydroxymethyl)cyclohexane-1,2,3-triol (1) Synthesis of (1R,2R,3S,4S,6R)-4-[2-Ethoxy-5-(4-ethylbenzyl)phenyl]-6-(hydroxymethyl)cyclohexane-1,2,3-triol To a solution of the (1S,2R,3S,4R,5R)-2,3,4-tris-benzyloxy-5-benzyloxymethyl-1-[2-ethoxy-5-(4-ethylbenzyl)-phenyl]cyclohexanol (402 mg, 0.517 mmol) in THF (4 ml) and methanol (2 mL) as obtained in Example 67, a 20% palladium hydroxide catalyst (78 mg) was added and the mixture solution was stirred under a hydrogen atmosphere for 19 hours. After filtering the catalyst, the filtrate was concentrated under reduced pressure. The obtained residue was purified by silica gel column chromatography [developing solution=methylene chloride:methanol (10:1)] to obtain the title compound (42 mg, 20%).
$^1$H-NMR (CD$_3$OD) δ: 1.18 (3H, t, J=7.6 Hz), 1.25-1.50 (1H, m), 1.38 (3H, t, J=7.0 Hz), 1.62 (1H, m), 1.78 (1H, m), 2.57 (2H, q, J=7.6 Hz), 2.95-3.15 (1H, br), 3.25-3.33 (2H, m), 3.54 (1H, dd, J=10.8, 6.1 Hz), 3.73 (1H, dd, J=10.8, 3.8 Hz), 3.65-3.85 (1H, m), 3.83 (2H, s), 4.00 (2H, q, J=7.0 Hz), 6.81 (1H, d, J=8.4 Hz), 6.94 (1H, dd, J=8.3, 2.1 Hz), 7.04 (1H, d, J=1.7 Hz), 7.06 (4H, s)
MS (ESI$^+$):401[M]$^+$
HPLC Retention Time: 12.98 minutes Examples 69 to 74

The target compounds were obtained by performing the same operation as in Example 67 or Example 68 with the use of the corresponding starting materials and reagents, respectively.

Example 69

(1R,2R,3S,4R,5R)-1-[5-(4-Ethylbenzyl)-2,4-dimethoxy-phenyl]-5-(hydroxymethyl)cyclohexane-1,2,3,4-tetraol $^1$H-NMR (CD$_3$OD) δ: 1.17 (3H, t, J=7.6 Hz), 1.61 (1H, dd, J=13.9, 3.8 Hz), 1.90-2.10 (1H, m), 2.22 (1H, dd, J=13.9, 13.2 Hz), 2.55 (2H, q, J=-7.6 Hz), 3.32-3.42 (1H, m), 3.58-3.70 (3H, m), 3.76-3.88 (2H, m), 3.80 (3H, s), 3.84 (3H, s), 4.19 (1H, d, J=9.1 Hz), 6.58 (1H, s), 7.00 (2H, d, J=8.2 Hz), 7.06 (2H, d, J=8.2 Hz), 7.35 (1H, s)
MS (ESI$^+$): 455 [M+Na]$^+$
HPLC Retention Time: 17.83 minutes
Measurement Conditions of HPLC
  Column: YMC-Pack ODS-A 6.0×150 mm, 5 μm
  Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes
  Flow Rate: 1.5 mL/minute
  Column Temperature Room temperature
  Detection Condition Total plot of the entire wavelength of 230 to 400 nm Example 70

(1R,2R,3S,4S,6R)-4-[5-(4-Ethylbenzyl)-2,4-dimethoxy-phenyl]-6-(hydroxymethyl)cyclohexane-1,2,3-triol $^1$H-NMR (CD$_3$OD) δ: 1.17 (3H, t, J=7.6 Hz), 1.24-1.48 (1H, m), 1.52-1.82 (2H, m), 2.56 (2H, d, J=7.6 Hz), 2.86-3.08 (1H, m), 3.24-3.29 (1H, m), 3.48-3.67 (2H, m), 3.68-3.84 (3H, m), 3.79 (3H, s), 3.81 (3H, s), 6.56 (1H, s), 6.93 (1H, s), 7.01 (2H, d, J=8.6 Hz), 7.05 (2H, d, J=8.6 Hz)
MS (ESI$^+$): 416 [M]$^+$
HPLC Retention Time: 18.26 minutes
Measurement Conditions of HPLC
  Column: YMC-Pack ODS-A 6.0×150 mm, 5 μm
  Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes Flow Rate: 1.5 mL/minute Column Temperature Room temperature Detection Condition Total plot of the entire wavelength of 230 to 400 nm

Example 71

(1R,2R,3S,4R,5R)-1-[5-(4-Ethylbenzyl)-2-methylphenyl]-5-(hydroxymethyl)cyclohexane-1,2,3,4-tetraol $^1$H-NMR (CD$_3$OD) δ: 1.19 (3H, t, J=7.6 Hz), 1.70 (1H, m), 1.94 (1H, m), 2.05 (1H, m), 2.53 (3H, s), 2.58 (2H, q, J=7.6 Hz), 3.40 (1H, d, J=9.2 Hz), 3.67 (2H, d, J=4.6 Hz), 3.73 (1H, d, J=9.2 Hz), 3.87 (2H, s), 4.01 (1H, d, J=9.2 Hz), 6.91 (1H, dd, J=7.6, 1.5 Hz), 7.01 (1H, d, J=7.6 Hz), 7.07 (4H, m), 7.42 (1H, s)
MS (ESI$^+$): 409 [M+Na]$^+$

Example 72

(1R,2R,3S,4S,6R)-4-[5-(4-Ethylbenzyl)-2-methylphenyl]-6-(hydroxymethyl)cyclohexane-1,2,3-triol $^1$H-NMR (CD$_3$OD) δ: 1.19 (3H, t, J=7.6 Hz), 1.24-1.37 (1H, m), 1.59-1.81 (2H, m), 2.30 (3H, s), 2.57 (2H, q, J=7.6 Hz), 2.93 (1H, m), 3.34 (2H, m), 3.50-3.63 (2H, m), 3.75 (1H, dd, J=10.7, 4.2 Hz), 3.86 (2H, s), 6.87 (1H, d, J=7.6 Hz), 7.03 (1H, d, J=7.6 Hz, 2.1 Hz), 7.07 (4H, s), 7.11 (1H, s)
MS (ESI$^-$): 369 [M−H]$^-$

Example 73

(1R,2R,3S,4R,5R)-1-[5-(4-Ethylbenzyl)-2-methoxyphenyl]-5-(hydroxymethyl)cyclohexane-1,2,3,4-tetraol $^1$H-NMR (CD$_3$OD) δ: 1.13 (3H, t, J=7.6 Hz), 1.56 (1H, dd, J=14.1, 3.9 Hz), 1.94-2.04 (1H, m), 2.24 (1H, dd, J=13.9, 13.2 Hz), 2.51 (2H, q, J=7.5 Hz), 3.24-3.37 (1H, m), 3.57-3.63 (3H, m), 3.74 (3H, s), 3.80-3.90 (2H, m), 4.22 (1H, d, J=9.1 Hz), 6.80 (1H, d, J=8.4 Hz), 6.95-7.01 (5H, m), 7.41 (1H, d, J=1.2 Hz)
MS (ESI$^+$): 425 [M+Na]$^+$
HPLC Retention Time: 11.69 minutes

Example 74

(1R,2R,3S,4S,6R)-4-[5-(4-Ethylbenzyl)-2-methoxyphenyl]-6-(hydroxymethyl)cyclohexane-1,2,3-triol $^1$H-NMR (CD$_3$OD) δ: 1.18 (3H, t, J=7.6 Hz), 1.24-1.50 (1H, m), 1.54-1.85 (2H, m), 2.57 (2H, d, J=7.6 Hz), 2.90-3.18 (1H, m), 3.24-3.34 (2H, m), 3.54 (1H, dd, J=10.7, 5.9 Hz), 3.60-3.78 (2H, m), 3.76 (3H, s), 3.83 (2H, s), 6.82 (1H, d, J=8.4 Hz), 6.96 (1H, dd, J=8.4, 2.0 Hz), 7.01-7.11 (5H, m)
MS (ESI$^+$): 404 [M+H$_2$O]$^+$
HPLC Retention Time: 12.33 minutes

Example 75

(1R,2R,3S,4R,5R)-1-[5-(4-Ethylbenzyl)-2-trifluoromethoxy-phenyl]-5-(hydroxymethyl)cyclohexane-1,2,3,4-tetraol The target compound was obtained by performing the same operation as in Example 67 with the use of the corresponding staring material and reagents.

$^1$H-NMR (CD$_3$OD) δ: 1.17 (3H, t, J=7.6 Hz), 1.73 (1H, d, J=10.1 Hz), 2.00-2.12 (2H, m), 2.58 (2H, q, J=7.5 Hz), 3.35 (1H, dd, J=9.3, 9.3 Hz), 3.58-3.72 (2H, m), 3.66 (1H, dd, J=9.2, 9.2 Hz), 3.93 (2H, s), 3.99 (1H, d, J=8.9 Hz), 7.09 (4H, s), 7.13 (2H, m), 7.69 (1H, d, J=1.4 Hz)
MS (ESI$^+$): 474 [M+Na]$^+$
HPLC Retention Time: 13.09 minutes

Examples 76 to 78

The target compounds were obtained by performing the same operation as in Example 68 with the use of the corresponding staring raw materials and reagents, respectively.

Example 76

(1R,2R,3S,4S,6R)-4-[5-(4-Isopropylbenzyl)-2-methoxy-phenyl]-6-(hydroxymethyl)cyclohexane-1,2,3-triol $^1$H-NMR (CD$_3$OD) δ: 1.21 (6H, d, J=6.9 Hz), 1.29-1.42 (1H, m), 1.59-1.81 (2H, m), 2.78-2.89 (1H, m), 3.06-3.10 (1H, m), 3.26-3.34 (2H, m), 3.55 (1H, dd, J=10.7, 6.0 Hz), 3.62-3.85 (5H, m), 3.84 (2H, s), 6.82 (1H, d, J=8.5 Hz), 6.96 (1H, dd, J=8.2, 2.2 Hz), 7.05-7.11 (5H, m)
MS (ESI$^+$): 400 [M]$^+$
HPLC Retention Time: 13.07 minutes

Example 77

(1R,2R,3S,4S,6R)-4-[3-(4-Ethylbenzyl)phenyl]-6-(hydroxy-methyl)cyclohexane-1,2,3-triol $^1$H-NMR (CD$_3$OD) δ: 1.24 (3H, t, J=7.5 Hz), 1.43-1.53 (1H, m), 1.61-1.78 (1H, m), 1.85 (1H, dt, J=13.4, 3.7 Hz), 2.56-2.68 (3H, m), 3.29-3.40 (2H, m), 3.50-3.66 (2H, m), 3.80 (1H, dd, J=10.9, 3.9 Hz), 3.94 (2H, s), 7.04-7.27 (8H, m)
MS (ESI$^+$): 357 [M]$^+$
HPLC Retention Time: 12.12 minutes

Example 78

(1R,2R,3S,4S,6R)-4-[3-(4-Hydroxybenzyl)phenyl]-6-(hydroxy-methyl)cyclohexane-1,2,3-triol $^1$H-NMR (CD$_3$OD) δ: 1.43-1.52 (1H, m), 1.64-1.78 (1H, m), 1.85 (1H, dt, J=12.5, 3.7 Hz), 2.55-2.66 (1H, m), 3.33-3.40 (2H, m), 3.50-3.64 (2H, m), 3.76-3.84 (1H, m), 3.88 (2H, s), 6.68-6.74 (2H, m), 7.00-7.14 (5H, m), 7.20-7.25 (1H, m)
MS (ESI$^+$): 362 [M+H$_2$O]$^+$
HPLC Retention Time: 13.70 minutes

Example 79

(1R,2R,3S,4S,6R)-4-[5-(4-Ethylbenzyl)-2-hydroxyphenyl-6-(hydroxymethyl)cyclohexane-1,2,3-triol In a nitrogen stream, a solution of the (1R,2R,3S,4S,6R)-4-[5-(4-ethylbenzyl)-2-methoxyphenyl]-6-(hydroxy-methyl)cyclohexane-1,2,3-triol (40 mg, 0.1 mmol) as obtained in Example 74 in methylene chloride (1 mL) was cooled to −78° C. and a BBr$_3$ methylene solution (1.0 M, 0.31 mL) was added dropwise thereto and the mixture was stirred at the same temperature for 10 minutes and under cooling with ice for two hours. Furthermore the BBr$_3$ methylene chloride solution (0.2 mL) was added dropwise thereto and the mixture solution was stirred at the same temperature for 3.5 hours, and then a sodium hydroxide methanol solution (0.93 mL) was added thereto. The residue obtained by distilling the solvent under reduced pressure was purified by silica gel column chromatography [developing solution=ethyl acetate: n-hexane (1:4)] to obtain the title compound (3.5 mg, 9.1%).

$^1$H-NMR (CD$_3$OD) δ: 0.87-0.98 (1H, s), 1.19 (3H, t, J=7.8 Hz), 1.39-1.52 (1H, m), 1.59-1.66 (1H, m), 1.78-1.83 (1H, dt, J=13.5, 3.6 Hz), 2.56 (2H, q, J=7.8, 7.5 Hz), 2.96-3.07 (1H, m), 3.34 (1H, s), 3.54-3.59 (1H, m), 3.62-3.69 (1H, m), 3.72 (1H, dd, J=6.6, 3.9 Hz), 3.80 (2H, s), 6.68 (1H, d, J=8.4 Hz), 6.80 (1H, dd, J=8.4, 2.0 Hz), 6.99 (1H, s), 7.05 (4H, s)

MS (ESI$^+$): 372 [M]$^+$

HPLC Retention Time: 11.2 minutes

Example 80

(1R,2R,3S,4S,6R)-4-[3-(4-Cyclopropylbenzyl)phenyl-6-(hydroxymethyl)cyclohexane-1,2,3-triol (1) Synthesis of 4-[3-((3aS,4S,5aR,9aR,9bR)-2,2,8,8-tetramethyl-hexahydro[1,3]dioxolo[4',5':3,4]benzo-[1,2-d][1,3]dioxin-4-yl)benzyl]phenol (1R,2R,3S,4S,6R)-4-[3-(4-Hydroxybenzyl)phenyl-6-(hydroxymethyl)cyclohexane-1,2,3-triol (47 mg, 0.136 mmol) as obtained in Example 78 was dissolved in N,N-dimethylformamide (1 mL) and the resulting mixture was stirred under cooling with ice. 2,2-Dimethoxypropane (142 mg, 1.36 mmol) and successively p-toluenesulfonic acid hydrate (2 mg) were added to the reaction mixture. The resulting mixture was stirred at room temperature for 30 minutes, and a saturated ammonium chloride aqueous solution was added thereto to stop the reaction. The mixture was extracted with ethyl acetate, and the organic layer was washed with water and dried over sodium sulfate. The residue obtained distilling the solvent under reduced pressure was purified by preparative TLC [developing solution=ethyl acetate: n-hexane (1:4)] to obtain the title compound (34 mg, 59%).

$^1$H-NMR (CDCl$_3$) δ: 1.11-1.24 (1H, m), 1.42 (6H, s), 1.46 (3H, s), 1.53 (3H, s), 1.73 (1H, dt, J=13.7, 3.9 Hz), 1.80-1.93 (1H, m), 2.94 (1H, dt, J=4.0, 11.0 Hz), 3.59-3.92 (7H, m), 4.85 (1H, s), 6.71-6.76 (2H, m), 7.00-7.08 (5H, m), 7.19-7.23 (1H, m)

(2) Synthesis of Trifluoromethanesulfonic Acid 4-[3-((3aS,4S,5aR,9aR,9bR)-2,2,8,8-tetramethyl-hexahydro-[1,3]dioxolo[4',5':3,4]benzo[1,2-d][1,3]dioxin-4-yl)benzyl]phenyl Ester 4-[3-((3aS,4S,5aR,9aR,9bR)-2,2,8,8-Tetramethyl-hexahydro[1,3]dioxolo[4',5':3,4]benzo[1,2-d][1,3]dioxin-4-yl)benzyl]phenol (34 mg, 0.08 mmol) was dissolved in methylene chloride (0.8 mL) and the mixture was stirred under cooling with ice. Pyridine (15 mg, 0.19 mmol), 2-[N,N-bis(trifluoromethanesulfonyl)amino]pyridine (34 mg, 0.096 mmol), and successively N,N-dimethylaminopyridine (1 mg) were added thereto and the reaction mixture was stirred at room temperature for 30 minutes, and water was added thereto to stop the reaction. The mixture was extracted with methylene chloride and the organic layer was washed with water and dried over sodium sulfate. The residue obtained by distilling the solvent under reduced pressure was purified by preparative TLC [developing solution=ethyl acetate:n-hexane (1:4)] to obtain the title compound (37 mg, 83%).

$^1$H-NMR (CDCl$_3$) δ: 1.11-1.24 (1H, m), 1.42 (6H, s), 1.43 (3H, s), 1.53 (3H, s), 1.74 (1H, dt, J=13.7, 3.9 Hz), 1.80-1.93 (1H, m), 2.96 (1H, dt, J=11.1, 3.6 Hz), 3.59-3.92 (5H, m), 3.98 (2H, s), 7.00-7.03 (2H, m), 7.10-7.35 (6H, m)

(3) Synthesis of (3aS,4S,5aR,9aR,9bR)-4-[3-(4-Cyclo-propylbenzyl)phenyl]-2,2,8,8-tetramethyl-hexahydro-[1,3]dioxolo[4',5':3,4]benzo[1,2-d][1,3]dioxin In a nitrogen stream, toluene (0.5 mL)-water (0.017 mL) was added to a mixture of trifluoromethanesulfonic acid 4-[3-((3aS,4S,5aR,9aR,9bR)-2,2,8,8-tetramethyl-hexa-hydro[1,3]dioxolo[4',5':3,4]benzo[1,2-d][1,3]dioxin-4-yl)benzyl] phenyl ester (38 mg, 0.068 mmol), K$_3$PO$_4$ (65 mg, 0.31 mmol), sodium bromide (7 mg, 0.068 mmol), cyclo-propylboronic acid (9 mg, 0.10 mmol) and Pd(PPh$_3$)$_4$ (8.0 mg, 0.007 mmol), and the reaction mixture was heated at 100° C. and stirred for six hours. The reaction mixture was cooled to 0° C. and water was added thereto. The resulting solution was extracted with ethyl acetate, and the organic layer was washed with a saturated sodium chloride aqueous solution and dried over sodium sulfate. The solvent was distilled under reduced pressure and the obtained residue was purified by preparative TLC [developing solution=ethyl acetate:n-hexane (1:4)] to obtain the title compound (10 mg, 33%).

$^1$H-NMR (CDCl$_3$) δ: 0.62-0.68 (2H, m), 0.89-0.96 (2H, m), 1.10-1.24 (1H, m), 1.42 (3H, s), 1.43 (3H, s), 1.46 (3H, s), 1.54 (3H, s), 1.74 (1H, dt, J=13.7, 3.9 Hz), 1.80-1.93 (2H, m), 2.94 (1H, dt, J=10.9, 3.6 Hz), 3.59-3.96 (8H, m), 6.96-7.07 (7H, m), 7.16-7.25 (1H, m)

(4) Synthesis of (1R,2R,3S,4S,6R)-4-[3-(4-Cyclopropyl-benzyl)phenyl]-6-(hydroxymethyl)cyclohexane-1,2,3-triol A solution of (3aS,4S,5aR,9aR,9bR)-4-[3-(4-cyclo-propylbenzyl)phenyl]-2,2,8,8-tetramethyl-hexahydro[1,3]-dioxolo[4',5':3,4]benzo[1,2-d][1,3]dioxin (10 mg, 0.022 mmol) in dioxane (0.2 mL) was cooled to 0° C. and a 2N hydro-chloric acid solution (0.2 mL) was added dropwise thereto. The reaction mixture was stirred at the same temperature for three hours, and then a saturated sodium hydrogencarbonate aqueous solution was added thereto. The resulting solution was extracted with methylene chloride and the organic layer was washed with a saturated sodium chloride aqueous solution and dried over sodium sulfate. The residue obtained by distilling the solvent under reduced pressure was purified by preparative TLC [developing solution=methanol: methylene chloride (1:10)] to obtain the title compound (4.5 mg, 51%).

$^1$H-NMR (CD$_3$OD) δ: 0.63-0.68 (2H, m), 0.91-0.98 (2H, m), 1.42-1.52 (1H, m), 1.62-1.78 (1H, m), 1.80-1.94 (2H, m), 2.54-2.66 (1H, m), 3.33-3.40 (2H, m), 3.50-3.68 (2H, m), 3.79 (1H, dd, J=10.9, 3.9 Hz), 3.93 (2H, s), 6.85-7.16 (7H, m), 7.21-7.26 (1H, m)

MS (ESI$^+$): 386 [M+H$_2$O]$^+$

HPLC Retention Time: 18.49 minutes

Measurement Conditions of HPLC

Column: YMC-Pack ODS-A 6.0×150 mm, 5 μm

Mobile Phase Elution by applying a gradient of from 10 mM AcONH$_4$/H$_2$O (95%) plus 10 mM AcONH$_4$/MeOH (5%) to 10 mM AcONH$_4$/MeOH (100%) for 20 minutes, and thereafter under the same condition [10 mM AcONH$_4$/MeOH (100%)] for five minutes Flow Rate: 1.5 mL/minute
Column Temperature Room temperature
Detection Condition Total plot of the entire wavelength of 230 to 400 nm

Example 81

(1R,2R,3S,4R,5R)-1-[5-(4-Ethylbenzyl)-2-fluorophenyl]-5-(hydroxymethyl)cyclohexane-1,2,3,4-tetraol (1) Synthesis of (1R,2R,3S,4R,5R)- and (1S,2R,3S,4R,5R)-2,3,4-Trisbenzyloxy-5-benzyloxymethyl-1-[5-(4-ethyl-benzyl)-2-fluorophenyl]cyclohexanol In a nitrogen stream, an n-butyllithium hexane solution (2.44 M, 0.368 mL) was added dropwise to an solution of 2-bromo-4-(4-ethylbenzyl)-1-fluorobenzene (0.263 g, 0.9000 mmol) in ether (3.0 mL) at −78° C. and the mixture solution was stirred at the same temperature for two hours. To this solution, a solution of 2,3,4-tris-benzyloxy-5-methylcyclohexane (0.483-g, 0.900 mmol) in THF (1.5 mL) was added thereto and the reaction mixture was stirred for two hours. The reaction was stopped by addition of a saturated ammonium chloride aqueous solution and the resulting mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:4)] to obtain a (1R)-isomer (0.117 g, 17.3%) and a (1S)-isomer (0.311 g, 46.1%) of the title compound.

(1R)-Isomer: $^1$H-NMR (CDCl$_3$) δ: 1.15-1.32 (3H, m), 1.81-1.92 (1H, br), 2.20-2.38 (2H, br), 2.62 (2H, q, J=9.8 Hz), 3.07 (1H, br), 3.40-3.55 (1H, m), 3.66-3.80 (2H, m), 3.84-4.06 (4H, m), 4.28 (1H, d, J=12.3 Hz), 4.45 (2H, s), 4.58 (2H, t, J=12.1 Hz), 4.80-4.96 (3H, m), 6.76-6.84 (2H, m), 6.86-7.00 (1H, m), 7.02-7.44 (23H, m), 7.52-7.60 (1H, m)

(1S)-Isomer: $^1$H-NMR (CDCl$_3$) δ: 1.13 (3H, t, J=1.5 Hz), 1.34-1.55 (1H, br), 1.84 (1H, t, J=2.4 Hz), 2.50 (2H, q, J=1.5 Hz), 2.75 (1H, dd, J=2.4, 0.9 Hz), 2.93 (1H, d, J=0.9 Hz), 3.37 (1H, dd, J=10.5, 6.6 Hz), 3.57-3.78 (3H, m), 3.86-4.06 (3H, m), 4.40-5.00 (8H, m), 6.80-7.60 (26H, m), 7.72-7.84 (1H, m)

(2) Synthesis of (1R,2R,3S,4R,5R)-1-[5-(4-Ethylbenzyl)-2-fluorophenyl]-5-(hydroxymethyl)cyclohexane-1,2,3,4-tetraol To a mixture solution of (1R,2R,3S,4R,5R)-2,3,4-trisbenzyloxy-5-benzyloxymethyl-1-[5-(4-ethylbenzyl)-2-fluorophenyl]cyclohexanol (271 mg, 0.361 mmol) in methanol-THF (1:1) mixed solvent (20 mL), a 20% palladium hydroxide catalyst (40 mg) was added thereto. The mixture was stirred under a hydrogen atmosphere for 30 minutes, and then the catalyst was filtered off. The solvent was distilled under reduced pressure and the obtained residue was purified by silica gel column chromatography [developing solution=methanol:methylene chloride (1:10)] to obtain the title compound (44.6 mg, 31.6%).

$^1$H-NMR (CD$_3$OD) δ: 1.18 (3H, t, J=7.2 Hz), 1.15-1.26 (1H, m), 1.48 (1H, dd, J=13.5, 13.2 Hz), 2.57 (2H, q, J=7.8 Hz), 2.73 (1H, dd, J=13.5, 3.0 Hz), 3.30-3.80 (1H, m), 3.50 (1H, dd, J=9.9, 5.7 Hz), 3.53-3.66 (2H, m), 3.83-3.92 (3H, m), 6.94 (1H, dd, J=12.3, 8.1 Hz), 7.00-7.25 (5H, m), 7.95 (1H, dd, J=7.8, 1.8 Hz)

MS (ESI$^+$): 413 [M+Na]$^+$
HPLC Retention Time: 10.9 minutes

Example 82

(1S,2R,3S,4R,5R)-1-[5-(4-Ethylbenzyl)-2-fluorophenyl]-5-(hydroxymethyl)cyclohexane-1,2,3,4-tetraol To a solution of (1S,2R,3S,4R,5R)-2,3,4-trisbenzyloxy-5-benzyloxymethyl-1-[5-(4-ethylbenzyl)-2-fluorophenyl]cyclohexanol (33 mg, 0.044 mmol) as obtained in Example 81 in methanol-THF (1:1) mixture (1.4 mL), a 20% palladium hydroxide catalyst (7.5 mg) was added. The mixture was stirred under a hydrogen atmosphere for 2.5 hours, and then the catalyst was filtered off. The solvent was distilled under reduced pressure and the obtained residue was purified by silica gel column chromatography [developing solution=methanol:methylene chloride (1:10)] to obtain the title compound (17.5 mg, 100%).

$^1$H-NMR (CD$_3$OD) δ: 1.18 (3H, t, J=7.5 Hz), 1.70-1.79 (1H, m), 1.98-2.11 (2H, m), 2.57 (2H, q, J=7.8 Hz), 3.32-3.45 (1H, m), 3.60-3.71 (3H, m), 3.90 (2H, s), 3.94 (1H, d, J=9.0 Hz), 6.91 (1H, dd, J=12.3, 8.1 Hz), 7.02-7.12 (5H, m), 7.53 (1H, dd, J=7.8, 2.4 Hz)

MS (ESI$^+$): 413 [M+Na]$^+$
HPLC Retention Time: 11.7 minutes

Example 83

(1R,2R,3S,4R,5R)-5-Hydroxymethyl-1-[3-(4-methoxybenzyl)-phenyl]cyclohexane-1,2,3,4-tetraol The target compound was obtained by performing the same operation as in Example 81 with the use of the corresponding starting material and reagents.

$^1$H-NMR (CD$_3$OD) δ: 1.62-1.80 (2H, m), 1.94-2.10 (1H, m), 3.40 (1H, dd, J=10.5, 8.7 Hz), 3.62-3.72 (4H, m), 3.73 (3H, s), 3.89 (2H, s), 6.70-6.82 (2H, m), 7.00-7.03 (2H, m), 7.06-7.12 (2H, m), 7.22 (1H, t, J=7.8 Hz), 7.27-7.32 (1H, m), 7.34-7.37 (1H, m)

MS (ESI$^+$): 375 [M+H]$^+$
HPLC Retention Time: 9.53 minutes

Example 84

(1S,2R,3S,4R,5R)-5-Hydroxymethyl-1-[3-(4-methoxybenzyl)-phenyl]cyclohexane-1,2,3,4-tetraol The target compound was obtained by performing the same operation as in Example 81 with the use of the corresponding starting material and reagents.

$^1$H-NMR (CD$_3$OD) δ: 1.28-1.44 (1H, m), 1.56 (1H, t, J=13.2 Hz), 2.35 (1H, dt, J=13.5, 3.0 Hz), 3.45 (1H, dd, J=11.1, 6.0 Hz), 3.60-3.70 (3H, m), 3.73 (3H, s), 3.89 (2H, s), 6.77-6.82 (2H, m), 7.00-7.05 (1H, m), 7.06-7.13 (2H, m), 7.20 (1H, t, J=7.8 Hz), 7.60-7.65 (1H, m), 7.68-7.70 (1H, m)

MS (ESI$^+$): 397 [M+Na]$^+$
HPLC Retention Time: 14.6 minutes

Example 85

(1R,2R,3S,4S,6R)-4-[1-(4-Ethylbenzyl)-1H-indol-3-yl]-6-(hydroxymethyl)-cyclohexane-1,2,3-triol (1) Synthesis of 1-(4-Ethylbenzyl)-1H-indole To a solution of indole (4.0 g, 34.1 mmol), potassium hydroxide (2.40 g, 42.6 mmol) in ethanol (200 mL) was added and the mixture solution was stirred at room temperature for two hours. The solvent was distilled under reduced pressure. The residue was dissolved in acetone (200 mL), and 1-chloromethyl-4-ethylbenzene (5.28 g, 34.1 mmol) was added thereto. The reaction mixture was stirred at room temperature a whole day and night, and then subjected to Celite filtration and the filtrate was distilled under reduced pressure. The obtained residue was purified by silica gel column chromatography [developing solution=ethyl acetate:n-hexane (1:500)] to obtain the title compound (3.8 g, 47%).

$^1$H-NMR (CDCl$_3$) δ: 1.19 (3H, t, J=7.6 Hz), 2.60 (2H, q, J=7.6 Hz), 5.27 (2H, s), 6.53 (1H, dd, J=3.1, 0.7 Hz), 7.03 (2H, d, J=7.6 Hz), 7.07-7.22 (5H, m), 7.29 (1H, d, J=8.0 Hz), 7.64 (1H, d, J=6.8 Hz)

(2) Synthesis of 3-Bromo-1-(4-ethylbenzy)-1H-indole

A solution of 1-(4-ethylbenzyl)-1H-indole (2.0 g, 8.50 mmol) in DMF (20 mL) was added dropwise to a solution of bromine (0.46 mL, 8.93 mmol) in DMF (20 mL) at room temperature. The reaction mixture was stirred for two hours, and then poured into an ice-cooled sodium pyrosulfurous acid aqueous solution. The resulting mixture was extracted with ethyl acetate, and the organic layer was washed with a saturated sodium hydrogencarbonate aqueous solution and a saturated sodium chloride aqueous solution and dried (anhydrous magnesium sulfate), and then the solvent was distilled under reduced pressure. The residue was recrystallized from ethyl acetate and n-hexane to obtain the title compound (1.68 g, 63%).

$^1$H-NMR (CDCl$_3$) δ: 1.20 (3H, t, J=7.6 Hz), 2.61 (2H, q, J=7.6 Hz), 5.23 (2H, s), 7.05 (2H, dd, J=8.0 Hz), 7.11-7.22 (5H, m), 7.30 (1H, dd, J=6.5, 1.9 Hz), 7.57 (1H, dd, J=6.5, 1.9 Hz)

(3) Synthesis of (2R,3S,4R,5R)-2,3,4-Trisbnezyloxy-5-benzyloxymethyl-1-[1-(4-ethylbenzyl)-1H-indol-3-yl]-cyclohexanol In a nitrogen stream, a solution of 3-bromo-1-(4-ethylbenzyl)-1H-indole (427 mg, 1.36 mmol) in THF (8 mL) was cooled to –78° C., and an n-butyllithium hexane solution (1.6 M, 0.89 mL, 1.43 mmol) was added thereto. The reaction mixture was stirred at the same temperature for five minutes. To this solution, a solution of (2R,3S,4R,5R)-2,3,4-trisbenzyloxy-5-(benzyloxymethyl)-cyclohexanone (875 mg, 1.63 mmol) in THF (5.6 mL) was added dropwise and the mixture was stirred at –78° C. for two hours. The reaction was stopped by addition of a saturated ammonium chloride aqueous solution. The resulting mixture was extracted with ethyl acetate, and the organic layer was washed with water and then dried over sodium sulfate. The residue obtained by distilling the solvent was purified by silica gel column chromatography [developing solution=ethyl acetate:n-hexane (1:10)] to obtain a less polar-isomer (354 mg, 34%) and a more polar-isomer (115 mg, 11%) of the title compound.

Less Polar-Isomer: $^1$H-NMR (CDCl$_3$) δ: 1.18 (3H, t, J=7.2 Hz), 1.93 (2H, m), 2.40 (1H, m), 2.61 (2H, q, J=7.2 Hz), 3.40-5.22 (15H, m), 7.02-7.40 (28H, m), 7.93 (1H, d, J=8.0 Hz) More Polar-Isomer: $^1$H-NMR (CDCl$_3$) δ: 1.18 (3H, t, J=7.6 Hz), 2.40 (1H, m), 2.38 (2H, m), 2.58 (2H, q, J=7.6 Hz), 3.41-5.24 (15H, m), 6.83 (1H, d, J=8.0 Hz), 7.03-7.34 (27H, m), 7.75 (1H, d, J=7.6 Hz)

(4) Synthesis of 1-(4-Ethylbenzyl)-3-[(1S,2S,3R,4R,5R)-2,3,4-trisbenzyloxy-5-(benzyloxymethyl)cyclohexyl]-1H-indole In a nitrogen stream, triethylsilane (0.21 mL, 1.22 mmol) was added dropwise to a solution of (2R,3S,4R,5R)-2,3,4-trisbenzyloxy-5-benzyloxymethyl-1-[1-(4-ethylbenzyl)-1H-indol-3-yl]cyclohexanol (469 mg, 0.61 mmol) in methylene chloride (6 mL) at 0° C. A boron trifluoride-diethyl ether complex (0.093 mL, 0.73 mmol) was added dropwise thereto over five minutes and the reaction mixture was stirred at 0° C. for two hours. A saturated sodium hydrogencarbonate aqueous solution was added to the reaction mixture and the resulting mixture was extracted with methylene chloride. The organic layer was washed with a saturated sodium chloride aqueous solution and dried over sodium sulfate. The residue obtained by distilling the solvent under reduced pressure was purified by silica gel column chromatography [developing solution=ethyl acetate:n-hexane (1:15)] to obtain the title compound (232 mg, 51%).

$^1$H-NMR (CDCl$_3$) δ: 1.17 (3H, t, J=7.6 Hz), 1.87 (2H, m), 2.27 (1H, m), 2.58 (2H, q, J=7.6 Hz), 3.36 (1H, dd, J=9.0, 1.7 Hz), 3.59-3.70 (2H, m), 3.88-4.00 (2H, m), 4.12 (1H, t, J=8.6 Hz), 4.38 (2H, s), 4.47 (1H, d, J=11.4 Hz), 4.54 (1H, d, J=2.7 Hz), 4.58 (1H, d, J=3.1 Hz), 4.80 (1H, d, J=10.7 Hz), 4.89 (1H, d, J=10.7 Hz), 4.98 (1H, d, J=10.7 Hz), 5.25 (2H, d, J=4.9 Hz), 6.97 (2H, d, J=8.4 Hz), 7.05 (2H, d, J=8.0 Hz), 7.08-7.35 (24H, m), 7.62 (1H, d, J=7.2 Hz)

(5) Synthesis of (1R,2R,3S,4S,6R)-4-[1-(4-Ethylbenzyl)-1H-indol-3-yl]-6-(hydroxymethyl)cyclohexane-1,2,3-triol In a nitrogen stream, dimethylsulfide (0.72 mL) and a boron trifluoride-diethyl ether complex (0.36 mL, 2.8 mmol) were added to a solution of 1-(4-ethylbenzyl)-3-[(1S,2S,3R,4R,5R)-2,3,4-tris-benzyloxy-5-(benzyloxymethyl)cyclohexyl]-1H-indole (213 mg, 2.28 mmol) in methylene chloride (4.7 mL) under cooling with ice. The mixture solution was stirred at room temperature for 64 hours, and then water was added thereto under cooling with ice and the resulting solution was extracted with methylene chloride. The organic layer was washed with a saturated sodium chloride aqueous solution and dried (anhydrous magnesium sulfate) and then the solvent was distilled under reduced pressure. The obtained residue was purified by silica gel column chromatography [developing solution=methylene chloride:methanol (50:1)] to obtain the title compound (45 mg, 41%).

$^1$H-NMR (CD$_3$OD) δ: 1.17 (3H, t, J=7.6 Hz), 1.66 (1H, m), 1.79 (1H, m), 2.16 (1H, m), 2.58 (2H, q, J=7.6 Hz), 3.33 (1H, m), 3.57 (1H, dd, J=10.7, 6.1 Hz), 3.69 (1H, dd, J=10.7, 4.2 Hz), 3.76-3.88 (3H, m), 5.29 (2H, s), 6.98-7.11 (6H, m), 7.24 (1H, d, J=8.0 Hz), 7.30 (1H, s), 7.62 (1H, d, J=7.6 Hz)

MS (ESI$^+$): 396 [M+H]$^+$

The structural Formulae of the compounds of the above-described Examples are shown in Table 1 to Table 10.

TABLE 1

| Example | Structural Formula |
|---------|-------------------|
| Example 1 | |

TABLE 1-continued
| Example | Structural Formula |
|---|---|
| Example 2 | 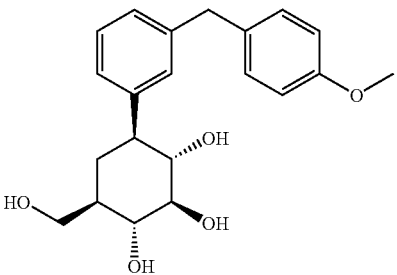 |
TABLE 2
| Example | Structural Formula |
|---|---|
| Example 3 | 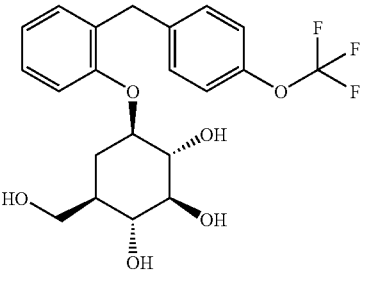 |
| Example 4 | 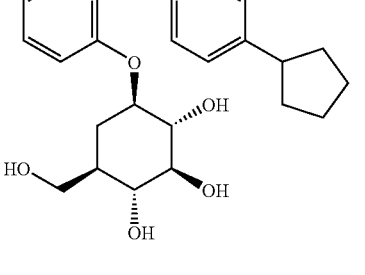 |
| Example 5 | 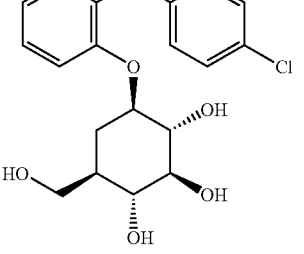 |
| Example 6 | 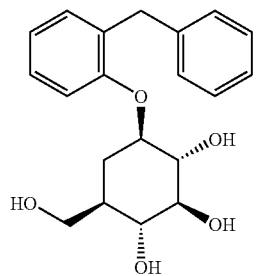 |
TABLE 2-continued
| Example | Structural Formula |
|---|---|
| Example 7 | 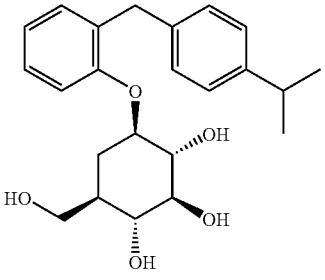 |
| Example 8 | 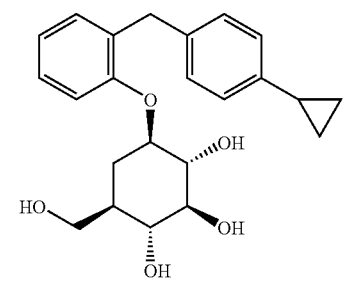 |
| Example 9 | 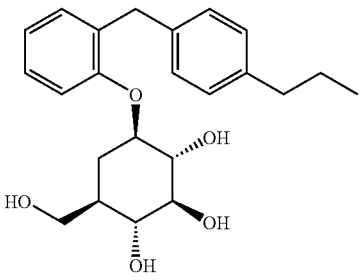 |
| Example 10 | 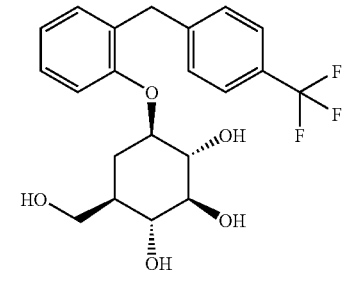 |
| Example 11 | 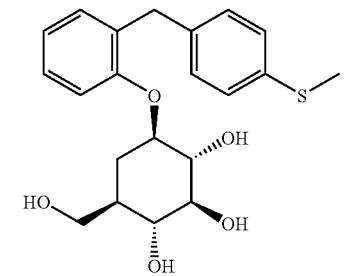 |

TABLE 2-continued
| Example | Structural Formula |
|---|---|
| Example 12 | 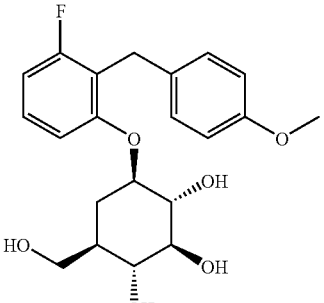 |
TABLE 3
| Example | Structural Formula |
|---|---|
| Example 13 | 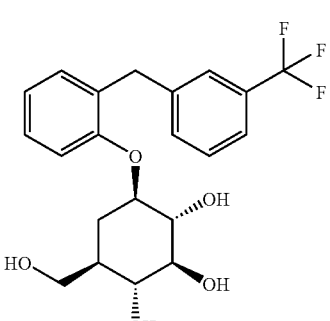 |
| Example 14 | 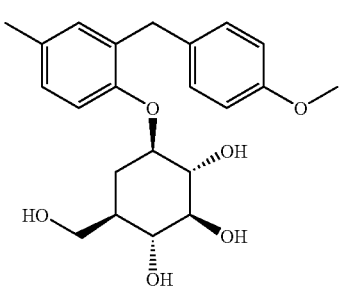 |
| Example 15 | 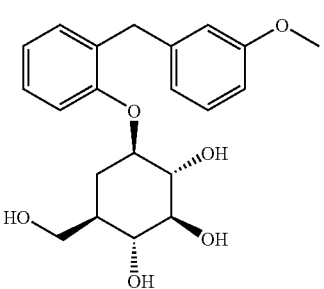 |
TABLE 3-continued
| Example | Structural Formula |
|---|---|
| Example 16 | 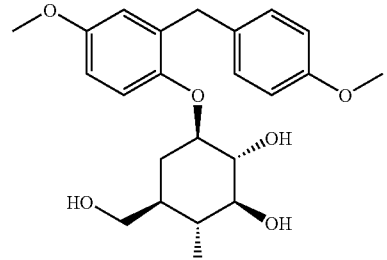 |
| Example 17 | 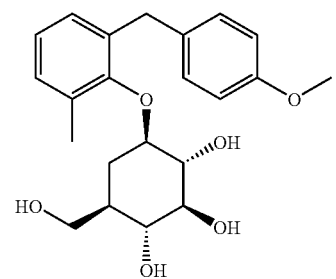 |
| Example 18 | 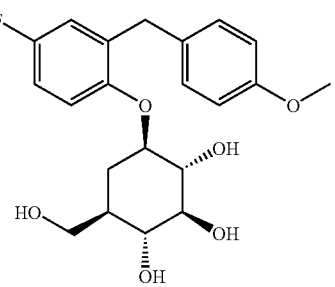 |
| Example 19 | 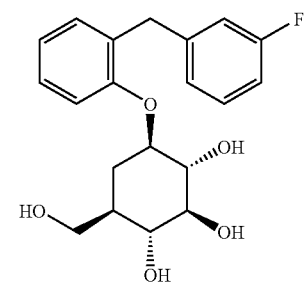 |
| Example 20 | 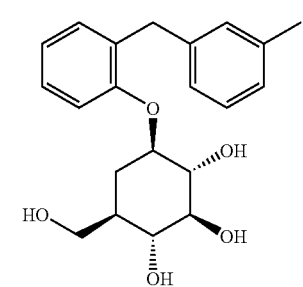 |

TABLE 3-continued
| Example | Structural Formula |
|---|---|
| Example 21 | 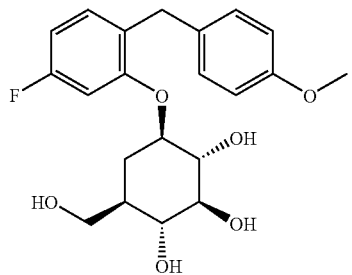 |
| Example 22 | 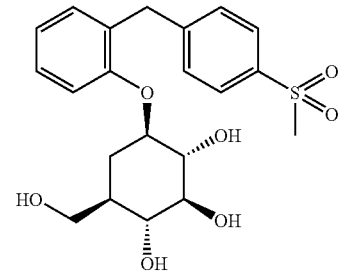 |
TABLE 4
| Example | Structural Formula |
|---|---|
| Example 23 | 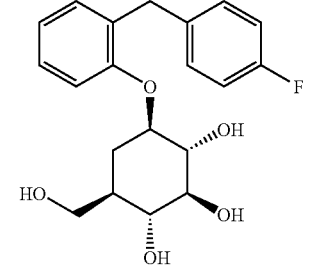 |
| Example 24 | 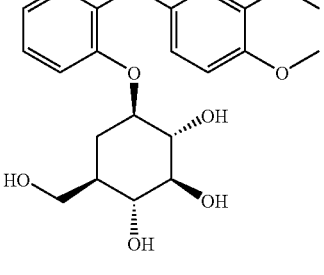 |
| Example 25 | 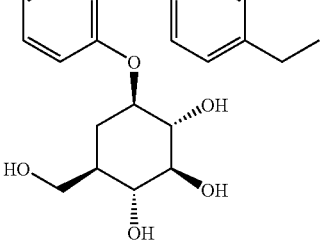 |
| Example 26 | 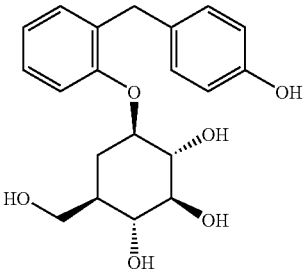 |
| Example 27 | 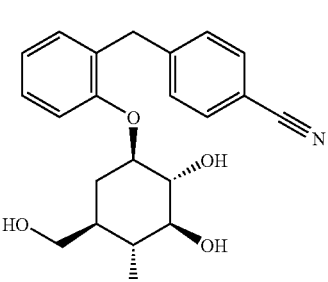 |
| Example 28 | 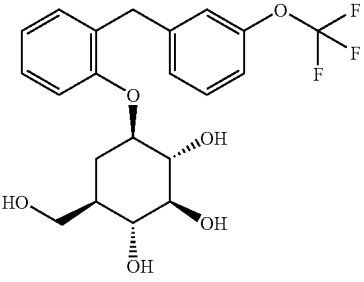 |
| Example 29 | 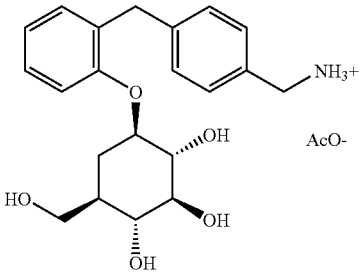 |
| Example 30 | 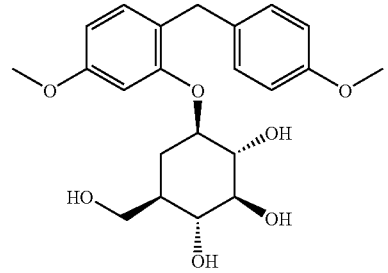 |

TABLE 4-continued
| Example | Structural Formula |
|---|---|
| Example 31 | 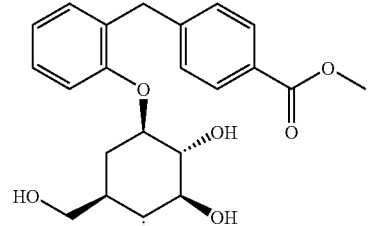 |
| Example 32 | 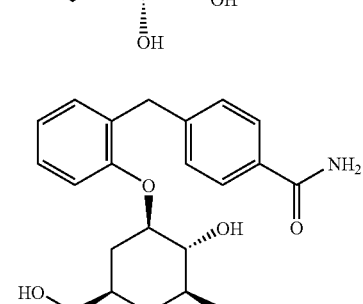 |
TABLE 5
| Example | Structural Formula |
|---|---|
| Example 33 | 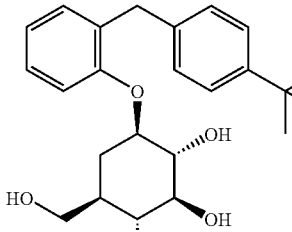 |
| Example 34 | 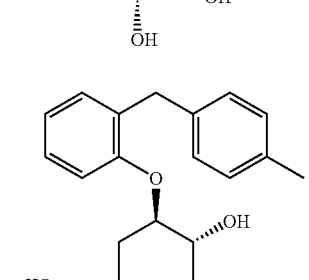 |
| Example 35 | 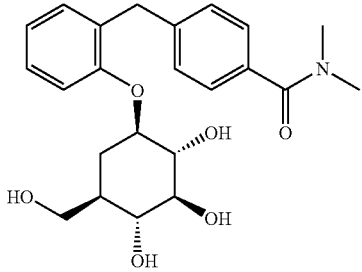 |
TABLE 5-continued
| Example | Structural Formula |
|---|---|
| Example 36 | 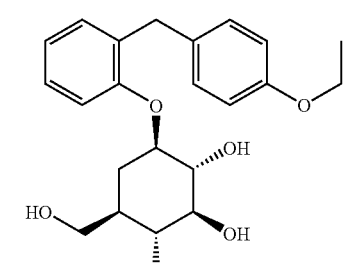 |
| Example 37 | 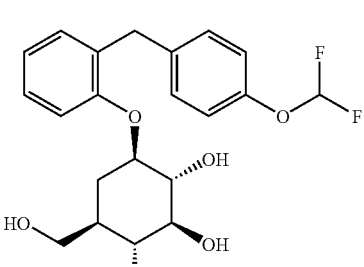 |
| Example 38 | |
| Example 39 | |
| Example 40 | |

TABLE 5-continued
| Example | Structural Formula |
|---|---|
| Example 41 | 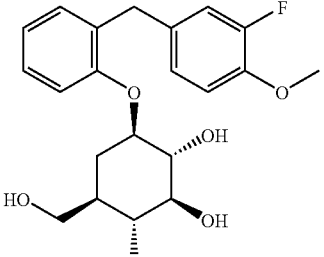 |
| Example 42 | 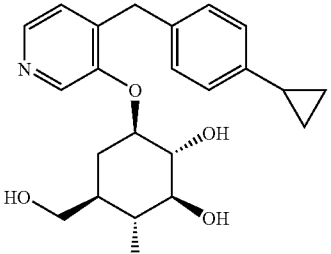 |
TABLE 6
| Example | Structural Formula |
|---|---|
| Example 43 | 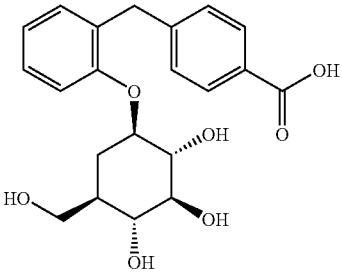 |
| Example 44 | 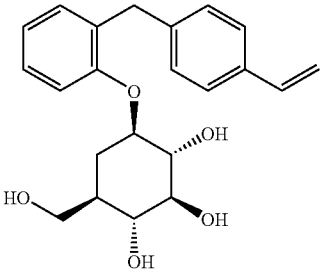 |
| Example 45 | 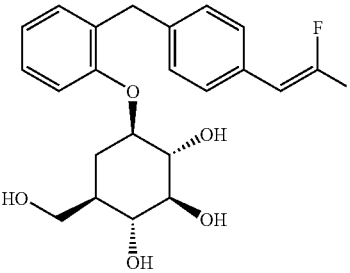 |
TABLE 6-continued
| Example | Structural Formula |
|---|---|
| Example 46 | 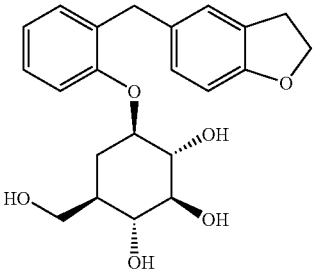 |
| Example 47 | 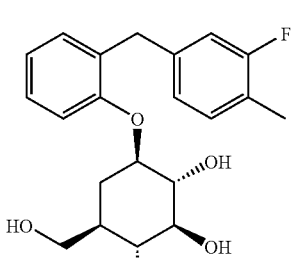 |
| Example 48 | 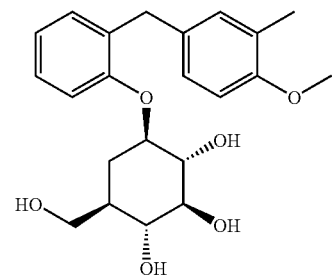 |
| Example 49 | 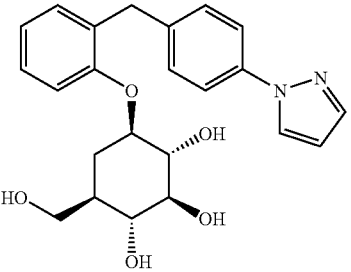 |
| Example 50 | 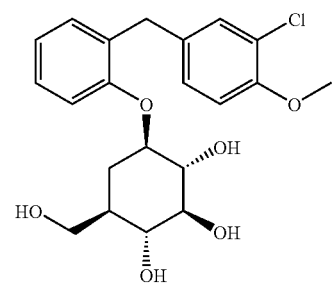 |

TABLE 6-continued

| Example | Structural Formula |
| --- | --- |
| Example 51 | (structure) |
| Example 52 | (structure) |

TABLE 7

| Example | Structural Formula |
| --- | --- |
| Example 53 | (structure) |
| Example 54 | (structure) |
| Example 55 | (structure) |

TABLE 7-continued

| Example | Structural Formula |
| --- | --- |
| Example 56 | (structure) |
| Example 57 | (structure) less polar-isomer |
| Example 58 | (structure) more polar-isomer |
| Example 59 | (structure) |
| Example 60 | (structure) |

TABLE 7-continued

| Example | Structural Formula |
|---|---|
| Example 61 | (structure) |
| Example 62 | (structure) |

TABLE 8

| Example | Structural Formula |
|---|---|
| Example 63 | (structure) |
| Example 64 | (structure) |
| Example 65 | (structure) |

TABLE 8-continued

| Example | Structural Formula |
|---|---|
| Example 66 | (structure) |
| Example 67 | (structure) |
| Example 68 | (structure) |
| Example 69 | (structure) |
| Example 70 | (structure) |

TABLE 8-continued

| Example | Structural Formula |
|---|---|
| Example 71 | |
| Example 72 | |

TABLE 9

| Example | Structural Formula |
|---|---|
| Example 73 | |
| Example 74 | |
| Example 75 | |

TABLE 9-continued

| Example | Structural Formula |
|---|---|
| Example 76 | |
| Example 77 | |
| Example 78 | |
| Example 79 | |
| Example 80 | |

131

TABLE 9-continued

| Example | Structural Formula |
|---------|-------------------|
| Example 81 | (structure) |
| Example 82 | (structure) |

TABLE 10

| Example | Structural Formula |
|---------|-------------------|
| Example 83 | (structure) |
| Example 84 | (structure) |
| Example 85 | (structure) |

132

Experimental Example 1

Test for Confirming Action of Inhibiting Human Na$^+$-Glucose Co-Transporters (SGLT1 and SGLT2)

(1) Preparation of Human SGLT1 Expression Vector

PCR was performed by KOD+DNA polymerase (a product of Toyobo Co., Ltd.) by taking a human small intestine-derived cDNA library (a product of Clontech) as a template with the use of a synthesized DNA primer to amplify human SGLT1 cDNA. Then, the amplified fragment was cloned to pcRII-Topo vector with the use of a Topo TA Cloning Dual Promoter kit (a product of Invitrogen) and introduced into *E. coli* competent cells (TOP10, a product of Invitrogen) and clones which exhibited resistance to ampicillin were proliferated in an LB medium containing ampicillin (50 mg/L). From the proliferated *E. coli*, a plasmid was purified according to the usual way (see Maniatis et al., Molecular Cloning). By taking this plasmid as a template, PCR was performed by KOD+DNA polymerase with the use of a synthetic DNA primer into which restriction enzyme recognition sites had been introduced to amplify human SGLT1 cDNA (a fragment added with an Eco RI recognition site on the upstream side and a Hind III recognition site on the downstream side). This amplified fragment was subjected to Eco RI and Hind III digestion, and the digested fragments were connected to the recognition sites of expression vector pcDNA 3.1(−) (a product of Invitrogen) with the use of a Rapid DNA Ligation kit (a product of Roche Diagonostic). The connected expression vector was introduced into *E. coli* competent cells (DH5α, a product of Invitrogen) and proliferated in an ampicillin-containing LB medium to obtain a human SGLT1 expression vector according to the usual way.

(2) Preparation of Human SGLT2 Expression Vector

PCR was performed by KOD+DNA polymerase by taking a human kidney-derived cDNA library (a product of Clontech) as a template with the use of a synthesized DNA primer to amplify human SGLT2 cDNA. Then, the amplified fragment was cloned to pcRII-Topo vector with the use of the Topo TA Cloning Dual Promoter kit and then introduced into *E. coli* competent cells (TOP10) and clones which exhibited resistance to ampicillin were proliferated in an LB medium containing ampicillin (50 mg/L). From the proliferated *E. coli*, a plasmid was purified according to the usual way. By taking this plasmid as a template, PCR was performed by KOD+DNA polymerase with the use of a synthetic DNA primer into which restriction enzyme recognition sites had been introduced to amplify human SGLT2 cDNA (a fragment added with Xho I recognition site on the upstream side and a Hind III recognition site on the downstream side). This amplified fragment was subjected to Xho I and Hind III digestion, and the digested fragments were connected to their recognition sites of the expression vector pcDNA 3.1(−) with the use of the Rapid DNA Ligation kit. The connected expression vector was introduced into *E. coli* competent cells (DH5α) and proliferated in an ampicillin-containing LB medium to obtain a human SGLT2 expression vector according to the usual way.

(3) Preparation of Human SGLT1 Stable Expression Cell and Human SGLT2 Stable Expression Cell The human SGLT1 expression vector or the human SGLT2 expression vector which was digested with restriction enzyme Pvu I was introduced into CHO-K1 cells with the use of FuGene (a product of Roche Diagonostics). After introduction of the gene, the cells were incubated in a DMEM medium (a product of Gibco) containing penicillin (50 U/mL, a product of Sigma), streptomycin (50 mg/L, a product of Sigma), Geneticin (200 mg/L, a product of Nakalai Tesque) and 20% bovine fetal serum in the presence of 5% $CO_2$ at 37° C. for about three weeks to obtain Genticin-resistant clones. From these clones, cells capable of stably expressing human SGLT1 or the human SGLT2 were selected and obtained by using sodium dependent sugar (methyl-α-D-glucopyranoside) intake activity as an index.

(4) Measurement of Methyl-α-D-glucopyranoside Intake Inhibition Activity

The human SGLT1 stable expression CHO cells or the human SGLT2 stable expression CHO cells was seeded in a 96-well plate to a density of 30,000 to 40,000 cells/well and incubated for four to six days. Next, the medium of the culture plate was removed, and a pretreatment buffer (a buffer containing 140 mM of choline chloride, 2 mM of potassium chloride, 1 mM of calcium chloride, 1 mM of magnesium chloride, 10 mM of 2-[4-(2-hydroxyethyl)-1-piperazinyl] ethanesulfonic acid and tris(hydroxymethyl)-aminomethane and having a pH of 7.4) was added in an amount of 150 μL per well and then left to stand at 37° C. for 20 minutes. The pretreatment buffer was removed and the pretreatment buffer was again added in an amount of 50 μL per well and then left to stand at 37° C. for 20 minutes. To 100 mL of a buffer (a buffer containing 140 mM of sodium chloride, 1 mM of potassium chloride, 1 mM of magnesium chloride, 1 mM of methyl-α-D-glucopyranoside, 10 mM of 2-[4-(2-hydroxyethyl)-1-piperazinyl]ethanesulfonic acid and tris(hydroxymethyl)aminomethane and having a pH of 7.4), there was added and mixed 6.3 mL of methyl-α-D-(U-$^{14}$C)glucopyranoside (200 mCi/L, a product of Amersham Pharmacia Biotech) to prepare an intake buffer, and a test compound was dissolved in this intake buffer and the resulting solution was used as a buffer for determining inhibition activity. Further, as a control, a test compound-free intake buffer was used. Furthermore, in order to determine a basic intake in the absence of the test compound and sodium, a basic intake buffer containing 140 mM of choline chloride instead of the sodium chloride was prepared in the same manner and used in the determination. The pretreatment buffer was removed from the wells of the culture plate and a buffer for determining inhibition activity was added in an amount of 35 μL per well and was left to stand at 37° C. for 45 minutes. Then, the buffer for determining inhibition activity was removed and a washing buffer (a buffer solution containing 140 mM of choline chloride, 2 mM of potassium chloride, 1 mM of calcium chloride, 1 mM of magnesium chloride, 10 mM of methyl-α-D-glucopyranoside, 10 mM of 2-[4-(2-hydroxy-ethyl)-1-piperazinyl] ethanesulfonic acid and tris-(hydroxymethyl)aminomethane and having a pH of 7.4) was added in an amount of 300 μL per well and immediately removed. This washing operation was repeated again and a cell solubilizing solution (1 M of sodium hydroxide and 0.1% of sodium lauryl sulfate) was added in an amount of 30 μL per well to solubilize cells. Thereto was added 15 μL of 2 M hydrochloric acid, and 40 μL of the obtained solution was transferred to a Luma-plate (a product of Packard) and was left to stand overnight at room temperature to evaporate the solvent. The radioactivity of the sample on the plate was determined on a Topcount (manufactured by Packard). The test compound concentration ($IC_{50}$ value) which inhibited 50% of intake, when the value obtained by deducting a basic intake from the intake of the control was taken as 100%, was calculated from the concentration-inhibition curve by using an arithmetic software (ELfit ver.3). As a result, the compounds of the present invention exhibited remarkable SGLT2 inhibition action. The $IC_{50}$ values for the SGLT2 inhibition of the representative compounds of the present invention are shown in Table 11.

[Table 11]

TABLE 11

| Test Compound | $IC_{50}$ Value (nM) |
|---|---|
| Example 1 | 61 |
| Example 2 | 111 |
| Example 8 | 7 |
| Example 11 | 14 |
| Example 12 | 18 |
| Example 25 | 31 |
| Example 42 | 7.7 |
| Example 44 | 16 |
| Example 55 | 17 |
| Example 59 | 8.9 |
| Example 62 | 7.1 |
| Example 64 | 6.6 |
| Example 68 | 18 |
| Example 69 | 5.1 |
| Example 70 | 7.4 |
| Example 73 | 11 |
| Example 54 | 14 |

Industrial Applicability

By the present invention, cyclohexane compounds which exhibit the action of inhibiting SGLT2 activity or their pharmaceutically acceptable salts can be provided. The compounds of the present invention are useful as prophylactic or therapeutic agents for diabetes, diabetes-related diseases or diabetic complications.

The invention claimed is:

1. A compound represented by formula (I)

wherein

A is —O—, —$CH_2$—, or —NH—;

n is an integer selected from 0 and 1;

$R^6$ and $R^7$ are each independently a hydrogen atom or a $C_1$-$C_6$ alkyl group m is an integer selected from 1 to 3;

Q is selected from $Q^1$ to $Q^5$ represented by the following formulae:

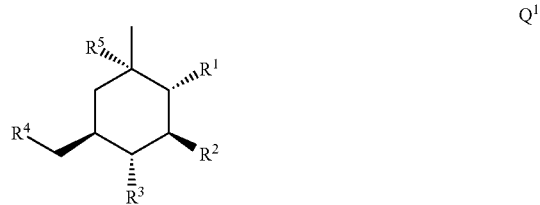

-continued

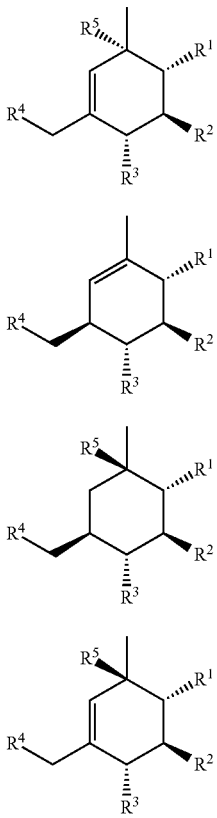

Wherein

R$^1$, R$^2$, R$^3$, and R$^4$ are each independently selected from a hydroxy group, a C$_1$-C$_6$ alkoxy group which may be substituted with one or more Ra, a C$_7$-C$_{14}$ aralkyloxy group which may be substituted with one or more Rb, and —OC(=O)Rx;

R$^5$ is selected from a hydrogen atom, a hydroxy group, a C$_1$-C$_6$ alkyl group which may be substituted with one or more Ra, a C$_1$-C$_6$ alkoxy group which may be substituted with one or more Ra, a C$_7$-C$_{14}$ aralkyloxy group which may be substituted with one or more Rb, and —OC(=O)Rx;

Rx is a C$_1$-C$_6$ alkyl group which may be substituted with one or more Ra, an aryl group which may be substituted with one or more Rb, a heteroaryl group which may be substituted with one or more Rb, a C$_1$-C$_6$ alkoxy group which may be substituted with one or more Ra, or —NReRf, Ar$^1$ is an arylene group which may be substituted with one or more Rb, or a heteroarylene group which may be substituted with one or more Rb, where the heteroarylene group may form a fused ring with an aromatic carbocycle or an aromatic heterocycle;

Ar$^2$ is an aryl group which may be substituted with one or more Rb, or a heteroaryl group which may be substituted with one or more Rb;

Ra is each independently selected from a halogen atom, a hydroxy group, a cyano group, a nitro group, a carboxy group, a C$_1$-C$_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a C$_1$-C$_6$ alkylthio group, a C$_1$-C$_6$ alkylsulfinyl group, a C$_1$-C$_6$ alkylsulfonyl group, —NRfRg, and a C$_1$-C$_6$ alkylcarbonyl group which may be substituted with one or more Rc;

Rb is each independently selected from a C$_1$-C$_6$ alkyl group which may be substituted with one or more Rc, a C$_1$-C$_6$ alkenyl group which may be substituted with one or more Rc, a C$_3$-C$_8$ cycloalkyl group which may be substituted with one or more Rc, a C$_7$-C$_{14}$ aralkyl group which may be substituted with one or more Rd, a halogen atom, a hydroxy group, a cyano group, a nitro group, a carboxy group, a C$_1$-C$_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a C$_1$-C$_6$ alkylthio group, a C$_1$-C$_6$ alkylsulfinyl group, a C$_1$-C$_6$ alkylsulfonyl group, —NRfRg, a C$_1$-C$_6$ alkylcarbonyl group which may be substituted with one or more Rc, a C$_1$-C$_3$ alkylenedioxy group, a heterocyclyl group, —CO$_2$Ri, and —CONRiRj;

Rc is each independently selected from a halogen atom, a hydroxy group, a cyano group, a nitro group, a carboxy group, a C$_1$-C$_6$ alkoxy group which may be substituted with one or more halogen atoms, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a C$_1$-C$_6$ alkylamino group, and a di(C$_1$-C$_6$ alkyl)amino group;

Rd is each independently selected from a C$_1$-C$_6$ alkyl group which may be substituted with one or more halogen atoms, a C$_1$-C$_6$ alkoxy group which may be substituted with one or more halogen atoms, a C$_7$-C$_{14}$ aralkyl group which may be substituted with one or more halogen atoms, a halogen atom, a hydroxy group, a cyano group, a nitro group, an amino group, a C$_1$-C$_6$ alkylamino group, and a di(C$_1$-C$_6$ alkyl)amino group;

Re is a hydrogen atom, a C$_1$-C$_6$ alkyl group which may be substituted with one or more Rc, an aryl group which may be substituted with one or more Rd, or a heteroaryl group which may be substituted with one or more Rd;

Rf is a hydrogen atom, or a C$_1$-C$_6$ alkyl group which may be substituted with one or more Rc;

Rg is a hydrogen atom, a C$_1$-C$_6$ alkyl group which may be substituted with one or more Rc, a C$_1$-C$_6$ alkylcarbonyl group which may be substituted with one or more Rc, an aryl group which may be substituted with one or more Rd, a heteroaryl group which may be substituted with one or more Rd, a carbamoyl group, a C$_1$-C$_6$ alkoxycarboxy group which may be substituted with one or more Rc, or a C$_1$-C$_6$ alkylsulfonyl group which may be substituted with one or more Rc;

Re and Rf, and Rf and Rg may form a 4- to 7-membered heterocycle together with the nitrogen atom to which they are bonded, respectively; and Ri and Rj are each independently selected from a hydrogen atom, a C$_1$-C$_6$ alkyl group which may be substituted with one or more Rc, a C$_3$-C$_8$ cyclo-alkyl group which may be substituted with one or more RC, and a C$_7$-C$_{14}$ aralkyl group which may be substituted with one or more Rd, or a pharmaceutically acceptable salt thereof.

2. The compound according to claim 1, wherein n is 1, or a pharmaceutically acceptable salt thereof.

3. The compound according to claim 1, wherein A is —O— or —NH—, or a pharmaceutically acceptable salt thereof.

4. The compound according to claim 2, wherein the substituent —$(CR^6R^7)_m$—$Ar^2$ is bonded to a ring atom adjacent to the ring atom to which the substituent A is bonded on $Ar^1$, or a pharmaceutically acceptable salt thereof.

5. The compound according to claim 1, wherein n is 0, or a pharmaceutically acceptable salt thereof.

6. The compound according to claim 5, wherein the substituent —$(CR^6R^7)_m$—$Ar^2$ is bonded to the second ring atom departing from the ring atom to which Q is bonded on $Ar^1$, or a pharmaceutically acceptable salt thereof.

7. The compound according to claim 1, wherein m is 1, or a pharmaceutically acceptable salt thereof.

8. The compound according to any claim 1, wherein $Ar^1$ is a phenylene group, a naphthylene group, a thienylene group, a pyridinylene group, an indolylene group, or a pyrazolylene group, where these groups may be substituted with one or more Rb, or a pharmaceutically acceptable salt thereof.

9. The compound according to claim 1, wherein $Ar^2$ is a phenyl group, a naphthyl group, a thienyl group, a benzofuranyl group, a benzothienyl group, a benzodioxolyl group, a 2,3-dihydrobenzofuranyl group, or a 2,3-dihyrobenzothienyl group, where these groups may be substituted with one or more Rb, or a pharmaceutically acceptable salt thereof.

10. The compound according to claim 1, wherein $R^1$, $R^2$, $R^3$, $R^4$ and $R^5$ are each independently selected from a hydroxy group and —OC(=O)Rx, or a pharmaceutically acceptable salt thereof.

11. The compound according to claim 1, wherein m is 1; n is 1; A is —O— or —NH—; $Ar^1$ is a phenylene group, a naphthylene group, a thienylene group, a pyridinylene group, an indolylene group, or a pyrazolylene group, where these groups may be substituted with one or more Rb; $Ar^2$ is a phenyl group, a naphthyl group, a thienyl group, a benzofuranyl group, a benzothienyl group, a benzodioxolyl group, a 2,3-dihydrobenzofuranyl group, or a 2,3-dihyrobenzothienyl group, where these groups may be substituted with one or more Rb; and $R^1$, $R^2$, $R^3$, $R^4$ and $R^5$ are each independently selected from a hydroxy group and —OC(=O)Rx, or a pharmaceutically acceptable salt thereof.

12. The compound according to claim 1, wherein m is 1; n is 0; $Ar^1$ is a phenylene group, a naphthylene group, a thienylene group, a pyridinylene group, an indolylene group or a pyrazolylene group, where these groups may be substituted with one or more Rb; $Ar^2$ is a phenyl group, a naphthyl group, a thienyl group, a benzofuranyl group, a benzothienyl group, a benzodioxolyl group, a 2,3-dihydrobenzofuranyl group, or a 2,3-dihyrobenzothienyl group, where these groups may be substituted with one or more Rb; and $R^1$, $R^2$, $R^3$, $R^4$ and $R^5$ are each independently selected from a hydroxy group and —OC(=O)Rx, or a pharmaceutically acceptable salt thereof.

13. A compound selected from:
[2-(4-methoxybenzyl)phenyl]-5a-carba-β-D-glucopyranoside; [1S,2R,3R,4R,6S]-4-hydroxymethyl-6-[3-(4-methoxybenzyl)-phenyl]cyclohexane-1,2,3-triol;
[2-(4-trifluoromethoxybenzyl)phenyl]-5a-carba-β-D-gluco-pyranoside;
[2-(4-cyclopentylbenzyl)phenyl]-5a-carba-β-D-glucopyranoside;
[2-(4-chlorobenzyl)phenyl]-5a-carba-β-D-glucopyranoside;
(2-benzylphenyl)-5a-carba-β-D-glucopyranoside;
[2-(4-isopropylbenzyl)phenyl]-5a-carba-β-D-glucopyranoside;
[2-(4-cyclopropylbenzyl)phenyl]-5a-carba-β-D-glucopyranoside;
[2-(4-n-propylbenzyl)phenyl]-5a-carba-β-D-glucopyranoside;
[2-(4-trifluoromethylbenzyl)phenyl]-5a-carba-β-D-glucopyranoside;
[2-(4-methylsulfanylbenzyl)phenyl]-5a-carba-β-D-glucopyranoside;
[3-fluoro-2-(4-methoxybenzyl)phenyl]-5a-carba-β-D-glucopyranoside;
[2-(3-trifluoromethylbenzyl)phenyl]-5a-carba-β-D-glucopyranoside;
[2-(4 methoxybenzyl)-4-methylphenyl]-5a-carba-β-D-glucopyranoside;
[2 (3-methoxybenzyl)phenyl]-5a-carba-β-D-glucopyranoside;
[2-(4-methoxybenzyl)-4-methoxyphenyl]-5a-carba-β-D-glucopyranoside;
[2-(4-methoxybenzyl)-6-methylphenyl]-5a-carba-β-D-glucopyranoside;
[2-(4-methoxybenzyl)-4-fluorophenyl]-5a-carba-β-D-glucopyranoside;
[2-(3-fluorobenzyl)phenyl]-5a-carba-β-D-glucopyranoside;
[2-(3-methylbenzyl)phenyl]-5a-carba-β-D-glucopyranoside;
[5-fluoro-2-(4-methoxybenzyl)phenyl]-5a-carba-β-D-glucopyranoside;
[2-(4-methylsulfonylbenzyl)phenyl]-5a-carba-β-D-glucopyranoside;
[2-(4-fluorobenzyl)phenyl]-5a-carba-β-D-glucopyranoside;
[2-(3,4-dimethoxybenzyl)phenyl]-5a-carba-β-D-glucopyranoside;
[2-(4-ethylbenzyl)phenyl]-5a-carba-β-D-glucopyranoside;
[2-(4-hydroxybenzyl)phenyl]-5a-carba-β-D-glucopyranoside;
[2-(4-cyanobenzyl)phenyl]-5a-carba-β-D-glucopyranoside;
[2-(3-trifluoromethoxybenzyl)phenyl]-5a-carba-β-D-glucopyranoside;
[2-(4-aminomethylbenzyl)phenyl]-5a-carba-β-D-glucopyranoside;
[5-methoxy-2-(4-methoxybenzyl)phenyl]-5a-carba-β-D-glucopyranoside;
[2-(4-methoxycarbonylbenzyl)phenyl]-5a-carba-β-D-glucopyranoside;
[2-(4-carbamoylbenzyl)phenyl]-5a-carba-β-D-glucopyranoside;
[2-(4-N,N-dimethylcarbamoylbenzyl)phenyl]-5a-carba-β-D-glucopyranoside;
[2-(4-ethoxybenzyl)phenyl]-5a-carba-β-D-glucopyranoside;
[2-(4-difluoromethoxybenzyl)phenyl]-5a-carba-β-D-glucopyranoside;
[2-(4-tert-butylbenzyl)phenyl]-5a-carba-β-D-glucopyranoside;
[2-(4-methylbenzyl)phenyl]-5a-carba-β-D-glucopyranoside;
[2-(4-methoxybenzyl)phenyl]-5-trifluoromethylthiophen-3-yl]-5a-carba-β-D-glucopyranoside;
[3-methoxy-2-(4-methoxybenzyl)phenyl]-5a-carba-β-D-glucopyranoside;

[2-(4-methoxybenzyl)-3-methylphenyl]-5a-carba-β-D-glucopyranoside;
[2-(3-fluoro-4-methoxybenzyl)phenyl]-5a-carba-β-D-glucopyranoside;
[4-(4-cyclopropylbenzyl)pyridin-3-yl]-5a-carba-β-D-glucopyranoside;
[2-(4-carboxybenzyl)phenyl]-5a-carba-β-D-glucopyranoside;
[2-(4-vinylbenzyl)phenyl]-5a-carba-β-D-glucopyranoside;
{2-[4-(2,2-difluorovinyl)benzyl]phenyl}-5a-carba-β-D-glucopyranoside;
[2-(2,3-dihydrobenzofuran-5-ylmethyl)phenyl]-5a-carba-β-D-glucopyranoside;
[2-(3-fluoro-4-methylbenzyl)phenyl]-5a-carba-β-D-glucopyranoside;
[2-(4-methoxy-3-methylbenzyl)phenyl]-5a-carba-β-D-glucopyranoside;
[2-(4-pyrazol-1-ylbenzyl)phenyl]-5a-carba-β-D-glucopyranoside;
[2-(3-chloro-4-methoxybenzyl)phenyl]-5a-carba-β-D-glucopyranoside;
[2-(3,4-methylenedioxybenzyl)phenyl]-5a-carba-β-D-glucopyranoside;
[2-(4-cyclobutylbenzyl)phenyl]-5a-carba-β-D-glucopyranoside;
[2-(4-acetylbenzyl)phenyl]-5a-carba-β-D-glucopyranoside;
[2-(4-methoxybenzyl)-5-methylphenyl]-5a-carba-β-D-glucopyranoside;
[2-(4-ethylbenzyl)thiophen-3-yl]-5a-carba-β-D-glucopyranoside;
[2-(benzothiophen-2-yl)methylphenyl]-5a-carba-β-D-glucopyranoside;
(R)-{2-[1-(4-cyclopropylphenyl)ethyl]phenyl}-5a-carba-β-D-glucopyranoside;
(S)-{2-[1-(4-cyclopropylphenyl)ethyl]phenyl}-5a-carba-β-D-glucopyranoside;
[2-(4-cyclopropylbenzyl)-5-methylthiophen-3-yl]-5a-carba-β-D-glucopyranoside;
[2-(4-ethylbenzyl)-5-methylthiophen-3-yl]-5a-carba-β-D-glucopyranoside;
[5-chloro-2-(4-cyclopropylbenzyl)thiophen-3-yl]-5a-carba-β-D-glucopyranoside;
(1R,2S,3R,6R)-6-[2-(4-cyclopropylbenzyl)phenoxy]-4-(hydroxymethyl)cyclohex-4-ene-1,2,3-triol;
(1R,2S,3R,6R)-4-hydroxymethyl-6-[2-(4-methoxybenzyl)-phenoxy]cyclohex-4-ene-1,2,3-triol;
(1R,2S,3S,6R)-4-[3-(4-ethylbenzyl)phenyl]-6-(hydroxymethyl)cyclohex-4-ene-1,2,3-triol;
(1R,2R,3S,4R,5R)-1-[3-(4-ethylbenzyl)-4-methoxyphenyl]-5-(hydroxymethyl)cyclohexane-1,2,3,4-tetraol;
(1R,2R,3S,4S,6R)-4-[3-(4-ethylbenzyl)-4-methoxyphenyl]-6-(hydroxymethyl)cyclohexane-1,2,3-triol;
(1R,2R,3S,4R,5R)-1-[2-ethoxy-5-(4-ethylbenzyl)phenyl]-5-(hydroxymethyl)cyclohexane-1,2,3,4-tetraol;
(1R,2R,3S,4S,6R)-4-[2-ethoxy-5-(4-ethylbenzyl)phenyl]-6-(hydroxymethyl)cyclohexane-1,2,3-triol;
(1R,2R,3S,4R,5R)-1-[5-(4-ethylbenzyl)-2,4-dimethoxyphenyl]-5-(hydroxymethyl)cyclohexane-1,2,3,4-tetraol;
(1R,2R,3S,4S,6R)-4-[5-(4-ethylbenzyl)-2,4-dimethoxyphenyl]-6-(hydroxymethyl)cyclohexane-1,2,3-triol;
(1R,2R,3S,4R,5R)-1-[5-(4-ethylbenzyl)-2-methylphenyl]-5-(hydroxymethyl)cyclohexane-1,2,3,4-tetraol;
(1R,2R,3S,4S,6R)-4-[5-(4-ethylbenzyl)-2-methylphenyl]-6-(hydroxymethyl)cyclohexane-1,2,3-triol;
(1R,2R,3S,4R,5R)-1-[5-(4-ethylbenzyl)-2-methoxyphenyl]-5-(hydroxymethyl)cyclohexane-1,2,3,4-tetraol;
(1R,2R,3S,4S,6R)-4-[5-(4-ethylbenzyl)-2-methoxyphenyl]-6-(hydroxymethyl)cyclohexane-1,2,3-triol;
(1R,2R,3S,4R,5R)-1-[5-(4-ethylbenzyl)-2-trifluoromethoxy-phenyl]-5-(hydroxymethyl)cyclohexane-1,2,3,4-tetraol;
(1R,2R,3S,4S,6R)-4-[5-(4-isopropylbenzyl)-2-methoxyphenyl]-6-(hydroxymethyl)cyclohexane-1,2,3-triol;
(1R,2R,3S,4S,6R)-4-[3-(4-ethylbenzyl)phenyl]-6-(hydroxy-methyl)cyclohexane-1,2,3-triol;
(1R,2R,3S,4S,6R)-4-[3-(4-hydroxybenzyl)phenyl]-6-(hydroxymethyl)cyclohexane-1,2,3-triol;
(1R,2R,3S,4S,6R)-4-[5-(4-ethylbenzyl)-2-hydroxyphenyl]-6-(hydroxymethyl)cyclohexane-1,2,3-triol;
(1R,2R,3S,4S,6R)-4-[3-(4-cyclopropylbenzyl)phenyl]-6-(hydroxymethyl)cyclohexane-1,2,3-triol;
(1R,2R,3S,4R,5R)-1-[5-(4-ethylbenzyl)-2-fluorophenyl]-5-(hydroxymethyl)cyclohexane-1,2,3,4-tetraol;
(1S,2R,3S,4R,5R)-1-[5-(4-ethylbenzyl)-2-fluorophenyl]-5-(hydroxymethyl)cyclohexane-1,2,3,4-tetraol;
(1R,2R,3S,4R,5R)-5-hydroxymethyl-1-[3-(4-methoxybenzyl)-phenyl]cyclohexane-1,2,3,4-tetraol;
(1S,2R,3S,4R,5R)-5-hydroxymethyl-1-[3-(4-methoxybenzyl)-phenyl]cyclohexane-1,2,3,4-tetraol; and
(1R,2R,3S,4S,6R)-4-[1-(4-ethylbenzyl)-1H-indol-3-yl]-6-(hydroxymethyl)-cyclohexane-1,2,3-triol,
or a pharmaceutically acceptable salt thereof.

14. A pharmaceutical composition comprising a compound according to claim 1 or a pharmaceutically acceptable salt thereof, and a pharmaceutically acceptable carrier.

15. A method of treating diabetes, diabetic complications caused by hyperglycemia, or obesity, which comprises administering a therapeutic effective amount of a compound according to claim 1 or a pharmaceutically acceptable salt thereof to a patient.

16. A method according to claim 15, wherein the diabetes is insulin-dependent diabetes (type I diabetes) or insulin-independent diabetes (type II diabetes).

17. A method of inhibiting $Na^+$-glucose co-transporter, which comprises administering a therapeutic effective amount of a compound according to claim 1 or a pharmaceutically acceptable salt thereof to a patient.

* * * * *